(12) United States Patent
Hodge

(10) Patent No.: US 7,655,432 B2
(45) Date of Patent: Feb. 2, 2010

(54) KINASES AND USES THEREOF

(75) Inventor: Martin R. Hodge, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/151,520

(22) Filed: May 7, 2008

(65) Prior Publication Data

US 2008/0274472 A1    Nov. 6, 2008

Related U.S. Application Data

(60) Division of application No. 11/358,419, filed on Feb. 21, 2006, now Pat. No. 7,425,424, which is a continuation of application No. 10/989,228, filed on Nov. 15, 2004, now abandoned, which is a division of application No. 09/862,027, filed on May 21, 2001, now Pat. No. 6,858,418, which is a division of application No. 09/345,473, filed on Jun. 30, 1999, now Pat. No. 6,558,903.

(51) Int. Cl.
    *C12Q 1/48* (2006.01)
(52) U.S. Cl. ........................................ 435/15
(58) Field of Classification Search .................. 435/15
    See application file for complete search history.

(56) References Cited

U.S. PATENT DOCUMENTS

| | | | |
|---|---|---|---|
| 5,663,314 | A | 9/1997 | Serge et al. |
| 5,817,479 | A | 10/1998 | Au-Young et al. |
| 5,962,265 | A | 10/1999 | Norris et al. |
| 6,034,228 | A | 3/2000 | Norris et al. |
| 6,300,098 | B1 * | 10/2001 | Norris et al. ............... 435/69.1 |
| 6,524,833 | B1 | 2/2003 | Zon et al. |
| 6,656,716 | B1 | 12/2003 | Plowman et al. |
| 6,680,170 | B2 | 1/2004 | Plowman et al. |

FOREIGN PATENT DOCUMENTS

| WO | 99/29857 | * 6/1999 |
|---|---|---|
| WO | WO 99/64576 A2 | 12/1999 |
| WO | WO 00/06728 A2 | 2/2000 |

OTHER PUBLICATIONS

Itoh et al., Arch. Biochem. Biophys., 340(2), 201-207, 1997.*
Pytowski et al., Arch. Biochem. Biopys., 359(2), 310-319, 1998.*
Colman, Research in Immunology, 1994; 145(1): 33-36.*
NCBI Entrez Protein Query, GenBank Report for Accession No. AAB71795, Federspiel et al., Direct Submission, Submitted Jun. 5, 1997. Amino Acid Residues 1-645 are SEQ ID Nos. 15 and 16.
NCBI Entrez Protein Query, GenBank Report for Accession No. AAB65490, Rounsley et al., Direct Submissions, Submitted Apr. 4, 1997. Amino Acid Residues 1-604 are SEQ ID No. 17.
NCBI Entrez Protein Query, GenBank Report for Accession No. AAC47047, Wilson et al., "2.2 Mb of Contiguous Nucleotide Sequence from Chromosome III of *C. elegans*," Nature, 1994 pp. 32-38, vol. 368; Waterston, Direct Submission, Submitted Apr. 8, 1994. Amino Acid Residues 1-328 are SEQ ID Nos. 18.
NCBI Entrez Protein Query, GenBank Report for Accession No. P80192, Dorow et al., "Identification of a New Family of Human Epithelial Protein Kinase Containing Two Leucine/Isoleucine-zipper Domains," Eur. J. Biochem., 1993, pp. 701-710, vol. 213. Amino Acid Residues 1-394 are SEQ ID No. 19.
Database EST, Accession No. AA740847, NCI-CGAP http://www.ncbi.nlm.nih.gov/ncicga;, National Cancer Genome Project (CGAP), Tumor Gene Index, Feb. 7, 1998. See their sequence for having at least 15 nucleotides of SEQ ID No. 1 and having the potential of encoding 15 amino acids (fragments) of SEQ ID O:2.
Colman, Research in Immunology, 1994; 145(1):33-36.

* cited by examiner

*Primary Examiner*—Maryam Monshipouri

(57) ABSTRACT

Novel kinase polypeptides, proteins, and nucleic acid molecules are disclosed. In addition to isolated, full-length kinase proteins, the invention further provides isolated kinase fusion proteins, antigenic peptides, and anti-kinase antibodies. The invention also provides kinase nucleic acid molecules, recombinant expression vectors containing a nucleic acid molecule of the invention, host cells into which the expression vectors have been introduced, and nonhuman transgenic animals in which a kinase gene has been introduced or disrupted. Diagnostic, screening, and therapeutic methods utilizing compositions of the invention are also provided.

5 Claims, 98 Drawing Sheets

```
Input file h12832; Output File h12832.pat
Sequence length 1586

GTCGACCCACGCGTCCGGTTCGAATTGCAACGGCAGCTGCCGGGCGTATGTGTTGGTGTGCTAGAGGCAGCTGCAGGGTCT                    79

CGCTGGGGGCCCGCTCCGGGACCAATTTGAAGAGGTACTTGGCCACGACTTATTTCACCTCCGACCTTTCCTTCCAGGC                     158

M   E   G   I   S   N   F   K   T   P   S                                                11
GGTGAGACTCTGGACTGAGAGTGGCTTTCACA ATG GAA GGG ATC AGT AAT TTC AAG ACA CCA AGC                        223

K   L   S   E   K   K   S   V   L   C   S   T   P   T   I   N   I   P   A                         31
AAA TTA TCA GAA AAG AAA AGT GTA TTA TGT TCA ACT CCA ACT ATA AAT ATC CCG GCC                         283

S   P   F   M   Q   K   L   G   F   G   T   G   V   N   V   Y   L   M   K   R                     51
TCT CCG TTT ATG CAG AAG CTT GGC TTT GGT ACT GGG GTA AAT GTG TAC CTA ATG AAA AGA                     343
```

FIG. 1A

| # | Amino acids / Codons | End position (aa / nt) |
|---|---|---|
| 1 | S P R G L S H P W A V K K I N P I C N<br>TCT CCA AGA GGT TTG TCT CAT CCT TGG GCT GTA AAA AAG ATT AAT CCT ATA TGT AAT | 71 / 403 |
| 2 | D H Y R S V Y Q K R L M D E A K I N S<br>GAT CAT TAT CGA AGT GTG TAT CAA AAG AGA CTA ATG GAT GAA GCT AAG ATT AAT AGC | 91 / 463 |
| 3 | L H P N I V G Y R A F T E A N D G S L<br>CTT CAT CCA AAC ATT GTT GGT TAT CGT GCT TTT ACT GAA GCC AAT GAT GGC AGT CTG | 111 / 523 |
| 4 | C L A M E Y G G E K S L N D L I E E R Y<br>TGT CTT GCT ATG GAA TAT GGA GGT GAA AAG TCT CTA AAT GAC TTA ATA GAA GAA CGA TAT | 131 / 583 |
| 5 | K A S Q D P F P A A K A E K N L V N M A<br>AAA GCC AGC CAA GAT CCT TTT CCA GCA GCC AAA GCA GAA AAG AAT TTG AAT ATG GCA | 151 / 643 |
| 6 | R G L K Y H Q L H K L L I K A C D I K S S<br>AGA GGG TTA AAG TAT CAC CAA CTG CAT AAA CTT CTT ATA AAA GCC GAA AAG TCT TCA | 171 / 703 |
| 7 | N P V I D F E T I K L L H G D V G K S L<br>AAT CCT GTT ATT GAC TTT GAA ACA ATT AAA CTG CTT CAT GGA GAT GTA GGA TCT CTA | 191 / 763 |
| 8 | P L E N M T V D P E A C Y I T D K A P E P<br>CCA CTG GAT GAA AAT ATG ACT GTG ACT GAC CCT GAG GCT TGT TAC ATT GGC ACA GAG CCA | 211 / 823 |
| 9 | W K P K E A V E N G E V I T D K A I F<br>TGG AAA CCC AAA GAA GCT GTG GAG GAG AAT GGT GTT ATT ACT GAC AAG GCA GCA TTT | 231 / 883 |

FIG. 1B

```
 A   F   G   L   T   L   W   E   M   M   T   L   S   I   P   H   I   N   L   S   251
GCC TTT GGC CTT ACT TTG TGG GAA ATG ATG ACT TTA TCG ATT CCA CAC ATT AAT CTT TCA  943
 N   D   D   D   E   D   K   T   F   D   E   S   D   F   D   D   E   A   Y       271
AAT GAT GAT GAT GAA GAT AAA ACT TTT GAT GAA AGT GAT TTT GAT GAT GAA GCA TAC     1003
 Y   A   A   L   G   T   R   P   P   I   N   M   E   E   L   D   E   S   Y   Q   291
TAT GCA GCG TTG GGA ACT AGG CCA CCT ATT AAT ATG GAA GAA CTG GAT GAA TCA TAC CAG 1063
 K   V   I   E   L   F   S   V   C   T   N   E   D   P   K   D   R   P   S   A   311
AAA GTA ATT GAA CTC TTC TCT GTA TGC ACT AAT GAA GAC CCT AAA GAT CGT CCT TCT GCT 1123
 A   H   I   V   E   A   L   E   T   D   V   *                                  322
GCA CAC ATT GTT GAA GCT CTG GAA ACA GAT GTC TAG                                 1159

TGATCATCTCAGCTGAAGTGTGCCTTGCGTAAATAACTGTTTATTCCAAAATATTTACATAGTTACTATCAGTAGTTAT 1238
TAGACTCTAAAATTGGCATATATTGAGGACCATAGTTTCTCTGTAACATATGGATAACTATTCTAATATGAAATATGCT 1317
TATATTGGCTATAAGCACTGGAATTGTACTGGGTTTCTGTAAAGTTTTAGAAACTAGCTACATAAGTACTTTGATAC   1396
TGCTCATGCTGACTTAAAACACTGTAAACGCTGTAAACTGTAACATTAAATTGAATGACCATTACTTTTATTAA     1475
TGATCTTTCTTAAATATTCTATATTTAATGGATCTACTGACATTAGCACTTTGTACAGTACAAAATAAAGTCTACATT 1554
TGTTTAAAAAAAAAAAAAAAGGGGCCCGC                                                   1586
```

FIG. 1C

```
                    LVNLKS-YLNDNNFSG-FPESLTSLHRLKT--LSRNRLSGKIPSSLLRLS  Majority
                       |         |         |         |         |
                      110       120       130       140       150

12   : : : : : : : : : : : : : : : : : : : : : : : : : : : : : : : : : : : : : : : : :  hl2832 pro
101   : LVNLKS·LYLNDNNFSG·EFPESLTSLHRLKT··VVLSRNRFSGKIPSSLLRLS  A. thal protein kinase homolog
101   : LVNLKS·LYLNDNNFSG·EFPESLTSLHRLKT··VVLSRNRFSGKIPSSLLRLS  A. thal putative Rc. Kinase
101   : LVNLKS·LYLNDNLTG·DFPESLTSLHRLKT··VVLSGNRLSGRIPSSLLRLS   A. thal Rc. Kinase isolog
 78   : VVNLKS·VYLNDNNFSG·DFPESLTSLHRLKT··IFLSGNRLSGRIPSSLLRLS  A. thal Rc. Kinase isolog
 44   : : : : : : : : : : : : : : : · · IQR··-··F2D············DDIQVGDH·IGVG·--TFG  C. ele. Tyr. Kinase
  1   : : : : : : : : : : : : : : : : : : : : : : : : : : : · ·AELT·EEII·GIG·--GFQ  hMLK1

ELY TFYVQDNLF GSIPPLNQASLR-FNVSNNQLSGHIPETQALNRFNE  Majority
                       |         |         |         |         |
                      160       170       180       190       200

17   : : : : : : : : : : : : : : : : : : : : : : : : : : : : : : : : : : : : : : : : :  hl2832 pro
151   : RLY·-TFYVQDNLF·SGSIPPLNQATLR·FFNVSNNQLSGHIPPTQALNRFNE  A. thal protein kinase homolog
151   : RLY·-TFYVQDNLF·SGSIPPLNQATLR·FFNVSNNQLSGHIPPTQALNRFNE  A. thal putative Rc. Kinase
128   : RLY·-TLNVEDNLF·TGSIPPLNQTSLR·YFNVSNNKLSGQIFLTRALKQFDE  A. thal Rc. Kinase isolog
 65   : AVFSGNW·-·····TLPDGSQR··TIALKKVFVLEKEAEIL·SKIRH  C. ele. Tyr. Kinase
 16   : KV·RAF·WIGD·EV·--·AVKAARHDPDE·-·DIS·-QTIENVRQEAKLFAMLXH  hMLK1
```

```
             K L Q A L L T I A T A C V A V K P E N R P A M R E V L K M V K D A R A E A A - F S F - N S S D H S P  Majority
                        |         |         |         |         |
                       610       620       630       640       650
389  S Y Q K V I E L F S V C T N E D P K D R P S A A H I - - - - - - - - - - - - - - - - - - - - - - - - - - -  h12832 pro
378  K L Q A L L T I A T A C V A V K P E N R P A M R E V L K M V R D A R A E A A L F S F - N S S D H S P        A. thal protein kinase homolog
378  K L Q A L L T I A T A C V A V K P E N R P A M R E V L K M V R D A R A E A A L F S F - N S S D H S P        A. thal putative Rc. Kinase
339  K L Q A L L S I A T V C V T I Q P D N R P V M R E V L K M V R D A R A E A P - F S S - N S S E H S P        A. thal Rc. kinase isolog
116  - - - - - - - - - - - - - - - - - - Q K V R V S K - - - - - - - - - - - - - L S L S - - - - - - - -        C. ele. Tyr. Kinase
142  - E E N - - I I H Q L G - - - - - - Q E K P R V K K R K G K F R K S R L A Q P V L P F P H G H S R C P      hMLK G - - - - R W S D T V Q S L P R D D - - S I   Majority
                        |         |
                       660       670
115  - - - - - - - - - - - V E A L E T D - - - - - v .                  h12832 pro
328  G - - - - R W S D T Q S L R P E D H M S I                          A. thal protein kinase homolog
328  G - - - - R W S D T Q S L R P E D H M S I                          A. thal putative Rc. Kinase
287  G - - - - R W S D T V Q S L R P D D Q V S I                        A. thal Rc. kinase isolog
127  - - - - - - - - - - - - - - - - - - - - S V                       C. ele. Tyr. Kinase
185  G G T G S S W G - - - - - - - - - - - - G Q                       hMLK Decoration 'Decoration #1': Shade (with solid black) residues that match the Consensus exactly.
```

FIG. 2G

Input file h14138new; Output File h14138new.pat
Sequence length 831

```
  Y   Y   R   E   F   G   P   R   G   Q   N   S   A   R   D   R   T   P   K   S      20
 TAC TAT AGG GAA TTT GGC CCT CGA GGC CAG AAT TCG GCA CGA GAC CGA ACT CCG AAG AGT      60

V   R   R   G   V   A   P   V   D   D   G   R   I   L   G   T   P   D   Y   L      40
 GTG AGA AGA GGG GTG GCC CCC GTT GAT GAT GGG CGA ATT CTA GGA ACC CCA GAC TAC CTT     120

A   P   E   L   L   G   R   A   H   G   P   A   V   D   W   A   L   G      60
 GCA CCT GAG CTG TTA CTA GGC AGG GCC CAT GGT CCT GCG GTA GAC TGG GCA CTT GGA        180
```

FIG. 4A

```
V   C   L   F   E   F   L   T   G   I   P   P   F   N   D   E   T   P   Q   Q       80
GTT TGC TTG TTT GAA TTT CTA ACA GGA ATT CCC CCT TTC AAT GAT GAA ACA CCA CAA CAA     240

V   F   Q   N   I   L   K   R   D   I   P   W   P   E   G   E   E   K   L   S      100
GTA TTC CAG AAT ATT CTG AAA AGA GAT ATC CCT TGG CCA GAA GGT GAA GAA AAG TTA TCT     300

D   N   A   Q   S   A   V   E   I   L   L   T   I   D   D   T   K   R   A   G      120
GAT AAT GCT CAA AGT GCA GTA GAA ATA CTT TTA ACC ATT GAT GAT ACA AAG AGA GCT GGA     360

M   K   E   L   K   R   H   P   L   F   S   D   V   D   W   E   N   L   Q   H      140
ATG AAA GAG CTA AAA CGT CAT CCT CTC TTC AGT GAT GTG GAC TGG GAA AAT CTG CAG CAT     420

Q   T   M   P   F   I   P   Q   P   Q   P   D   E   T   D   T   S   Y   F   E   A  160
CAG ACT ATG CCT TTC ATC CCC CAG CCA CAG GAT GAA ACA GAT ACC TCC TAT TTT GAA GCC     480

R   N   T   A   Q   H   L   T   V   S   G   F   S   L   *                          174
AGG AAT ACT GCT CAG CAC CTG ACC GTA TCT GGA TTT AGT CTG TAG                         525

CACAAAAATTTCCTTTTAGTCTAGCCCTCGTGTTATAGAATGAACTTGCATAATTATATACTCCTTAATACTAGATTGA     604

TCTAAGGGGAAAGATCATTATTAACCTAGTTCAATGTGCTTTAATGTACGTTACAGCTTTCACAGAGTTAAAAGGC       683

TGAAAGGAATATAGTCAGTAATTATCTTAACCTCAAAACTGTATATAAATCTTCAAAGCTTTTTTCATCTATTTATTT    762

TGTTTATTGCACTTTATGAAAACTGAAGCATCAATAAAATTAGAGGACACTATTGAGAGTGAGCCACTA             831
```

FIG. 4B

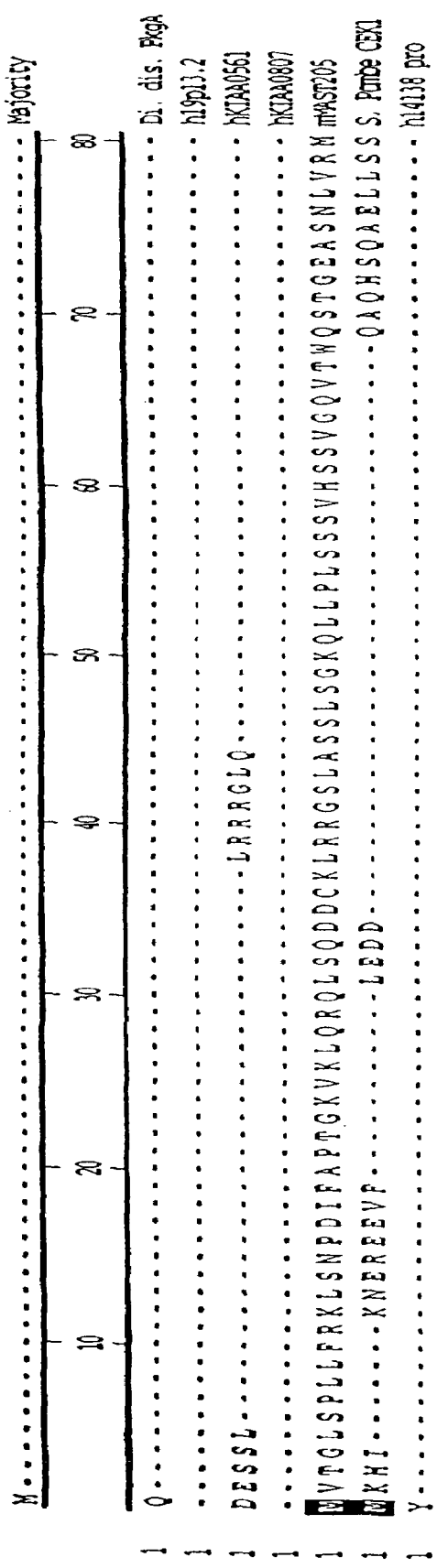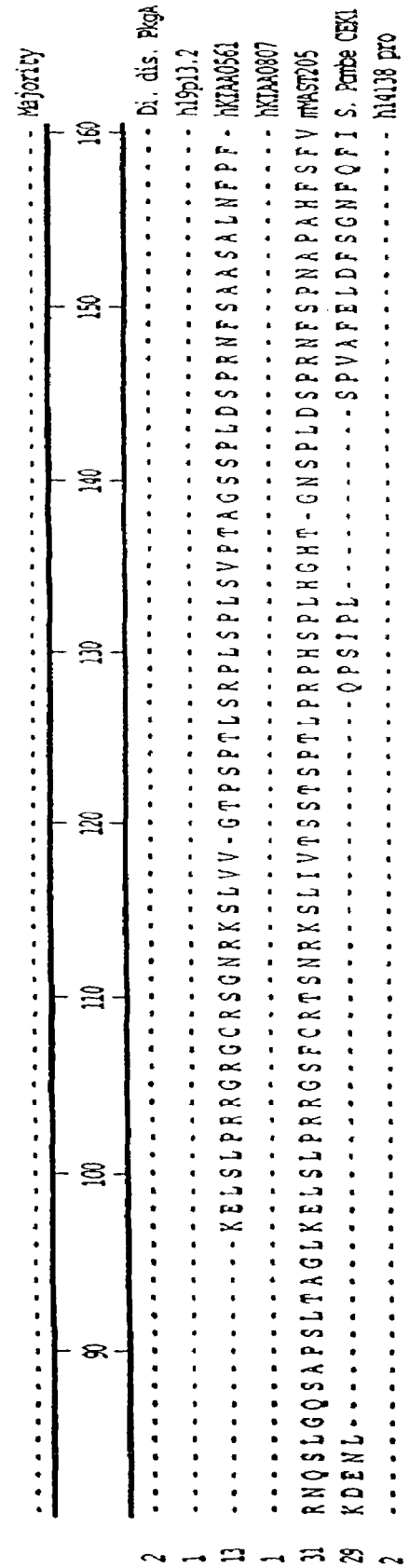
FIG. 5A

```
Input file h14833; Output File h14833.pat
Sequence length 2060

TTTTGCCTTCATTCACTCCCATGTGGGGCCCTTGAGAATTAACATCTTAAGTTGCCTCCTGCCCTGCCTCCCACTCA          79

M           1
TCGAGGATGCTCTGACTGCTCACTGCCTCTACAGAACCAGCTGGGCTCCATGAGGATGTG ATG                       156

T   M   D   G   L   L   Y   D   L   T   E   K   Q   V   Y   H   I   G   K   Q         21
ACT ATG GAT GGT CTT CTC TAT GAT CTC ACA GAA AAA CAA GTA TAT CAC ATC GGA AAG CAG        216

V   L   A   L   E   F   L   Q   E   K   H   L   F   H   G   D   V   A   A   A         41
GTC CTT TTG GCG CTG GAA TTC CTG CAG GAG AAG CAT TTG TTC CAT GGG GAT GTG GCA GCC        276

R   N   I   L   M   Q   S   D   L   T   A   K   L   C   G   L   G   L   A   Y         61
AGG AAT ATT CTG ATG CAA AGT GAT CTC ACT GCT AAG CTC TGT GGA TTA GGC CTG GCT TAT        336

E   V   Y   T   R   G   A   I   S   T   Q   T   I   P   L   K   W   L   A             81
GAA GTT TAC ACC CGA GGG GCC ATC TCC ACT CAA ACC ATA CCT CTC AAG TGG CTT GCC            396
```

FIG. 7A

```
P   E   R   L   L   L   R   P   A   S   I   R   A   D   V   W   S   F   G   I   101
CCA GAA CGG CTT CTC CTG AGA CCT GCT AGC ATC AGA GCA GAT GTC TGG TCT TTT GGG ATC     456

L   L   Y   E   M   V   T   L   G   A   P   P   Y   P   E   V   P   P   T   S   121
CTG CTC TAT GAG ATG GTG ACT CTA GGA GCA CCA CCG TAT CCT GAA GTC CCT ACC AGC     516

I   L   E   H   L   Q   R   K   I   M   K   R   P   S   S   C   T   H   T   141
ATC CTA GAG CAT CTC CAA AGA AAG ATC ATG AAG AGA CCC AGT AGC TGC ACA CAT ACC     576

M   Y   S   I   M   K   S   C   W   R   W   R   E   A   D   D   R   P   S   R   161
ATG TAC AGT ATC ATG AAG TCC TGC TGG CGT TGG CGA GAG GCT GAC GAT GAC CGC TCA CCT AGA 636

E   L   R   L   R   L   E   A   A   I   K   T   A   D   E   A   V   L   Q   181
GAG CTG CGC TTG CGC CTA GAA GCT GCC ATT AAA ACT GCA GAT GAG GCT GTG TTA CAA     696

V   P   E   L   V   V   P   E   L   Y   A   A   V   A   G   I   R   V   E   S   201
GTA CCA GAG TTG GTG GTA CCT GAA CTG TAT GCA GCT GTG GCC GGC ATC AGA GTG GAG AGC 756

L   F   Y   N   Y   S   M   L   *                                                209
CTC TTC TAC AAC TAT AGC ATG CTT TGA                                              783

AGAGTCTCGGGCAAGAAACATTCATGCATGAGTATATGTTCTTGGAATCAATTCCTCTAAGAACAGAGAATGGTCTTTC  862

CCAGGGACACAAGGGAGAAATGGGACATGGATTCTTCCTTTACACATTTCTCGGGAAATCTGAAATGATGCT        941

GGATGGACTCTACACATCCCTGAGCTAAGACATACTGTCAGTCTCACTTCTGCTGTCCCAGTCCTAGAAATCCTGGGTA 1020
```

FIG. 7B

```
GAAGTGGTGGACCTGTGCAAAGGAGGTTTAGAACTCTGCAGTATTGTTGGGGCATGGCACAAATAAGCTCATCCCTC  1099
CCGTCCGAGGCTAGTTCCTCTGGAACCACATTTTATCTAGATGAAATGAAGGAATAGAAATCCA                1178
ATAAAGAGTTGAAGGAAAGAAAATTAAGGTTCTTCTGCTCAGGATTACAGATATGGACCAACACCTCCTTCAAGA     1257
AAAGGTGGTAGGACACAAAGTTCTTCAGTCCTGAGCCCTACATGTGGGGTTGGAGGAGAACTATAACGGAAAAACCTCT 1336
GAGTTTCACCTTAGGTATAGATAAAGAAGATGGTCCCCTTTATCTCGATTCTGAGACAGGTAAATTCTGTTTGTTAC   1415
TACGTTTAATTAGAAGGTGGAGGAGTCATTTCATGATTAAGAACATTCAACATGTATTGTTCATTAAGCTAGCTTCCTA 1494
GTTCCGATTAGACTAAGGAGACTAAGCCTAGAGAGTCAATGTTAGAACAGTGAAAAGAATTCTGTGTGTGTGTGTGT   1573
GTGTGCACAATAAATAGGAAATGTAGAAACCAAGCAAGAAGGCTTAGTAGCTCAGTCTTTAACAAGGCTAGAAAGAA   1652
TGTAATCTGATATGGAAGGATAGCAGCTTCTAATTTCAATCATCTGTGATATACTGTGAAACTTATTGTATTAAATT   1731
AATATTTATTAAATGAAATAAATATGCTTTTCTCGGTTTATAACTACTAAAAATATCATAGGAGGATAAAGTAAATAAGTG 1810
AAAGTTAATGCCAATAGAAAAATTCAAGAGATAATGTCAGAAAAGGATTCTTTATGTGTAAATGGGGATAA         1889
TACCTATTCACAAGGTTGTTCTGAGGATTGATACGTTTGAGTATGTATTGTACACTATCTGGCACATATGCGCTCA    1968
ATAAACGTGTTTCTCCTTTAAAAAAAAAAAAAAAAAAAAAAAAAAAAAAAANAAATAAAAAA                  2047
AAAGGGGCCGC                                                                     2060
```

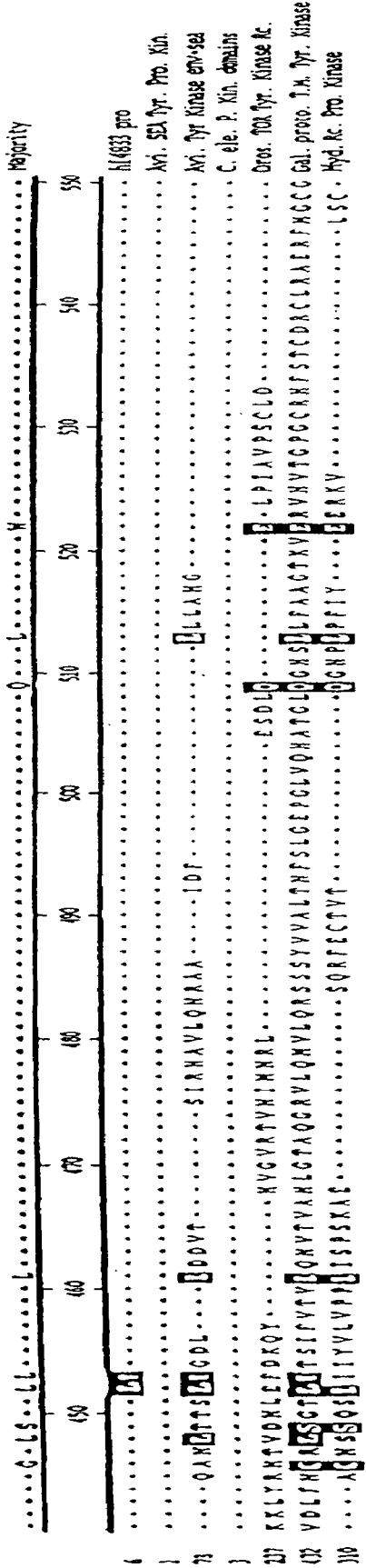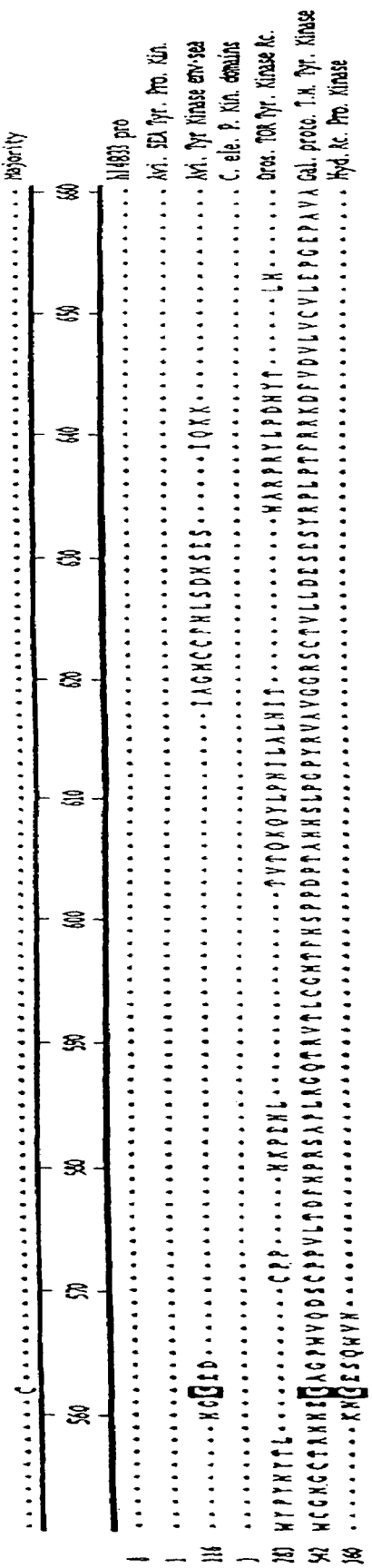
FIG. 8C

```
Input file h15590; Output File h15590.pat
Sequence length 1697

E   N   Q   E   L   V   G   K   G   G   F   G   T   V   F   R   A   Q   H      19
 G GAG AAC CAG GAG CTC GTC GGC AAA GGC GGG TTC GGC ACA GTG TTC CGG GCG CAA CAT      58

ACC TCA ACT TTC AGA AAC CAG ATG CCC AGC CCT ACC TCA ACT GGA ACA CCA AGT CCT GGA    1198
                                                                                   419
   P   R   G   N   Q   G   A   E   R   Q   G   M   N   W   S   C   R   T   P   E
 CCC CGA GGG AAT CAG CAG GCT GAG AGA CAA GGC ATG AAC TGG TCC TGC AGG ACC CCG GAG   1258

439
   P   N   P   V   T   G   R   P   L   V   N   I   Y   N   C   S   G   V   Q   V
 CCA AAT CCA GTA ACA GGG CGA CCG CTC GTT AAC ATA TAC AAC TGC TCT GGG GTG CAA GTT   1318

459
   G   D   N   Y   L   T   M   Q   T   T   A   L   P   T   W   G   L   A
 GGA GAC AAC TAC TTG ACT ATG CAA CAG ACA ACT GCC TTG CCC ACA TGG GGC TTG GCA       1378

479
   P   S   G   K   G   R   G   L   Q   H   P   P   V   G   S   Q   E   G   P
 CCT TCG GGC AAG GGG AGG GGC TTG CAG CAC CCC CCA GTA GGT TCG CAA GAA GGC CCT       1438

497
   K   D   P   E   A   W   S   R   P   Q   G   W   Y   N   H   S   G   K   *      1495
 AAA GAT CCT GAA GCC TGG AGC AGG CCA CAG GGT TGG TAT AAT CAT AGC GGG AAA TAA

AGCACCTTCCAAGCTTGCCTCCAAGAGTTACGAGTTAAGGAAGAGTGCCACCCCTTGAGGCCCCTGACTTCCTTCTAGG   1574

GCAGTCTGGCCTGCCCACAACTGACTTTGTGACCTGTCCCCCAGGAGTCAATAAACATGATGGAATGCTAAAAAAAAA   1653

AAAAAAAAAAAAAAAAAAAAAAAAAAAAAAAAAAAAAAAAAGGGGGCCCGC                                1697
```

FIG. 10A

```
E   L   P   T   E   P   S   L   V   Y   E   A   V   C   N   R   Q   N   R   P    219
GAG TTG CCA ACC GAA CCA TCA CTC GTG TAC GAA GCA GTG TGC AAC AGG CAG AAC CGG CCT   658

S   L   A   E   L   P   Q   A   G   P   E   T   P   C   L   E   G   Q   K   E    239
TCA TTG GCT GAG CTG CCC CAA GCC GGG CCT GAG ACT CCC TTA GAA GGA CTG AAG AAG GAG   718

L   M   Q   L   C   W   S   E   P   K   D   R   P   S   F   Q   E   C   L        259
CTA ATG CAG CTC TGC TGG AGT GAG CCC AAG GAC AGA CCC TCC TTC CAG GAA TGC CTA       778

P   K   T   D   F   V   Q   M   V   N   E   N   R   A   V   I   P   H   S   T    279
CCA AAA ACT GAT TTC GTC CAG ATG GTG GAG AAC AAT AGG GCT GTC ATC CCA CAC TCC ACG   838

V   K   D   F   L   S   Q   L   R   S   N   R   F   T   I   E   N   Q   E   S    299
GTA AAG GAT TTC CTG TCT CAG CTC AGG AGC AAT AGG TTT ACC ATA GAA AAC CAG GAG TCA   898

G   Q   G   T   E   M   D   R   G   F   R   R   T   N   L   E   P   P   S   R    319
GGC CAA GGA ACA GAA ATG GAT AGG GGC TTT AGG AGA ACC AAT CTA GAG CCT CCC AGC CGT   958

N   D   V   M   V   S   E   W   L   N   K   L   T   S   R   A   Q   E   V   P    339
AAT GAT GTC ATG GTT TCT GAG TGG CTA AAC AAA CTG ACT AGC AGG GCA CAA GAG GTT CCA   1018

V   P   K   K   C   P   S   L   T   K   R   S   D   S   M   A   Q   P   P   E    359
GTT CCT AAA AAA TGC CCG AGC CTT ACC AAG AGG AGC GAT TCG ATG GCA CAG CCA CCA GAG   1078

Q   A   W   T   A   G   T   S   S   D   S   M   A   Q   P   P   Q   T   P   E    379
CAA GCC TGG ACA GCA GGC ACA TCT TCA GAT TCG ATG GCC CAA CCT CCC CAG ACT CCA GAG   1138
```

FIG. 10B

```
T   S   T   F   R   N   Q   M   P   S   P   T   S   P   S   G                          399
ACC TCA ACT TTC AGA AAC CAG ATG CCC AGC CCT ACC TCA CCA AGT GGA                         1198

P   R   G   N   Q   A   E   R   Q   G   M   N   W   T   P   E                          419
CCC CGA GGG AAT CAG GCT GAG AGA CAA GGC ATG AAC TGG TCC ACC CCG GAG                     1258

P   N   P   V   T   G   R   P   L   V   N   I   Y   N   C   S   G   V   Q   V          439
CCA AAT CCA GTA ACA GGG CGA CCG CTC GTT AAC ATA TAC AAC TGC TCT GGG CAA GTG             1318

G   D   N   N   Y   L   T   M   Q   T   T   A   L   P   P   V   G   S   L   A          459
GGA GAC AAC AAC TAC TTG ACT ATG CAA CAG ACA ACT GCC TTG CCC CCA GTA GGG TTG GCA         1378

P   S   G   K   G   R   G   L   Q   H   P   P   P   V   G   S   Q   E   G   P          479
CCT TCG GGC AAG GGG AGG GGC TTG CAG CAC CCC CCA CCA GGT TCG CAA GAA GGC CCT             1438

K   D   P   E   A   W.  S   R   P   Q   G   W   Y   N   H   S   G   K   *              497
AAA GAT CCT GAA GCC TGG AGC AGG CCA CAG GGT TGG TAT AAT CAT AGC GGG AAA TAA             1495

AGCACCCTTCCAAGCTTGCCTCCAAGAGTTACGAGTTAAGGAAGAGTGCCACCCCTGAGGCCCCTGACTTCCTTCTAGG        1574

GCAGTCTGGCCTGCCCACACAACTGACTTTGTGACCTGTCCCCAGGAGTCAATAAACATGATGGAATGCTAAAAAAAAA        1653

AAAAAAAAAAAAAAAAAAAAAAAAAAAAAAAAAAAAAAAAAAAGGGGCGGCCGC                                 1697
```

```
                              K - - VRKL - - - - - - - D - - - - QD - - - - GLQEKVYQILQAWSSREG - -   Majority
                  |              |              |              |              |              |
                 660            670            680            690            700

AMTE - - - - - - - - VRKL - - - - - - - LE - - - - - - - - - - - - - - - - - VIKLSTRSSF              A. thal. BAC clone
          SMSS - - - - - - - - VIQF - - - - - - - LDGVAQ - - - - - - - - - - - - - - - DIVKARENVGAIE           A. thal. Ser/Thr kin-like pro
          - - - - - SGKGRGL - - - - - - - - - - - QHPPPVGSQEGP - KDPEAMSRPQG -                                  h15990 partial pro
          - - - - - - RVIVQKL - - - - - - - - - - - - - - - - - - - - - - - QPYP - ELVVSRGPSL - -              hBAC clone
          NLGKHWKNCARKL - - - - - - GFTQSQIEIDHDYERDGLKEKVYQMLQKWVMREGIK                                        hSer/Thr Kin. RIP
          NLGRQWKNCARKL - - - - - - GFTESQIEIDHDYERDGLKEKVYQMLQKWLMREGTK                                        mSer/Thr Pro. Kin. RIP
                                                                                                               rHomocysteine respondent protei G - - - - G - - - - A - - L - - - - - - - - - - L - - - - XLIXXGQ -   Majority
                  |              |              |              |
                 710            720            730

G     FGEAESEAEPCSVATETETEPFVSHGR                                      A. thal. BAC clone
                              WYNHSGK                                            A. thal. Ser/Thr kin-like pro
                   - NLQNKSM                                                     h15990 partial pro
          - - - - - - - - - - - - - SLYYVSN                                      hBAC clone
          GATVGKLQAHQCSRIDLLS - -                                                 hSer/Thr Kin. RIP
          GATVGKLQAHQCCRIDLN - -                                                  mSer/Thr Pro. Kin. RIP
          - - - - - - - - - - - - - HLRASQS - - - - - - - - - - - - - - - Y     rHomocysteine respondent protei
```

Decoration'Decoration #1': Shade (with solid black) residues that match the Consensus exactly.

FIG. 11H

```
Input file h15993; Output File h15993.pat
Sequence length 981

A   Q   R   A   V   A   W   A   G   R   T   M   A   A   P   E   P   A   P        19
  C GCG CAG AGG GCG GTG GCC TGG GCT GGC CGA ACC ATG GCG GCC CCG GAG CCG GCG CCG        58

R   R   A   R   E   R   E   E   D   E   S   E   D   E   S   D   I                 39
  AGG CGG GCC CGG GAA CGG GAG GAG GAC GAG AGC GAG GAC GAG AGC GAC ATC                 118

L   E   E   S   P   C   G   R   W   Q   K   R   E   Q   V   N   Q   G   N         59
  CTG GAG GAA AGC CCG TGT GGT CGC TGG CAA AAG CGA GAG CAG GTA AAC CAA GGG AAC        178

M   P   G   L   Q   S   T   F   L   A   M   D   T   E   G   E   V   V             79
  ATG CCA GGG CTT CAG AGC ACC TTC CTA GCC ATG GAC ACG GAG GGG GTA GAG GTG GTG        238

W   N   E   L   H   F   G   D   R   K   A   F   A   A   H   E   E   K   I   Q     99
  TGG AAC GAG CTC CAC TTC GGA GAC AGG AAG GCC TTC GCG GCG CAC GAG GAG AAG ATC CAG    298

T   V   F   E   Q   Q   L   V   D   H   P   N   I   V   K   L   H   K   Y        119
  ACC GTG TTC GAG CAG CAG CTG GTG GAC CAC CCG AAC ATC GTG AAG TTG CAC AAG TAC        358

W   L   D   T   S   E   A   C   A   R   V   I   F   I   T   E   Y   V   S        139
  TGG CTG GAT ACC TCT GAG GCC TGC GCG AGG GTC ATC TTC ATC ACA GAG TAC GTG TCA TCA    418
```

FIG. 13A

```
G   S   L   K   Q   F   L   K   K   T   K   K   N   H   K   A   M   N   A   R      159
GGC AGC CTC AAG CAA TTC CTC AAA AAG ACC AAG AAG AAC CAC AAG GCC ATG AAC GCC CGG    478

A   W   K   R   W   C   T   Q   I   L   S   A   L   C   A   C   G   L        179
GCC TGG AAG CGC TGG TGC ACG CAG ATC CTG TCT GCG CTC TGC GCC TGC GGC CTC AGC       538

P   I   H   G   H   N   L   T   S   D   T   I   F   I   Q   H   N   G   L        199
CCC ATC ATC CAC GGG AAC CTG ACC AGC GAC ACC ATC TTC ATT CAG CAC AAC GGC CTC       598

I   K   I   G   S   V   W   H   R   I   F   S   N   A   L   H   D   L   R        219
ATC AAG ATC GGG TCC GTG TGG CAC CGA ATC TTC TCC AAT GCA CTT CAC GAT CTC CGA       658

S   P   I   R   A   E   R   E   E   L   N   L   H   F   F   G   M   C   P   E   Y  239
AGC CCC ATC CGC GCT GAG CGA GAG GAA CTT CGG AAC CTG CAC TTC TTT GGG ATG TGC CCA TAT 718

G   E   V   A   D   G   T   A   V   D   I   F   F   R   T   E   E   A   L   E      259
GGA GAG GTG GCC GAT GGG ACC GCT GTG GAC ATC TTC TTC CGG ACA GAG GAG GCG CTG GAG    778

M   A   V   L   E   H   S   I   Q   T   N   G   D   T   R   M   E   F   I   A      279
ATG GCT GTA CTG GAA CAC TCG AGT CAG AAT GGG GAC ACC CGG ATG GAG TTC ATC GCT        838

R   A   R   H   S   R   R   P   S   V   H   N   P   V   S   L   F   L   C   L   A  299
CGC GCC AGG CAC TCG CGG CGG CCC TCT GTC CAC AAC CCC GTC AGT CTG TTC CTC TGC CTG GCC 898

R   D   P   A   R   R   P   R   P   S   V   H   S   L   F   H   X   R   A   L   X  319
CGG GAC CCT GCC GCC CGG CGG CCC CGG CCC AGC GTC CAC AGC CTC TTC CAC NCG CGT GCT CTT NGA 958

G   A   L   A   E   A   P                                                         326
GGT GCA CTC GCA GAA GCT CCT GG                                                     982
```

```
                                                                Majority
        |         |         |         |         |
       710       720       730       740       750
                                                                h15993 partial pro
293 - - - - - - - - - - - - - - - - - - - - - - - - - - - - -  A. tha. MAPK (putative)
13  - - - - - - - - - - - - - - - - - - - - - - - - - - - - -  A. tha. Ste20-like Kinase homo.
337 - - - - - - - - - - - - - - - - - - - F D L - - - - - - -  A. Thal. cosmid
407 - - - - - - - - - - - - - - - - C - - - - - - - - - - - -  A. Thal. cosmid
263 - - - - - - - - - - - - - - - - - - - - - - - - - - - - -  C. ele. Kinase like
216 V N T S L P G Q S S Q P S G T T T N T N - - - - - - - - -  C. ele. Tyr. Kinase like
109 - - - - - - - - - - - - - - - - - - - - - C H N - - - - -  hMARKK (putative partial)
60  - - - - - - - - - - - - - - - - - - - - - - - - - C G S   O. sat. MEKI
88  - - - - - - - K K D L A L A V - - - E R V F E E - - - - -  P. bla. PKA
90  P T T T D G G A A A S T T T E N K E E K R K S N K R K V V M E I L G C D E S R N F A L V S C R L C. ele. Ser/Thr Kinase like Majority
        |         |         |         |         |
       760       770       780       790       800
                                                                h15993 partial pro
293 - - - - F I L C - - - - - - - - - - - C L - - - - - - - -  A. tha. MAPK (putative)
13  - - - - - - - - - - - - - - - - - - - - - H E S F G H E D D E D  A. tha. Ste20-like Kinase homo.
337 - - - - - - - - - - - - - - - - - - - - - - - - - - - - -  A. Thal. cosmid
407 - L S S P E T L H L - - - - - - - - - - - D R F P S G R K F W  A. Thal. cosmid
263 - - - - - - - - - - - L - - - - - - - - - - - - - - - - -  C. ele. Kinase like
216 - - - - - F T G Y - - - - - - - - C - - - - - - - - - - -  C. ele. Tyr. Kinase like
109 N V S S C G S L Y A Y M S C A A R G C - - - - H C A D L H G R F - E D I T F Q  hMARKK (putative partial)
60  - - - - - - - - - - - A E K K C E - - - - - - - - - - - -  O. sat. MEKI
88  - - - - - - - - - - - - - - - - - - - - - L L E Q H N I I A E E R - - - - -  P. bla. PKA
90  D T S H K S V T F Q F A P G T D K P C T I A T K L L A E D C L L K V H V H I V E A Q L G E V I Q L I  C. ele. Ser/Thr Kinase like
```

FIG. 141

```
                                                    Majority
             1110        1120        1130        1140        1150
- - - - - - - - - - - - - - - L - S L - - - - - - - - - - - - - - - - - - - - - -

- - - - - - - - - - - - - - - - - - - - - - - - - - - - - - - - - - - - - - - -   h15993 partial pro
- - - - - - - R R R V R L - - - - - - - - - - - - - - - - - - - - - - - - - - -   A. tha. MAPK (putative)
- - - - - - - - - - - - - L P A L G Y Q V G I I S N E S N - - - - - - - - - - -    A. tha. Ste20-like Kinase homo.
- - - V I - - - V E K L E S L - - - - - - - - - - - - - - - - - - - - - - - - -   A. Thal. cosmid
- - - - - - - - - - - - - Q M H R Q L - - T T S I N K G D N P E F L T E N L I -    T H G F M  C. ele. Kinase like
- - - - - - - - - - - - - - - - - - - - - - - - - - - - - - - - - - - - - - - -   C. ele. Tyr. Kinase like
- - - - M A K Y K A R K M A H L - - - - - - - - - - - - - - - - - - - - - - - -   hMAPKKK (putative partial)
P T S D D N S T N S T M C S L E S E L S K L - - - - - - - - - - - - - - - - - -   O. sat. MEK1
Q E P L V I D H H S D V L T Q L D S E L R K V S G V S H S A S P S T V V E S L T S M T P Q T I P L A   P. bla. PKFA
                                                                                   C. ele. Ser/Thr Kinase like Majority
             1160        1170        1180        1190        1200
- - - - - - - - - - - - - - - - - - - - - - - - - - - - - - - - - - - - - - - -

- - - - - - - - - - - - - - - - - - - - - - - - - - - - - - - - - - - - - - - -   h15993 partial pro
- - - - - - - - - - - - - - - - - - - - - - - - - Q Q K M R S L V D                A. tha. MAPK (putative)
- - - - - - - - - - - - - - - - R A A E K L A F E E P R Q V L H P L A D            A. tha. Ste20-like Kinase homo.
- - - - - - - - - - - - - - - - - - - - - - - L R K Q R E E I E                    A. Thal. cosmid
C N S S D - - - - - - - - - - - - - - - - - - - - - - - - - - - - - - - - - - -   C. ele. Kinase like
- - - - - - - - - - - - - - - - - - - - - - - - - - - - - - - - - - - - - - - -   C. ele. Tyr. Kinase like
C Q L D S E G V E K A I A V A F D I R A A R I - - - - - - - - - - - - - - - - -   hMAPKKK (putative partial)
- - - - - - - - - - - - - - - - - - - - - - - R R G I H P S L D                    O. sat. MEK1
C V S - - - - - - - - - - - - - - - - - - - - - - - - - - - - - - - - - - - - -   P. bla. PKFA
C Q T V P A S I G Q A P A V I A A A H A A S L I P N A S V P Q S P S R L D A E T G L A G L H E K L E   C. ele. Ser/Thr Kinase like
```

FIG. 14L

```
                                                                    - - Majority 1210           1220           1230           1240           1250
- - - R - - - - - - - - - - - - - - - - - - - - - - - - - - - - - - - -    h15993 partial pro
- - - - - - - - - - - - - - - - - - - - - - - - - - - L M E L I N K R - -  A. tha. MARK (putative)
T R T Q V L H R S - - - - - - - - - - - - - - - - - - - - - - - - - - - -  A. tha. Ste20-like Kinase homo.
T K K I R K A G S D Q - - - - - Q E K P K N G Y A D S P V N - - - - R E    A. Thal. cosmid
E M Q R D Q E R I - - - - - - - - - - - - - - - - - - - - - V T E F L K -  C. ele. Kinase like
- - - - - - A E G V Q E E E N E T S T R E S N S E A P I - - - - - - - - -  C. ele. Tyr. Kinase like
                                                                            hMAPKKK (putative partial)
F D N L N G E R R - - - - - - - - - - - - - - - - - - - - M K S S L N K L  O. sat. MEK1
- - - - - - - - G D E Q V E T T T - - - - - - - - - - - - - - - - - - - -  P. bla. PKPA
A L K M E Q D R R E D M G D D A I G T T T T T D G K D E I P I D T L K G L A E A L G K V I H A D G R E  C. ele. Ser/Thr Kinase like

- - Majority 1260           1270           1280           1290           1300
- - - - - - - - - - - - - - - - - - - - - - - - - - - - - - - - - - - - -  h15993 partial pro
- - - - - - - - - - - - - - - - - - - - - - - - - - - - - - - - - - - - -  A. tha. MARK (putative)
- - - - - - - - - - - - - - - - - - - - - - - - - - - - - - - - - - - - -  A. tha. Ste20-like Kinase homo.
S S T L S K E P - - L A D T K - - - - - - - - - - - - - - - - - - - - - -  A. Thal. cosmid
- - - - - - - - - - - - - - - - - - - - - - - E H G T S S I T N S V K P -  C. ele. Kinase like
- - - - - - - - - - - - - - - - - - - - - - - - - - - - - - - - - - - - -  C. ele. Tyr. Kinase like
                                                                            hMAPKKK (putative partial)
- - - - - H S A L M E - - - - - - - - - - - - - - - - - - - - - - - - - -  O. sat. MEK1
- - - - - - - - - - - - - - - - - - - - - - - - - - - - N V L A - - - - -  P. bla. PKPA
T T P M P P D H P D L T D A S T Q Q L I S P S N P D V L T T M S S A V E G S A S S T M I E D I D A S  C. ele. Ser/Thr Kinase like
```

FIG. 14M

| | | | | | Majority |
|---|---|---|---|---|---|
| 1310 | 1320 | 1330 | 1340 | 1350 | |

```
   90  - - - - - - - - - - - - - - - - - - - - - - - - - - - - - - - - - - - - - - - - - - - -   h15993 partial pro
   25  - - - - - - - - - - - - - - - - - - - - - - - - - - - - - - - - - - - - - - - - - - - -   A. tha. MAPK (putative)
   84  - - - - - - - - - - - - - - - - - - - - - - - - - - - - - - - - - - - - - - - - - - - -   A. tha. ste20-like Kinase homo.
   93  - - - - - - - - - - - - - - - - - - - - - - - - - - - - - - - - - - - - - - - - - - - -   A. Thal. cosmid
   44  - - - I V D S V A P S S Q T P T T T S S - - - - - - - - - - - - - - - - - - - - - - - -   C. ele. Kinase like
   23  - - - - - - - - - - - - - - - - - - - - - - - - - - - - - - - - - - - - - - - - - - - -   C. ele. Tyr. Kinase like
   60  - - - - - - - - - - - - - - - - - - - - - - - - - - - - - - - - - - - - - - - - - - - -   hMAPKK (putative partial)
   13  - - - - - - - - - - - - - - - - - - - - - - - - - - - - - - - - - - - - - - - - - - - -   O. sat. MEK1
   80  - - - - - - - - - - - - - - - - - - - - - - - - - - - - - - - - - - - - - - - - - - - -   P. bla. PKA
  280  T S A V D A S M M N S M P P G A Q N S T D Q I P A A M T L S M D Q E C A Q S M T S S I T R N T T G T   C. ele. Ser/Thr Kinase like
```

| | | | | | Majority |
|---|---|---|---|---|---|
| 1360 | 1370 | 1380 | 1390 | 1400 | |

```
   90  - - - - - - - - - - - - - - - - - - - - - - - - - - - - - - - - - - - - - - - - - - - -   h15993 partial pro
   25  - - - - - - - - - - - - - - - - - - - - - - - - - - - - - - - - - - - - - - - - - - - -   A. tha. MAPK (putative)
   84  - - - - - - - - - - - - - - - - - - - - - - - - - - - - - - - - - - - - - - - - - - - -   A. tha. Ste20-like Kinase homo.
   93  - - - - - - - - - - - - - - - - - - - - - - - - - - - - - - - - - - - - - - - - - - - -   A. Thal. cosmid
   61  - - - - - - - Q V R K P G N - - - - - - - - - - - - - - - - - - - - - - - - - - - - - -   C. ele. Kinase like
   23  - - - - - - - - - - - - - - - - - - - - - - - - - - - - - - - - - - - - - - - - - - - -   C. ele. Tyr. Kinase like
   60  - - - - - - - - - - - - - - - - - - - - - - - - - - - - - - - - - - - - - - - - - - - -   hMAPKK (putative partial)
   13  - - - - - - - - - - - - - - - - - - - - - - - - - - - - - - - - - - - - - - - - - - - -   O. sat. MEK1
   80  - - - - - - - - - - - - - - - - - - - - - - - - - - - - - - - - - - - - - - - - - - - -   P. bla. PKA
  330  K L A T F E N L E T A L S S T L G T H I R Q P N A P S S R D E T T A P M T P S F T N E R I G G G G G   C. ele. Ser/Thr Kinase like
```

FIG. 14N

```
                                   S------F-------------------P---------------------                  Majority

|---------|---------|---------|---------|---------|
      1410      1420      1430      1440      1450
 6   - - - - - - - - - - - - - - - - - - - - - - - - - - -   hl5993 partial pro
 5   - - - - - - - - - - - - - - - - - - - - - - - - - - -   A. tha. MARK (putative)
 1   - - - R G R G - - E - - - - - - - - - - - E S V H S L L F H X R A - -   A. tha. Ste20-like Kinase homo.
 3   - - - E Q E K P K N G Y I V S - - - - - - - - - D N T N E L - - - - -   A. Thal. cosmid
 1   - - - - - E - - - E P P E I C E E A L - - - - - - - - - - - - - - - -   C. ele. Kinase like
 9   - - - - - - - - - - - - - - - - - - - - - Y S D K M - - - - - - - - -   C. ele. Tyr. Kinase like
 3   - - Q S F H I G K N H N - - F R I P T C E R S P - G A R D A E - E D E D I F N L A - -   hMARKK (putative partial)
 8   G K A K Y Y E Y S N D T S I D K F V M D T A G A T N R S K D - - K Q K Q W A   O. sat. MEK1
 80  G G A T S F S I G T P P S H S P F P V S E C D Y D L K G Q M D L E S E D E V I Q M I V R H R M E Q   P. bla. PKPA
                                                                                                       C. ele. Ser/Thr Kinase like ----------------------------------------              Majority

|---------|---------|---------|---------|---------|
      1460      1470      1480      1490      1500
 8   - - - - - - - - - - - - - - - - - - - - - - - L X G A L A E A   hl5993 partial pro
 7   - - - - - - - - - - - - - - - - - - - - - - - - - - - - - - -   A. tha. MARK (putative)
 3   - - - - - - - - - H V N R E S S T S E E I - - - - - - - - - - -   A. tha. Ste20-like Kinase homo.
 4   - - - - - - - - - - - - - - - - - - - - - L P L L Q S L L V Q N   A. Thal. cosmid
 1   - - - - - - - - - - - - - - - - - - - - - - - - - - - - - - - -   C. ele. Kinase like
 8   - - - - - - - - - - - - - - - - - - - - - - V K N - - - - - - -   C. ele. Tyr. Kinase like
 9   - - - - - - - - - - - - - - - - - - - - - - - - - - - - - - - -   hMARKK (putative partial)
 8   - - - - - - - - - - - - - - - - - - - - - - - - - - - - - - - -   O. sat. MEK1
 4   A K L Q D Q D I M T V G D L R - - - - - - - D L H D E D W S G I G L T - -   P. bla. PKPA
 30  H K L L E K Q R V E I E R L R S K I R V P R A T S V N P E M I G D D E A D T T T A L Q S A L G N A   C. ele. Ser/Thr Kinase like
```

```
                    1510              1520              1530              1540              1550                   Majority 6  P - - - - - - - - - - - - - - - - - - - - - - - - - - - - - - - - - - - - - - - - - - - - - - - - - - - -    h15993 partial pro
7  - - - - - - - - - - - - - - - - - - - - - - - - - - - - - - - - - - - - - - - - - - - - - - - - - - - - -    A. tha. MARK (putative)
6  D I - - - - - - - - - - - - - - - - - - - - - Q R V C V L S V S T A S C G Y T S P K W - - - - - - - - - -    A. tha. Ste20-like Kinase homo.
4  - - - - - - - - - - - - - - - - - - - - - - - - - - - - - - - - - - - - - - - - - - - - - - - - - - - - -    A. Thal. cosmid
1  - - - - - - - - - - - - - - - - - - - - - - - - - - - - - - - - - - - - - - - - - - - - - - - - - - - - -    C. ele. Kinase like
1  H - - - - - - - - - - - - - - - - - - - - - - - - - - - - - - - - - - - - - - - - - - - - - - - - - - - -    C. ele. Tyr. Kinase like
9  - - - - - - - - - - - - - - - - - - - - - - - - - - V F A L R A L K N M L A G K K A A V T - - - - - - -    hMARKK (putative partial)
8  - - - - - - - - - - - - - - - - - - - - - - - - - - - - - - - - - - - - - - - - - - - Q R P. bla. PKA      O. sat. MEKI
2  S L S L P A S P P P N T E T T K V N T T V I P S D V L A T R M T M S Q S S T K S S N V S V S S R H R       C. ele. Ser/Thr Kinase like
80

1560              1570              1580              1590              1600                  Majority 26 - - - - - - - - - - - - - - - - - - - - - - - - - - - - - - - - - - - - - - - - - - - - - - - - - - - - -    h15993 partial pro
7  - - - - - - - - - - - Q P Q P S S T D F I R R - - - - - - - - - - - - - - - - - - - - - - - - - - - - -    A. tha. MARK (putative)
48 - - - - - - - - - - - - - - - L L R F G F - - - - - - - - - - - - - - - - C - - - - - - - - - - - - - -    A. tha. Ste20-like Kinase homo.
4  - - - - - - - - - - - - - - - - - - - - - - - - - - - - - - - - - V R L Q V K D - - - - - - - - - - - -    A. Thal. cosmid
1  - - - - - - - - - - - - - - - - - - - - - - - - - - - - - - - - - - - - - - - - - - - - - - - - - - - -    C. ele. Kinase like
1  - - - - - - - - - - - - - - - - - - - - - - - - - - - - - - - - - - - - - - - - - - - - - - - - - - - -    C. ele. Tyr. Kinase like
9  - - - - - - - - - - - - - - - - - - - - - - - - - - - - - - - - - - - - - - - - - - - - - - - - - - - -    hMARKK (putative partial)
8  - - - - Y H S R H P D P G A Q R - A R H - - - - - - - - - - - - - - - C E - - - V D A Q S S P             O. sat. MEKI
3  G - - - - - - - - - - - - - - - - - - - - - - - - - - - - - - - - - - - - - - - - - - - L Q G T R        P. bla. PKA
30 D N Q S A P P R H H H H Q P H P P H H P H L Q N H Y H P P Q N H T S A T A P C P S A M V Q L Q A V S       C. ele. Ser/Thr Kinase like
```

|       |                               | 1610 | 1620 |                                      | Majority                            |
|-------|-------------------------------|------|------|--------------------------------------|-------------------------------------|
|       |                               |      |      |                                      |                                     |
| 6     |                               |      |      |                                      | h15993 partial pro                  |
| 9     |                               |      |      |                                      | A. tha. MARK (putative)             |
| 3     |                               |      |      |                                      | A. tha. Ste20-like Kinase homo.     |
| 1     | S D N L L - - - - - - - - - - - - - - C |      |      |                                      | A. Thal. cosmid                     |
| 1     |                               |      |      |                                      | C. ele. Kinase like                 |
| 1     |                               |      |      |                                      | C. ele. Tyr. Kinase like            |
| 9     |                               |      |      |                                      | hMARKK (putative partial)           |
| 2     | D G H V Y - - - - - - - - - - - - - - S |      |      |                                      | O. sat. MEK1                        |
| 9     | S G A S T P V E E Q E Q E L M |      |      |                                      | P. bla. PKPA                        |
| 80    | N N N V N P L H Q P P H P V S S Q I P P Q A |  |  |                                  | C. ele. Ser/Thr Kinase like         |

Decoration 'Decoration #1': Shade (with solid black) residues that match the Consensus exactly.

FIG. 14Q

Input file h16341; Output File h16341.pat
Sequence length 518

```
                  N   G   I   Q   L   Q   D   F   L   H   V   W   S   R   L   E   E   F   X    19
                A AAC GGA ATT CAA TTG CAG GAT TTC CTC CAC GTG TGG AGC CGT CTT GAA GAG TTT GAN   58

G   G   G   G   E   G   N   V   S   Q   V   G   R   V   W   P   S   Y              39
GGA GGT GGT GGA GAA GGA AAT GTG AGC CAG GTG GGA AGA GTT TGG CCA TCT TCG TAT          118

R   A   L   I   S   A   F   S   R   L   T   R   L   D   F   T   C   E   K          59
CGA GCT CTT ATA AGT GCC TTT TCC AGA CTG ACG CGT TTG GAT TTC ACC TGT GAA AAA          178

I   G   S   G   F   F   S   E   V   F   K   V   R   H   R   A   S   G   Q   V      79
ATA GGG TCT GGC TTC TTT TCT GAA GTG TTC AAG GTA CGA CAC CGA GCT TCT GGT CAG GTG      238

M   A   L   K   M   N   T   L   S   S   N   R   A   N   M   L   K   E   V   Q      99
ATG GCT CTT AAG ATG AAC ACA TTG AGC AGT AAC CGG GCA AAC ATG CTG AAA GAA GTA CAG      298

L   M   N   R   L   S   H   P   N   I   L   R   F   M   G   V   C   V   H   Q      119
CTC ATG AAT AGA CTC TCC CAT CCC AAC ATC CTT AGG TTC ATG GGT GTT TGT CAT CAA          358

G   Q   L   H   A   L   T   E   Y   I   N   G   N   L   E   Q   L   L   D          139
GGA CAA TTG CAT GCA CTT ACA GAG TAT ATC AAC GGG AAC CTG GAA CAG CTA GAC              418

S   N   L   H   L   P   W   T   V   R   V   K   L   A   Y   D   I   A   V   G      159
AGT AAC CTG CAT TTG CCT TGG ACT GTG AGG GTA AAA CTG GCC TAT GAC ATA GCA GTG GGC      478

L   S   Y   L   H   F   K   G   I   F   H   R   D                                  173
CTC AGC TAC CTT CAC TTC AAA GGC ATT TTT CAT CGG GAC C                                520
```

Input file h2252con; Output File h2252con.pat
Sequence length 1737

ACCCTACTAAAGGGAACAAAAGCTGGAGCTCCACGCGGTGGGCCGCTCTAGAACTAGTGGATCCCCCGGGCTGCAG   79

GAATTCGGCACGAGTAACAGCCCACCTCCTAGCCCCGGCTACGCGCCAGTAACCCCACTTTGTGTCC   158

TCCCAGGCCCCGATCGAAAAGCCTGGGAGGGCCGCCGAACTACCCCCGGAGGAGGAGCCAGTCCGAACCCAAGGCGCC   237

FIG. 19A

```
                                                                          M   A   H   S   P   V   A   V   Q   V      10
ACCGCCGCAGAAGCGGAGGCAGCATTCGCCTCC ATG GCC CAC TCG CCG GTG GCT GTC CAA GTG     304

P   G   M   Q   N   I   A   D   P   E   E   L   F   T   K   L   E   R   I    30
CCT GGG ATG CAG AAT AAC ATA GCT GAT CCA GAA GAA CTG TTC ACA AAA TTA GAG CGC ATT   364

G   K   G   S   F   G   E   V   F   K   G   I   D   N   R   T   Q   V   V    50
GGG AAA GGC TCA TTT GGG GAA GTT TTC AAA GGA ATT GAT AAC CGT ACC CAG GTC GTT   424

A   I   K   I   I   D   L   E   E   A   E   D   I   E   I   Q   Q   E    70
GCT ATT AAA ATC ATA GAC CTT GAG GAA GCC GAA GAT ATA GAA ATT CAG CAA GAA   484

I   T   V   L   S   Q   C   D   S   Y   V   T   K   Y   Y   G   S   Y   L    90
ATA ACT GTC TTG AGT CAA TGT GAC AGC TAT GTA ACA AAA TAC TAT GGG TCA TAT TTA   544

K   G   S   K   L   W   I   I   M   E   Y   L   G   G   G   S   A   L   D   L    110
AAG GGG TCT AAA TTA TGG ATA ATA ATG GAA TAC CTG GGT GGT GGG TCA GCA CTG GAT CTT   604

L   R   A   G   P   F   D   E   F   Q   I   A   T   M   L   K   E   I   L   K    130
CTT CGA GCT GGT CCA TTT GAT GAG TTC CAG ATT GCT ACC ATG CTA AAG GAA ATT TTA AAA   664

G   L   D   Y   L   H   S   E   K   K   I   H   R   D   I   K   A   A   N   V    150
GGT CTG GAC TAT CTG CAT TCA GAA AAG AAA ATT CAC CGA GAC ATA AAA GCT GCC AAT GTC   724
```

FIG. 19B

```
L   S   E   Q   G   D   V   K   L   A   D   F   G   V   A   G   Q   L   T          170
TTG TCA GAA CAA GGA GAT GTT AAA CTT GCT GAT TTT GGA GTT GCT GGT CAG CTG ACA         784
D   T   Q   S   A   Y   D   K   A   M   P   W   F   E   P   V   I   A   E   V      190
GAT ACA CAG TCA GCT TAT GAC AAA GCT ATG CCA TGG TTT GAA CCT GTG GCT GAA GAA GTT    844
I   Q   Q   A   K   G   E   P   N   P   T   L   V   G   I   T   A   M   I          210
ATT CAG CAG GCC AAA GGA GAG CCT AAC CCT ACT CTT GGA GGA ATT ACT ATG GCT ATT         904
E   L   A   K   G   N   P   P   T   L   V   G   I   T   A   M   R   V   F   L      230
GAA CTA GCC AAG GGA AAT CCT CCA ACT CTT GTT GGA ATA ACA ATG AGA GTT TTT CTT         964
I   P   K   N   A   C   L   N   D   P   S   F   R   S   T   A   K   E   L   K      250
ATT CCC AAA AAC AAC GCT TGC CTG AAC GAT CCA TCA TTT CGT TCT ACT GCA AAA GAA CTT   1024
I   D   A   L   N   K   S   K   T   Y   K   T   P   R   P   S   T   E   L   I      270
ATT GAT GCT TGC CTG AAC AAA TCA AAG ACT TAT AAG ACT CCT CGT TCA ACT GAA CTG ATA   1084
H   K   F   I   V   K   N   S   D   E   H   S   D   E   S   G   D   R              290
CAC AAA TTC ATT GTA AAA AAT TCA GAT GAA CAC AGT GAT GAA TCC GAG GGC CGT             1144
F   K   R   W   K   A   E   G   H   S   D   D   D   S   E   S   D                  310
TTT AAG AGA TGG AAG GCA GAA GGA CAC AGT GAT GAT GAT AGT GAA TCT GAT                1204
```

FIG. 19C

```
  S   E   S   T   S   R   E   N   N   T   H   P   E   W   S   F   T   T   V   R   330
TCG GAA TCT ACC AGC AGG GAA AAC AAT ACT CAT CCT GAA TGG AGC TTT ACC GTA CGA  1264

K   K   P   D   P   K   V   Q   K   V   Q   A   E   Q   D   L   V   Q   T   L   350
AAG AAG CCT GAT CCA AAG AAA GTA CAG AAT GGG GCA GAG CAA GAT CTT GTG CAA ACC CTG  1324

S   C   L   S   M   I   I   T   P   A   F   A   E   L   K   Q   Q   D   E   N   370
AGT TGT TTG TCT ATG ATA ATC ACA CCT GCA TTT GCT GAA CTT AAA CAG CAG GAC GAG AAT  1384

N   A   S   R   N   Q   A   I   E   E   L   S   K   I   A   V   E   A   390
AAC GCT AGC AGG AAT CAG GCG ATT GAA GAA CTC GAG AAA AGT ATT GCT GTG GCT GAA GCC  1444

A   C   P   G   I   T   D   K   M   V   K   L   I   E   K   F   Q   K   C   410
GCC TGT CCC GGC ATC ACA GAT AAA ATG GTG AAG AAA CTA ATT GAA TTT CAA AAG TGT  1504

S   A   D   E   S   P   *                                                  416
TCA GCA GAC GAA TCC CCC TAA                                                  1525

GAAACTTATTATTGGCTTCTGKTTCATATGGACCCAGAGAGCCCCACCAAACCTACGTCAAGATAACAATGCTTAACCC  1604

ATGAGCTCCATGTGCCTTTTGGATCTTTGCAACACTTGAAGATTTGGAAGAAGCTATTAAACTATTTGGGATGGCGG  1683

TTATCATTTTATATTTGGAAGGATTATTTGTAAGGATAACTTTTAATACTAT  1737
```

FIG. 20G

KINASES AND USES THEREOF

CROSS-REFERENCE TO RELATED APPLICATIONS

The present application is a divisional application of U.S. patent application Ser. No. 11/358,419, filed on Feb. 21, 2006 now U.S. Pat. No. 7,425,424, which is a continuation application of U.S. patent application Ser. No. 10/989,228, filed on Nov. 15, 2004 (abandoned), which is a divisional of U.S. patent application Ser. No. 09/862,027, filed on May 21, 2001, now U.S. Pat. No. 6,858,418, which is divisional of U.S. application Ser. No. 09/345,473, filed Jun. 30, 1999, now U.S. Pat. No. 6,558,903. The entire contents of each of these applications are herein incorporated by reference.

FIELD OF THE INVENTION

The invention relates to novel kinase nucleic acid sequences and proteins. Also provided are vectors, host cells, and recombinant methods for making and using the novel molecules.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786-791; Birchmeier et al. (1993) *Bioessays* 15:185-189). They serve as growth factor receptors and signal transducers and have been implicated in cellular transformation and malignancy (Hunter et al. (1992) *Cell* 70:375-387; Posada et al. (1992) *Mol. Biol. Cell* 3:583-592; Hunter et al. (1994) *Cell* 79:573-582). For example, protein kinases have been shown to participate in the transmission of signals from growth-factor receptors (Sturgill et al. (1988) *Nature* 344:715-718; Gomez et al. (1991) *Nature* 353:170-173), control of entry of cells into mitosis (Nurse (1990) *Nature* 344:503-508; Maller (1991) *Curr. Opin. Cell Biol.* 3:269-275) and regulation of actin bundling (Husain-Chishti et al. (1988) *Nature* 334:718-721).

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42-52).

Kinases play critical roles in cellular growth. Therefore, novel kinase polynucleotides and proteins are useful for modulating cellular growth, differentiation and/or development.

SUMMARY OF THE INVENTION

Isolated nucleic acid molecules corresponding to kinase nucleic acid sequences are provided. Additionally amino acid sequences corresponding to the polynucleotides are encompassed. In particular, the present invention provides for isolated nucleic acid molecules comprising nucleotide sequences encoding the amino acid sequences shown in SEQ ID NOs:2, 4, 6, 8, 10, 12, and 14. Further provided are kinase polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The kinase molecules of the present invention are useful for modulating cellular growth and/or cellular metabolic pathways particularly for regulating one or more proteins involved in growth and metabolism. Accordingly, in one aspect, this invention provides isolated nucleic acid molecules encoding kinase proteins or biologically active portions thereof, as well as nucleic acid fragments suitable as primers or hybridization probes for the detection of kinase-encoding nucleic acids.

Another aspect of this invention features isolated or recombinant kinase proteins and polypeptides. Preferred kinase proteins and polypeptides possess at least one biological activity possessed by naturally occurring kinase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the kinase polypeptides and fragments are provided. Such antibodies are useful in detecting the kinase polypeptides as well as in modulating cellular growth and metabolism.

In another aspect, the present invention provides a method for detecting the presence of kinase activity or expression in a biological sample by contacting the biological sample with an agent capable of detecting an indicator of kinase activity such that the presence of kinase activity is detected in the biological sample.

In yet another aspect, the invention provides a method for modulating kinase activity comprising contacting a cell with an agent that modulates (inhibits or stimulates) kinase activity or expression such that kinase activity or expression in the cell is modulated. In one embodiment, the agent is an antibody that specifically binds to kinase protein. In another embodiment, the agent modulates expression of kinase protein by modulating transcription of a kinase gene, splicing of a kinase mRNA, or translation of a kinase mRNA. In yet another embodiment, the agent is a nucleic acid molecule having a nucleotide sequence that is antisense to the coding strand of the kinase mRNA or the kinase gene.

In one embodiment, the methods of the present invention are used to treat a subject having a disorder characterized by aberrant kinase protein activity or nucleic acid expression by administering an agent that is a kinase modulator to the subject. In one embodiment, the kinase modulator is a kinase protein. In another embodiment, the kinase modulator is a kinase nucleic acid molecule. In other embodiments, the kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a kinase protein; (2) misregulation of a gene encoding a kinase protein; and (3) aberrant post-translational modification of a kinase protein, wherein a wild-type form of the gene encodes a protein with a kinase activity.

In another aspect, the invention provides a method for identifying a compound that binds to or modulates the activity of a kinase protein. In general, such methods entail measuring a biological activity of a kinase protein in the presence and absence of a test compound and identifying those compounds that alter the activity of the kinase protein.

The invention also features methods for identifying a compound that modulates the expression of kinase genes by measuring the expression of the kinase sequences in the presence and absence of the compound.

Other features and advantages of the invention will be apparent from the following detailed description and claims.

BRIEF DESCRIPTION OF THE DRAWINGS

FIGS. 1A-1C provide the nucleotide (SEQ ID NO:1) and amino acid (SEQ ID NO:2) sequences for h12832.

Figure 2C:
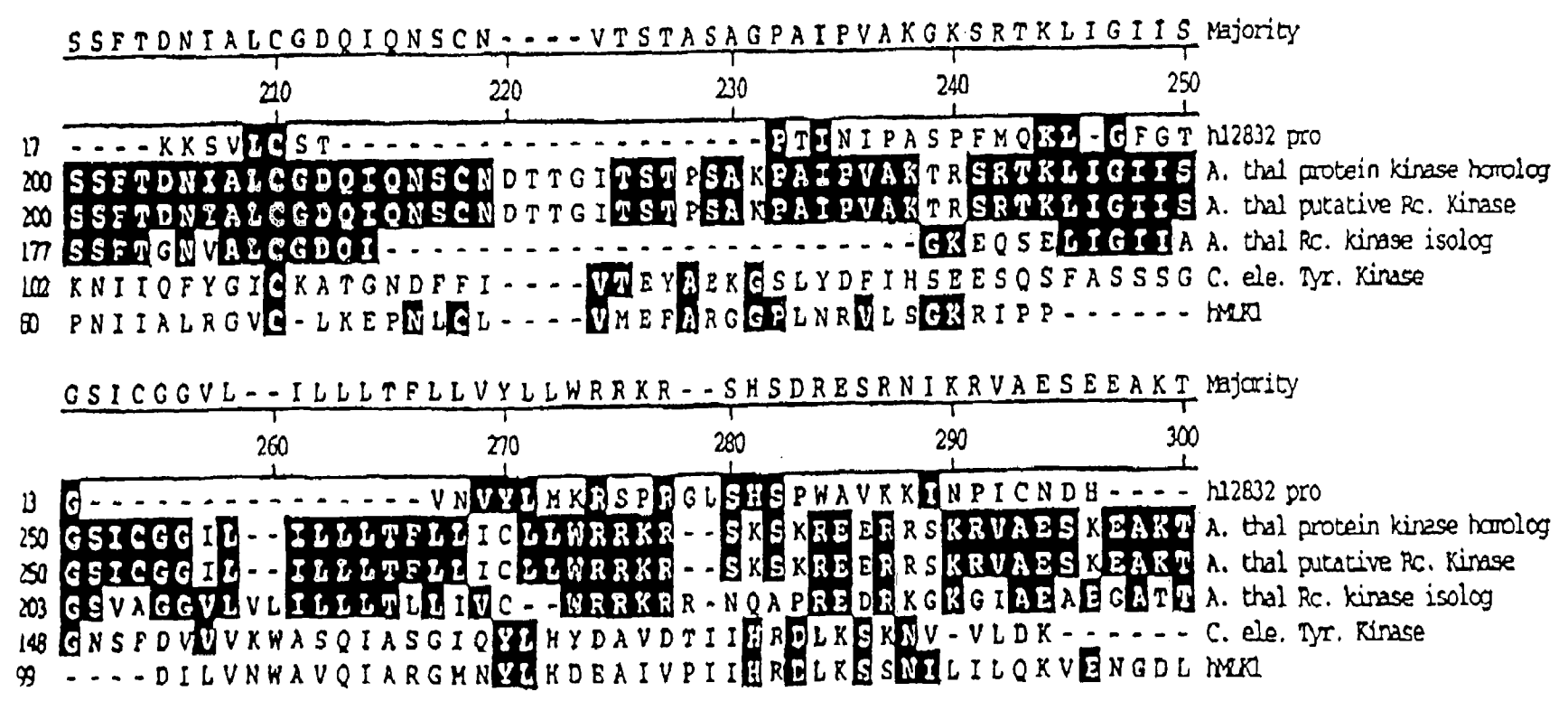
Figure 2D:
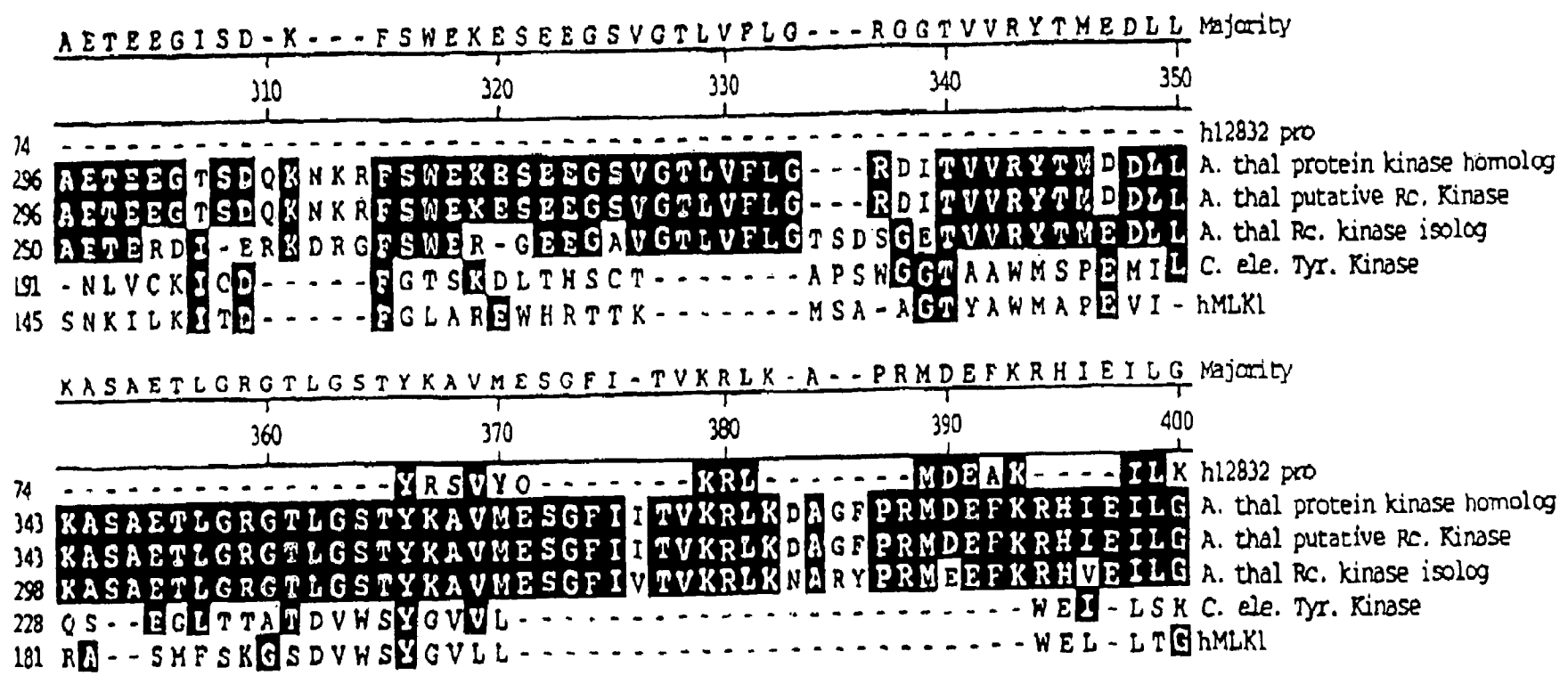
Figure 2E:
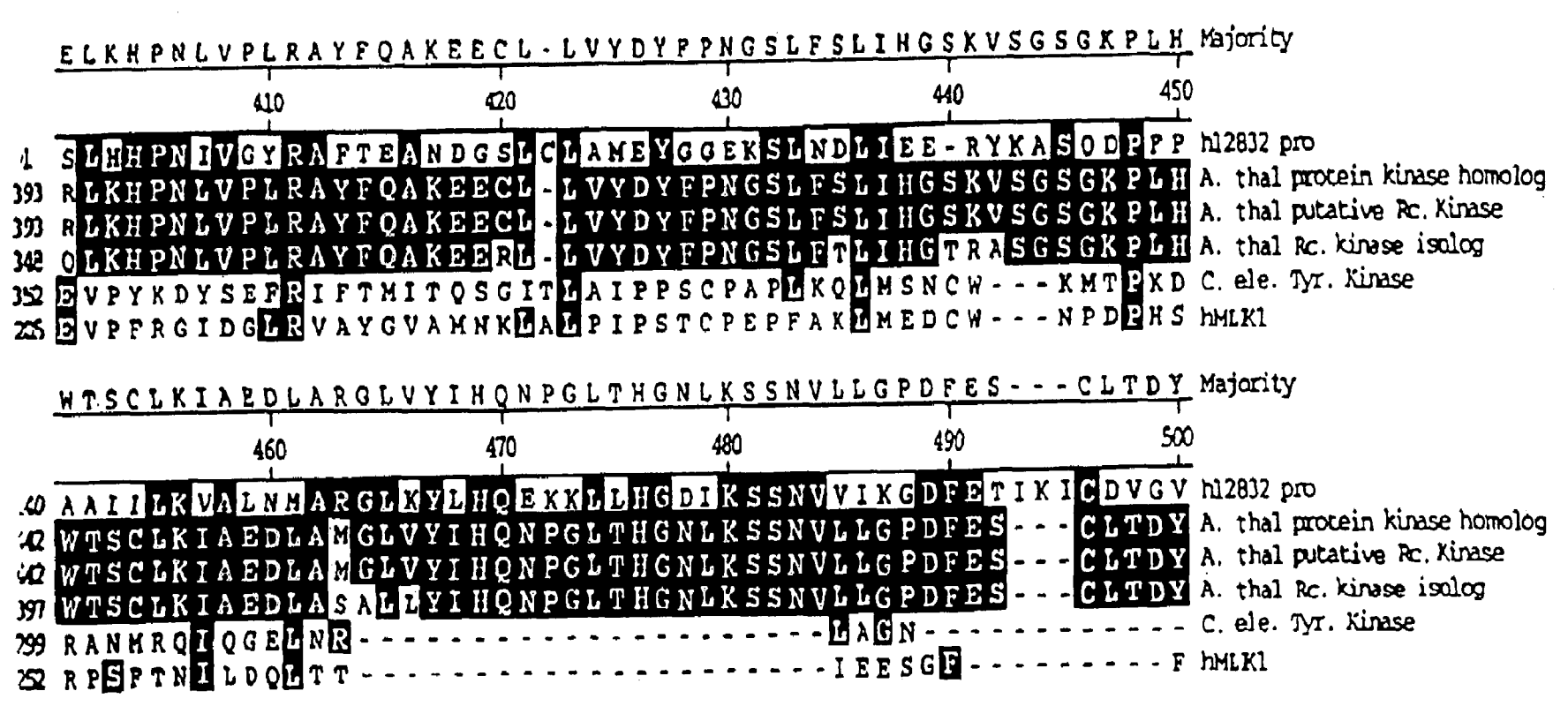
Figure 2F:
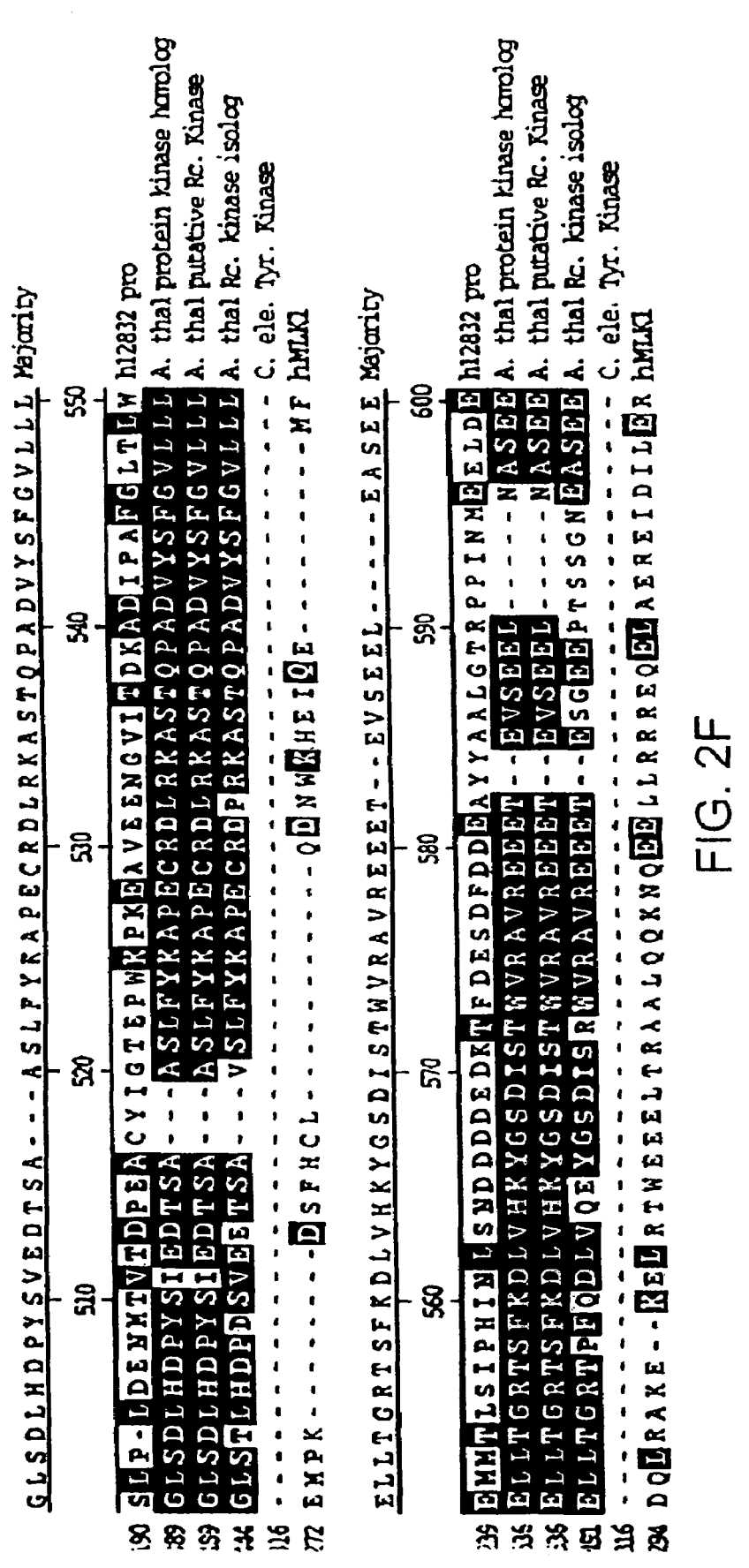

FIGS. 2A-2G show the amino acid sequence alignment for the protein (h12832; SEQ ID NO:2) encoded by human 12832 (SEQ ID NO:1) with the *Arabidopsis thaliana* protein kinase homologue (A. thal. protein kinase homolog; GenBank Accession Number AAB71975; SEQ ID NO:15), the *Arabidopsis thaliana* putative receptor kinase (A. thal. putative Rc. Kinase; GenBank Accession Number AAB71975; SEQ ID NO:16), the *Arabidopsis thaliana* receptor-kinase isolog (A. thal. Rc. kinase isolog; GenBank Accession Number AAB65490; SEQ ID NO:17), the *C. elegans* tyrosine kinase (C. ele. Tyr. Kinase;; GenBank Accession Number AAC47047; SEQ ID NO:18) and the human mixed lineage kinase 1 (hMLK1; SP Accession Number P80192; SEQ ID NO:19).

FIGS. 4A-4B provide the nucleotide (SEQ ID NO:3) and amino acid (SEQ ID NO:4) sequences for h14138.

Figure 5B:
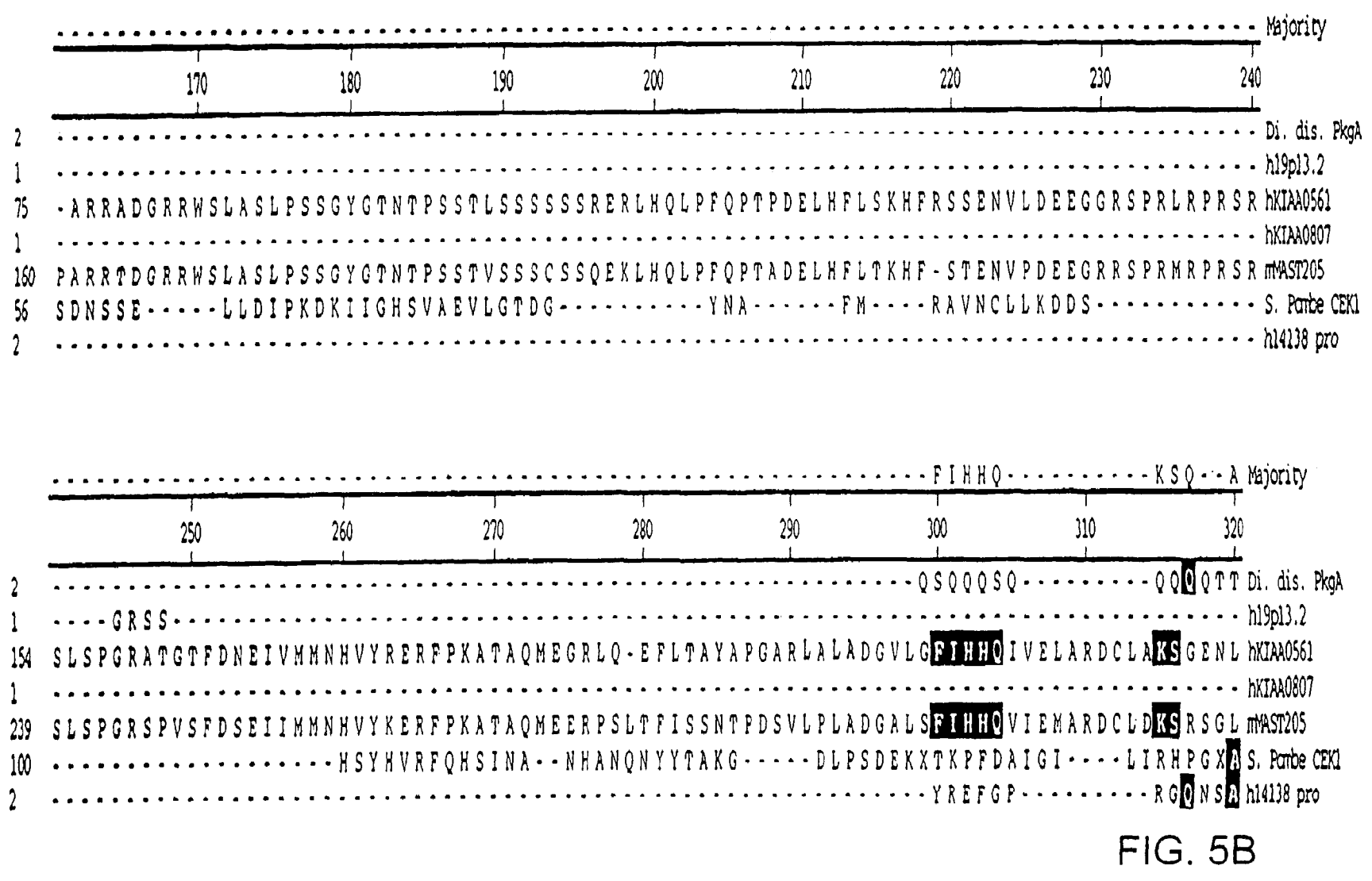
Figure 5C:
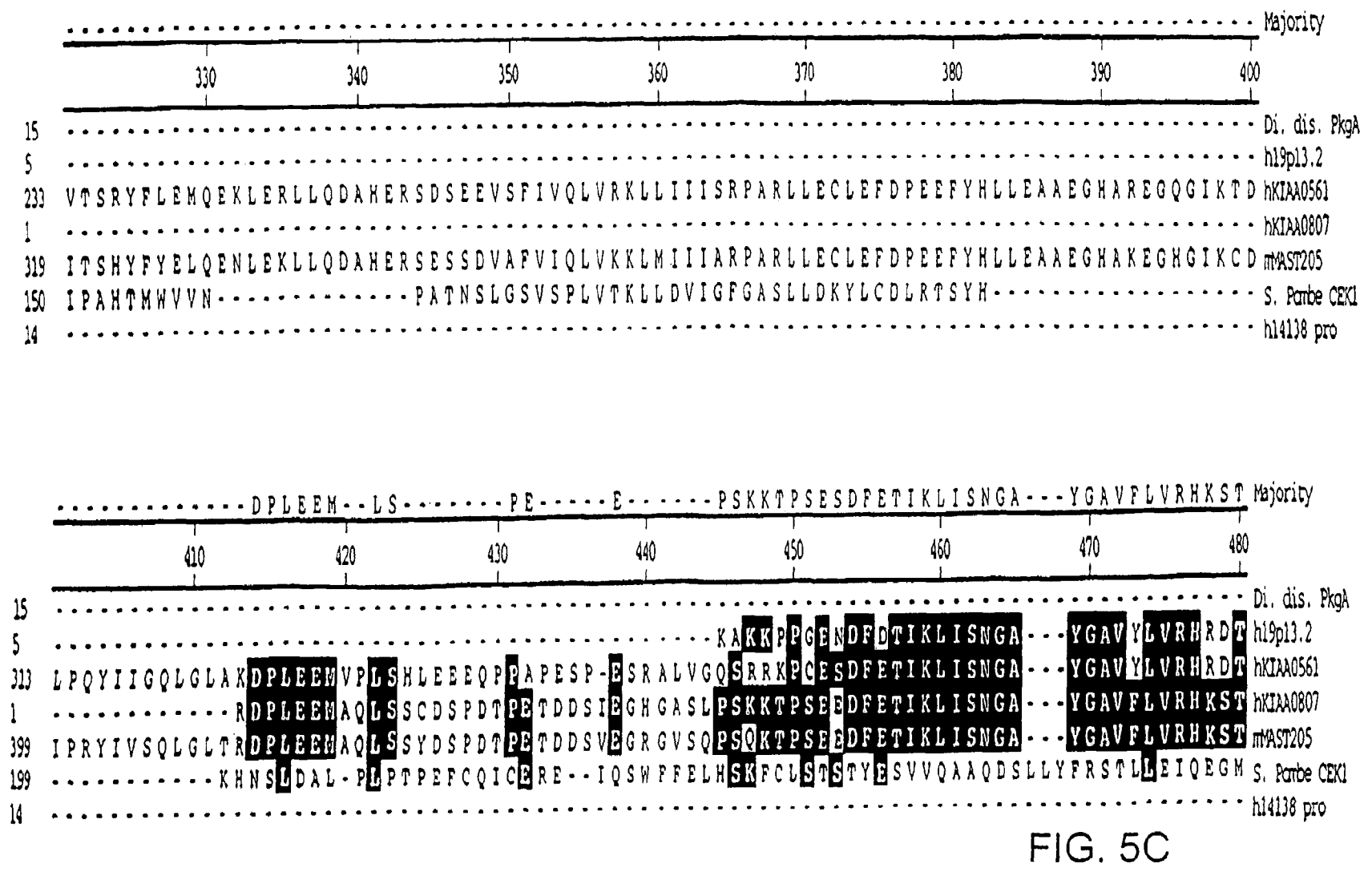
Figure 5E:
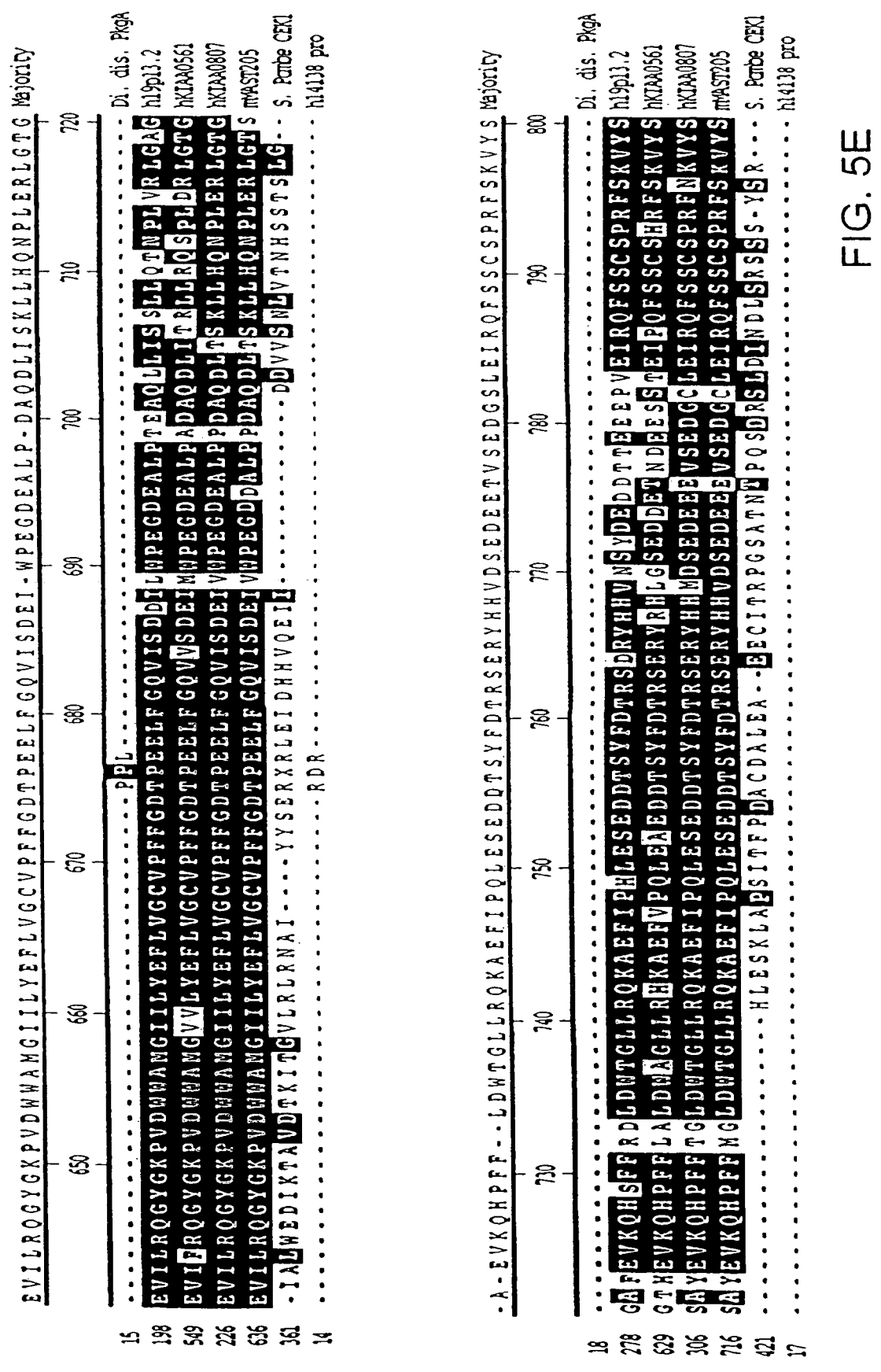
Figure 5F:
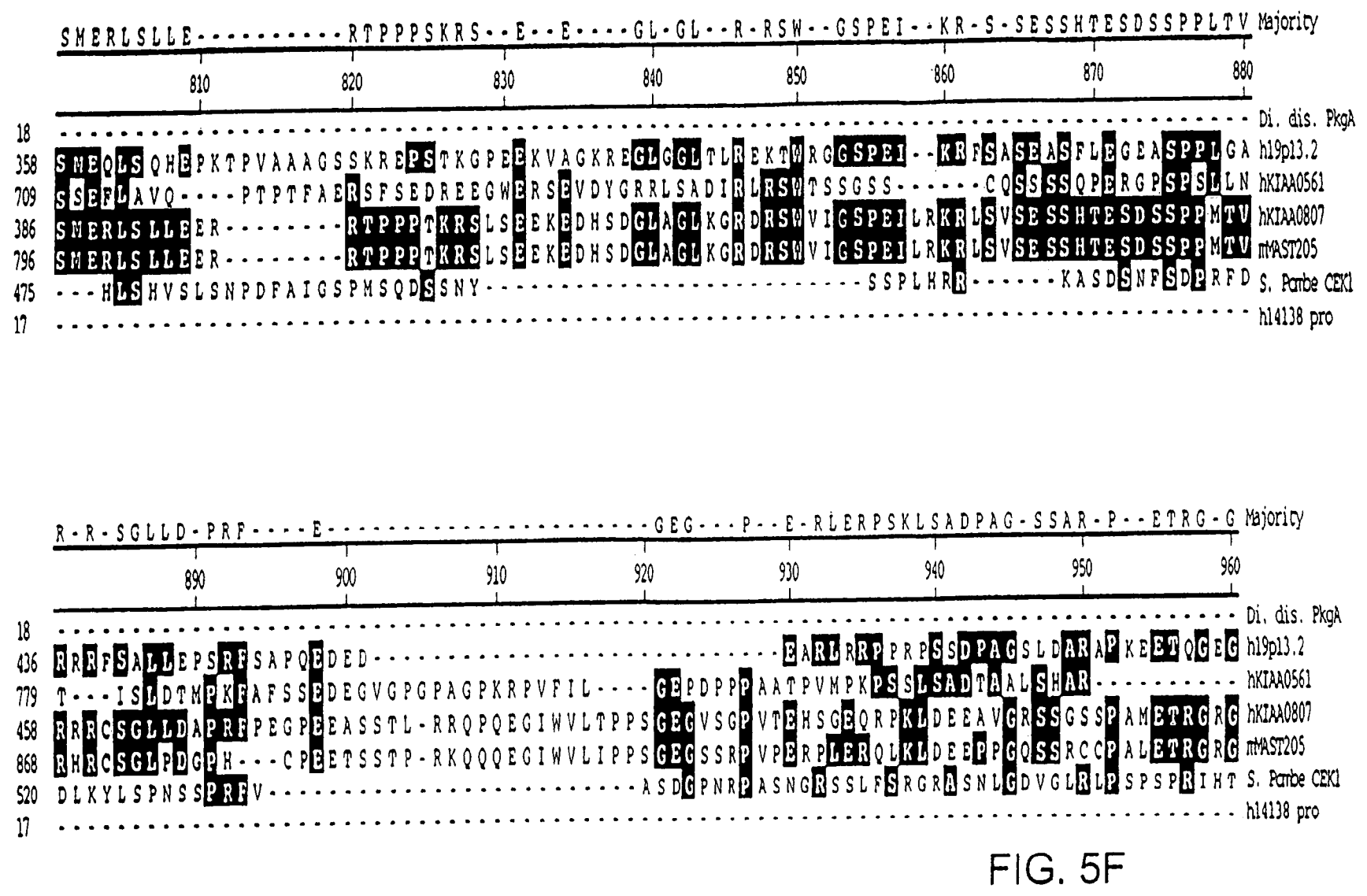
Figure 5G:
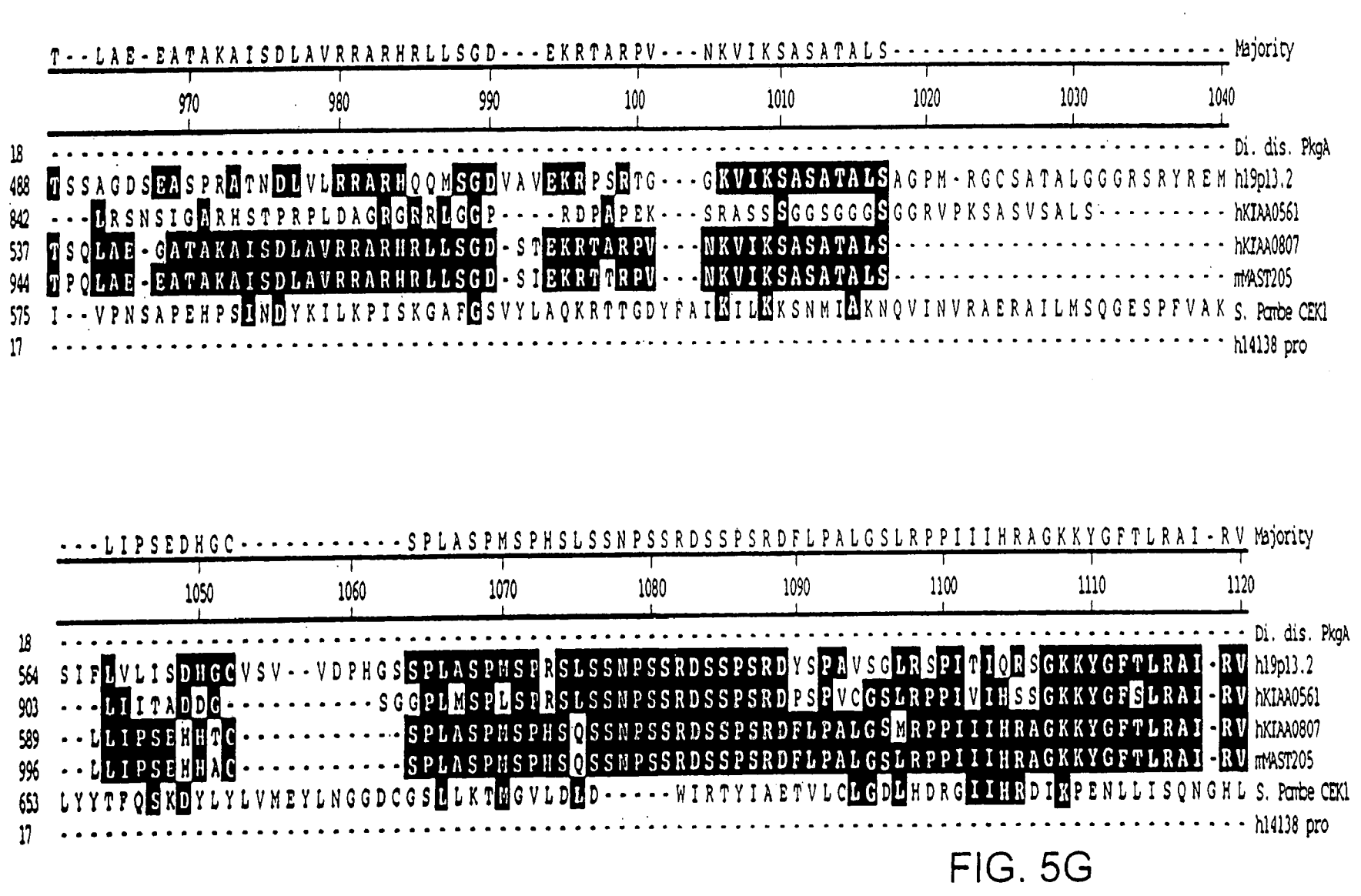
Figure 5H:
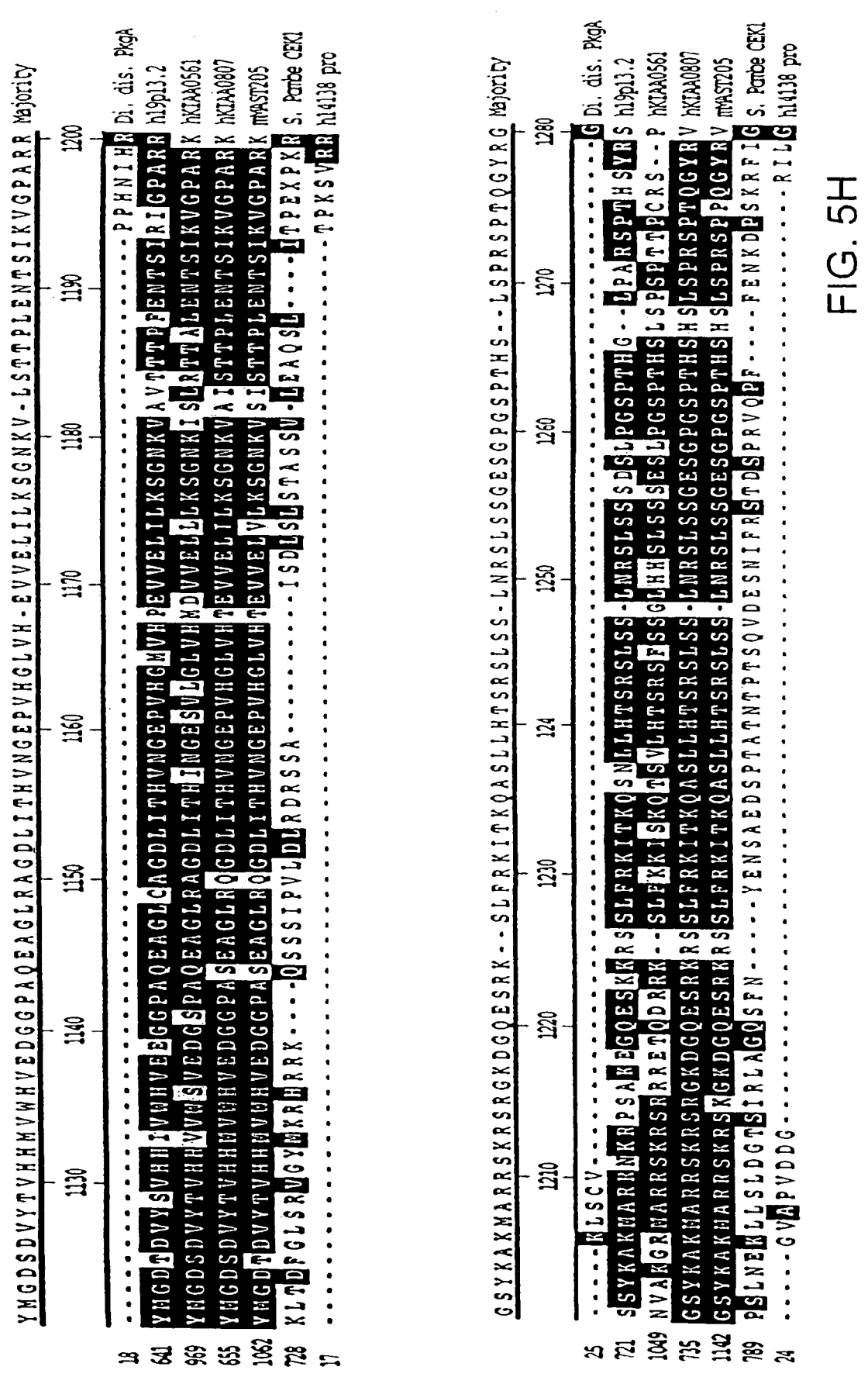
Figure 5J:
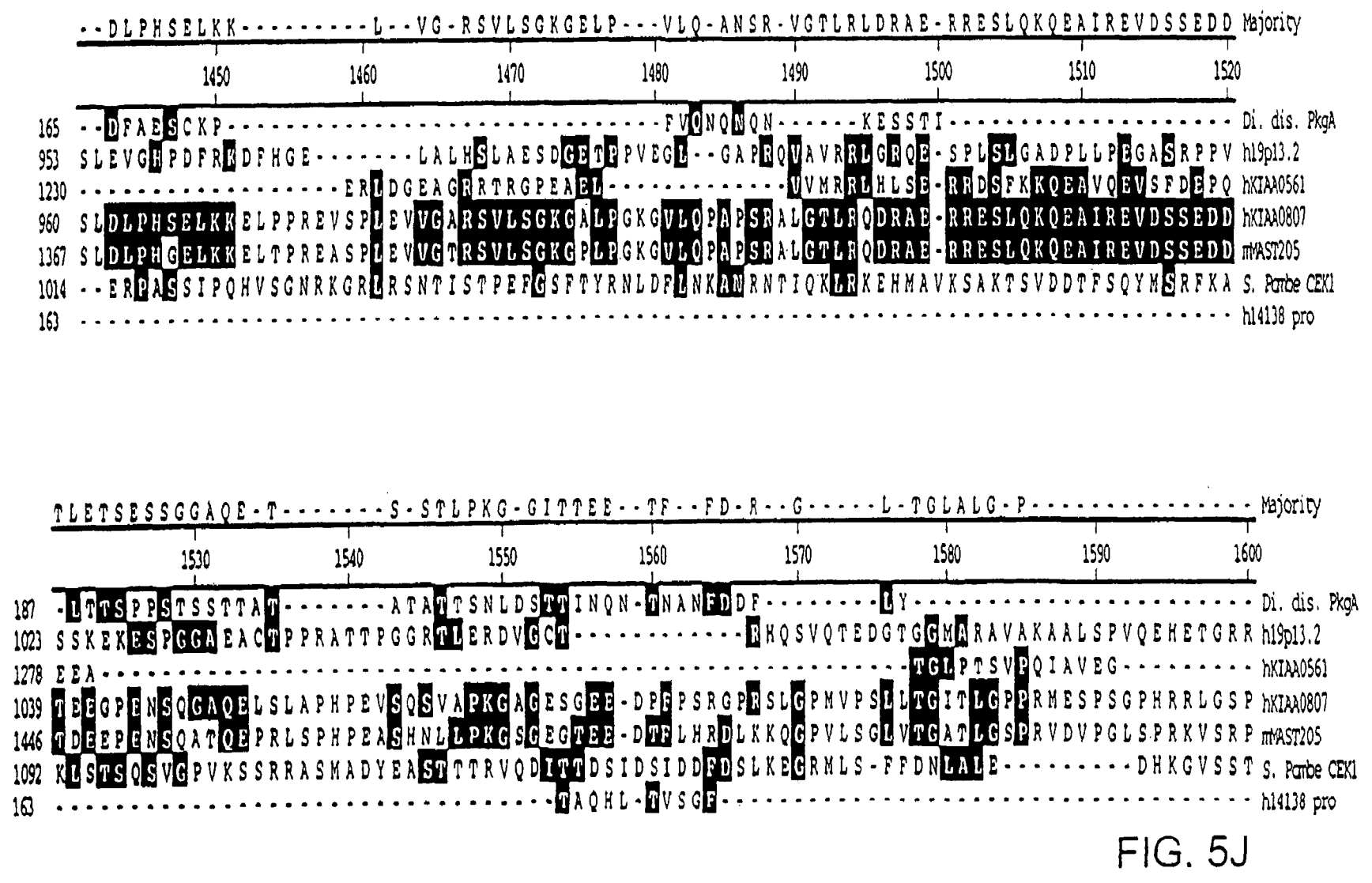
Figure 5K:
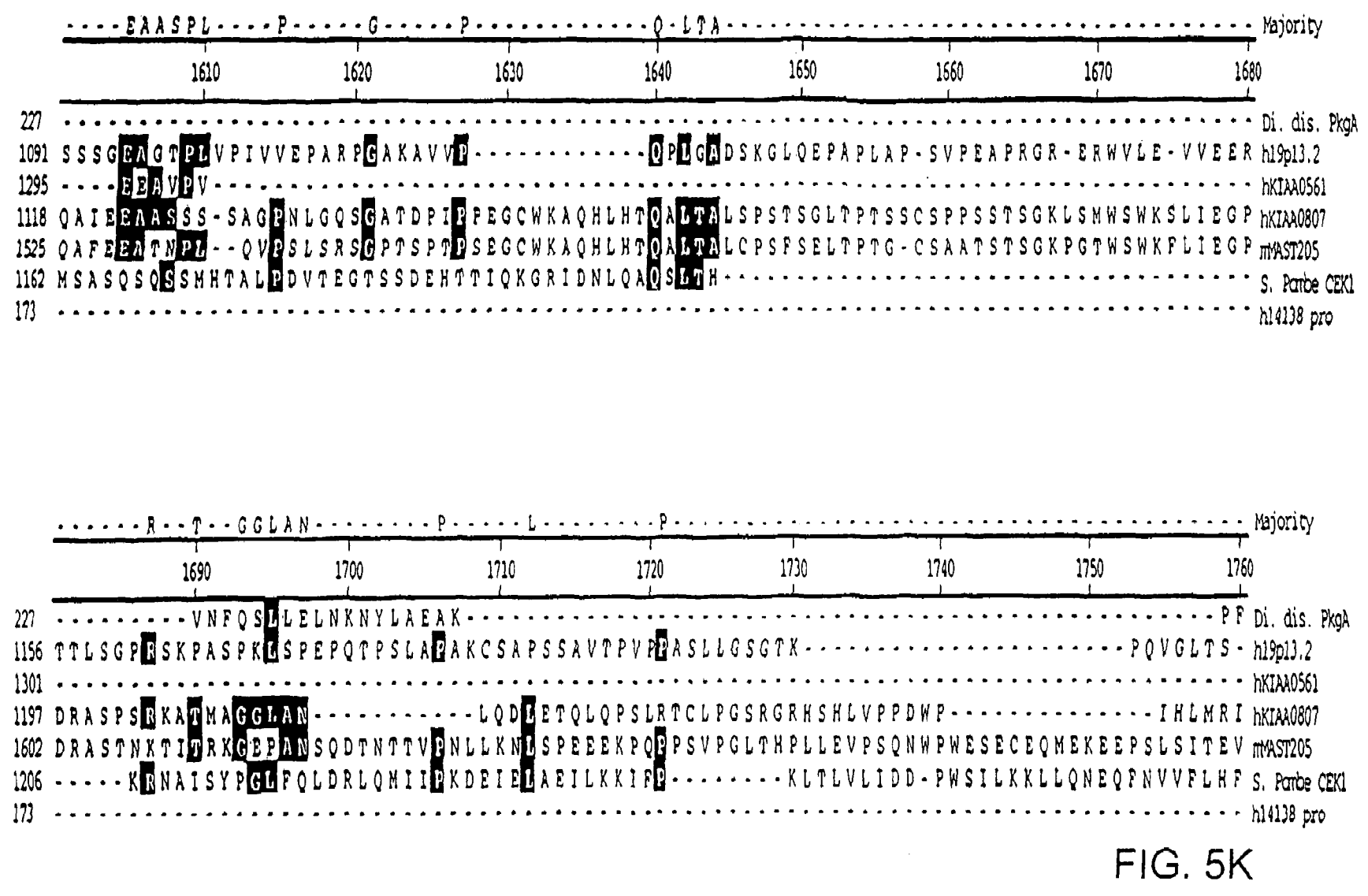

FIGS. 5A-5L show the amino acid sequence alignment for the protein (h14138; SEQ ID NO:4) encoded by human 14138 (SEQ ID NO:3) with the *Dictyostelium discoideum* PkgA protein (Di. Dis. PkgA; GenBank Accession Number AAB70848, SEQ ID NO:77), the hypothetical human serine-threonine protein kinase R31240_1 (h19p13.2; GenBank Accession Number AAB51171; SEQ ID NO:78), the human KIAA0561 protein (hKIAA0561; DBJ Accession Number BAA20762; SEQ ID NO:79), the human KIAA0807 protein (hKIAA0807; DBJ Accession Number BAA34527; SEQ ID NO:80), the mouse protein kinase (mMAST205; GenBank Accession Number AAC04132; SEQ ID NO:81) and the *S. pombe* protein kinase CEK1 (CEK1, SP Accession Number P38938; SEQ ID NO:82).

FIGS. 7A-7C provide the nucleotide (SEQ ID NO:5) and amino acid (SEQ ID NO:6) sequences for h14833.

Figure 8A:
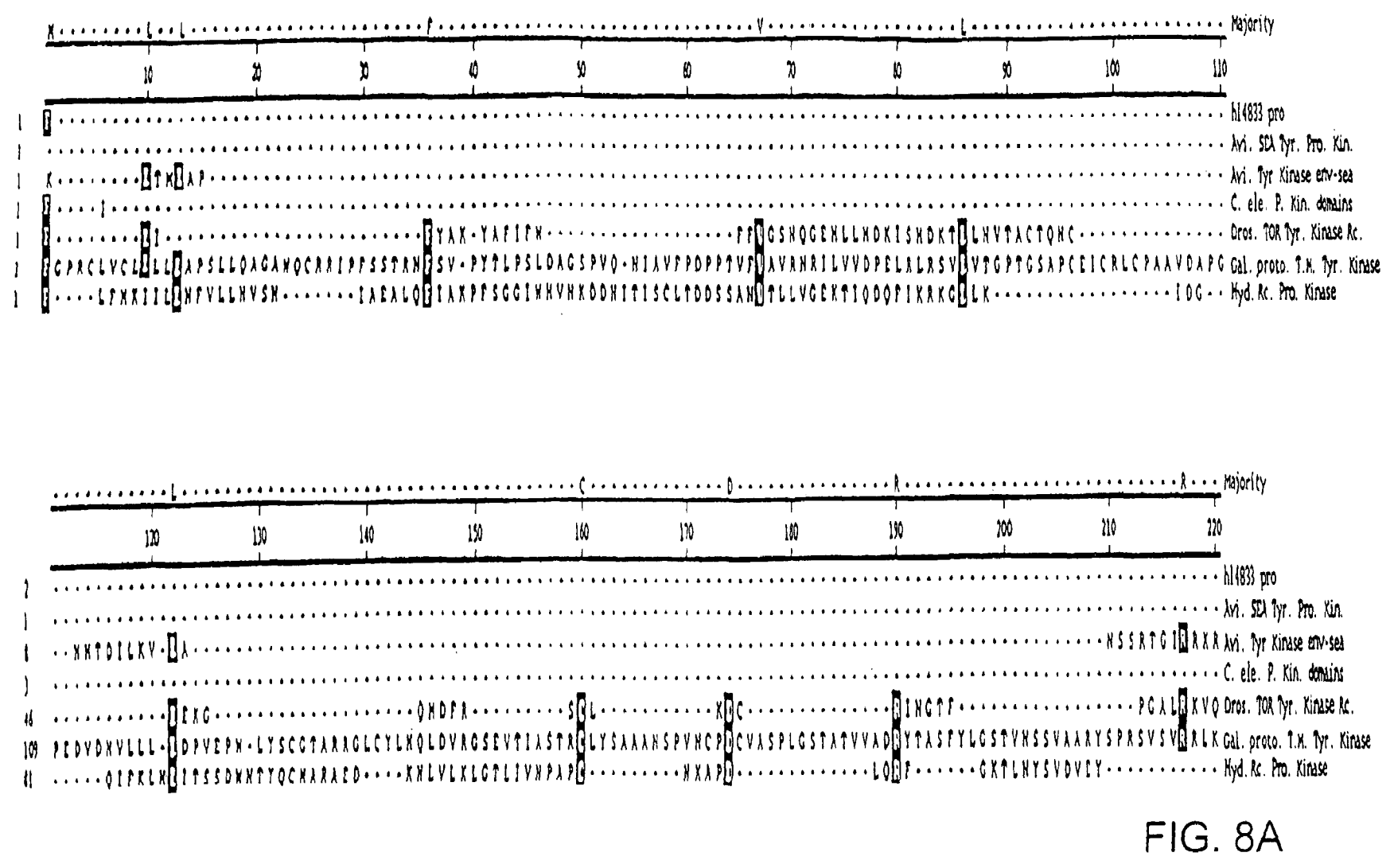
Figure 8B:
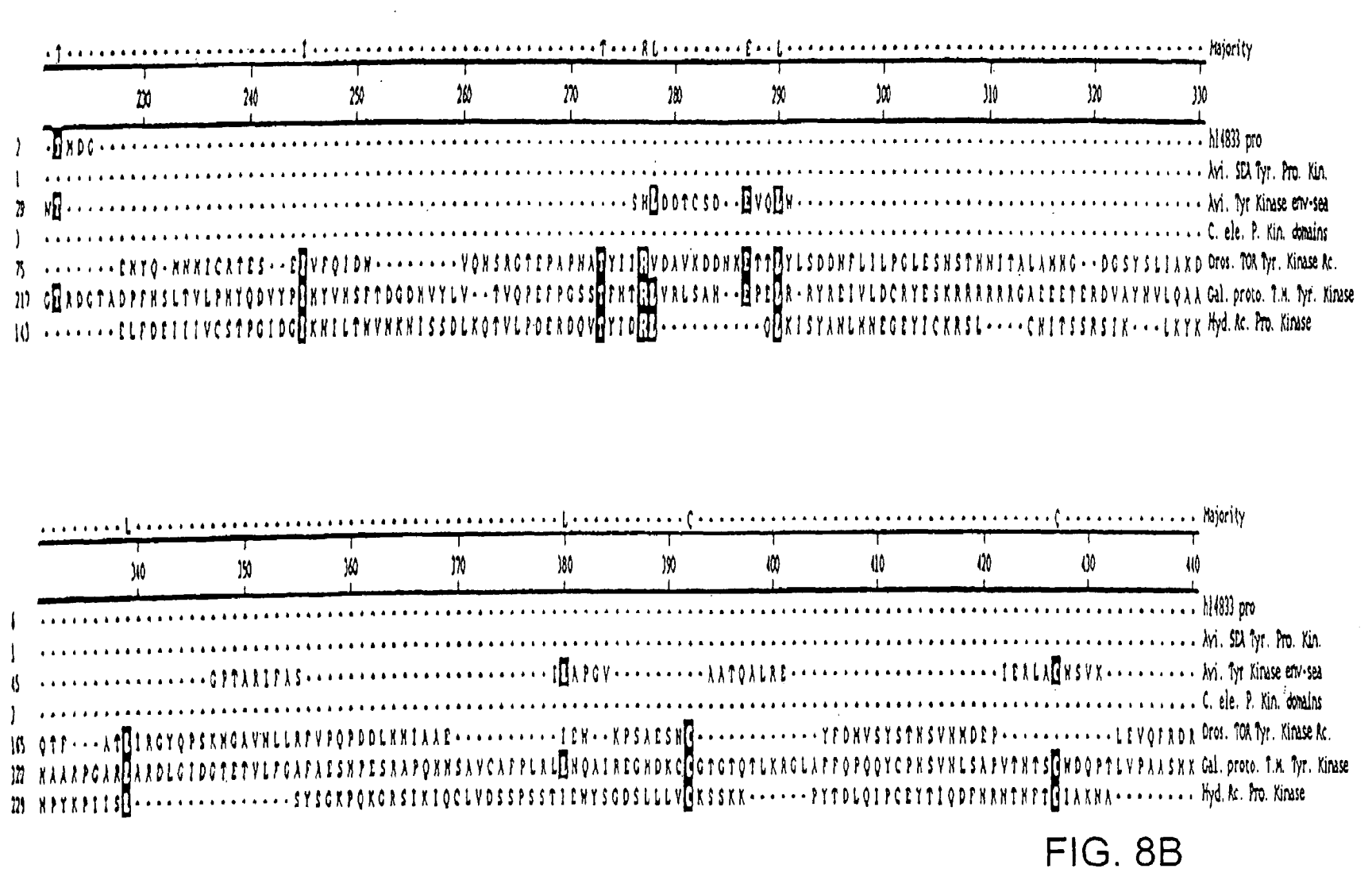
Figure 8E:
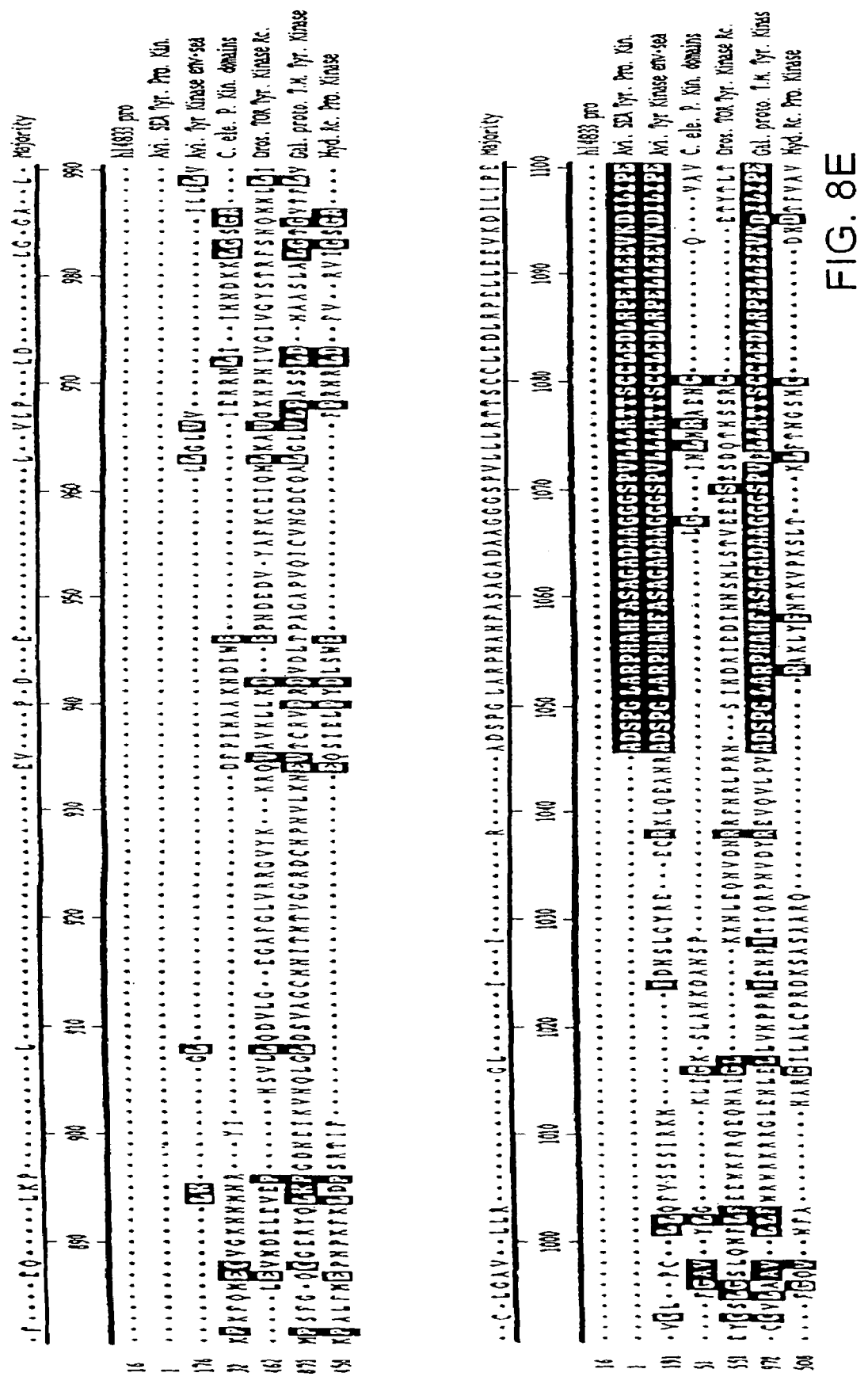
Figure 8F:
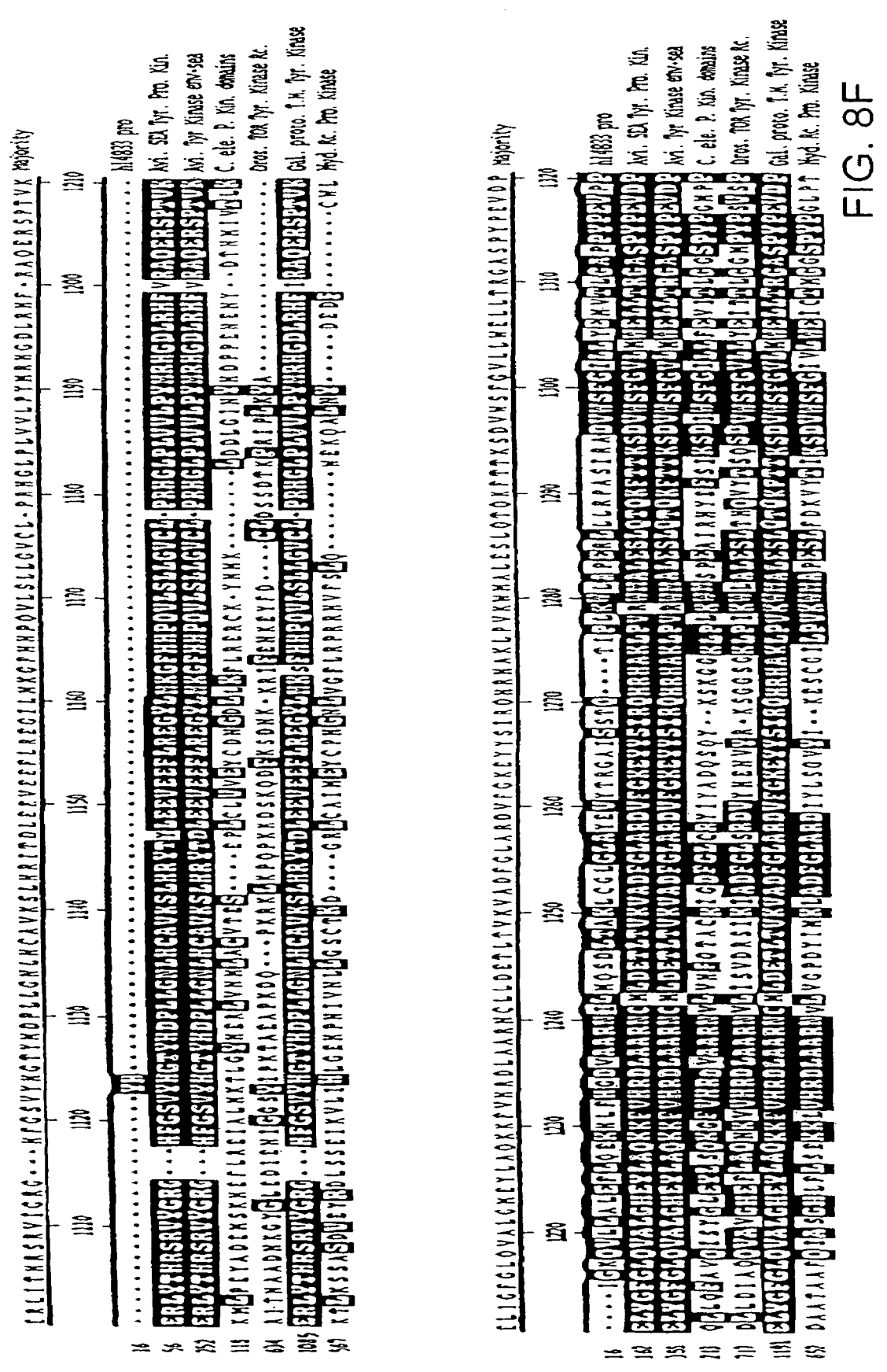
Figure 8G:
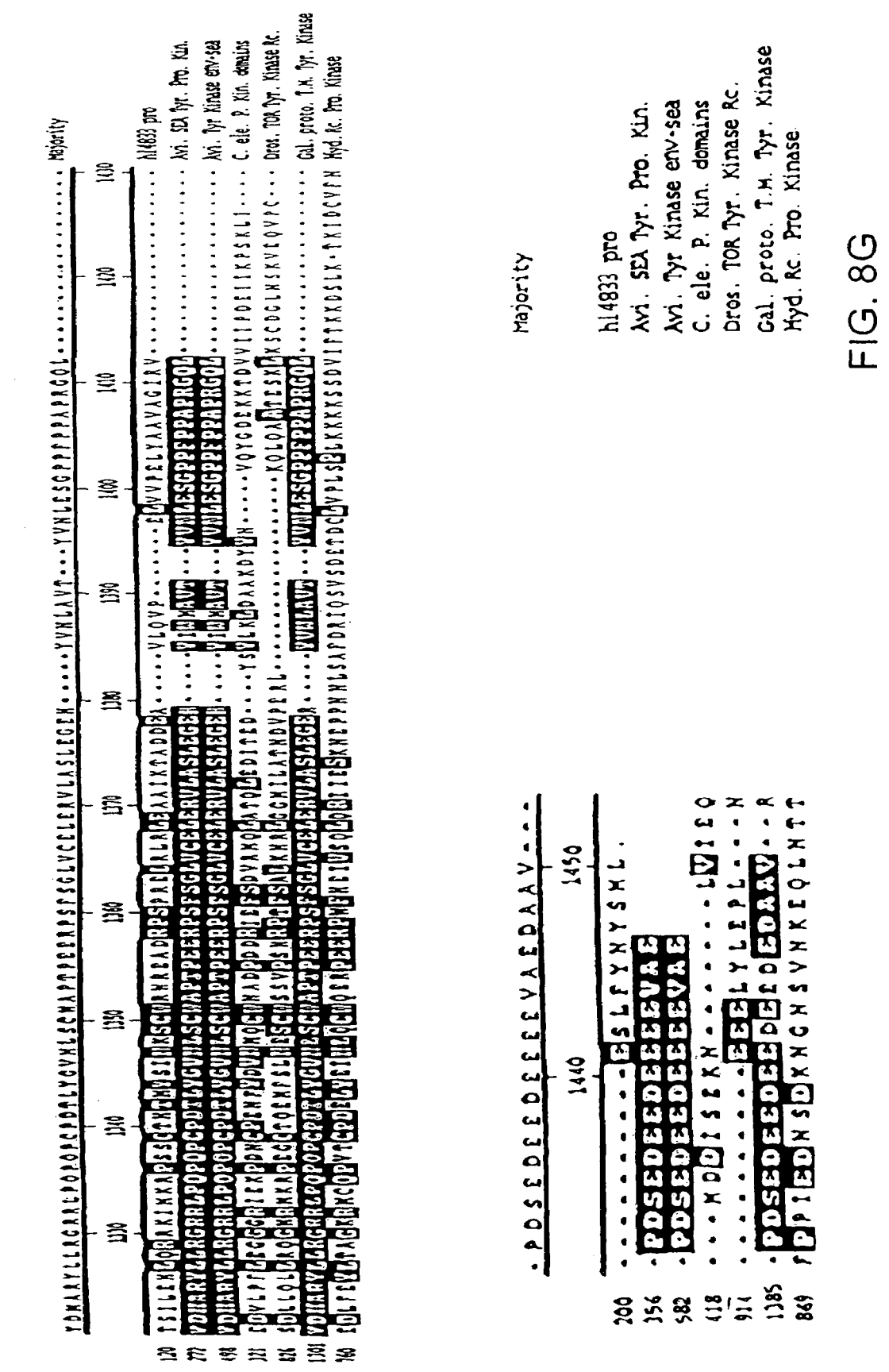

FIGS. 8A-8G show the amino acid sequence alignment for the protein (h14833; SEQ ID NO:6) encoded by human 14833 (SEQ ID NO:5) with the avian erythroblastosis virus (strain S13) sea tyrosine-protein kinase transforming protein (Avi. SEA Tyr. Pro. Kin.; SP Accession Number P23049; SEQ ID NO:20), the avian erythroblastosis virus env-sea polyprotein (Avi. Tyr. Kinase env-sea; NB Accession Number A33902; SEQ ID NO:21), the *Caenorhabditis elegans* protein containing similarity to protein kinase domains (C. ele. P. Kin. Domains; GenBank Accession Number AAC19211; SEQ ID NO:22), the putative fruit fly (*Drosophila melanogaster*) torso tyrosine-protein kinase receptor (Dros. TOR Tyr. Kinase Rc.; SP Accession Number P18475; SEQ ID NO:23), the c-sea chicken (*gallus gallus*) transmembrane protein-tyrosine kinase (Gal. Proto. T. M. Tyr. Kinase; GenBank Accession Number AAA48729; SEQ ID NO:24), and the *Hydra vulgaris* receptor protein-tyrosine kinase (Hyd. Rc. Pro. Kinase; GenBank Accession Number AAA65223; SEQ ID NO:25). The sequence alignment was generated using the Clustal method with PAM 250 residue weight table.

FIGS. 10A-10C provide the nucleotide (SEQ ID NO:7) and amino acid (SEQ ID NO:8) sequences for h15590.

Figure 11B:
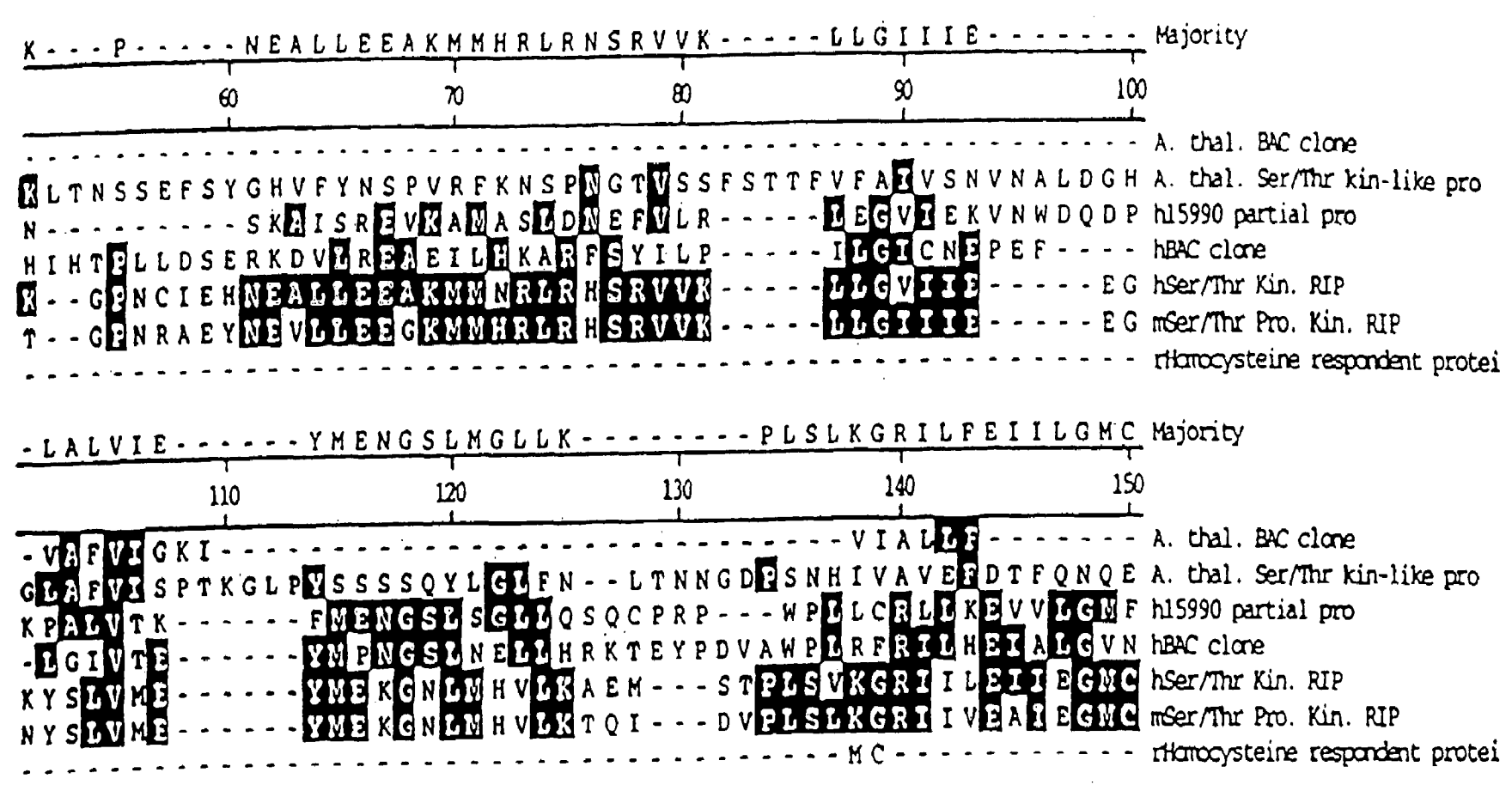
Figure 11C:
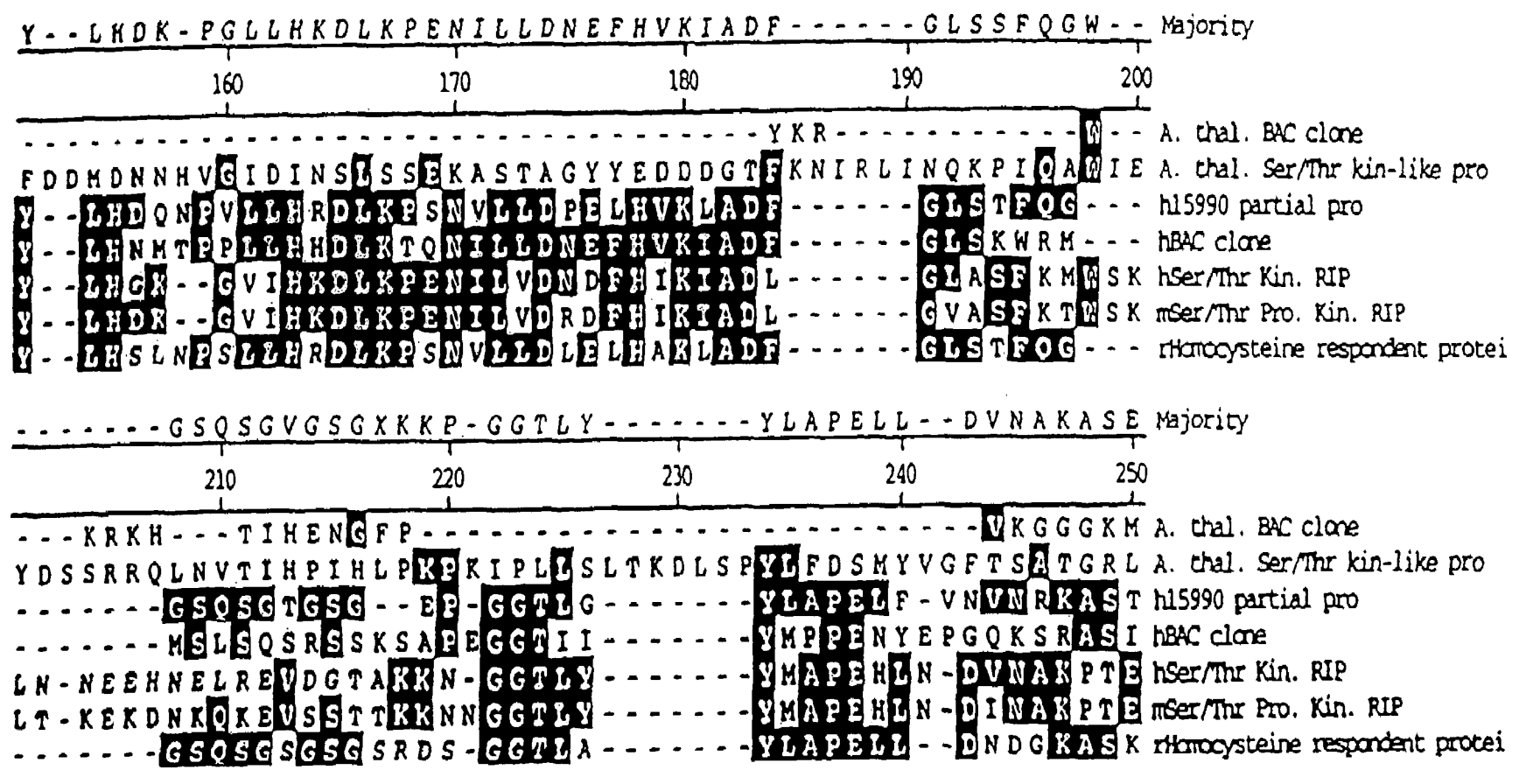
Figure 11D:
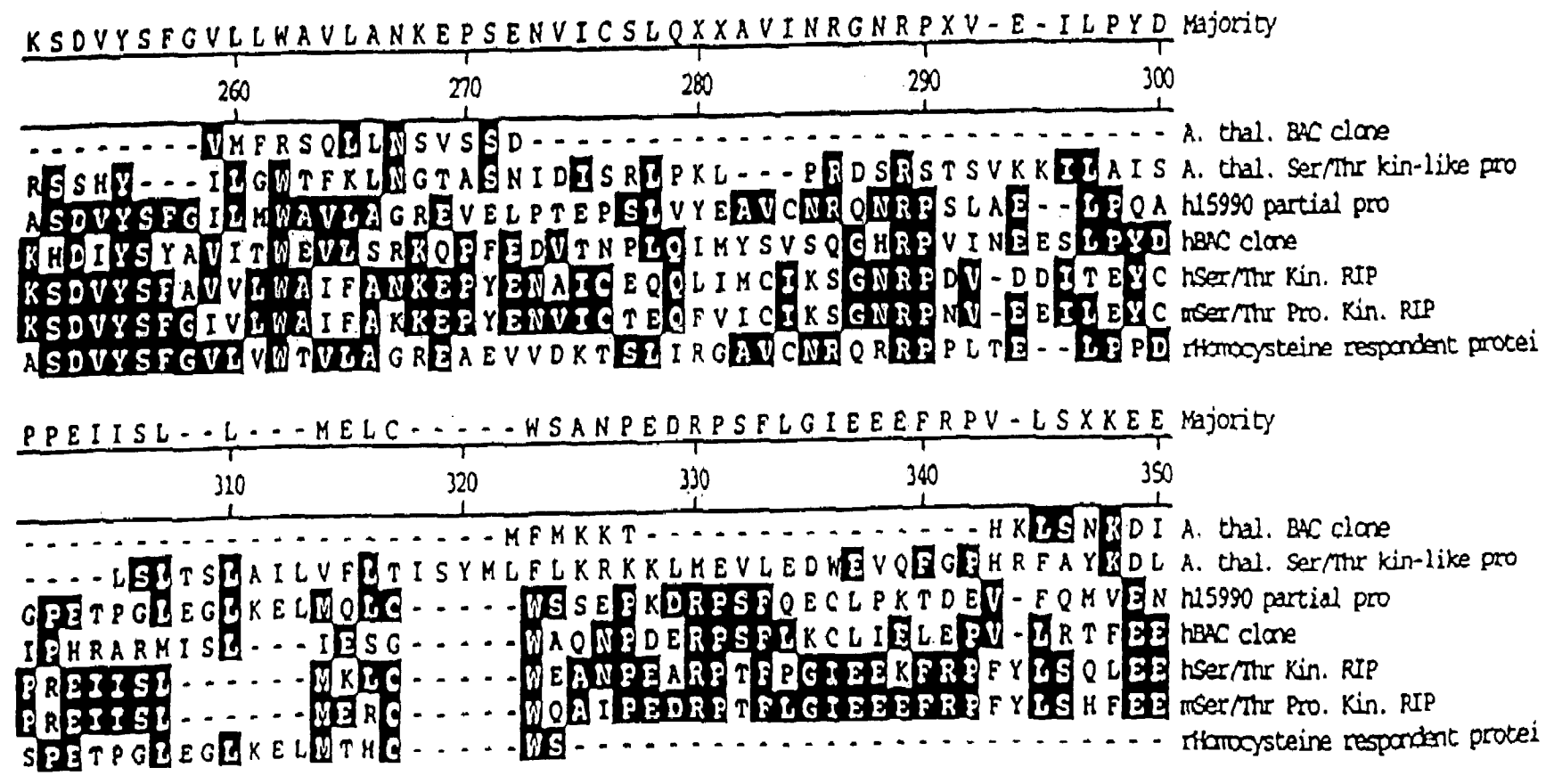
Figure 11E:
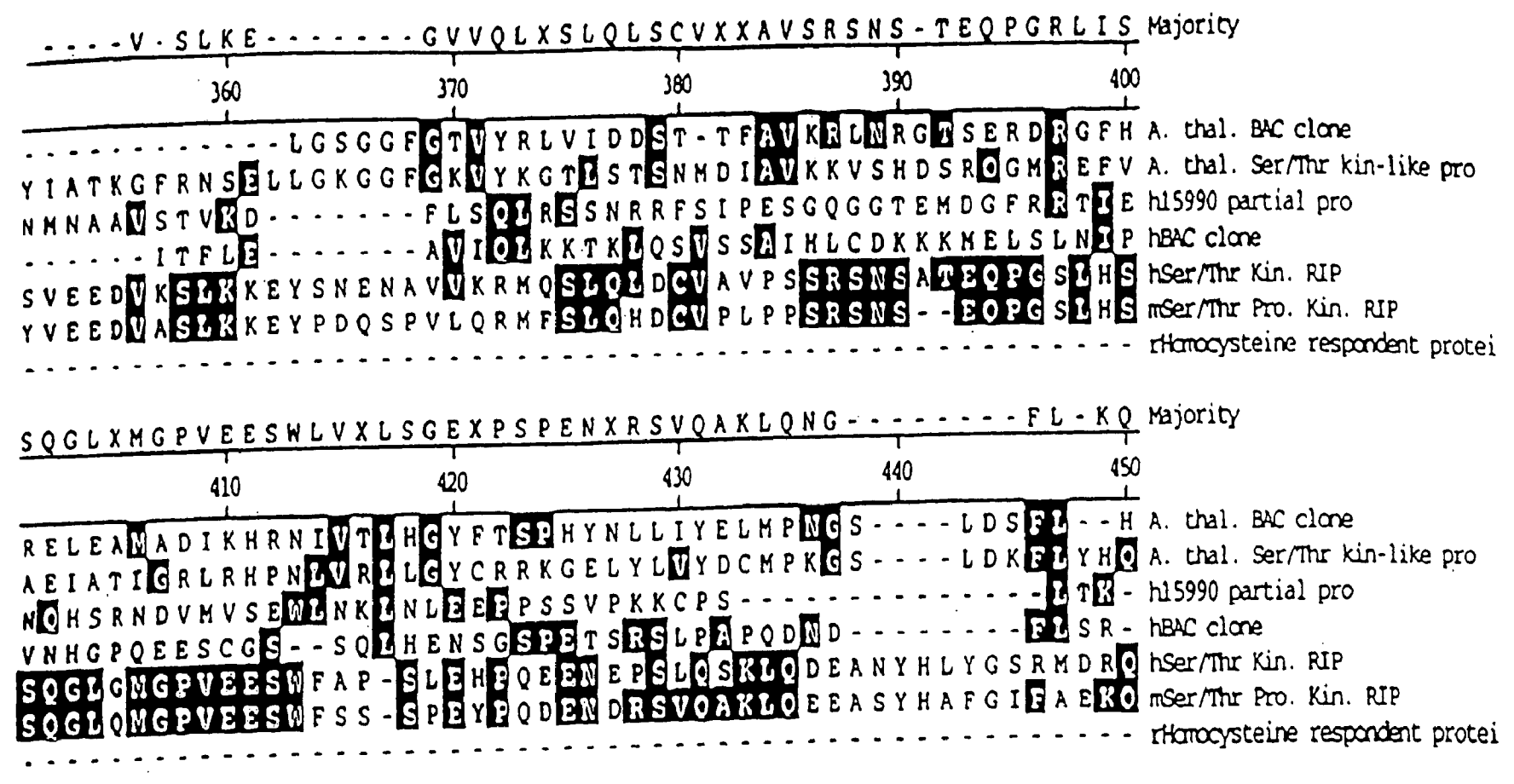
Figure 11F:
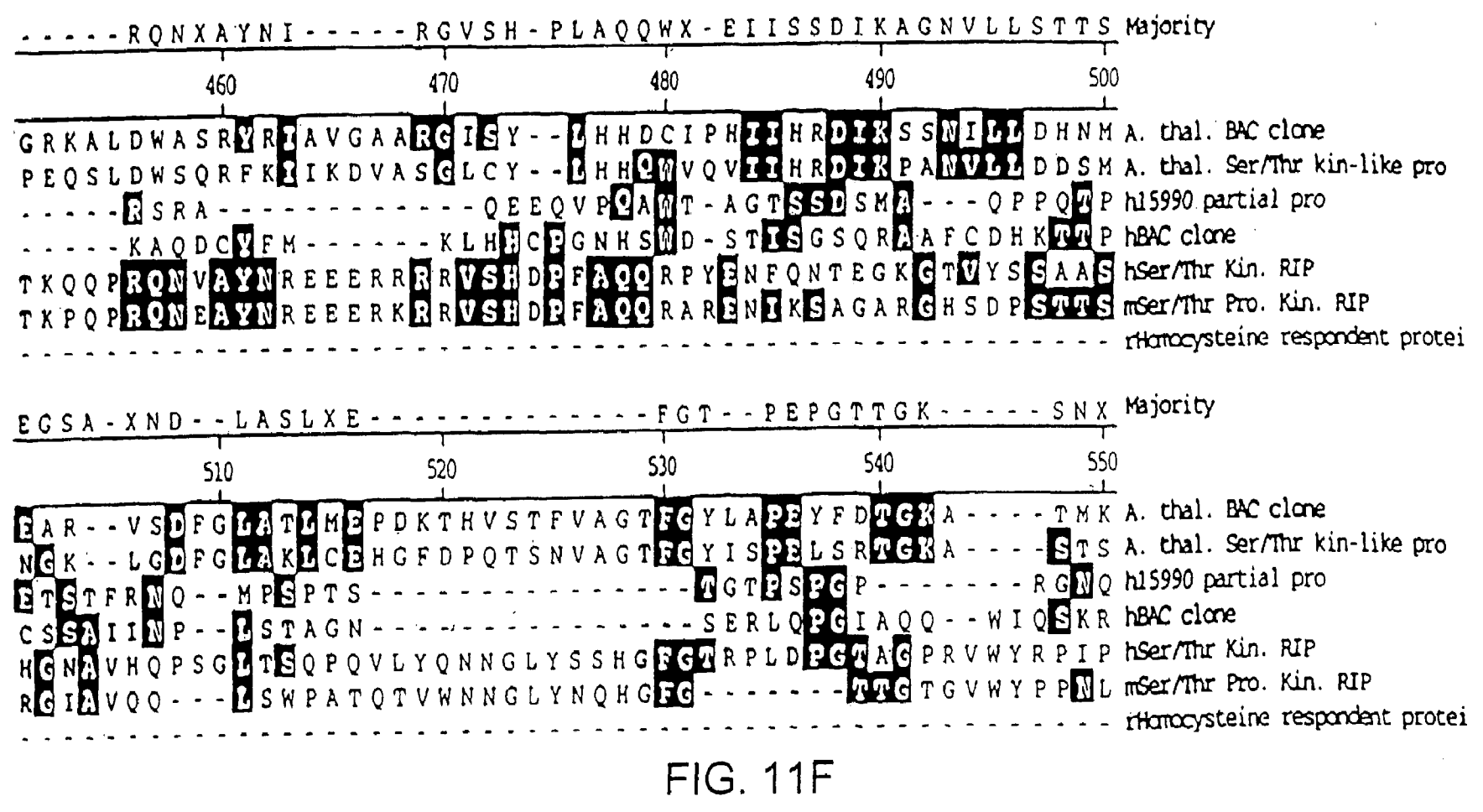
Figure 11G:
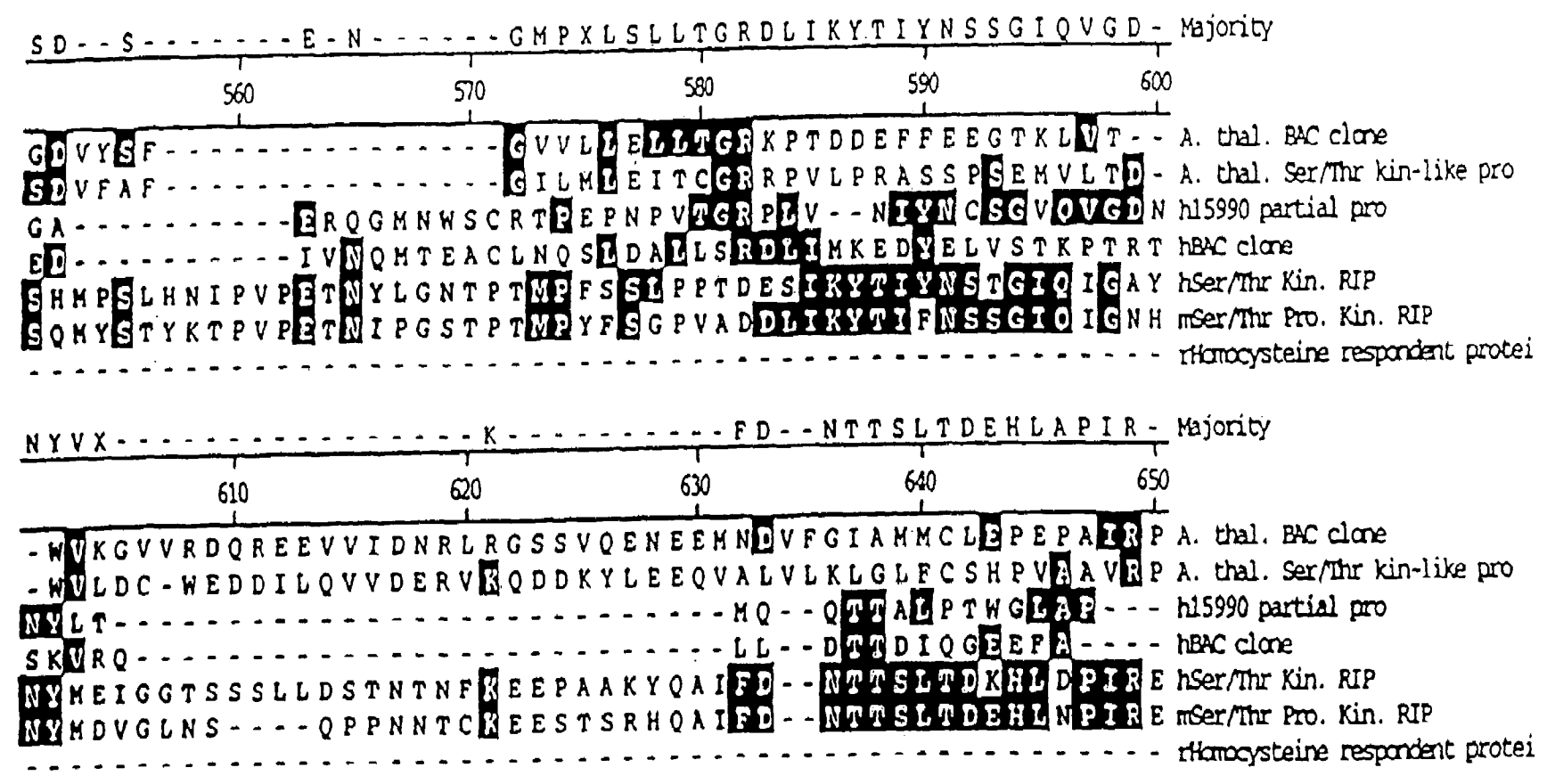

FIGS. 11A-11H show the amino acid sequence alignment for the protein (h15990; SEQ ID NO:8) encoded by human 15990 (SEQ ID NO:7) with the *Arabidopsis thaliana* putative protein kinase (A. thal. BAC clone; GenBank Accession Number AAD30583; SEQ ID NO:26), the *Arabidopsis thaliana* serine/threonine kinase-like protein (A. thal. Ser/Thr kin-like pro; EMB Accession Number CAB43919; SEQ ID NO:27), the human serine/threonine kinase RICK (hBAC clone; GenBank Accession Number AAC24561; SEQ ID NO:28), the human serine/threonine kinase receptor interacting protein (hSer/Thr Kin. RIP; SP Accession Number Q13546; SEQ ID NO:29), the murine serine/threonine kinase receptor interacting protein (mSer/Thr Pro. Kin. RIP; SP Accession Number Q60855; SEQ ID NO:30), and the *Rattus norvegicus* homocysteine respondent protein (GenBank Accession Number AAD02059; SEQ ID NO:31). The sequence alignment was generated using the Clustal method.

FIGS. 13A-13B provide the nucleotide (SEQ ID NO:9) and amino acid (SEQ ID NO: 10) sequences for h15993.

FIG. 16 provides the nucleotide (SEQ ID NO:11) and amino acid (SEQ ID NO: 12) sequences for h16341.

Figure 17C:
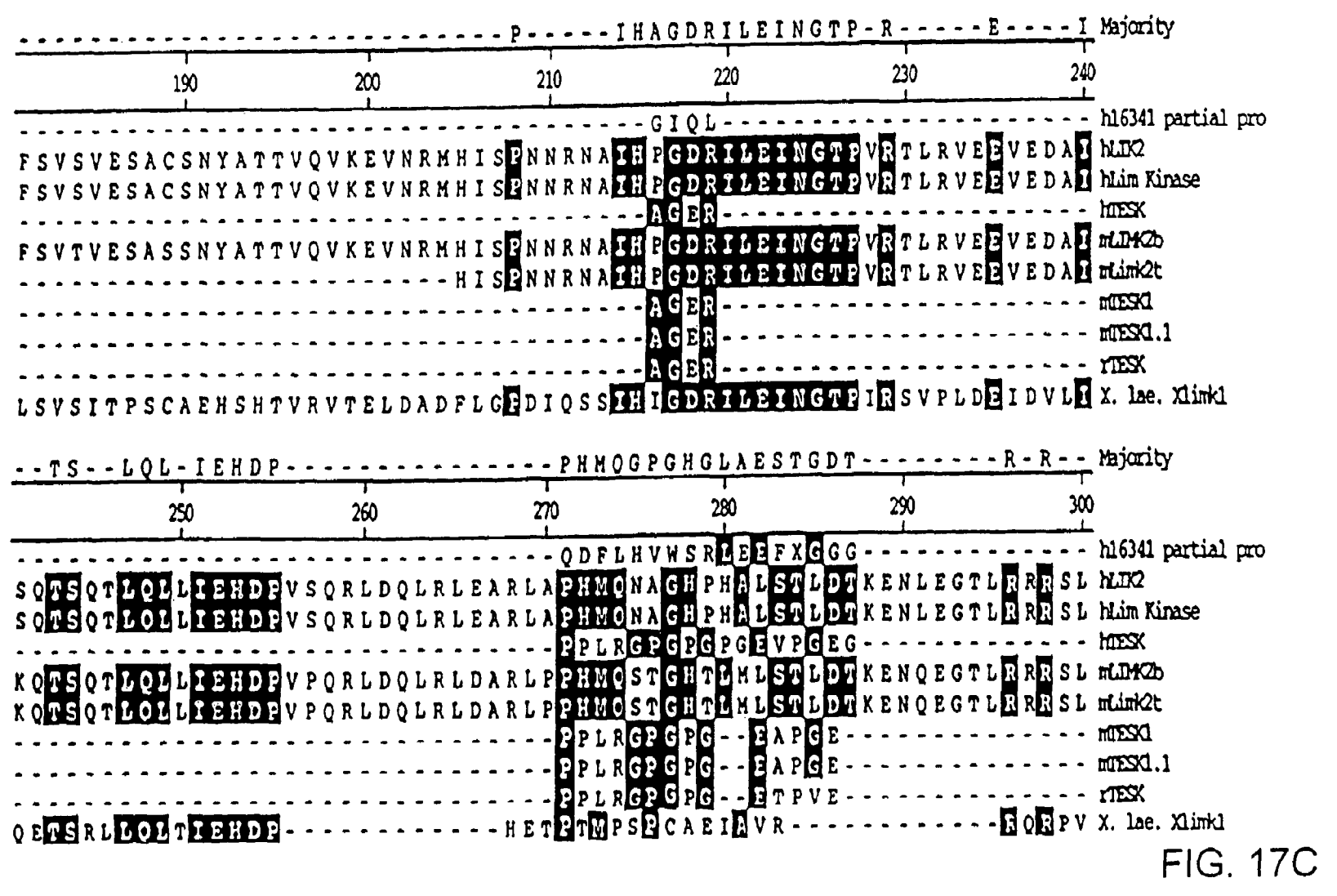
Figure 17D:
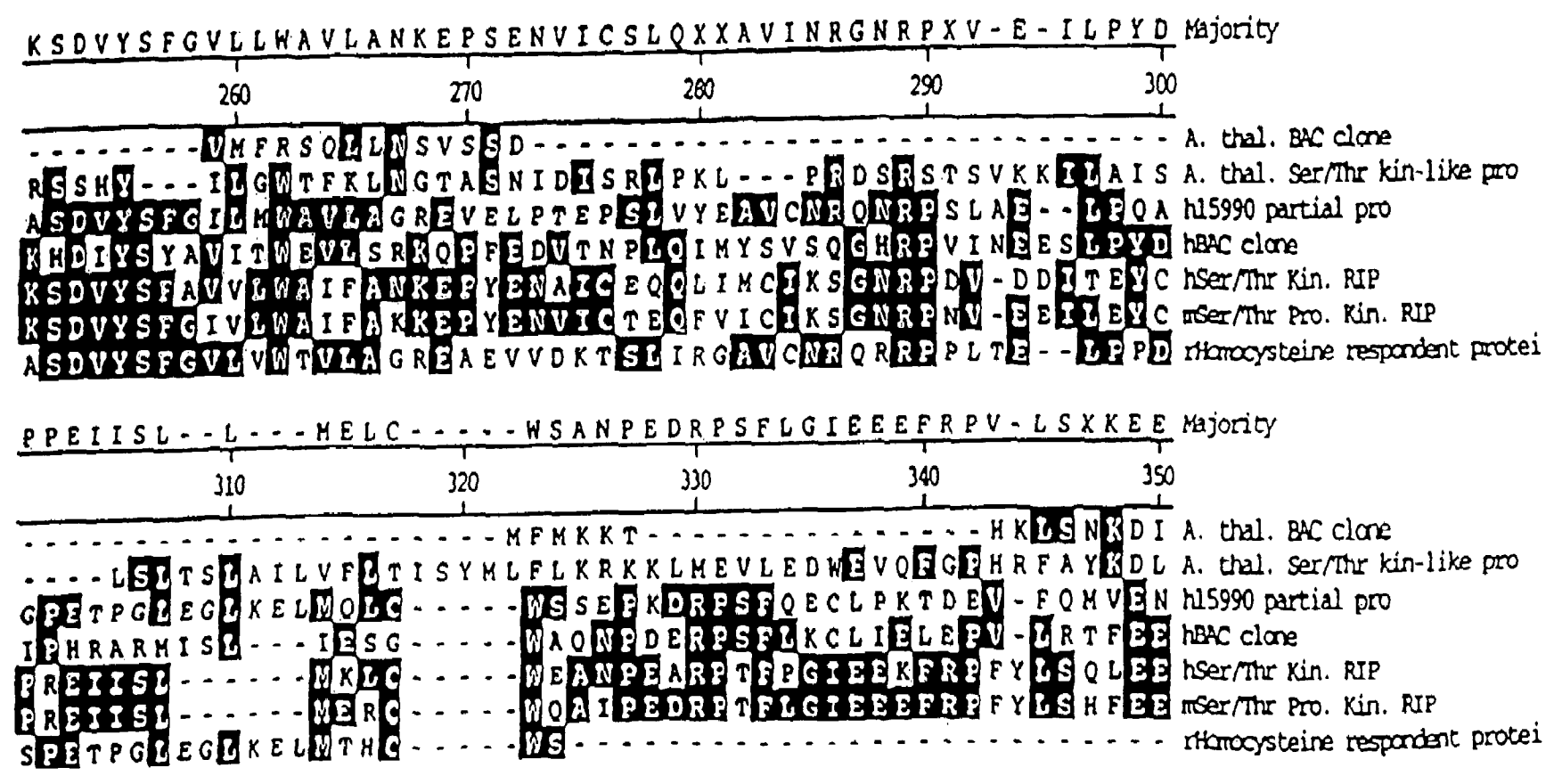
Figure 17E:
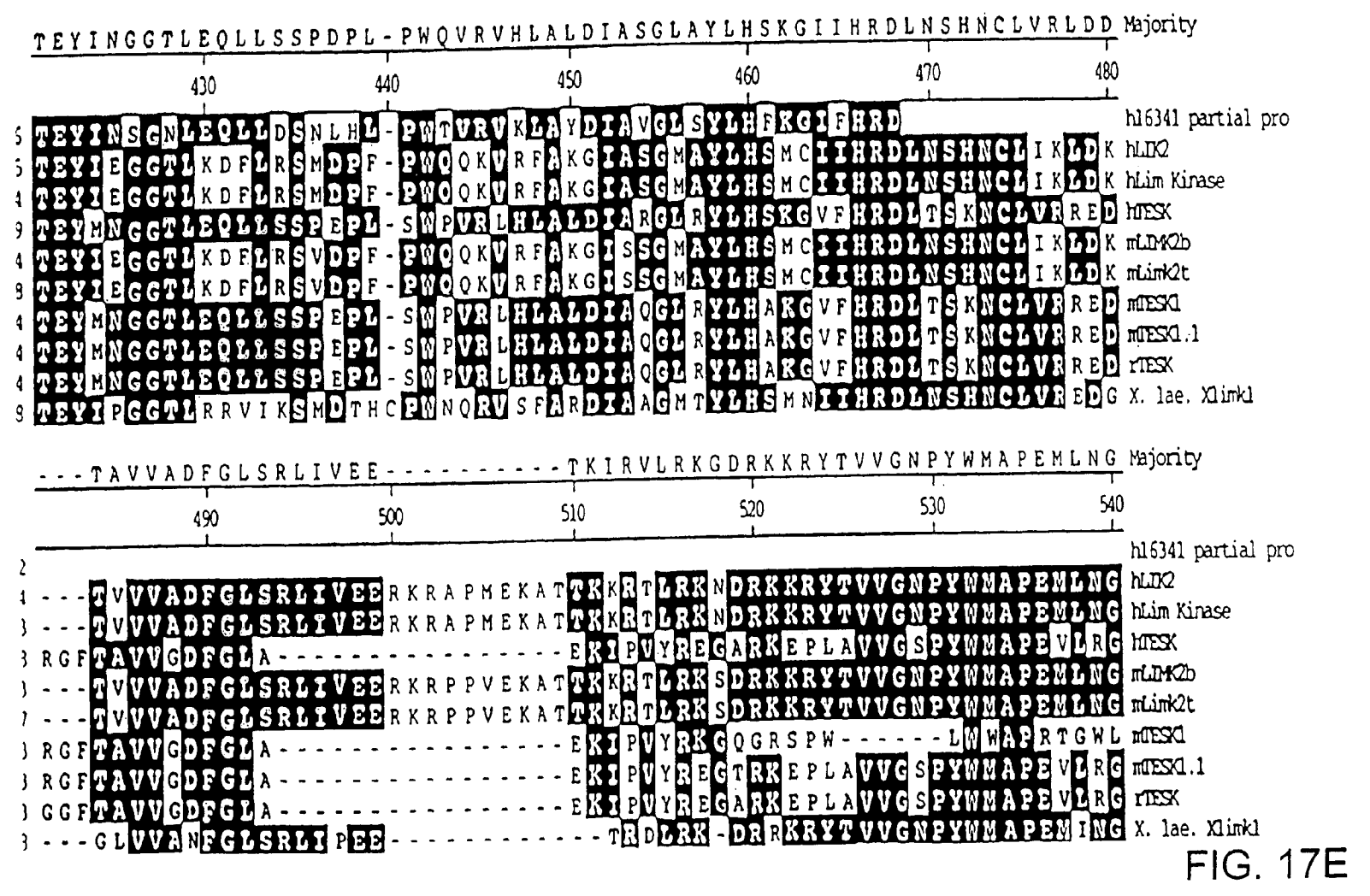
Figure 17F:
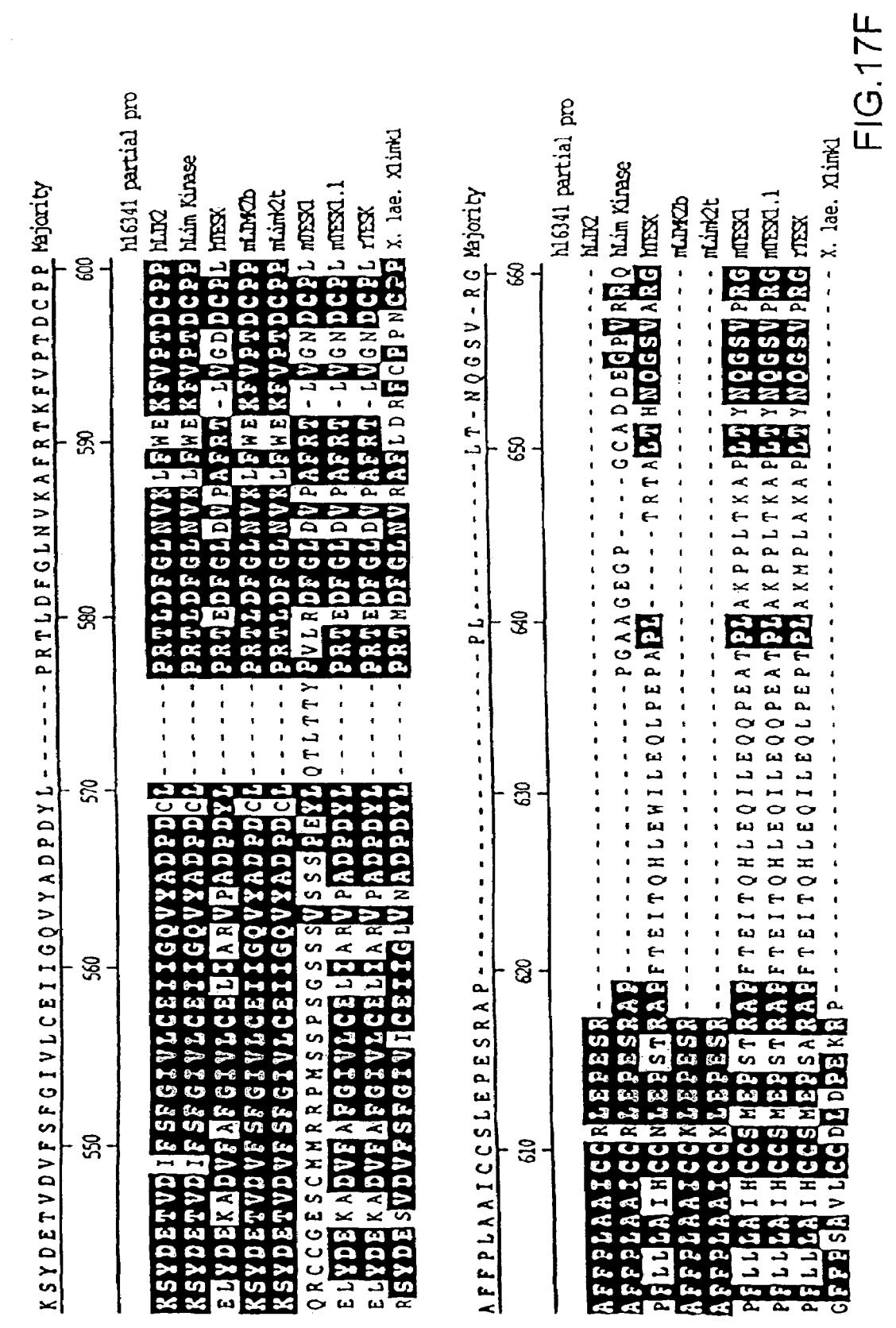
Figure 17G:
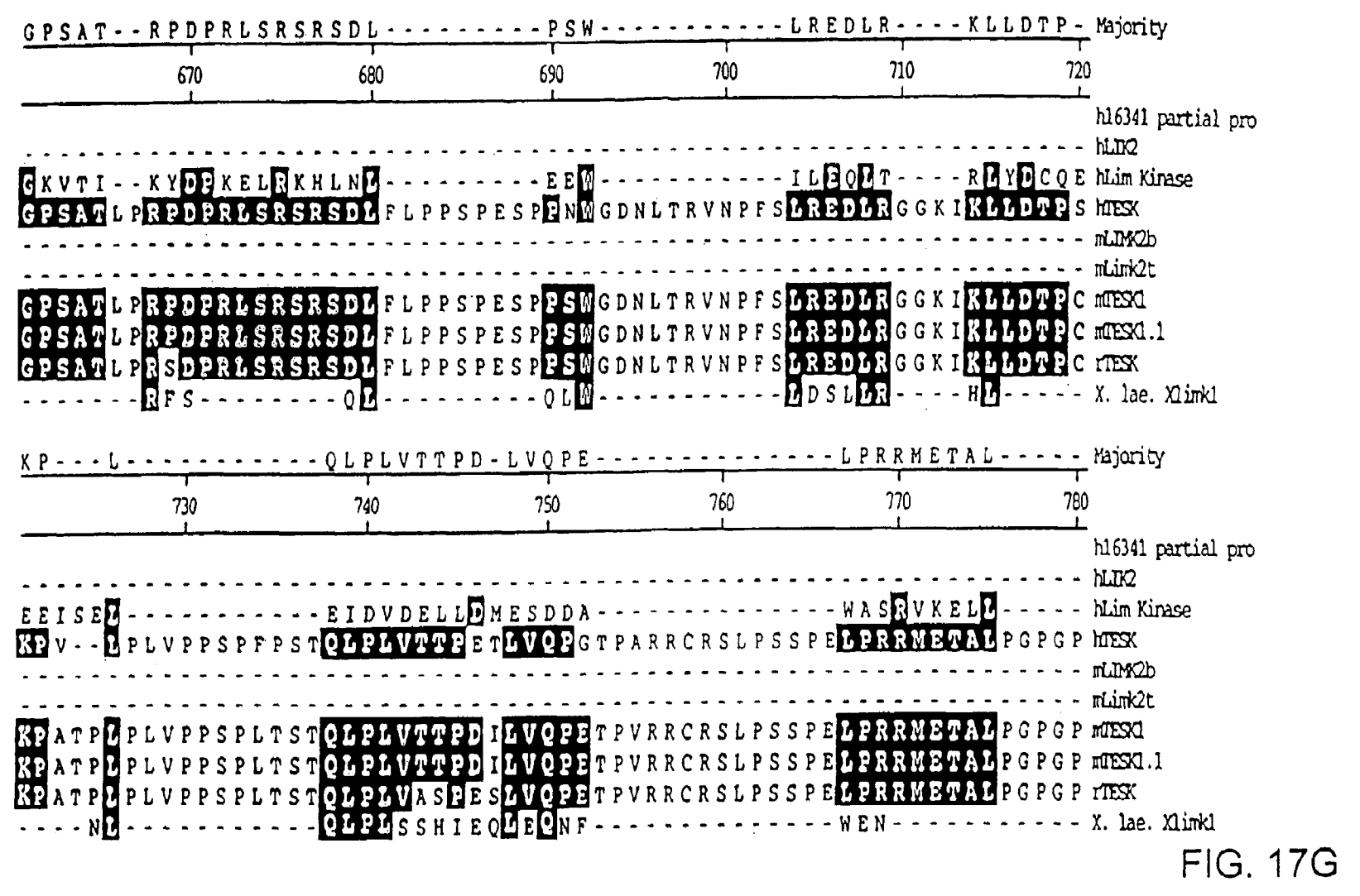
Figure 17H:
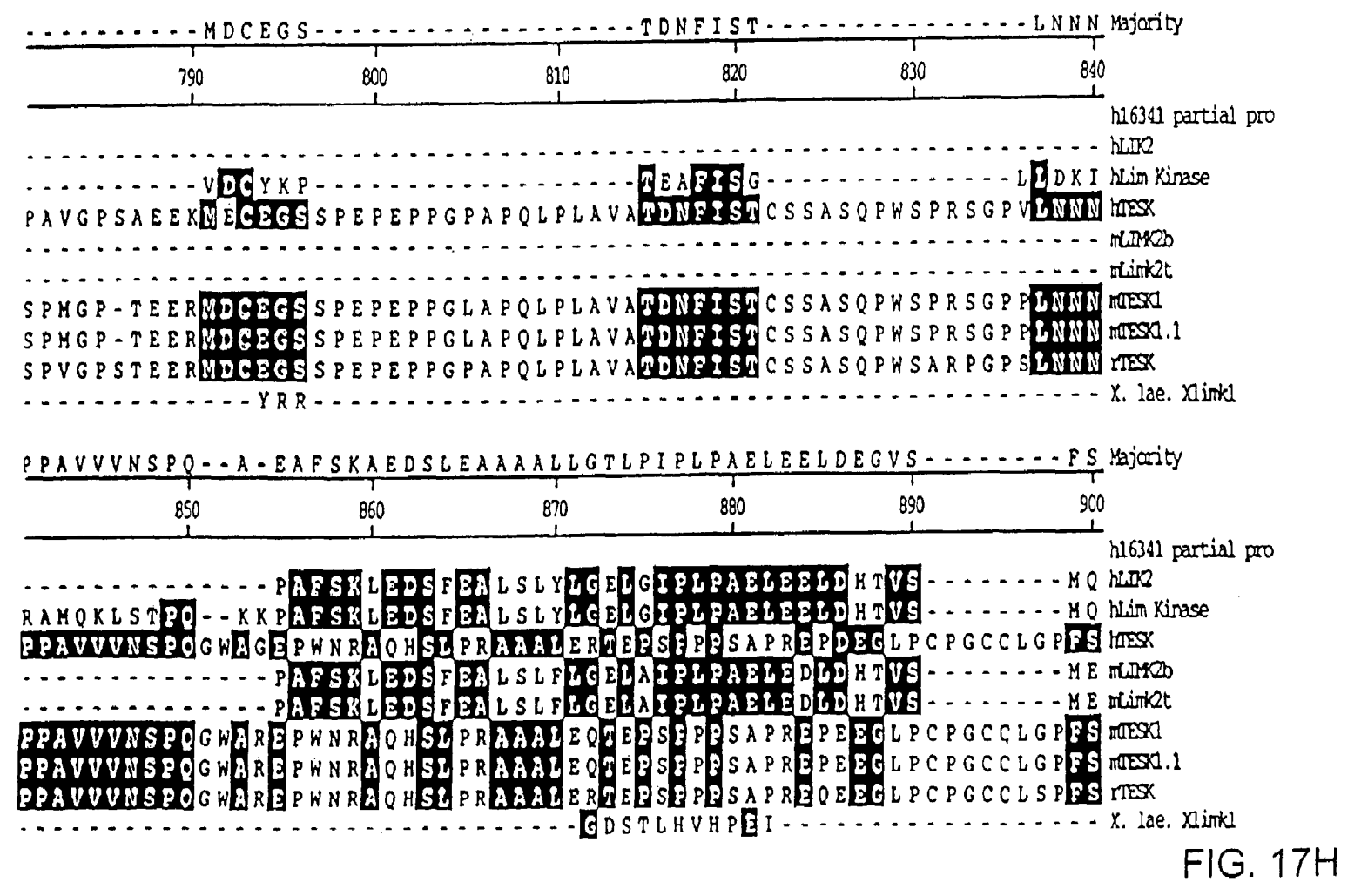

FIGS. 17A-17I show the amino acid sequence alignment for the protein (h16341; SEQ ID NO: 12) encoded by human 16341 (SEQ ID NO:11) with the human lim domain kinase 2 (hLIK2; SP accession Number P53671; SEQ ID NO:41), the human lim kinase (hLim Kinase; GenBank Accession Number AAB54055; SEQ ID NO:42), the human testis-specific protein kinase 1 (hTESK; SP accession Number Q15569; SEQ ID NO:43), the murine lim kinase 2b (mLIMK2b; DBJ Accession Number BAA24489; SEQ ID NO:44), the murine testis-specific lim-kinase 2 (mLimk2t; DBJ Accession Number BAA31147; SEQ ID NO:45), the murine testis-specific protein kinase 1 (mTESK1; DBJ Accession Number BAA25124; SEQ ID NO:46), and mTESK1.1; DBJ Accession Number BAA25125; SEQ ID NO:47), the *R. norvegicus* testis-specific protein kinase 1 (rTESK; SP Accession Number Q63572; SEQ ID NO:48), and *Xenopus laevis* LIM motif-containing protein kinase, Xlimk1 (S. lae. Xlimk1; DBJ Accession Number BAA21488; SEQ ID NO:49). The sequence alignment was generated using the Clustal method.

FIGS. 19A-19D provide the nucleotide (SEQ ID NO:13) and amino acid (SEQ ID NO:14) sequences for h2252.

Figure 20B:
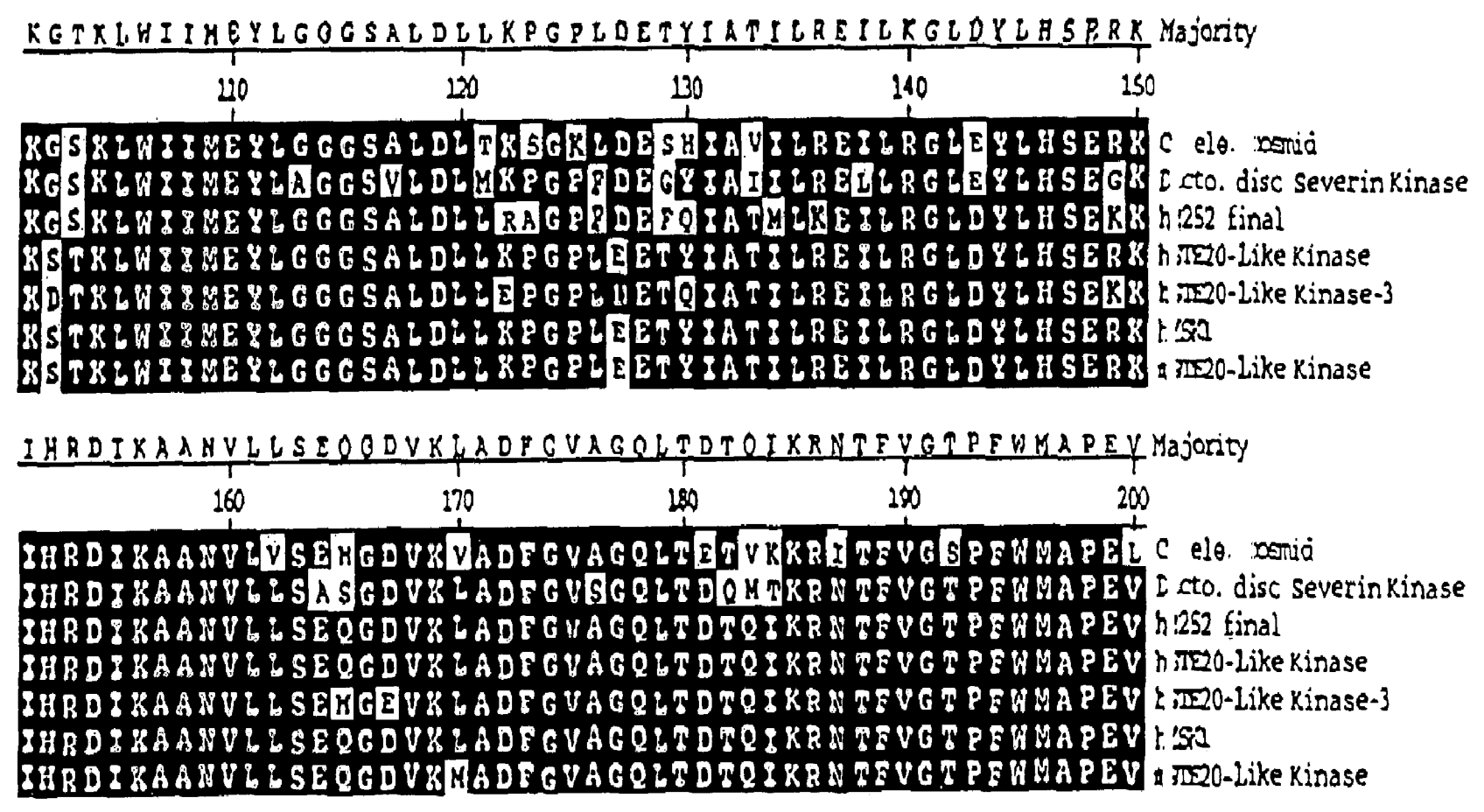
Figure 20C:
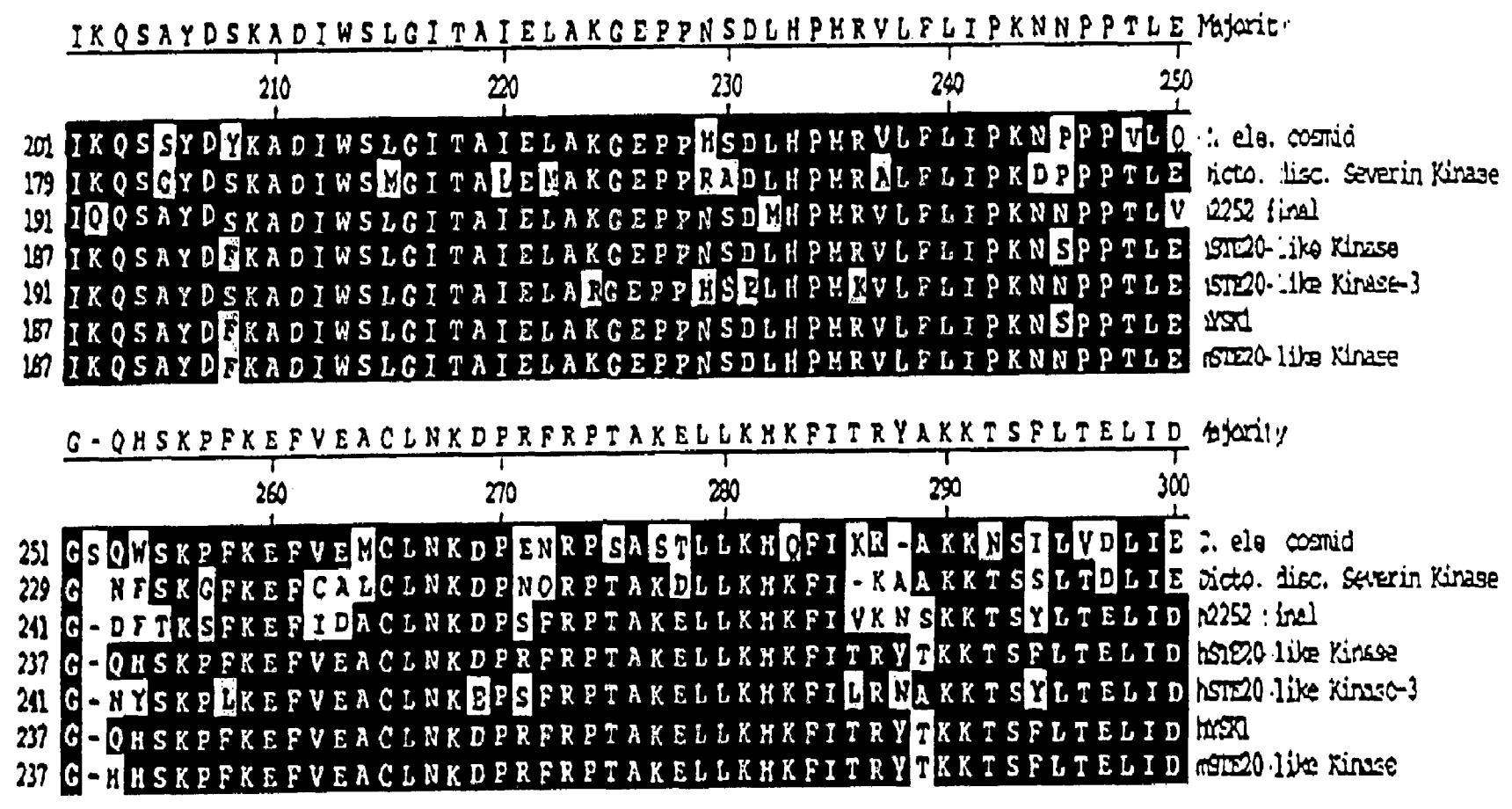
Figure 20D:
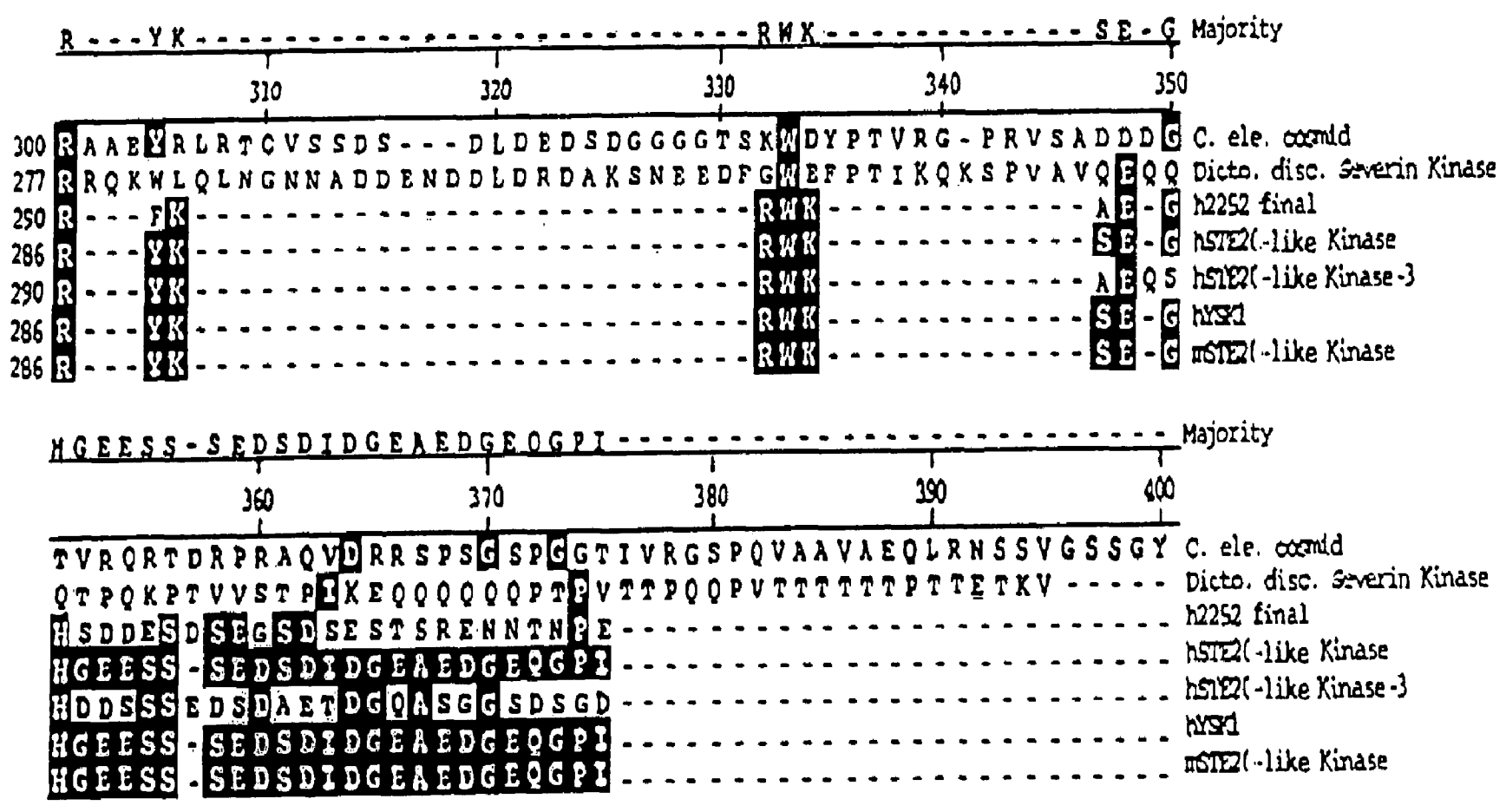
Figure 20E:
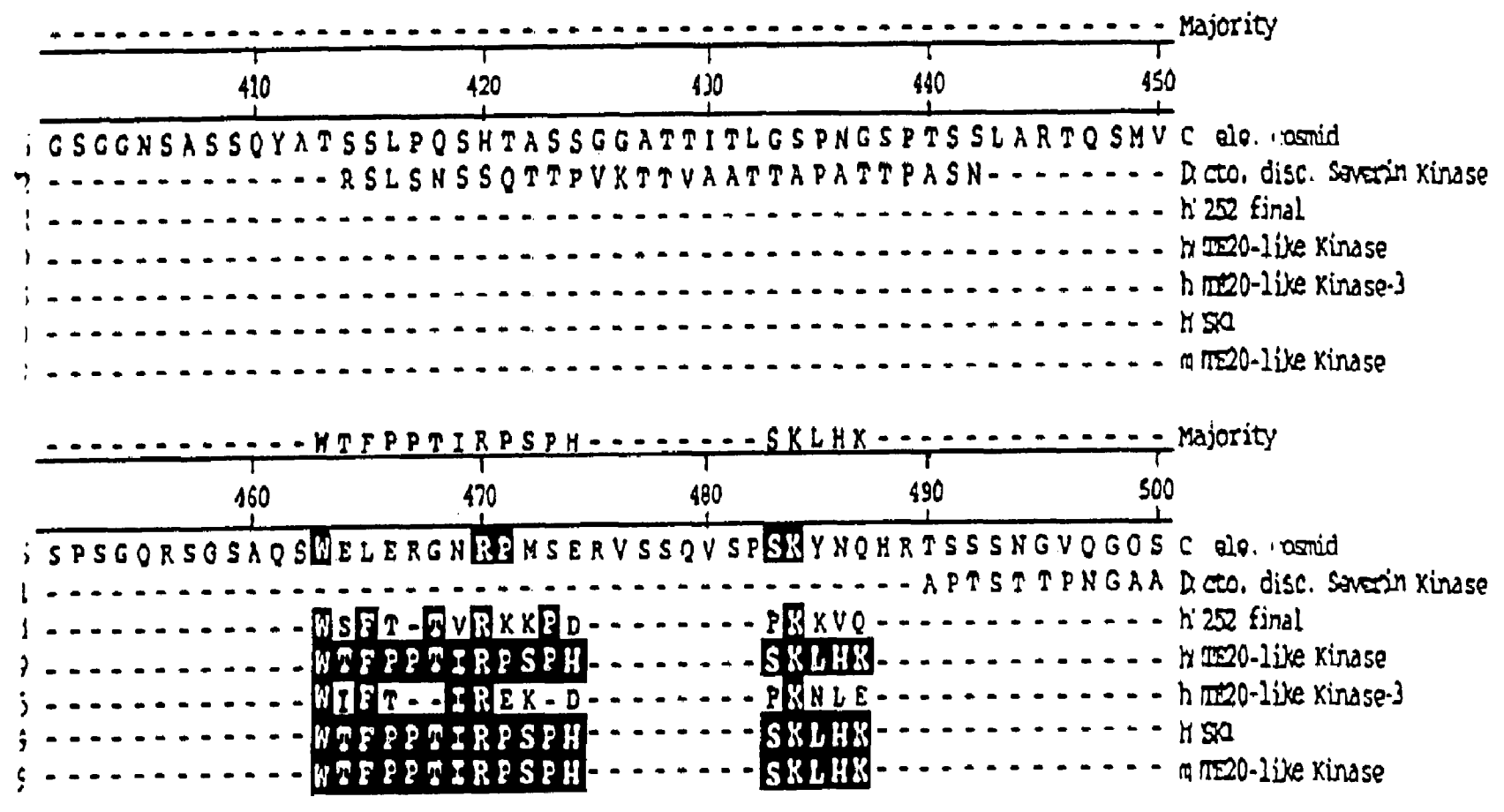
Figure 20F:
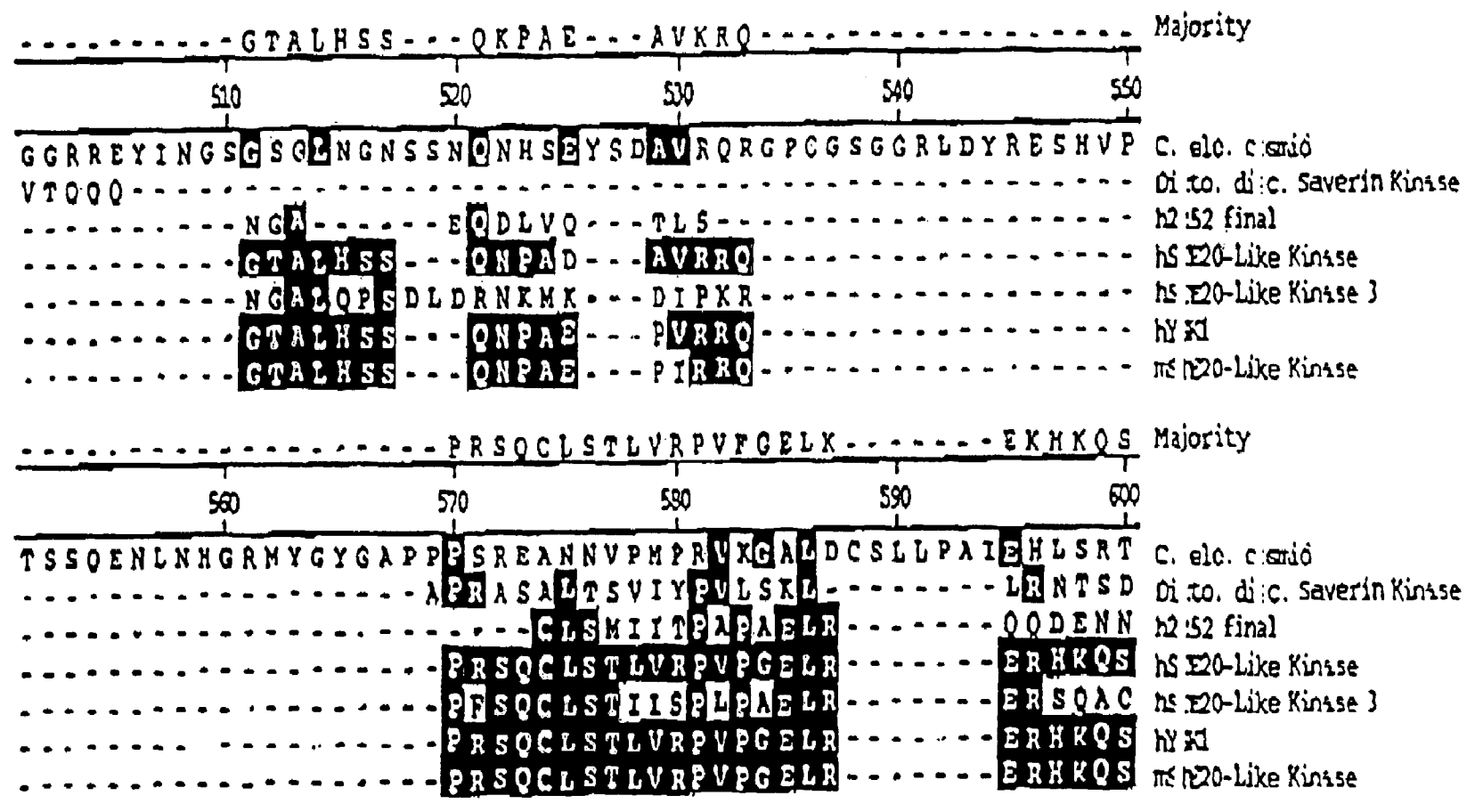
Figure 20G:
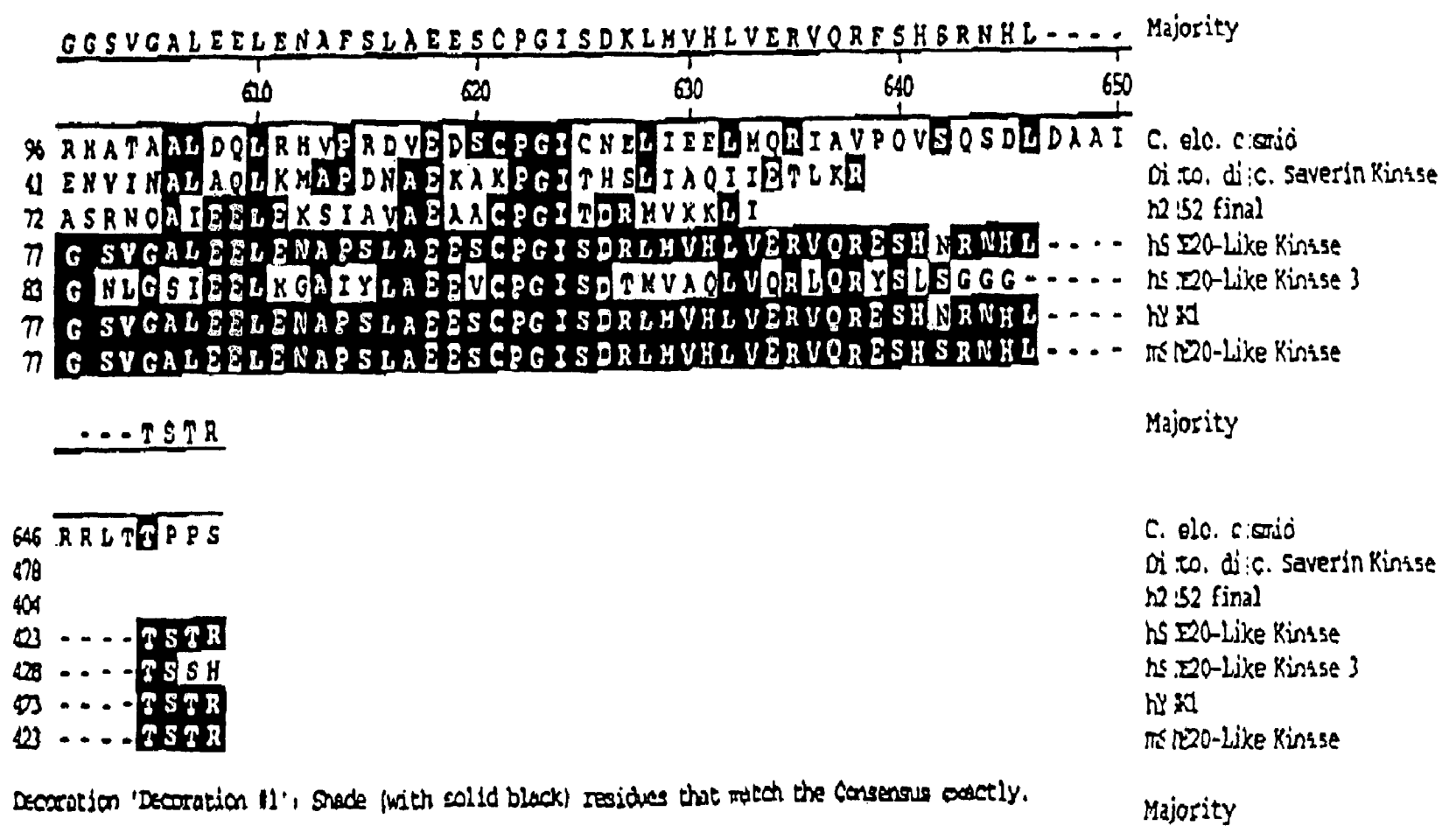

FIGS. 20A-20G show the amino acid sequence alignment for the protein (h2252; SEQ ID NO:14) encoded by human 2252 (SEQ ID NO:13) with the *C. elegans* serine/threonine kinase (C. ele. cosmid, GenBank Accession Number AAC69038; SEQ ID NO:50), the *Dictyostelium discoideum* severin kinase (Disto. Disc. Severin Kinase., GenBank Accession Number AAC24522; SEQ ID NO: 51), the human Ste20-like kinase (hSTE20-like Kinase; EMB Accession Number CAA67700; SEQ ID NO:52), the human Ste20-like kinase 3 (hSTE20-like Kinase-3; GenBank Accession Number AAB82560; SEQ ID NO:53), the human YSK1 protein (hYSK1, DBJ Accession Number BAA20420; SEQ ID NO:54) and the mouse Ste20-like kinase (mSTE20-like Kinase; GenBank Accession Number AAD01208; SEQ ID NO:55).

DETAILED DESCRIPTION OF THE INVENTION

Figure 2A:
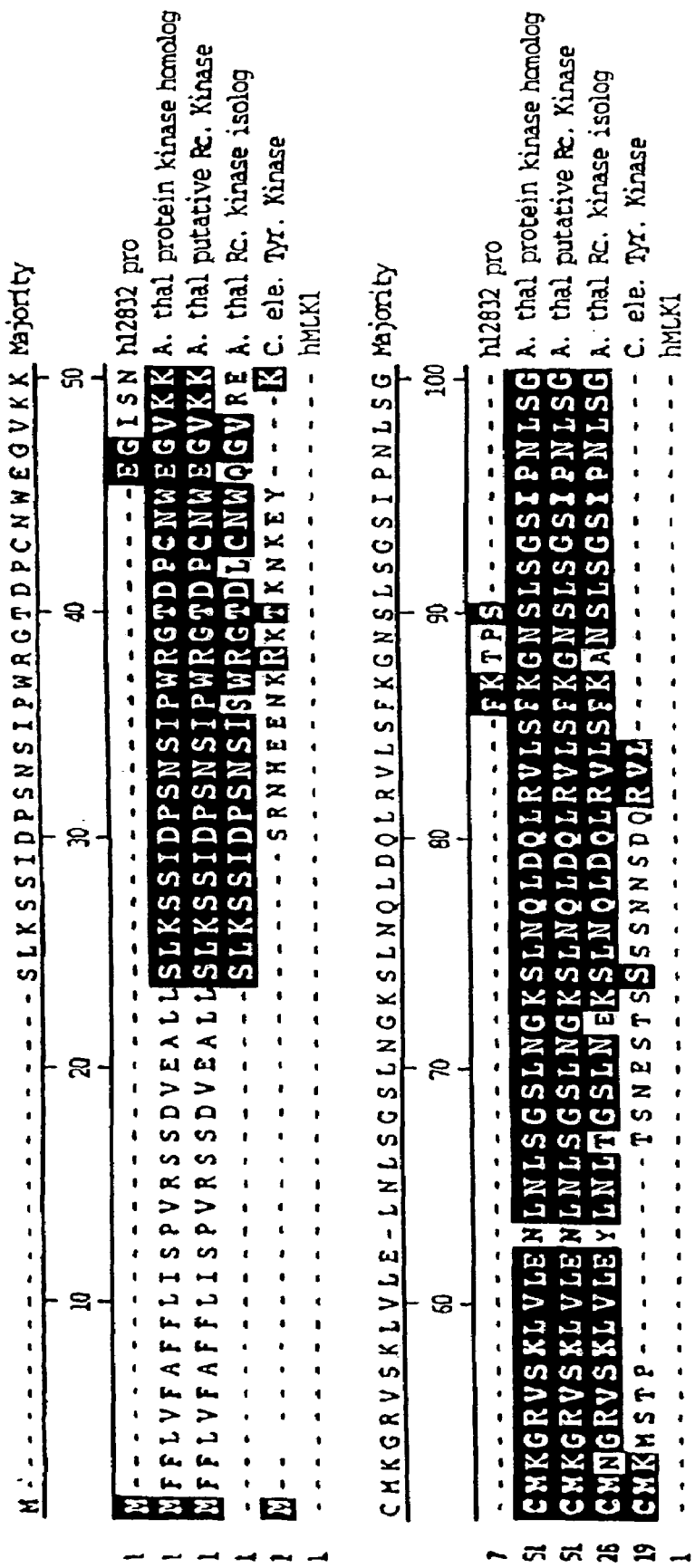

The present invention is based, at least in part, on the discovery of novel molecules, referred to herein as "kinase" nucleic acid and polypeptide molecules, which play a role in, or function in, signaling pathways associated with cellular growth and/or cellular metabolic pathways. These growth and metabolic pathways are described in Lodish et al. (1995) *Molecular Cell Biology* (Scientific American Books Inc., New York, N.Y.) and Stryer *Biochemistry*, (W. H. Freeman, New York), the contents of which are incorporated herein by reference. In one embodiment, the kinase molecules modulate the activity of one or more proteins involved in cellular growth or differentiation, e.g., cardiac, epithelial, or neuronal cell growth or differentiation. In another embodiment, the kinase molecules of the present invention are capable of modulating the phosphorylation state of a kinase molecule or the phosphorylation state of one or more proteins involved in cellular growth or differentiation, e.g., cardiac, epithelial, or neuronal cell growth or differentiation, as described in, for example, Lodish et al. and Stryer, supra. In addition, kinases of the present invention are targets of drugs described in Goodman and Gilman (1996), *The Pharmacological Basis of Therapeutics* ($9^{th}$ ed.) Hartman & Limbard Editors, the contents of which are incorporated herein by reference. Particularly, the kinases of the invention may modulate phosphorylation in tissues and cells including lymph node, spleen, thymus, brain, lung, skeletal muscle, fetal liver, tonsil, colon, heart, liver, immune cells, including T cells, Th1 and Th2 cells, leukocytes, blood marrow, etc.

As used herein, the term "kinase" includes a protein, polypeptide, or other non-proteinaceous molecule that is capable of modulating its own phosphorylation state or the phosphorylation state of a different protein, polypeptide, or other non-proteinaceous molecule. Kinases can have a specificity for (i.e., a specificity to phosphorylate) serine/threonine residues, tyrosine residues, or both serine/threonine and tyrosine residues, e.g., the dual-specificity kinases. As referred to herein, kinases such as protein kinases preferably include a catalytic domain of about 200-400 amino acid residues in length, preferably about 200-300 amino acid residues in length, or more preferably about 250-300 amino acid residues in length, which includes preferably 5-20, more preferably 5-15, or most preferably 11 highly conserved motifs or subdomains separated by sequences of amino acids with reduced or minimal conservation. Specificity of a kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52, the contents of which are incorporated herein by reference). These subdomains are also described in further detail herein.

Kinases play a role in signaling pathways associated with cellular growth. For example, protein kinases are involved in the regulation of signal transmission from cellular receptors, e.g., growth-factor receptors, entry of cells into mitosis, and the regulation of cytoskeleton function, e.g., actin bundling.

Assays for measuring Kinase activity are well known in the art depending on the particular kinase. Specific assay protocols are available in standard sources known to the ordinarily skilled artisan. For example, see "Kinases" in Ausueel et al., eds. (1994-1998) *Current Protocols in Molecular Biology* (3) and references cited therein.

Inhibition or over stimulation of the activity of kinases involved in signaling pathways associated with cellular growth can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma. Disorders associated with the following cells or tissues are also encompassed: lymph node, spleen, thymus, brain, lung, skeletal muscle, fetal liver, tonsil, colon, heart, liver, immune cells, including T cells, Th1 and Th2 cells, leukocytes, blood marrow, etc. The compositions are also useful for the treatment of liver fibrosis and other liver-related disorders.

The disclosed invention relates to methods and compositions for the modulation, diagnosis, and treatment of immune, inflammatory, respiratory, and hematological disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Hematologic disorders include but are not limited to anemias including sickle cell and hemolytic anemia, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VIII and IX deficiencies, hemarthrosis, hematemesis, hematomas, hematuria, hemochromatosis, hemoglobinuria, hemolytic-uremic syndrome, thrombocytopenias including HIV-associated thrombocytopenia, hemorrhagic telangiectasia, idiopathic thrombocytopenic purpura, thrombotic microangiopathy, hemosiderosis.

The present invention is based, at least in part, on the discovery of novel molecules, referred to herein as kinase protein and nucleic acid molecules, that comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features kinase nucleic acid molecules, preferably human kinase molecules, that were identified based on a consensus motif or protein domain characteristic of a kinase family of proteins. Specifically, seven novel human genes, termed clones h12832, h14138 (partial-length), h14833, h15990 (partial length), 15993 (partial length), h16341 (partial length), and h2252, are provided. Such sequences are referred to as "kinase" sequences indicating that the genes and the partial gene sequences share sequence similarity with kinase genes. The kinases of the invention fall within the eukaryotic protein kinase family.

A. The Eukaryotic Protein Kinase Nucleic Acid and Polypeptide Molecules

In one embodiment, the isolated nucleic acid molecules of the present invention encode eukaryotic protein kinase polypeptides. Eukaryotic protein kinases (described in, for example, Hanks et al. (1995) *FASEB J.* 9:576-596) are enzymes that belong to an extensive family of proteins that share a conserved catalytic core common to both serine/threonine and tyrosine protein kinases. There are a number of conserved regions in the catalytic domain of protein kinases. One of these regions, located in the N-terminal extremity of the catalytic domain, is a glycine-rich stretch of residues in the vicinity of a lysine residue, which has been shown to be involved in ATP binding. Another region, located in the central part of the catalytic domain, contains a conserved aspartic acid residue which is important for the catalytic activity of the enzyme (Knighton et al. (1991) *Science* 253:407-414). Two signature patterns have been described for this region: one specific for serine/threonine kinases and one for tyrosine kinases.

Eukaryotic protein kinase polypeptides of the present invention preferably include one of the following consensus sequences:

```
                                         (SEQ ID NO:83)
[LIV]-G-{P}-G-{P}-[FYWMGSTNH]-[SGA]-{PW}-[LIVCAT]-

{PD}-x-[GSTACLIVMFY]-x(5,18)-[LIVMFYWCSTAR]-

[AIVP]-[LLLVMFAGCKR]-K[K binds ATP]

(SEQ ID NO:84)
[LIVMFYC]-x-[HY]-x-D-[LIVMFY]-K-x(2)-N-[LIVMIFYCT]

(3)

[D is an active site residue]

(SEQ ID NO:85)
[LIVMFYC]-x-[HY]-x-D-[LIYMFY]-[RSTAC]-x(2)-N-

[LIVMFYC](3)

[D is an active site residue]
```

B. The Adenylate Kinase Nucleic Acid and Polypeptide Molecules

In one embodiment, the isolated nucleic acid molecules of the present invention encode adenylate kinase polypeptides. Adenylate kinase (AK) (described in Schulz (1987) *Cold Spring Harbor Symp. Quant. Biol.* 52:429-439) is a monomeric enzyme that catalyzes the reversible transfer of MgATP to AMP (MgATP+AMP=MgADP+ADP).

In mammals there are three different isozymes: AK1 (or myokinase), which is cytosolic; AK2, which is located in the outer compartment of mitochondria; and AK3 (or GTP:AMP phosphotransferase), which is located in the mitochondrial matrix and which uses MgGTP instead of MgATP.

Several regions of AK family enzymes are well conserved, including the ATP-binding domains. This region includes an aspartic acid residue that is part of the catalytic cleft of the enzyme and is involved in a salt bridge.

It also includes an arginine residue whose modification leads to inactivation of the enzyme. Adenylate kinase polypeptides of the present invention preferably include the following consensus sequence:

```
[LIVMFYW](3)-D-G-[FYI]-P-R-x(3)-[NQ]    (SEQ ID NO:86)
```

C. The Guanylate Kinase Nucleic Acid and Polypeptide Molecules

In one embodiment, the isolated nucleic acid molecules of the present invention encode guanylate kinase polypeptides. Guanylate kinase (described in Stehle (1992) *J. Mol. Biol.* 224:1127-1141) catalyzes the ATP-dependent phosphorylation of GMP into GDP and it is essential for recycling GMP and indirectly, cGMP. In prokaryotes (such as *Escherichia coli*), lower eukaryotes (such as yeast) and in vertebrates, guanylate kinase is a highly conserved monomeric protein of about 200 amino acids.

Guanylate kinases are characterized by the presence of one or more of a DHR domain, and an SH3 domain (Woods et al. (1994) *Mech. Dev.* 44:85-89). There is also an ATP-binding site (P-loop) in the N-terminal section of guanylate kinases. Guanylate kinase polypeptides of the present invention contain a highly conserved region that contains two arginine residues and a tyrosine residue, which are involved in GMP-binding. This conserved region is shown below:

```
T-[ST]-R-x(2)-[KR]-x(2)-[DE]-x(2)-G-x(2)-Y-x-[FY]-[LIVMK]    (SEQ ID NO:87)
```

D. The Pyruvate Kinase Nucleic Acid and Polypeptide Molecules

In one embodiment, the isolated nucleic acid molecules of the present invention encode pyruvate kinase polypeptides. Pyruvate kinase (PK) (described in Muirhead (1990) *Biochem. Soc. Trans.* 18:193-196) catalyzes the final step in glycolysis, the conversion of phosphoenolpyruvate to pyruvate with the concomitant phosphorylation of ADP to ATP. PK requires both magnesium and potassium ions for its activity. PK is found in all living organisms. In vertebrates there are four, tissue-specific isozymes: (L) liver, R (red cells), M1 (muscle, heart, and brain), and M2 (early fetal tissues).

All PK isozymes appear to be tetramers of identical subunits of about 500 amino acid residues. PKs contain a conserved region that includes a lysine residue that appears to be the acid/base catalyst responsible for the interconversion of pyruvate and enolpyruvate, and a glutamic acid residue implicated in the binding of the magnesium ion.

The pyruvate kinase polypeptides of the present invention preferably include the following consensus sequence:

```
                                                  (SEQ ID NO:88)
[LIVAC]-x-[LIVM](2)-[SAPCV]-K-[LIV]-E-[NKRST]-x-

[DEQH]-[GSTA]-[LIVM]

[K is the active site residue]
[E is a magnesium ligand]
```

E. The Phosphatidylinositol-3 Kinase Nucleic Acid and Polypeptide Molecules

In one embodiment, the isolated nucleic acid molecules of the present invention encode phosphatidylinositol 3-kinase polypeptides. Phosphatidylinositol 3-kinase (PI3-kinase) (described in Hiles et al. (1992) *Cell* 70:419-429) is an enzyme that phosphorylates phosphoinositides on the 3-hydroxyl group of the inositol ring.

The three products of PI3-kinase [PI-3-P, PI-3,4-P(2), and PI-3,4,5-P(3)] function as second messengers in cell signaling. The mammalian PI3 kinase is a heterodimer of a 110 kDa catalytic chain (p110) and an 85 kDa subunit (p85) which allows it to bind to activated tyrosine protein kinases. The PI3-kinases share a well conserved domain at their C-terminal section (Kunz et al. (1993) *Cell* 73:585-596).

The phosphatidylinositol 3-kinase polypeptides of the present invention preferably include the following consensus domains:

```
                                                  (SEQ ID NO:89)
[LIVMFAC]-K-x(1,3)-[DEA]-[DE]-[LIVMC]-R-Q-[DE]-x (4)-Q[GS]-x-[AV]-x(3)-[LIVM]-x(2)-[FYH]-[LIVM](2)- x-[LIVMIF]-x-D-R-H-x(2)-N
```

Novel Kinase Sequences

The kinase genes and partial gene sequences of the invention were identified in a variety of cell or tissue libraries including Th2 cell library (h12832, h15993, h16341); natural killer T cell library (h14833, h2252); microvascular endothelial cells (h14138); mixed lymphocyte reaction (h15990). The first of these clones, h12832, encodes an approximately 1.6 kb mRNA transcript having the corresponding cDNA sequence set forth in SEQ ID NO:1. This transcript has a 966 nucleotide open reading frame (nucleotides 191-1156 of SEQ ID NO:1), which encodes a 322 amino acid protein (SEQ ID NO:2). The molecule may have transmembrane segments from amino acids (aa) 19-35 and 230-250 as predicted by MEMSAT. Prosite program analysis was used to predict various sites within the h12832 protein. N-glycosylation sites were predicted at aa 196-199 and 249-252. A cAMP- and cGMP-dependent protein kinase phosphorylation site was predicted at aa 16-19. Protein kinase C phosphorylation sites were predicted at aa 14-16, 52-54, 181-183, and 225-227. Casein kinase II phosphorylation sites were predicted at aa 122-125, 198-201, 236-239, 251-254, 260-263, 264-267, and 301-304. N-myristoylation sites were predicted at aa 41-46 and 118-123. A serine/threonine protein kinase active-site signature sequence was predicted at aa 163-175. The h12832 protein possesses a eukaryotic protein kinase domain, from aa 32 to aa 316, as predicted by HMMer, Version 2. Within this domain, critical residues are conserved at amino acid (aa) positions 39, 41, 46, 62, 64, 85, 94, 96, 116, 123, 153, 156-158, 165, 167, 169, 172, 183, 186, 188, 208, 209, 216, 229, 234, 237, 239, 246, 296, 304, 305, and 308. Critical residues are missing at aa positions 166, 187, 214, and 215, while important residues are missing at aa positions 44, 121, 149, 173, 174, 212, 231, 232, and 284. "Critical residues" are those residues that are recognized as important for activity and are highly conserved in known kinases. "Important residues" are those residues generally conserved among kinases.

Figure 3:
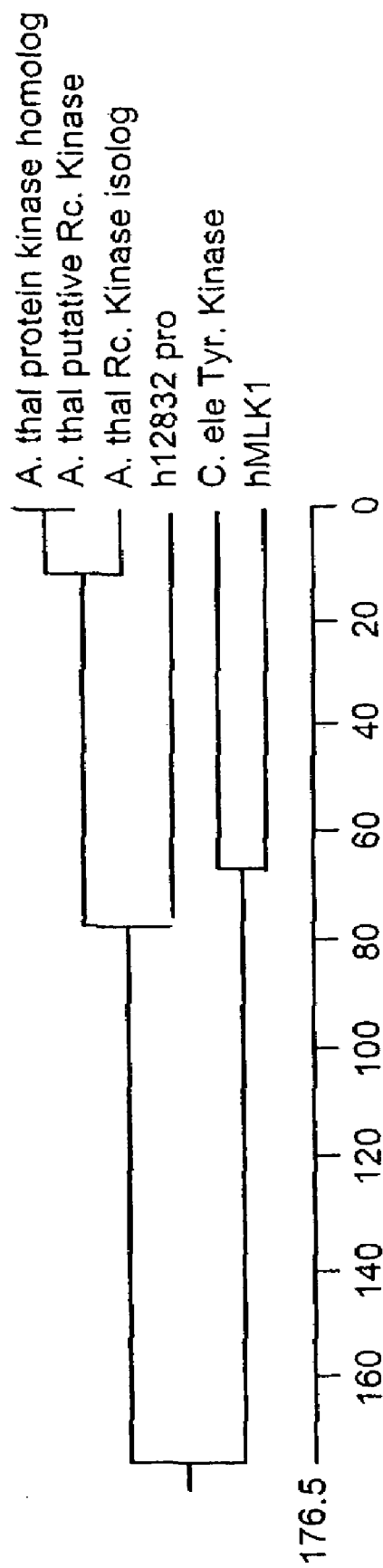
FIG. 3 shows a dendrogram for the h12832 gene.
Figure 5L:
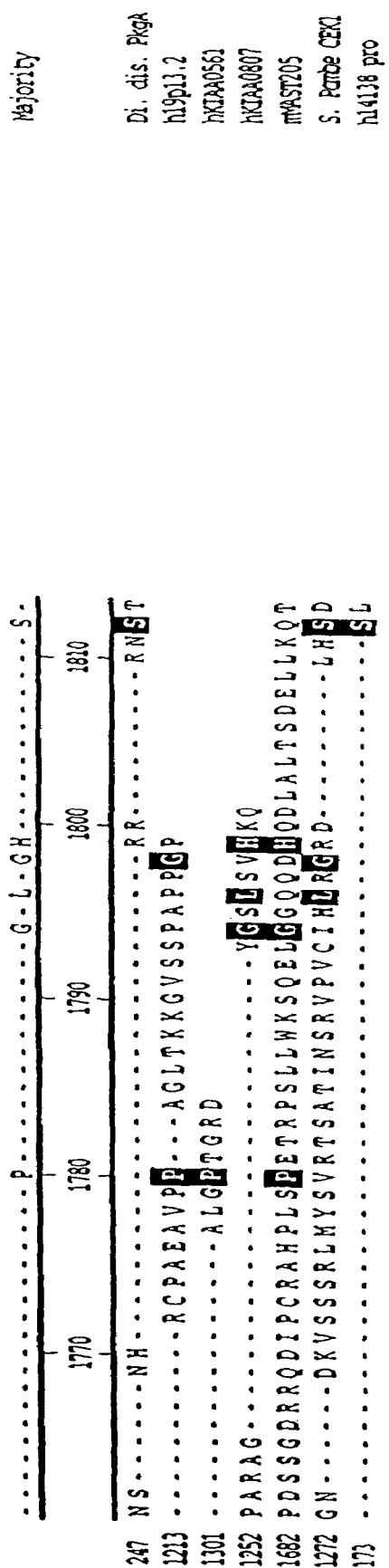

The h12832 protein shares similarity with several protein kinases (see FIGS. 2A-2G). Dendrogram analysis of this gene indicates it shares closest homology with *C. elegans* tyrosine kinase (C. ele. Tyr. Kinase; GenBank Accession Number AAC47047; SEQ ID NO:18). The h12832 protein shares approximately 26% identity with this protein kinase receptor as determined by pairwise alignment (see Needleman and Wunsch (1970) *J. Mol. Biol.* 48:444). (see FIG. 3).

The partial gene sequence designated clone h14138 encodes an approximately 0.83 kb transcript mRNA having the corresponding cDNA set forth in SEQ ID NO:3. This transcript has a 522 nucleotide open reading frame (nucleotides 1-522 of SEQ ID NO:3), which encodes a 174 amino acid polypeptide (SEQ ID NO:4). An analysis of the disclosed h14138 polypeptide sequence (SEQ ID NO:4) using the MEMSAT program predicts a transmembrane segment from aa 56-73. Prosite program analysis was also used to predict various sites within this partial-length protein sequence. Protein kinase C phosphorylation sites were predicted at aa 12-14, 17-19, 20-22, and 116-118. Casein kinase II phosphorylation sites were predicted at aa 12-15, 105-108, 112-115, 131-134, and 156-159. An N-myristoylation site was predicted at aa 9-14. The partial-length h14138 protein possesses a eukaryotic protein kinase domain, from aa 35-130, and a protein kinase C terminal domain, from aa 131-159, as predicted by HMMer Version 2.

Figure 6:
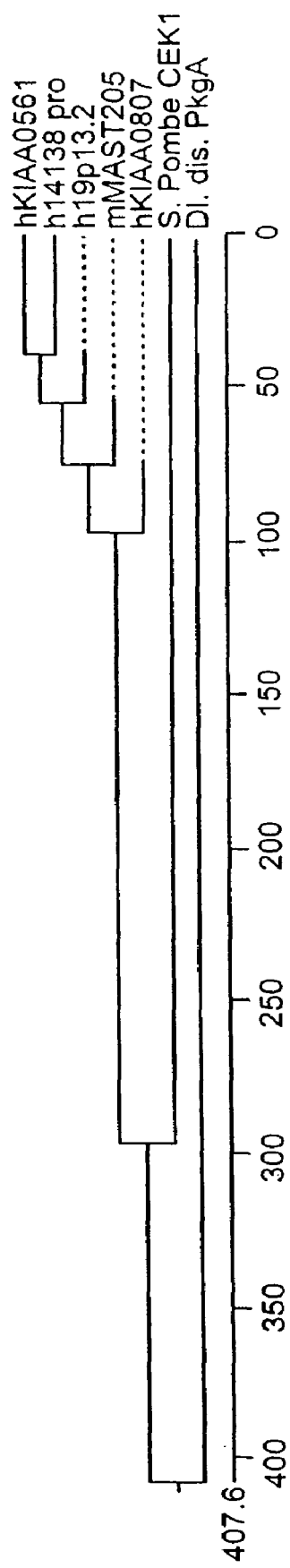
FIG. 6 shows a dendrogram for the h14138 gene.
Figure 8D:
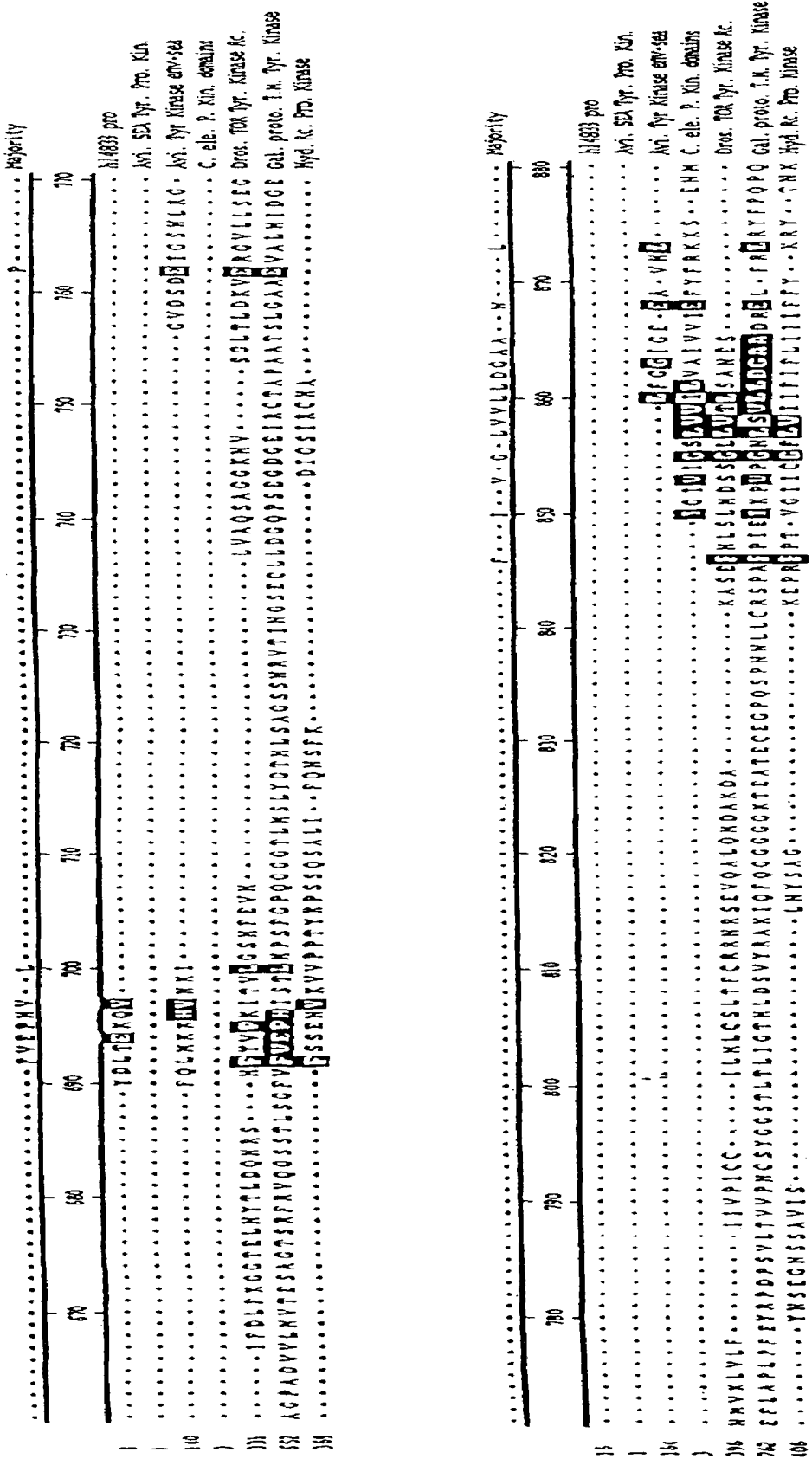

The partial length h14138 protein displays similarity to several protein kinases (see FIGS. 5A-5L). Dendrogram analysis of this gene indicates it shares closest homology with human KIAA0807 protein; DBJ Accession Number BAA34527; SEQ ID NO: 80). The h14138 protein shares approximately 35% identity with this protein kinase receptor as determined by pairwise alignment (see Needleman and Wunsch (1970) J. Mol. Biol. 48:444). (see FIG. 6).

The third novel gene, designated clone h14833, encodes an approximately 2.1 kb transcript mRNA having the corresponding cDNA set forth in SEQ ID NO:5. This transcript has a 627 nucleotide open reading frame (nucleotides 154-780 of SEQ ID NO:5), which encodes a 209 amino acid protein (SEQ ID NO:6) having a molecular weight of approximately 23.8 kDa. An analysis of the full-length h14833 protein sequence using the MEMSAT program predicted no transmembrane domains. Prosite program analysis of this protein predicted an N-glycosylation site at amino acid (aa) 205-208 and a cAMP- and cGMP-dependent protein kinase phosphorylation site at aa 133-136. Protein kinase C phosphorylation sites were predicted at aa 11-13, 51-53, 91-93, and 159-161. Casein kinase II phosphorylation sites were predicted at aa 121-124, 159-162, and 173-176. N-myristoylation sites were predicted at aa 56-61 and 67-72. A tyrosine protein kinase specific active-site signature was predicted at aa 34-46. The h14833 protein possesses a eukaryotic protein kinase domain from aa 10 to aa 163.

Figure 9:
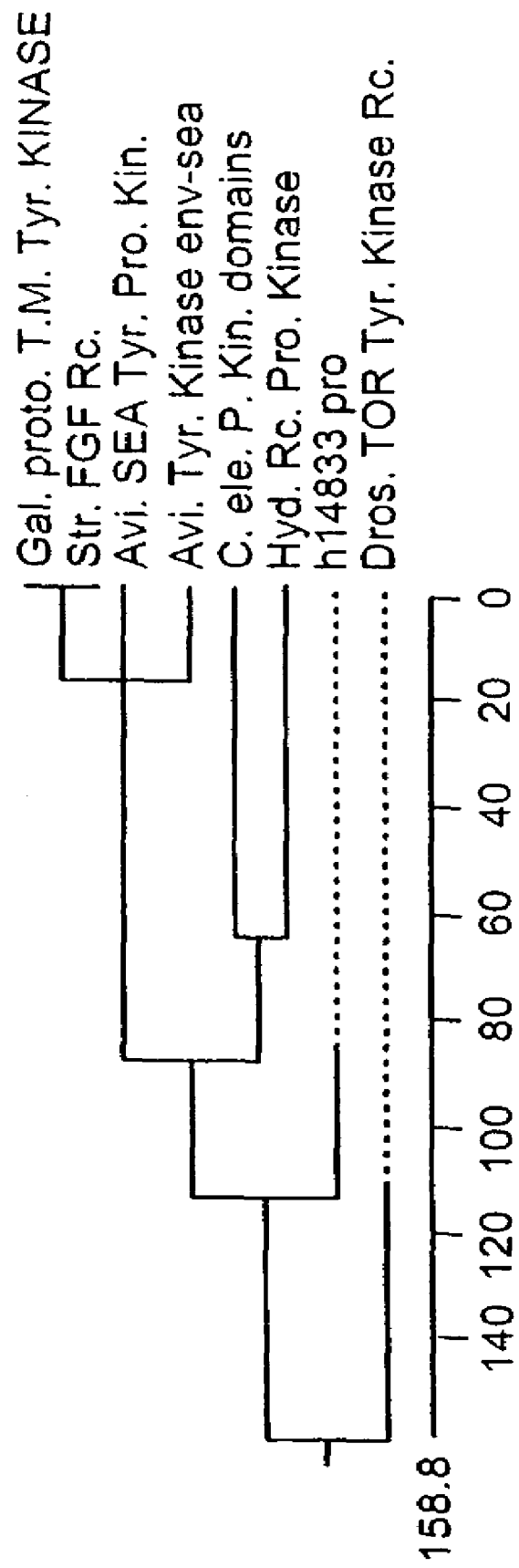
FIG. 9 shows a dendrogram for the h14833 gene.
Figure 11A:
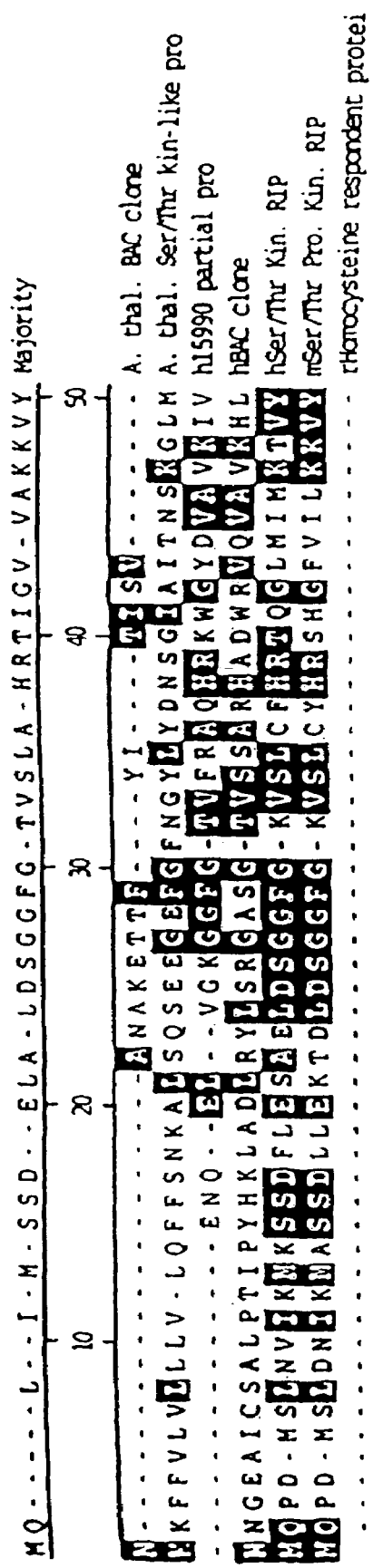

The h14833 protein displays similarity to several protein kinases (see FIGS. 8A-8G). Dendrogram analysis of this gene indicates that the encoded h14833 protein shares closest homology with a putative fruit fly (Drosophila melanogaster) torso tyrosine-protein kinase receptor (SP Accession Number P18475; SEQ ID NO:23) (see FIG. 9). The h14833 protein shares approximately 34% identity over a 209 amino-acid overlap with this protein kinase receptor as determined by pairwise alignment (see Needleman and Wunsch (1970) J. Mol. Biol. 48:444).

The partial gene sequence designated clone h15990 encodes an approximately 1.7 kb transcript mRNA having the corresponding cDNA set forth in SEQ ID NO:7. This transcript has a 1491 nucleotide open reading frame (nucleotides 2-1492 of SEQ ID NO:7), which encodes a 497 amino acid polypeptide (SEQ ID NO:8). An analysis of the partial-length h15990 protein sequence using the MEMSAT program predicted no transmembrane domains. Prosite program analysis of this partial-length protein predicted N-glycosylation sites at amino acids (aa) 78-81, 412-415, 433-436, and 493-496. Glycosaminoglycan attachment sites were predicted at aa 151-154, 299-302, and 461-464. cAMP- and cGMP-dependent protein kinase phosphorylation sites were predicted at aa 175-178 and 292-295. Protein kinase C phosphorylation sites were predicted at aa 279-281, 290-292, 348-350, 382-384, 414-416, 424-426, 461-463, and 495-497. Casein kinase II phosphorylation sites were predicted at aa 179-182, 220-223, 254-257, 279-282, 295-298, 304-307, 318-321, and 366-369. N-myristoylation sites were predicted at aa 9-14, 79-84, 147-152, 159-164, 300-305, 402-407, 410-415, 436-441, and 457-462. A protein kinase ATP-binding region signature sequence was predicted at aa 6-14. A serine/threonine protein kinase active-site signature sequence was predicted at aa 117-129. The partial-length h15990 protein possesses a eukaryotic protein kinase domain, from aa 1-259, as predicted by HMMer Version 2.

Figure 12:
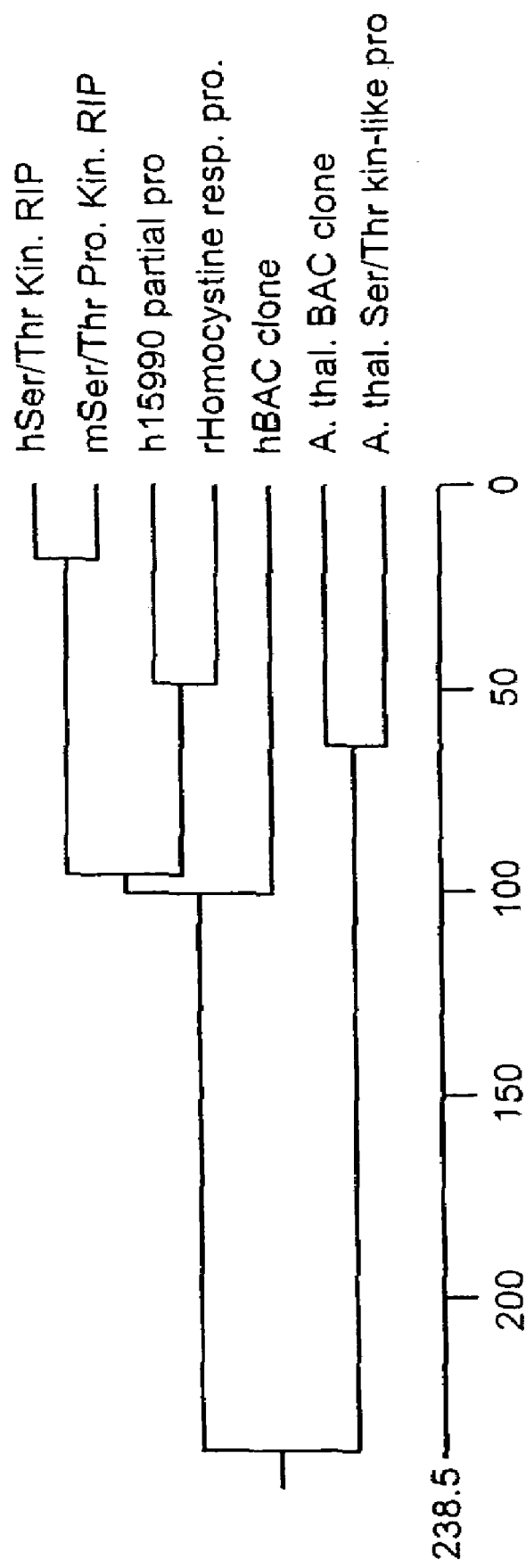
FIG. 12 shows a dendrogram for the h15990 gene.

The partial-length h15990 protein displays similarity to several protein kinases (see FIGS. 11A-11H). Dendrogram analysis of this gene indicates that the encoded h15990 protein shares closest homology with a Rattus norvegicus homocysteine respondent protein (GenBank Accession Number AAD02059; SEQ ID NO:31) (see FIG. 12). The partial-length h15990 protein shares approximately 74.3% identity over a 142 amino-acid overlap with this homocysteine respondent protein as determined by pairwise alignment.

The partial gene sequence designated clone h15993 encodes an approximately 0.98 kb transcript mRNA having the corresponding cDNA set forth in SEQ ID NO:9. This transcript has a 978 nucleotide open reading frame (nucleotides 2-979 of SEQ ID NO:9), which encodes a 326 amino acid polypeptide (SEQ ID NO:10) having a molecular weight of approximately 37.2 kDa. Transmembrane segments from amino acids (aa) 168-185 and 247-263 were predicted by MEMSAT. Prosite program analysis of the partial-length h15993 protein predicted an N-glycosylation site at aa 186-189, and a cAMP and cGMP-dependent protein kinase phosphorylation site at aa 304-307. Protein kinase C phosphorylation sites were predicted at aa 141-143 and 149-151. Casein kinase II phosphorylation sites were predicted at aa 33-36, 100-103, 246-249, 267-270, and 284-287. N-myristoylation sites were predicted at aa 58-63 and 185-190. The partial-length h15993 protein possesses two eukaryotic protein kinase domains, from aa 108 to 203 and from aa 283 to 314, as predicted by HMMer Version 2.

Figure 14A:
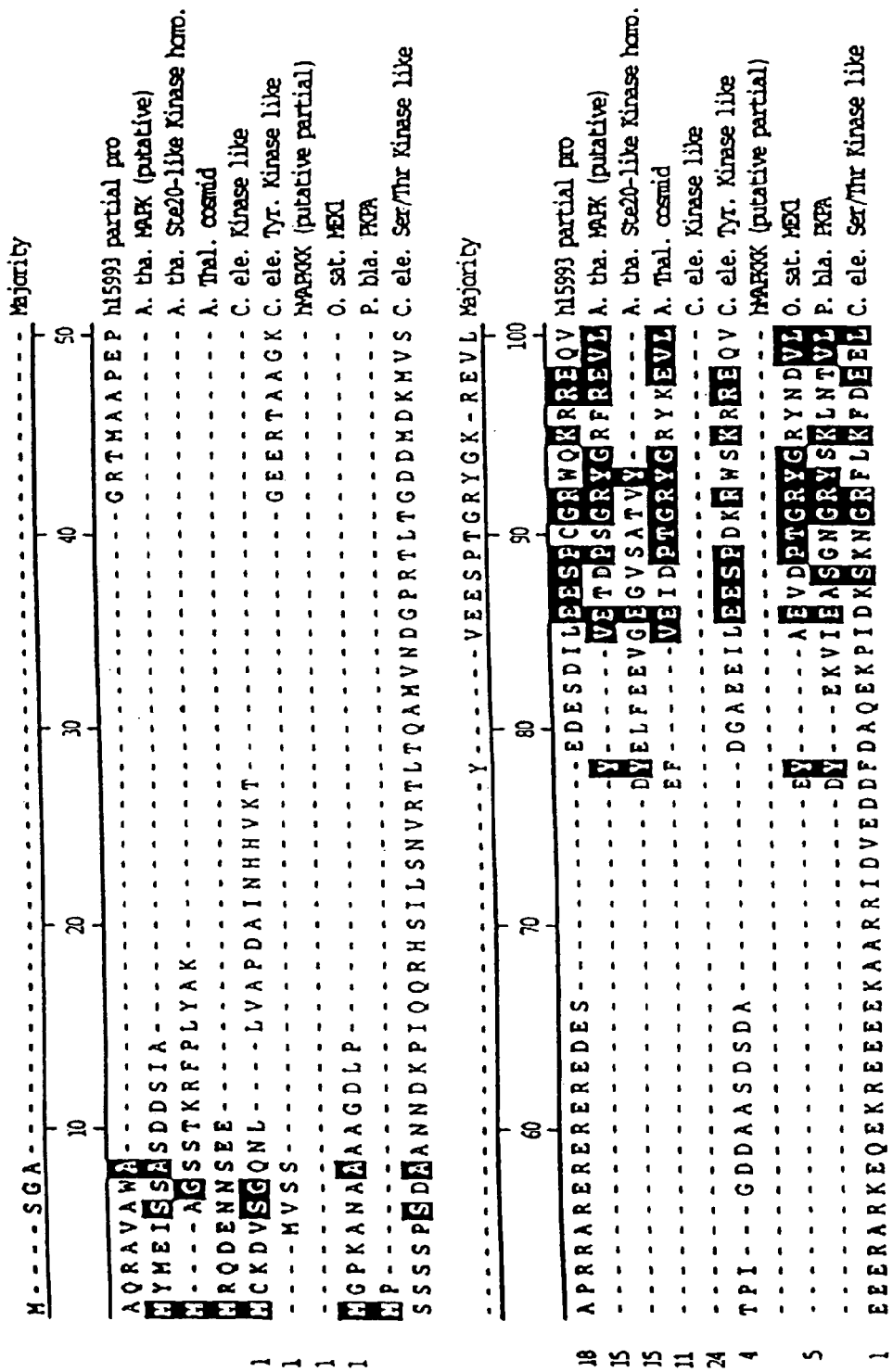
FIGS. 14A-14Q show the amino acid sequence alignment for the protein (h15993; SEQ ID NO:10) encoded by human 15993 (SEQ ID NO:9) with the *Arabidopsis thaliana* putative MAP kinase (A. thal. MAPK; EMB Accession Number CAB43520; SEQ ID NO:32), the *Arabidopsis thaliana* Step 20-like kinase homolog (A. tha. Sete20-like Kinase homo.; GenBank Accession Number AAC18797; SEQ ID NO:33), the *Arabidopsis thaliana* protein kinase-like protein (A. thal. cosmid; EMB Accession Number CAB41172; SEQ ID NO:34), the *C. elegans* protein having weak similarity with many protein kinases (C. ele. Kinase-like; EMB Accession Number CAA99887; SEQ ID NO:35), the *C. elegans* tyrosine-protein kinase-like protein (C. ele. Tyr. Kinase-like; EMB Accession Number CAA15621; SEQ ID NO:36), the human putative mitogen-activated protein kinase kinase kinase (hMAPKKK; EMB Accession Number CAB44308; SEQ ID NO:37), the *Oryza sativa* mitogen activated protein kinase kinase (O. sat. MEK1; GenBank Accession Number AAC32599; SEQ ID NO:38), the Phycomyces blakesleeanus serine/threonine protein kinase pkpa (P. bla. PKPA; SP Accession Number Q01577; SEQ ID NO:39), and the *C. elegans* serine/threonine-protein kinase-like protein (C. ele. Ser/thr Kinase-like; EMB Accession Number CAA92591; SEQ ID NO:40). The sequence alignment was generated using the Clustal method.
Figure 14B:
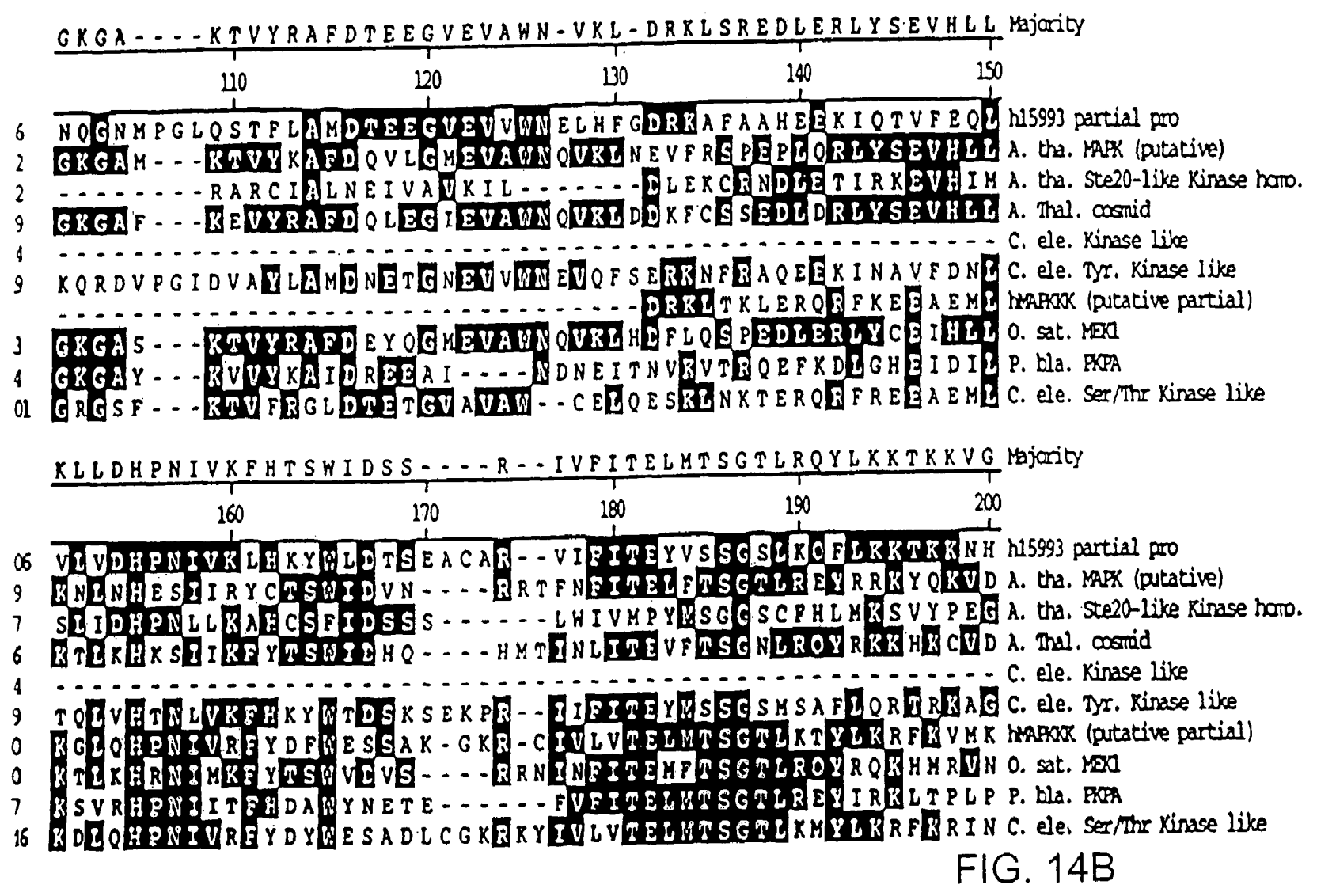
Figure 14C:
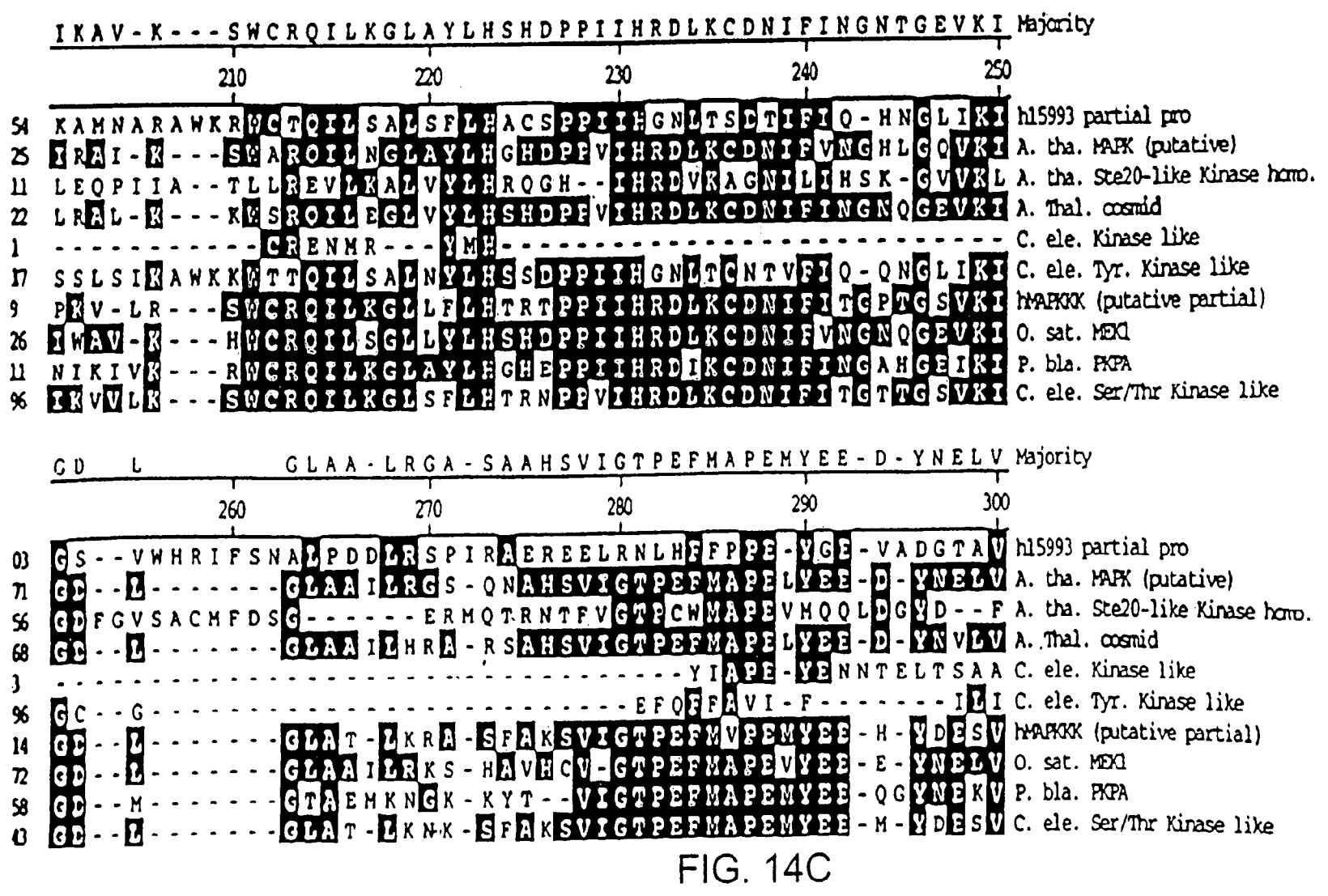
Figure 14D:
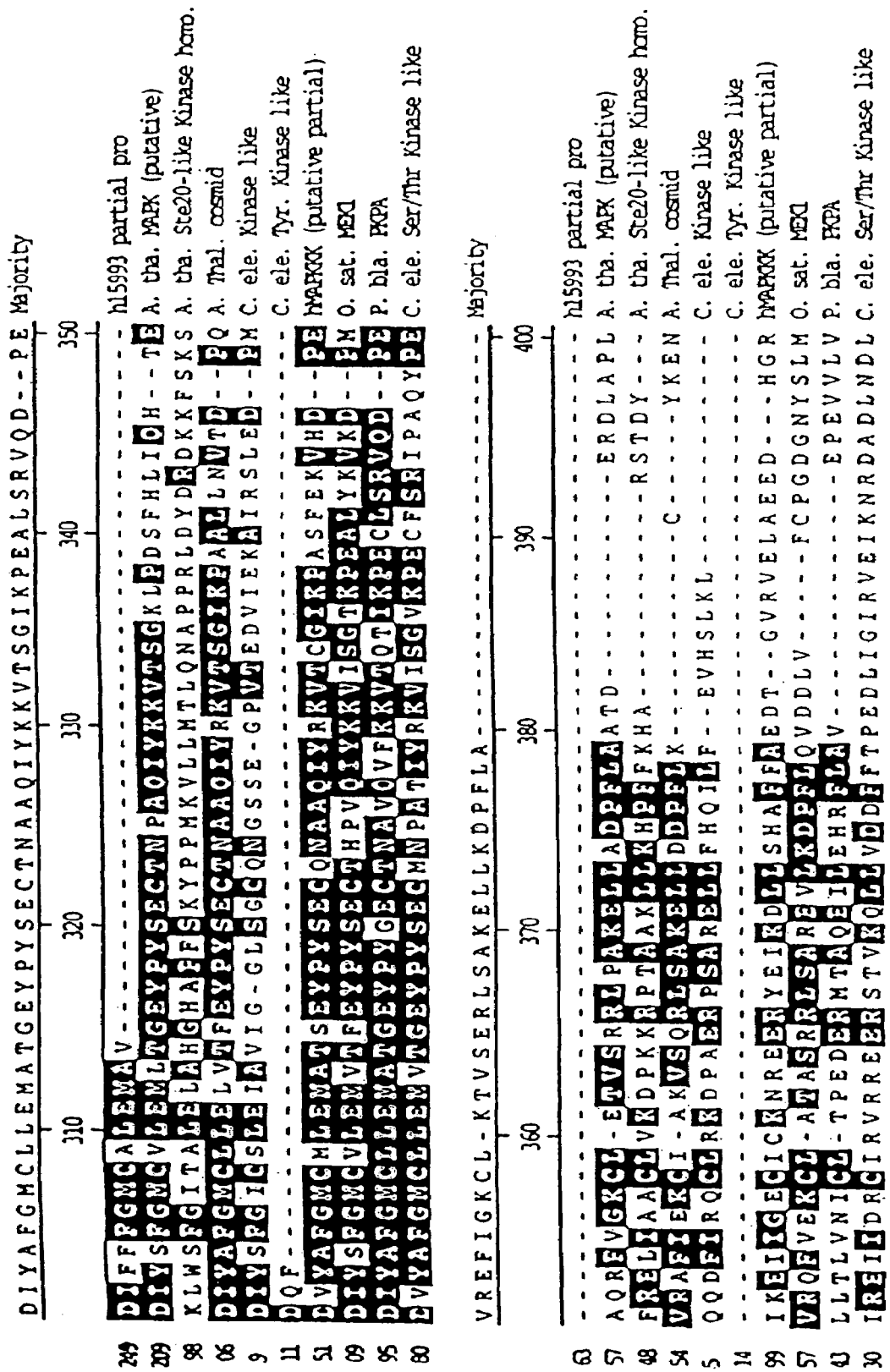
Figure 14E:
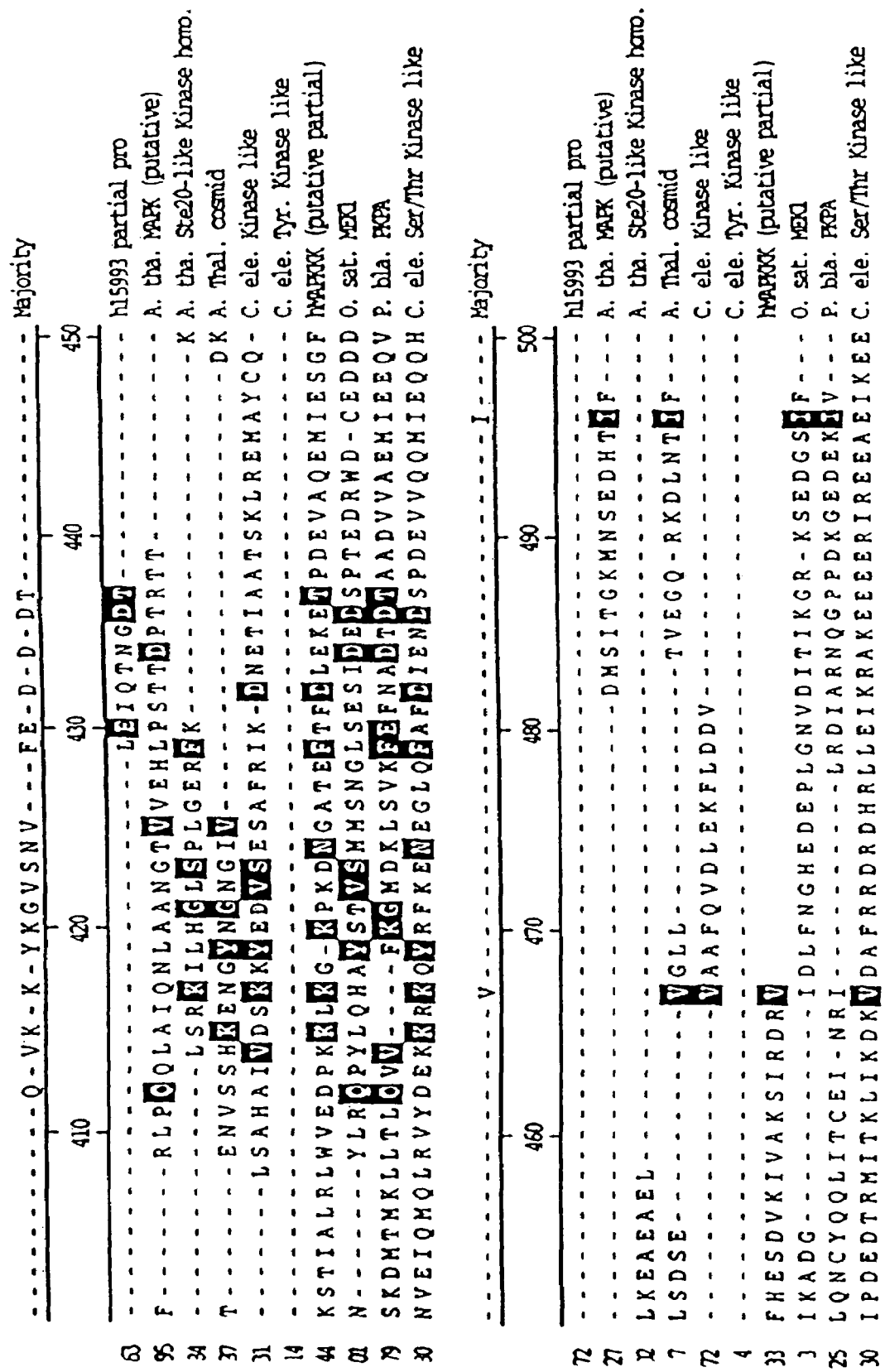
Figure 14F:
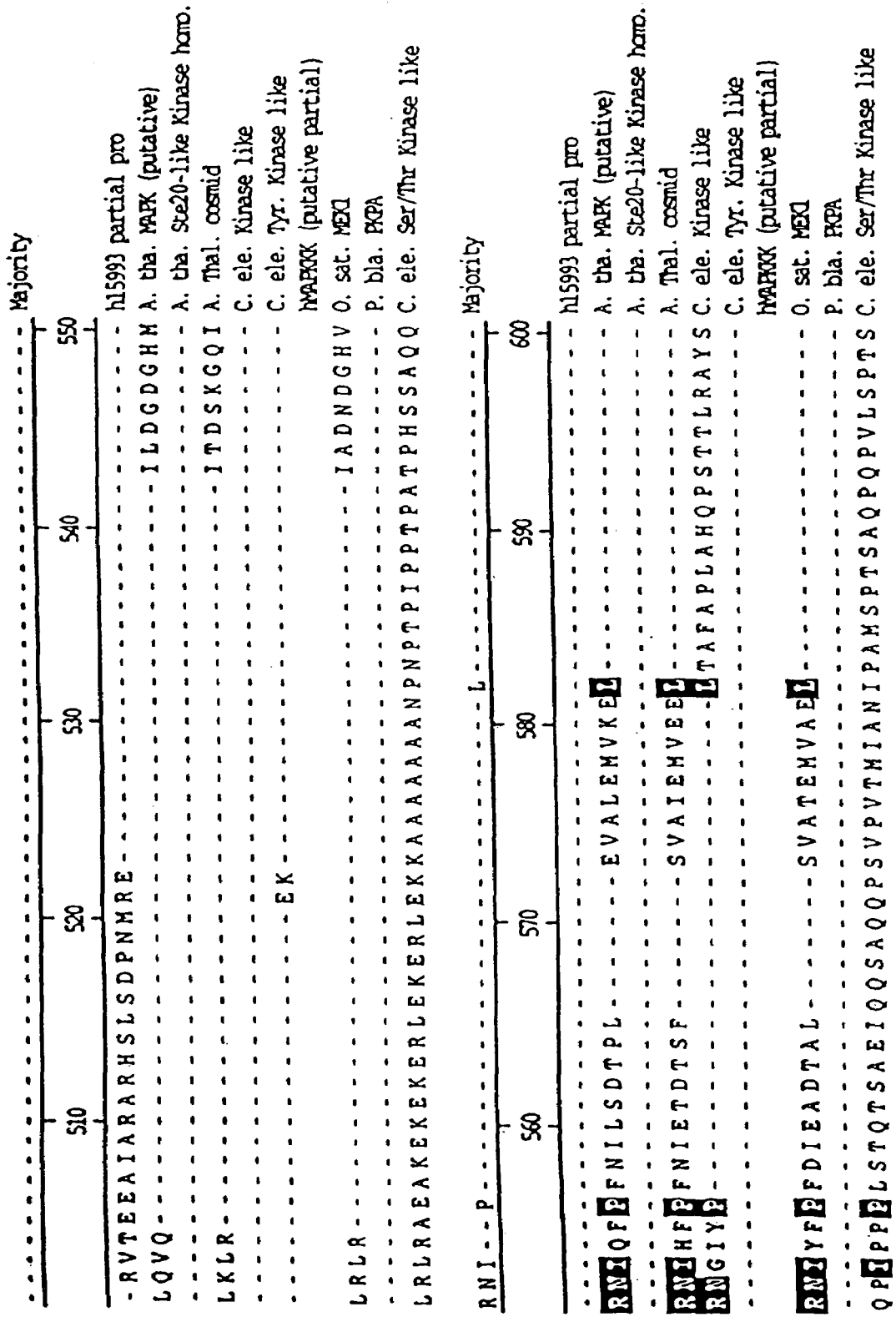
Figure 14G:
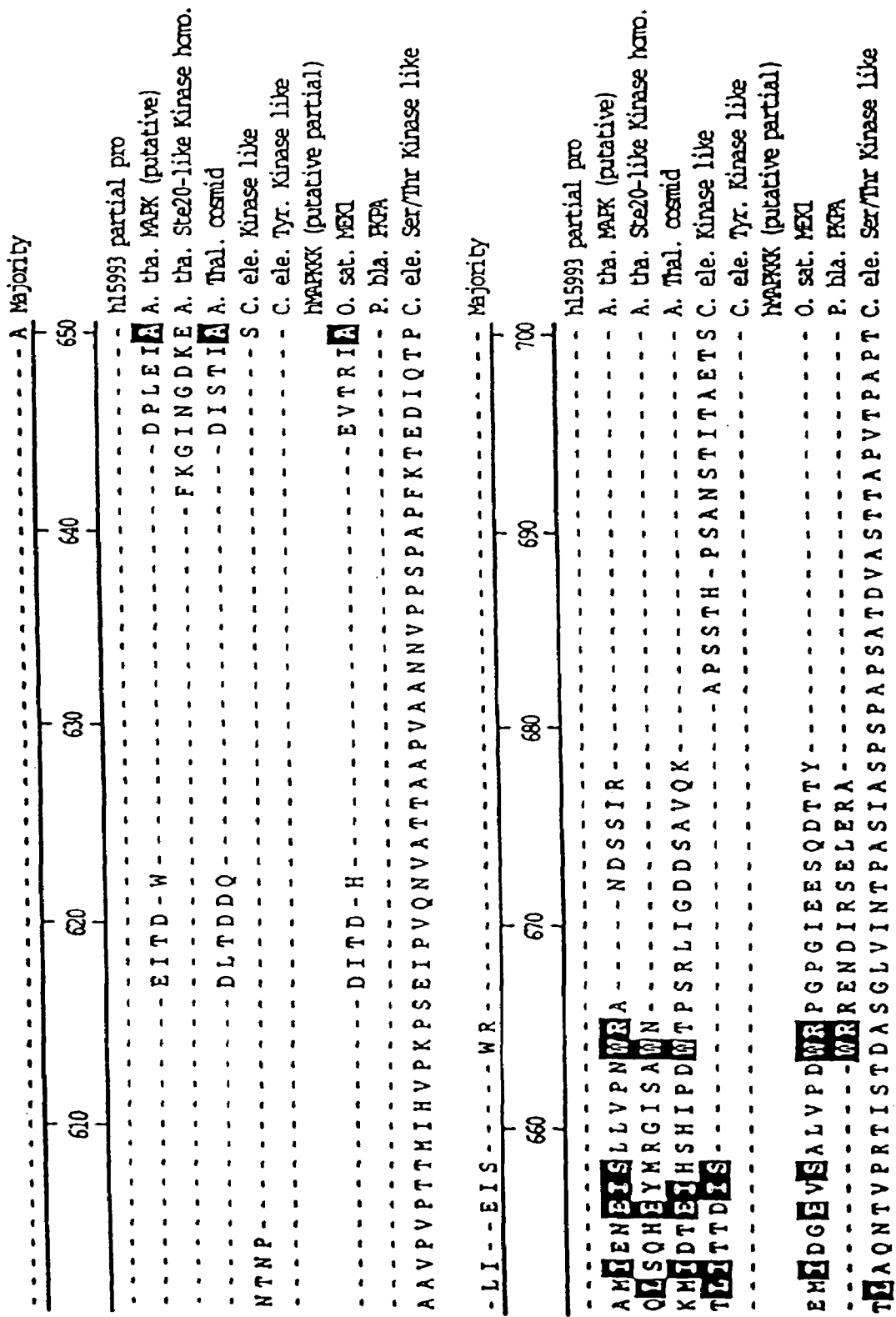
Figure 14J:
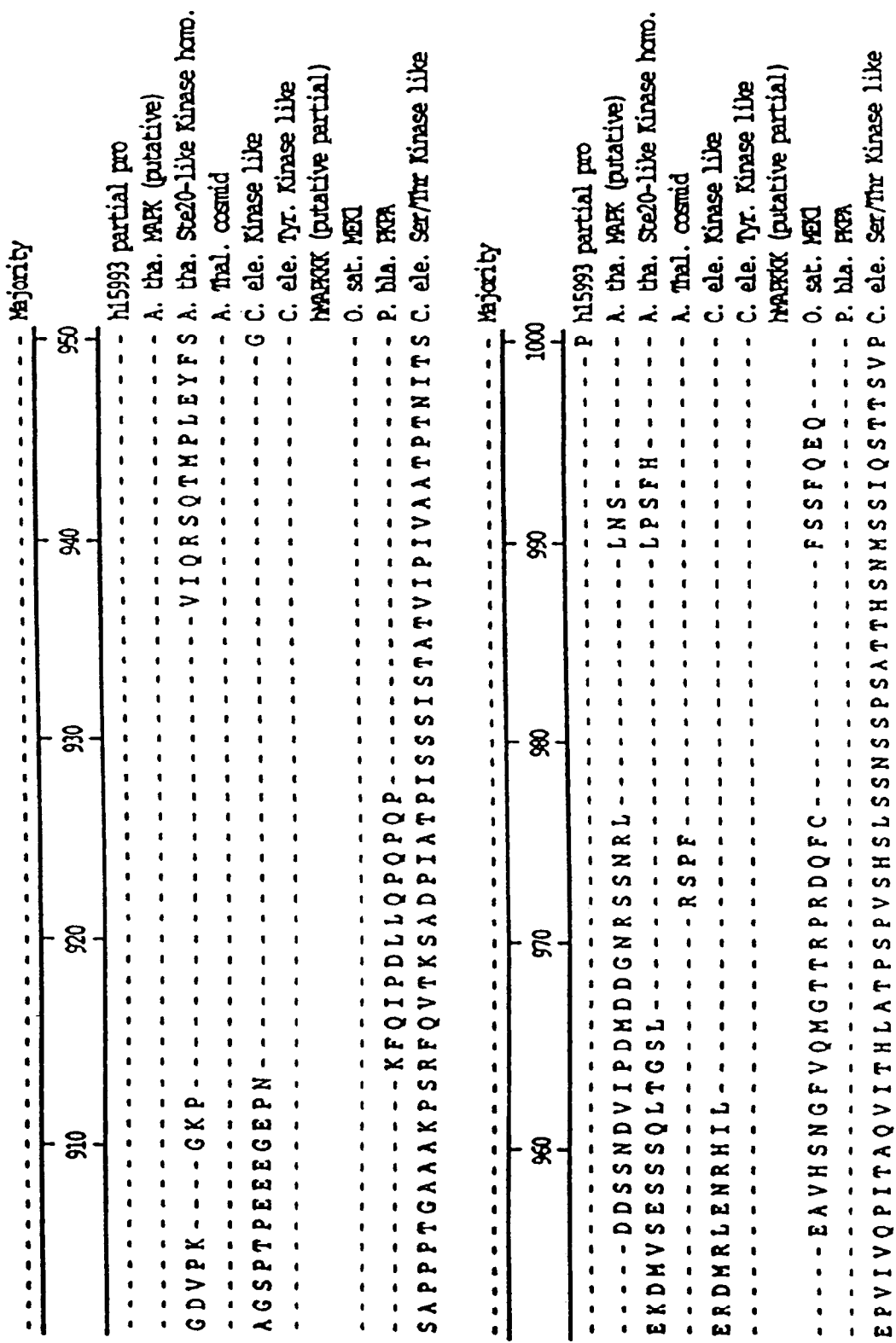
Figure 14K:
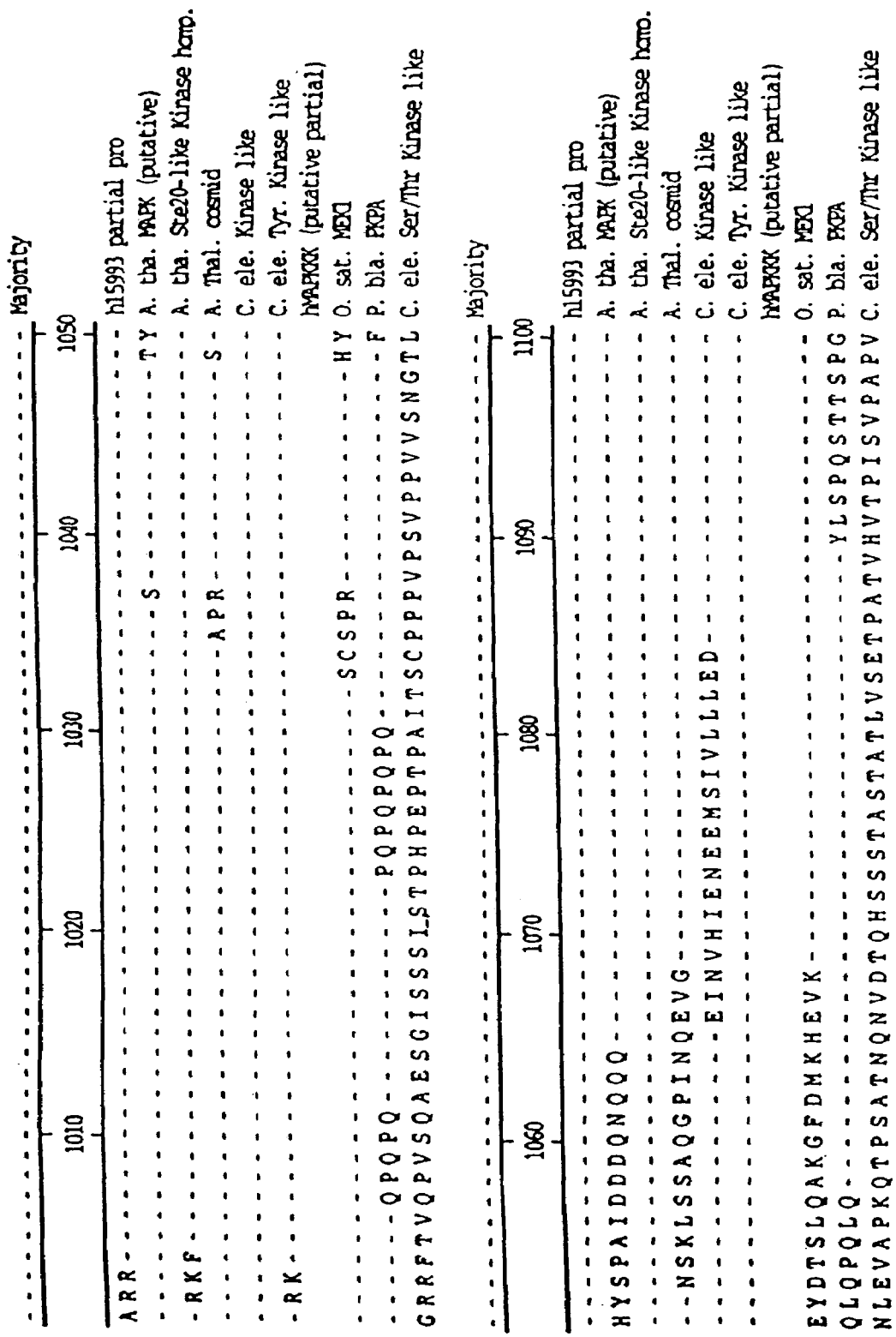
Figure 15:
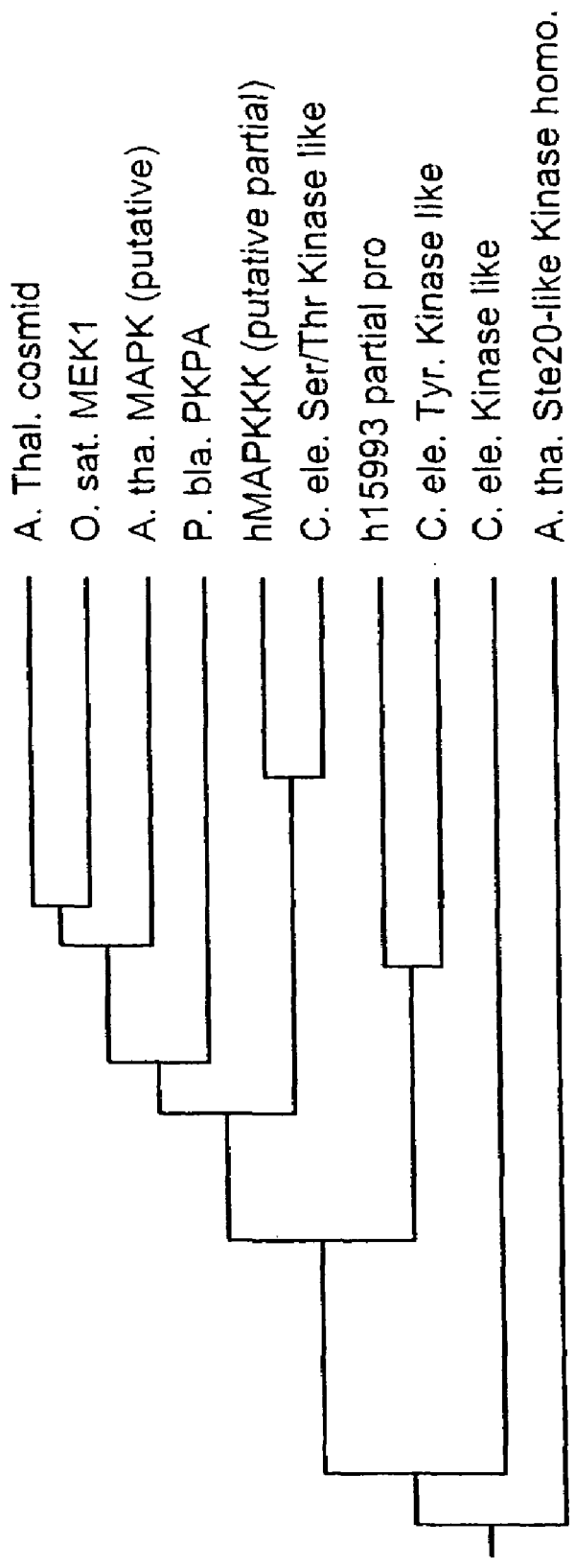
FIG. 15 shows a dendrogram for the h15993 gene.
Figure 17A:
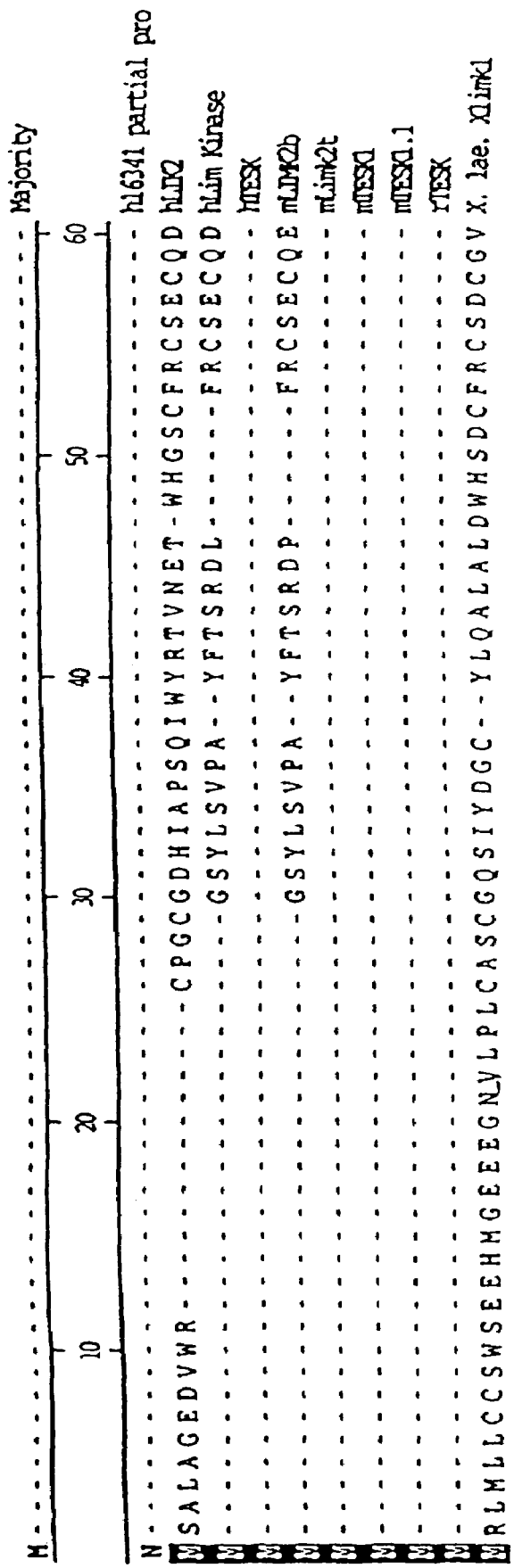
Figure 17B:
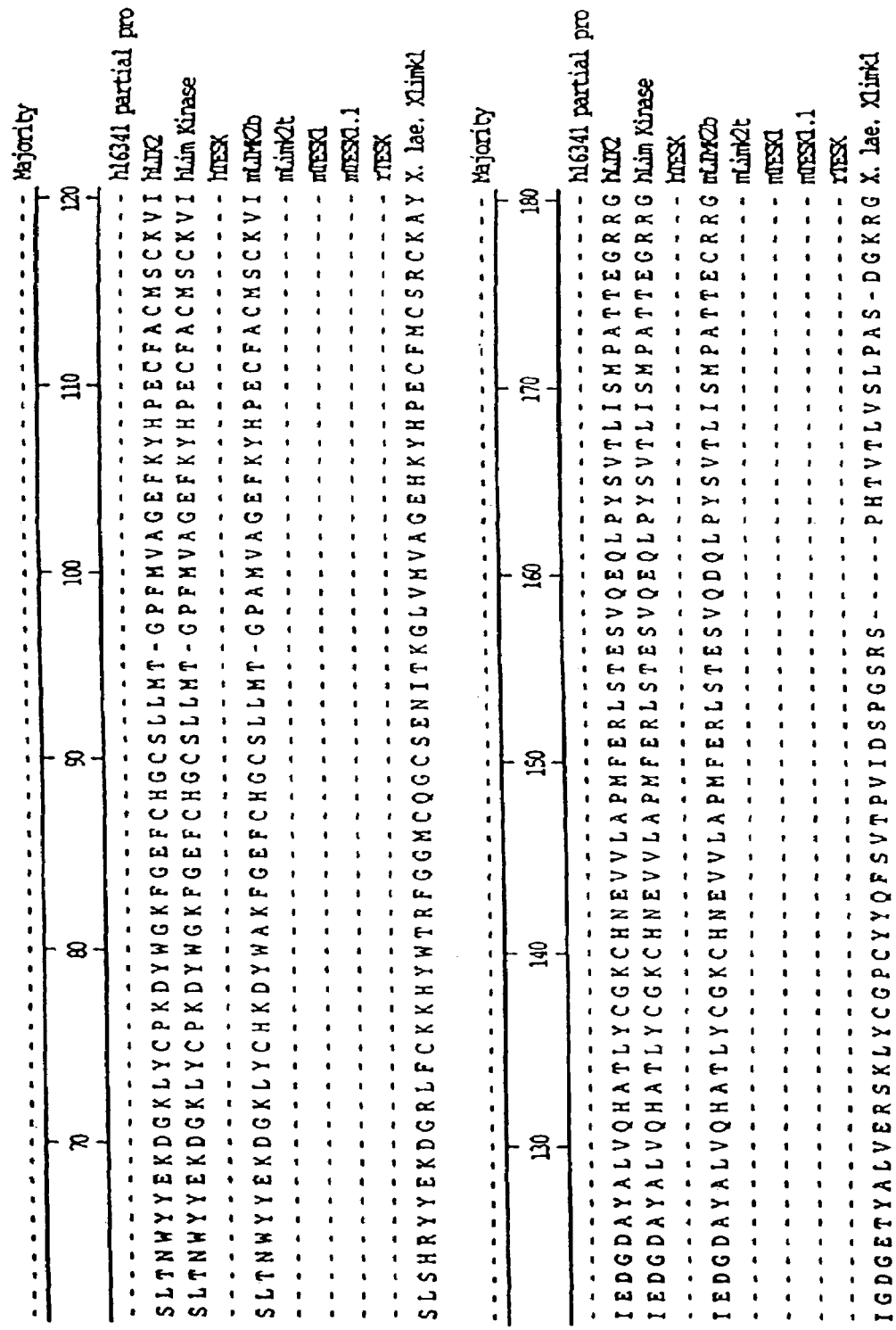
Figure 171:
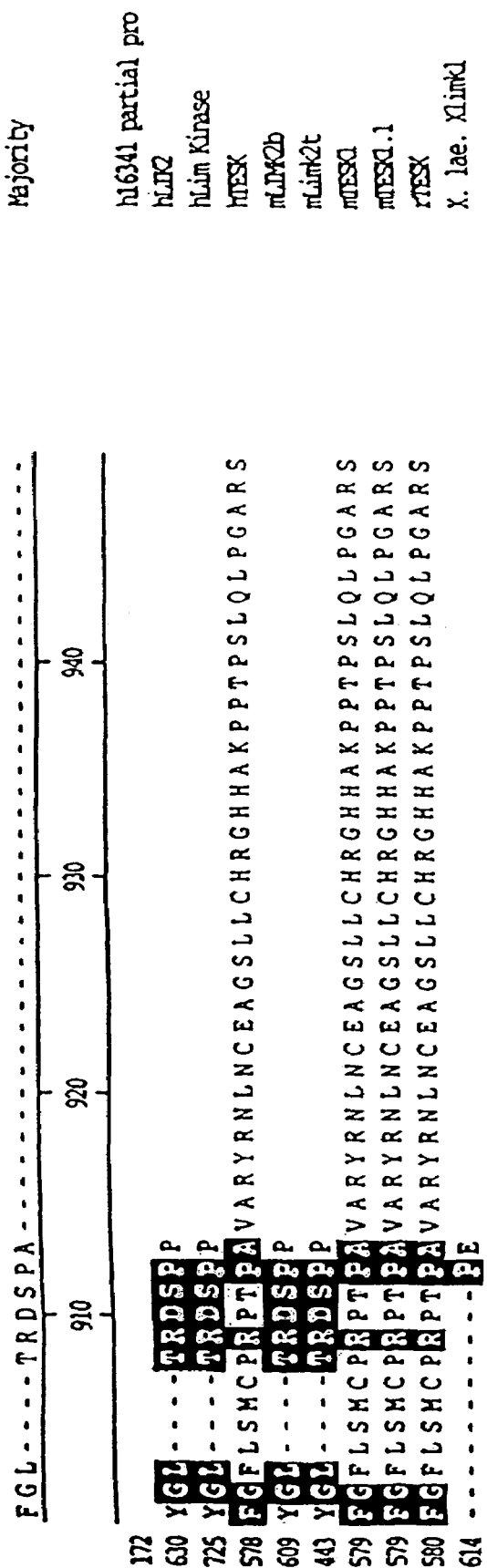

The partial-length h15993 protein displays similarity to several protein kinases (see FIGS. 14A-14Q). Dendrogram analysis of this gene indicates that the encoded h15993 protein shares closest homology with a C. elegans tyrosine-protein kinase-like protein (EMB Accession Number CAA15621; SEQ ID NO:36) (see FIG. 15). The partial-length h15993 protein shares approximately 45.1% identity over a 231 amino-acid overlap with this tyrosine-protein kinase-like protein as determined by pairwise alignment.

The partial gene sequence designated clone h16341 encodes an approximately 0.52 kb transcript mRNA having the corresponding cDNA set forth in SEQ ID NO:9. This transcript has a 516 nucleotide open reading frame (nucleotides 2-517 of SEQ ID NO:9), which encodes a 172 amino acid polypeptide (SEQ ID NO:10) having a molecular weight of approximately 19.5 kDa. An analysis of the partial-length h16341 protein sequence using the MEMSAT program predicted no transmembrane domains. Prosite program analysis of this partial-length protein predicted an N-glycosylation site at amino acids (aa) 27-30, and protein kinase C phosphorylation sites at aa 38-40, 89-91, and 147-149. Casein kinase II phosphorylation sites were predicted at aa 13-16 and 50-53. N-myristoylation sites were predicted at aa 20-25, 77-82, and 120-125. A protein kinase ATP-binding region signature sequence was predicted at aa 60-68. The partial-length h16341 protein possesses a eukaryotic protein kinase domain, from aa 58 to aa 172, as predicted by HMMer Version 2.

Figure 18:
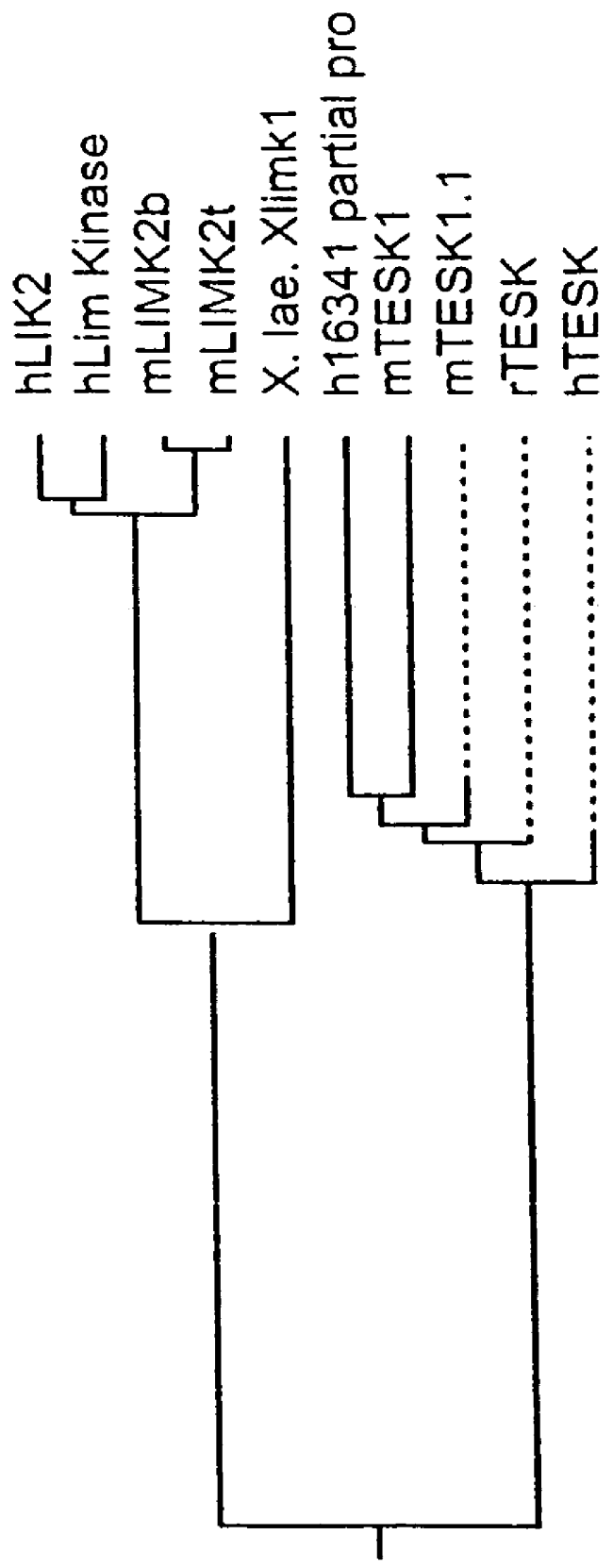
FIG. 18 shows a dendrogram for the h16341 gene.
Figure 20A:
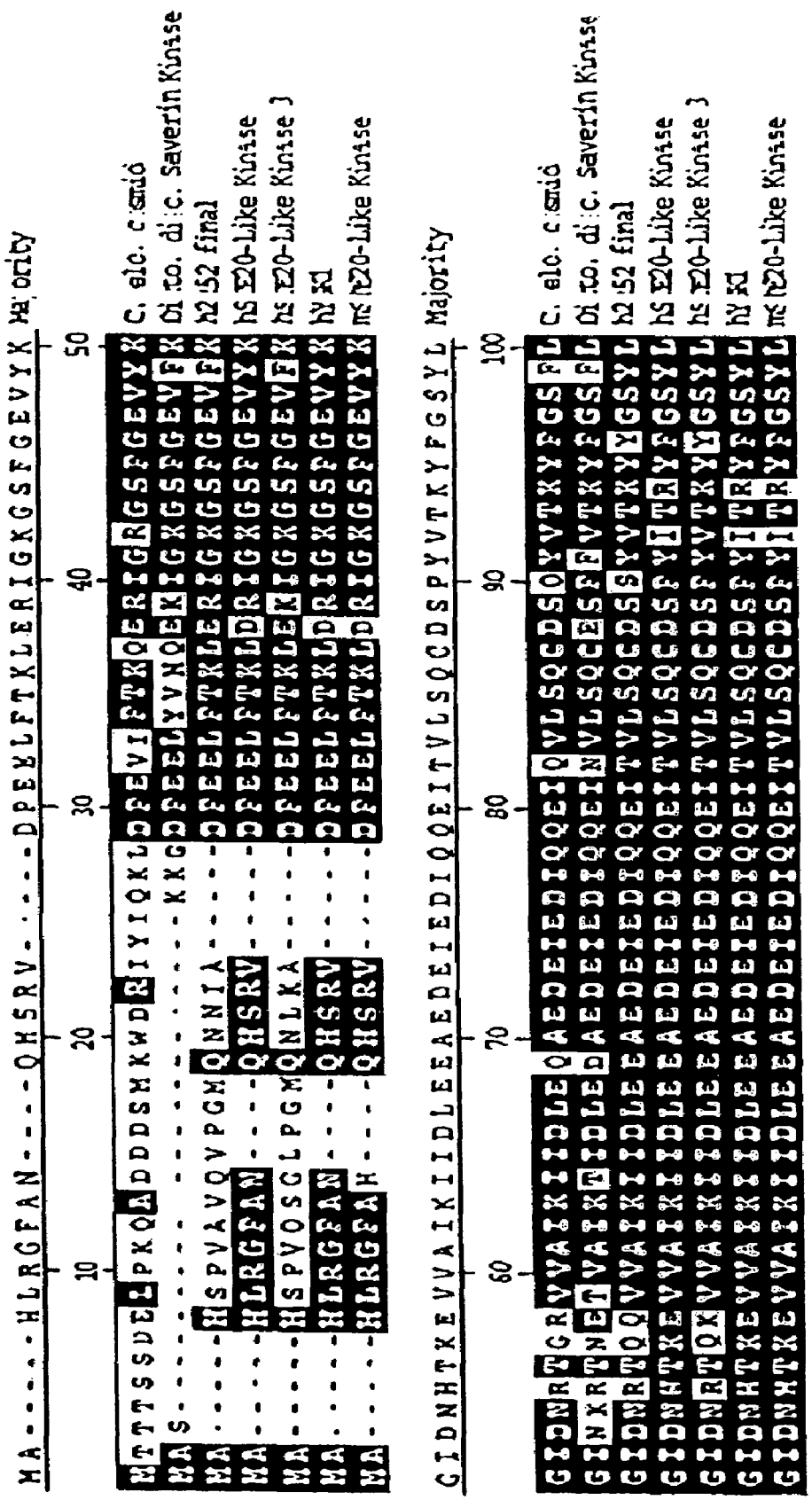

The partial-length h16341 protein displays similarity to several protein kinases (see FIGS. 17A-17I). Dendrogram analysis of this gene indicates that the encoded partial-length h16341 protein shares closest homology with a murine testis-specific protein kinase 1 (DBJ Accession Number BAA25124; SEQ ID NO:46) (see FIG. 18). The partial-length h16341 protein shares approximately 91.7% identity over a 172 amino-acid overlap with this tyrosine-protein kinase-like protein as determined by pairwise alignment.

The last of these novel genes, designated clone h2252, encodes an approximately 1.7 kb transcript mRNA having the corresponding cDNA set forth in SEQ ID NO:13. This transcript has a 1248 nucleotide open reading frame (nucleotides 275-1522 of SEQ ID NO:13), which encodes a 416 amino acid protein (SEQ ID NO:14). Transmembrane segments were predicted at aa 95-111 and 346-362 using the MEMSAT program. Prosite analysis of the full-length h2252 protein predicted N-glycosylation sites at aa 44-47, 318-321, and 371-374. cAMP- and cGMP-dependent protein kinase phosphorylation sites were predicted at aa 175-178 and aa 279-282. Protein kinase C phosphorylation sites were predicted at aa 137-139, 246-248, 260-262, 264-266, 278-280, 314-316, 328-330, and 396-398. Casein kinase II phosphorylation sites were predicted at aa 25-28, 34-37, 75-78, 106-109, 194-197, 198-201, 208-211, 246-249, 264-267, 300-303, 304-307, 309-312, 314-317, 320-323, and 411-414. N-myristoylation sites were predicted at aa 12-17 and 103-108. A protein kinase ATP-binding region signature sequence was predicted at aa 30-38. The h2252 protein possesses a eukaryotic protein kinase domain, from aa 24-274, and a phosphofructokinase domain, from aa 385-406, as predicted by HMMer Version 2.0.

Figure 21:
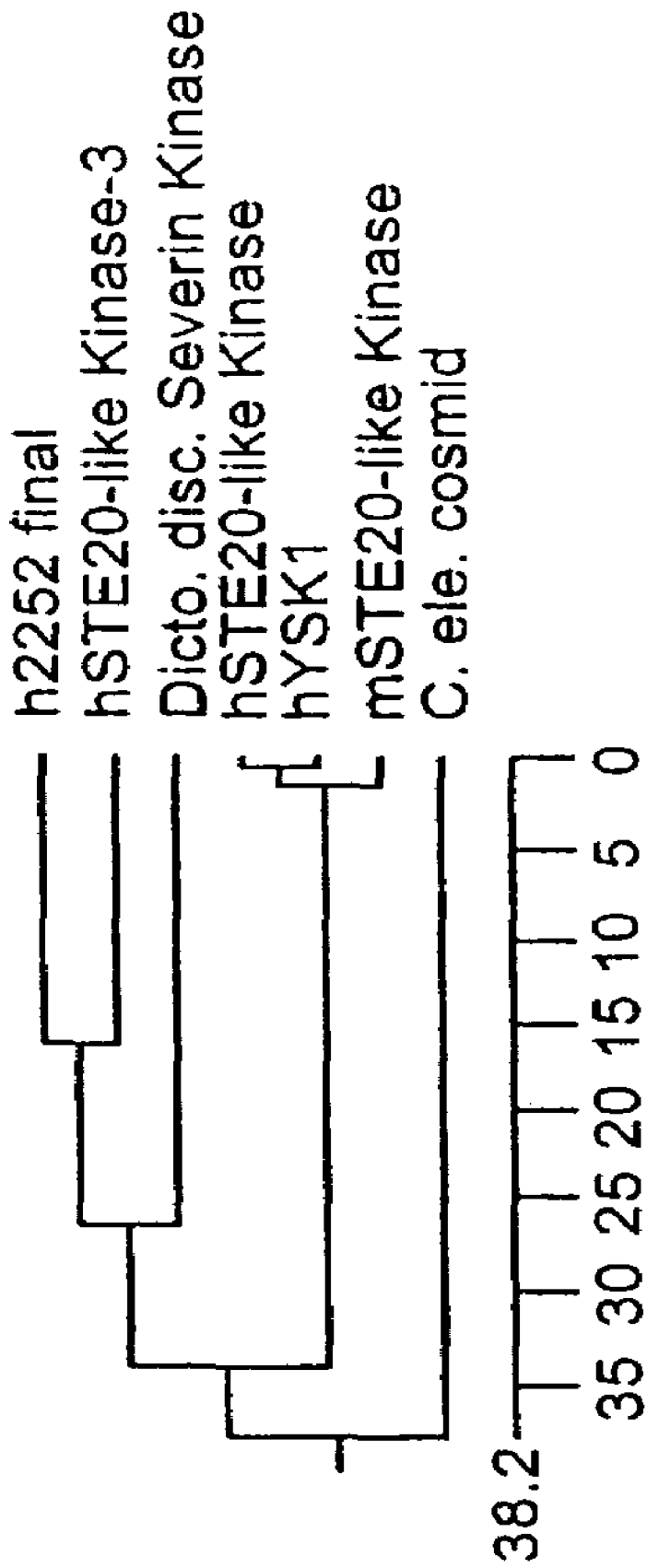
FIG. 21 shows a dendrogram for the h2252 gene.

The partial length h2252 protein displays similarity to several protein kinases (see FIGS. 20A-20G). Dendrogram analysis of this gene indicates it shares closest homology with the human Ste2O-like kinase 3 (hSTE20-like Kinase-3; GenBank Accession Number AAB82560; SEQ ID NO:53). The h2252 protein shares approximately 73% identity with this protein kinase receptor as determined by pairwise alignment (see Needleman and Wunsch (1970) *J. Mol. Biol.* 48:444). (see FIG. 21).

Preferred kinase polypeptides of the present invention have an amino acid sequence sufficiently identical to the amino acid sequence of SEQ ID NO:2, 4, 6, 8, 10, 12, or 14, or a domain thereof. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to kinase nucleic acid molecules of the invention. BLAST protein searches can be performed with the XBLAST program, score=50, wordlength=3, to obtain amino acid sequences homologous to kinase protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. When utilizing BLAST, Gapped BLAST, and PSI-Blast programs, the default parameters of the respective programs (e.g., XBLAST and NBLAST) can be used (accessible at the website maintained by the National Center for Biotechnology Information, Bethesda, Md.). Another preferred, example of an algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. A preferred program is the Pairwise Alignment Program (Sequence Explorer), using default parameters.

Accordingly, another embodiment of the invention features isolated kinase proteins and polypeptides having a kinase protein activity. As used interchangeably herein, a "kinase protein activity", "biological activity of a kinase protein", or "functional activity of a kinase protein" refers to an activity exerted by a kinase protein, polypeptide, or nucleic acid molecule on a kinase-responsive cell as determined in vivo, or in vitro, according to standard assay techniques. A kinase activity can be a direct activity, such as an association with or an enzymatic activity on a second protein, or an indirect activity, such as a cellular signaling activity mediated by interaction of the kinase protein with a second protein. In a preferred embodiment, a kinase activity includes at least one or more of the following activities: (1) modulating (stimulating and/or enhancing or inhibiting) cellular proliferation, growth and/or metabolism (e.g. in those cells in which the sequence is expressed, including, lymph node, spleen, thymus, brain, lung, skeletal muscle, fetal liver, tonsil, colon, heart, liver, immune cells, including Th1, Th2, T cells, natural killer T cells, lymphocytes, leukocytes, blood marrow, etc.); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function, e.g., actin bundling.

An "isolated" or "purified" kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For purposes of the invention, "isolated"

when used to refer to nucleic acid molecules excludes isolated chromosomes. For example, in various embodiments, the isolated kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase protein that is substantially free of cellular material includes preparations of kinase protein having less than about 30%, 20%, 10%, or 5% (by dry weight) of non-kinase protein (also referred to herein as a "contaminating protein"). When the kinase protein or biologically active portion thereof is recombinantly produced, preferably, culture medium represents less than about 30%, 20%, 10%, or 5% of the volume of the protein preparation. When kinase protein is produced by chemical synthesis, preferably the protein preparations have less than about 30%, 20%, 10%, or 5% (by dry weight) of chemical precursors or non-kinase chemicals.

Various aspects of the invention are described in further detail in the following subsections.

I. Isolated Nucleic Acid Molecules

One aspect of the invention pertains to isolated nucleic acid molecules comprising nucleotide sequences encoding kinase proteins or biologically active portions thereof, as well as nucleic acid molecules sufficient for use as hybridization probes to identify kinase-encoding nucleic acids (e.g., kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the kinase proteins of the present invention include sequences set forth in SEQ ID NOs: 1, 3, 5, 7, 9, 11, and 13, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the kinase proteins encoded by these nucleotide sequences are set forth in SEQ ID NOs:2, 4, 6, 8, 10, 12, and 14, respectively.

Nucleic acid molecules that are fragments of these kinase nucleotide sequences are also encompassed by the present invention. By "fragment" is intended a portion of the nucleotide sequence encoding a kinase protein of the invention. A fragment of a kinase nucleotide sequence may encode a biologically active portion of a kinase protein, or it may be a fragment that can be used as a hybridization probe or PCR primer using methods disclosed below. A biologically active portion of a kinase protein can be prepared by isolating a portion of one of the kinase nucleotide sequences of the invention, expressing the encoded portion of the kinase protein (e.g., by recombinant expression in vitro), and assessing the activity of the encoded portion of the kinase protein. Generally, nucleic acid molecules that are fragments of a kinase nucleotide sequence comprise at least 15, 20, 50, 75, 100, 325, 350, 375, 400, 425, 450 or 500 nucleotides, or up to the number of nucleotides present in a full-length kinase nucleotide sequence disclosed herein (for example, 1586, 831, 2060, 1697, 981, 518 or 1737 nucleotides for SEQ ID NO:1, 3, 5, 7, 9, 11, or 13, respectively) depending upon the intended use.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a kinase nucleotide sequence that encodes a biologically active portion of a kinase protein of the invention will encode at least 15, 25, 30, 50, 75, 100, 125, 150, 160, or 170 contiguous amino acids, or up to the total number of amino acids present in a full-length kinase protein of the invention (for example, 322, 174, 209, 503, 326, 172, or 416 amino acids for SEQ ID NO:2, 4, 6, 8, 10, 12, or 14, respectively). Fragments of a kinase nucleotide sequence that are useful as hybridization probes for PCR primers generally need not encode a biologically active portion of a kinase protein.

Nucleic acid molecules that are variants of the kinase nucleotide sequences disclosed herein are also encompassed by the present invention. "Variants" of the kinase nucleotide sequences include those sequences that encode the kinase proteins disclosed herein but that differ conservatively because of the degeneracy of the genetic code. These naturally-occurring allelic variants can be identified with the use of well-known molecular biology techniques, such as polymerase chain reaction (PCR) and hybridization techniques as outlined below. Variant nucleotide sequences also include synthetically-derived nucleotide sequences that have been generated, for example, by using site-directed mutagenesis but which still encode the kinase proteins disclosed in the present invention as discussed below. Generally, nucleotide sequence variants of the invention will have at least 45%, 55%, 65%, 75%, 85%, 95%, or 98% identity to the nucleotide sequences disclosed herein. A variant kinase nucleotide sequence will encode a kinase protein that has an amino acid sequence having at least 45%, 55%, 65%, 75%, 85%, 95%, or 98% identity to an amino acid sequence of a kinase protein disclosed herein.

In addition to the kinase nucleotide sequences shown in SEQ ID NOs:1, 3, 5, 7, 9, 11, and 13, it will be appreciated by those skilled in the art that DNA sequence polymorphisms that lead to changes in the amino acid sequences of kinase proteins may exist within a population (e.g., the human population). Such genetic polymorphism in a kinase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a kinase protein, preferably a mammalian kinase protein. As used herein, the phrase "allelic variant" refers to a nucleotide sequence that occurs at a kinase locus or to a polypeptide encoded by the nucleotide sequence. Such natural allelic variations can typically result in 1-5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding kinase proteins from other species (kinase homologues), which have a nucleotide sequence differing from that of the kinase sequences disclosed herein, are intended to be within the scope of the invention. Nucleic acid molecules corresponding to natural allelic variants and homologues of the kinase cDNAs of the invention can be isolated based on their identity to the mouse kinase nucleic acids disclosed herein using the mouse cDNAs, or a portion thereof, as a hybridization probe according to standard hybridization techniques under stringent hybridization conditions as disclosed below.

In addition to naturally-occurring allelic variants of the kinase sequence that may exist in the population, the skilled artisan will further appreciate that changes can be introduced by mutation into the nucleotide sequences of the invention thereby leading to changes in the amino acid sequence of the encoded kinase protein, without altering the biological activity of the kinase protein. Thus, an isolated nucleic acid molecule encoding a kinase protein having a sequence that differs from that of SEQ ID NO:2, 4, 6, 8, 10, 12, or 14 can be created by introducing one or more nucleotide substitutions, additions, or deletions into the nucleotide sequences disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a kinase protein (e.g., the sequence of SEQ ID NO:2, 4, 6, 8, 10, 12, or 14) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the critical eukaryotic protein kinase domain of all disclosed clones, and the phosphofructo-kinase domain of clone h2252, where such residues are essential for protein activity.

Alternatively, variant kinase nucleotide sequences can be made by introducing mutations randomly along all or part of a kinase coding sequence, such as by saturation mutagenesis, and the resultant mutants can be screened for kinase biological activity to identify mutants that retain activity. Following mutagenesis, the encoded protein can be expressed recombinantly, and the activity of the protein can be determined using standard assay techniques.

Thus the nucleotide sequences of the invention include those sequences disclosed herein as well as fragments and variants thereof. The kinase nucleotide sequences of the invention, and fragments and variants thereof, can be used as probes and/or primers to identify and/or clone kinase homologues in other cell types, e.g., from other tissues, as well as kinase homologues from other mammals. Such probes can be used to detect transcripts or genomic sequences encoding the same or identical proteins. These probes can be used as part of a diagnostic test kit for identifying cells or tissues that misexpress a kinase protein, such as by measuring levels of a kinase-encoding nucleic acid in a sample of cells from a subject, e.g., detecting kinase mRNA levels or determining whether a genomic kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Kinase nucleotide sequences isolated based on their sequence identity to the kinase nucleotide sequences set forth herein or to fragments and variants thereof are encompassed by the present invention.

In a hybridization method, all or part of a known kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase nucleic acid molecule hybridizes under stringent conditions to a probe that is a nucleic acid molecule comprising one of the kinase nucleotide sequences of the invention or a fragment thereof. In another embodiment, the previously unknown kinase nucleic acid molecule is at least 300, 325, 350, 375, 400, 425, 450, 500, 550, 600, 650, 700, 800, 900, 1000, 2,000, 3,000, or 4,000 nucleotides in length and hybridizes under stringent conditions to a probe that is a nucleic acid molecule comprising one of the kinase nucleotide sequences disclosed herein or a fragment thereof.

Accordingly, in another embodiment, an isolated previously unknown kinase nucleic acid molecule of the invention is at least 300, 325, 350, 375, 400, 425, 450, 500, 518, 550, 600, 650, 700, 800, 831, 900, 981, 1000, 1,100, 1,200, 1,300, 1,400, 1,500, 1,600, 1,700, 1,800, 1,900, 2,000, or 2,060 nucleotides in length and hybridizes under stringent conditions to a probe that is a nucleic acid molecule comprising one of the nucleotide sequences of the invention, preferably the coding sequence set forth in SEQ ID NO:1, 3, 5, 7, 9, 11, or 13, or a complement, fragment, or variant thereof.

As used herein, the term "hybridizes under stringent conditions" is intended to describe conditions for hybridization and washing under which nucleotide sequences having at least 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50-65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a kinase sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the kinase nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the kinase nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequences encoding a kinase protein disclosed herein (e.g., SEQ ID NOs:1, 3, 5, 7, 9, 11, and 13), antisense nucleic acids of the invention can be designed according to the rules of Watson and Crick base pairing. The antisense nucleic acid molecule can be complementary to the entire coding region of kinase mRNA, but more preferably is an oligonucleotide that is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave kinase mRNA transcripts to thereby inhibit translation of kinase mRNA. A ribozyme having specificity for a kinase-encoding nucleic acid can be designed based upon the nucleotide sequence of a kinase cDNA disclosed herein (e.g., SEQ ID NO:1, 3, 5, 7, 9, 11, or 13). See, e.g., Cech et al., U.S. Pat. No. 4,987,071; and Cech et al., U.S. Pat. No. 5,116,742. Alternatively, kinase mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, kinase gene expression can be inhibited by targeting nucleotide sequences complementary to the regulatory region of the kinase protein (e.g., the kinase promoter and/or enhancers) to form triple helical structures that prevent transcription of the kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al.

(1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a kinase molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra, or as probes or primers for DNA sequence and hybridization (Hyrup (1996), supra; Perry-O'Keefe et al. (1996), supra).

In another embodiment, PNAs of a kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357-63; Mag et al. (1989) *Nucleic Acids Res.* 17:5973; and Peterser et al. (1975) *Bioorganic Med. Chem. Lett.* 5:1119.

II. Isolated Kinase Proteins and Anti-kinase Antibodies

Kinase proteins are also encompassed within the present invention. By "kinase protein" is intended proteins having the amino acid sequence set forth in SEQ ID NO: 2, 4, 6, 8, 10, 12, or 14, as well as fragments, biologically active portions, and variants thereof.

"Fragments" or "biologically active portions" include polypeptide fragments suitable for use as immunogens to raise anti-kinase antibodies. Fragments include peptides comprising amino acid sequences sufficiently identical to or derived from the amino acid sequences of a kinase protein of the invention and exhibiting at least one activity of a kinase protein, but which include fewer amino acids than the full-length kinase proteins disclosed herein. Typically, biologically active portions comprise a domain or motif with at least one activity of the kinase protein. A biologically active portion of a kinase protein can be a polypeptide which is, for example, 10, 25, 50, 100 or more amino acids in length. Such biologically active portions can be prepared by recombinant techniques and evaluated for one or more of the functional activities of a native kinase protein.

By "variants" is intended proteins or polypeptides having an amino acid sequence that is at least about 45%, 55%, 65%, preferably about 75%, 85%, 95%, or 98% identical to the amino acid sequence of SEQ ID NO: 2, 4, 6, 8, 10, 12, or 14. Variants also include variants of polypeptides encoded by a nucleic acid molecule that hybridizes to a nucleic acid molecule of SEQ ID NO: 1, 3, 5, 7, 9, 11, or 13, or a complement thereof under stringent conditions. Such variants generally retain the functional activity of the kinase proteins of the invention. Variants include polypeptides that differ in amino acid sequence due to natural allelic variation or mutagenesis.

The invention also provides kinase chimeric or fusion proteins. As used herein, a kinase "chimeric protein" or "fusion protein" comprises a kinase polypeptide operably linked to a non-kinase polypeptide. A "kinase polypeptide" refers to a polypeptide having an amino acid sequence corresponding to a kinase protein, whereas a "non-kinase polypeptide" refers to a polypeptide having an amino acid sequence corresponding to a protein that is not substantially identical to the kinase protein, e.g., a protein that is different from the kinase protein and which is derived from the same or a different organism. Within a kinase fusion protein, the kinase polypeptide can correspond to all or a portion of a kinase protein, preferably at least one biologically active portion of a kinase protein. Within the fusion protein, the term "operably linked" is intended to indicate that the kinase polypeptide and the non-kinase polypeptide are fused in-frame to each other. The non-kinase polypeptide can be fused to the N-terminus or C-terminus of the kinase polypeptide.

One useful fusion protein is a GST-kinase fusion protein in which the kinase sequences are fused to the C-terminus of the GST sequences. Such fusion proteins can facilitate the purification of recombinant kinase proteins.

In yet another embodiment, the fusion protein is a kinase-immunoglobulin fusion protein in which all or part of a kinase protein is fused to sequences derived from a member of the immunoglobulin protein family. The kinase-immunoglobulin fusion proteins of the invention can be incorporated into pharmaceutical compositions and administered to a subject to inhibit an interaction between a kinase ligand and a kinase protein on the surface of a cell, thereby suppressing kinase-mediated signal transduction in vivo. The kinase-immunoglobulin fusion proteins can be used to affect the bioavailability of a kinase cognate ligand. Inhibition of the kinase ligand/kinase interaction may be useful therapeutically, both for treating proliferative and differentiative disorders and for modulating (e.g., promoting or inhibiting) cell survival. Moreover, the kinase-immunoglobulin fusion proteins of the invention can be used as immunogens to produce anti-kinase antibodies in a subject, to purify kinase ligands, and in screening assays to identify molecules that inhibit the interaction of a kinase protein with a kinase ligand.

Preferably, a kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-encoding nucleic acid can be cloned into a commercially available expression vector such that it is linked in-frame to an existing fusion moiety. Variants of the kinase proteins can function as either kinase agonists (mimetics) or as kinase antagonists. Variants of the kinase protein can be generated by mutagenesis, e.g., discrete point mutation or truncation of the kinase protein. An agonist of the kinase protein can retain substantially the same or a subset of the biological activities of the naturally-occurring form of the kinase protein. An antagonist of the kinase protein can inhibit one or more of the activities of the naturally-occurring form of the kinase protein by, for example, competitively binding to a downstream or upstream member of a cellular signaling cascade that includes the kinase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the kinase proteins.

Variants of the kinase protein that function as either kinase agonists or as kinase antagonists can be identified by screening combinatorial libraries of mutants, e.g., truncation mutants, of the kinase protein for kinase protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods that can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang (1983) *Tetrahedron* 39:3; Itakura et al. (1984)*Annu. Rev. Biochem.* 53:323; Itakura et al. (1984) *Science* 198:1056; Ike et al. (1983) *Nucleic Acid Res.* 11:477).

In addition, libraries of fragments of the kinase protein coding sequence can be used to generate a variegated population of kinase fragments for screening and subsequent selection of variants of a kinase protein. In one embodiment, a library of coding sequence fragments can be generated by treating a double-stranded PCR fragment of a kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase proteins. The most widely used techniques, which are amenable to high throughput analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase variants (Arkin and Yourvan (1992) *Proc. Natl. Acad. Sci. USA* 89:7811-7815; Delgrave et al. (1993) *Protein Engineering* 6(3):327-331).

An isolated kinase polypeptide of the invention can be used as an immunogen to generate antibodies that bind kinase proteins using standard techniques for polyclonal and monoclonal antibody preparation. The full-length kinase protein can be used or, alternatively, the invention provides antigenic peptide fragments of kinase proteins for use as immunogens. The antigenic peptide of a kinase protein comprises at least 8, preferably 10, 15, 20, or 30 amino acid residues of the amino-acid sequence shown in SEQ ID NO:2, 4, 6, 8, 10, 12, or 14 and encompasses an epitope of a kinase protein such that an antibody raised against the peptide forms a specific immune complex with the kinase protein. Preferred epitopes encompassed by the antigenic peptide are regions of a kinase protein that are located on the surface of the protein, e.g., hydrophilic regions.

Accordingly, another aspect of the invention pertains to anti-kinase polyclonal and monoclonal antibodies that bind a kinase protein. Polyclonal anti-kinase antibodies can be prepared by immunizing a suitable subject (e.g., rabbit, goat, mouse, or other mammal) with a kinase immunogen. The anti-kinase antibody titer in the immunized subject can be monitored over time by standard techniques, such as with an enzyme linked immunosorbent assay (ELISA) using immobilized kinase protein. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B-cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550-52; Kenneth (1980) in *Monoclonal Antibodies: A New Dimension In Biological Analyses* (Plenum Publishing Corp., NY; and Lerner (1981) *Yale J. Biol. Med.*, 54:387-402).

Alternative to preparing monoclonal antibody-secreting hybridomas, a monoclonal anti-kinase antibody can be identified and isolated by screening a recombinant combinatorial immunoglobulin library (e.g., an antibody phage display library) with a kinase protein to thereby isolate immunoglobulin library members that bind the kinase protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) Science 246:1275-1281; Griffiths et al. (1993) *EMBO J.* 12:725-734.

Additionally, recombinant anti-kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125, 023, and 173,494; U.S. Pat. Nos. 4,816,567 and 5,225,539;

European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139: 3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *Bio/Techniques* 4:214; Jones et al. (1986) *Nature* 321:552-525; Verhoeyan et al. (1988) *Science* 239:1534; and Beidler et al. (1988) *J. Immunol.* 141: 4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

An anti-kinase antibody (e.g., monoclonal antibody) can be used to isolate kinase proteins by standard techniques, such as affinity chromatography or immunoprecipitation. An anti-kinase antibody can facilitate the purification of natural kinase protein from cells and of recombinantly produced kinase protein expressed in host cells. Moreover, an anti-kinase antibody can be used to detect kinase protein (e.g., in a cellular lysate or cell supernatant) in order to evaluate the abundance and pattern of expression of the kinase protein. Anti-kinase antibodies can be used diagnostically to monitor protein levels in tissue as part of a clinical testing procedure to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include $^{125}$I, $^{131}$I, $^{35}$S, or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp.

475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676, 980.

III. Recombinant Expression Vectors and Host Cells

Another aspect of the invention pertains to vectors, preferably expression vectors, containing a nucleic acid encoding a kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication-defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., kinase proteins, mutant forms of kinase proteins, fusion proteins, etc.).

The recombinant expression vectors of the invention can be designed for expression of kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301-315) and pET 11d (Studier et al. (1990) in *Gene Expression Technology: Methods in Enzymology* 185 (Academic Press, San Diego, Calif.), pp. 60-89). Strategies to maximize recombinant protein expression in *E. coli* can be found in Gottesman (1990) in *Gene Expression Technology: Methods in Enzymology* 185 (Academic Press, CA), pp. 119-128 and Wada et al. (1992) *Nucleic Acids Res.* 20:2111-2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39)); yeast cells (examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), particular promoters of T-cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Patent Publication No. 264,166). Developmentally-regulated promoters are also encompassed, for example the murine hox promoters (Kessel and Gruss (1990) *Science* 249:374-379), the α-fetoprotein promoter (Campes and Tilghman (1989) *Genes Dev.* 3:537-546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase protein. Accordingly, the invention further provides methods for producing kinase protein using the host cells of the invention. In one embodiment, the method comprises culturing the host cell of the invention, into which a recombinant expression vector encoding a kinase protein has been introduced, in a suitable medium such that kinase protein is produced. In another embodiment, the method further comprises isolating kinase protein from the medium or the host cell.

The host cells of the invention can also be used to produce nonhuman transgenic animals. For example, in one embodiment, a host cell of the invention is a fertilized oocyte or an embryonic stem cell into which kinase-coding sequences have been introduced. Such host cells can then be used to create nonhuman transgenic animals in which exogenous kinase sequences have been introduced into their genome or homologous recombinant animals in which endogenous kinase sequences have been altered. Such animals are useful for studying the function and/or activity of kinase genes and proteins and for identifying and/or evaluating modulators of kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinase-encoding nucleic acid into the male pronuclei of a fertilized oocyte, e.g., by microinjection, retroviral infection, and allowing the oocyte to develop in a pseudopregnant female foster animal. The kinase cDNA sequence can be introduced as a transgene into the genome of a nonhuman animal. Alternatively, a homologue of the mouse kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase transgene to direct expression of kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase transgene in its genome and/or expression of kinase mRNA in tissues or cells of the animals. A transgenic founder animal can then be used to breed additional animals, carrying the transgene. Moreover, transgenic animals carrying a transgene encoding kinase gene can further be bred to other transgenic animals carrying other transgenes.

To create a homologous recombinant animal, one prepares a vector containing at least a portion of a kinase gene or a homologue of the gene into which a deletion, addition, or substitution has been introduced to thereby alter, e.g., functionally disrupt, the kinase gene. In a preferred embodiment, the vector is designed such that, upon homologous recombination, the endogenous kinase gene is functionally disrupted (i.e., no longer encodes a functional protein; such vectors are also referred to as "knock out" vectors). Alternatively, the vector can be designed such that, upon homologous recombination, the endogenous kinase gene is mutated or otherwise altered but still encodes functional protein (e.g., the upstream regulatory region can be altered to thereby alter the expression of the endogenous kinase protein). In the homologous recombination vector, the altered portion of the kinase gene is flanked at its 5' and 3' ends by additional nucleic acid of the kinase gene to allow for homologous recombination to occur between the exogenous kinase gene carried by the vector and an endogenous kinase gene in an embryonic stem cell. The additional flanking kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced kinase gene has homologously recombined with the endogenous kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810-813 and PCT Publication Nos. WO 97/07668 and WO 97/07669.

IV. Pharmaceutical Compositions

The kinase nucleic acid molecules, kinase proteins, and anti-kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, NJ), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase protein or anti-kinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328, 470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express kinase protein (e.g., via a recombinant expression vector in a host cell in gene therapy applications), to detect kinase mRNA (e.g., in a biological sample) or a genetic lesion in a kinase gene, and to modulate kinase activity. In addition, the kinase proteins can be used to screen drugs or compounds that modulate cellular growth and/or metabolism as well as to treat disorders characterized by insufficient or excessive production of kinase protein or production of kinase protein forms that have decreased or aberrant activity compared to kinase wild type protein. In addition, the anti-kinase antibodies of the invention can be used to detect and isolate kinase proteins and modulate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to kinase proteins or have a stimulatory or inhibitory effect on, for example, kinase expression or kinase activity.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869), or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

Determining the ability of the test compound to bind to the kinase protein can be accomplished, for example, by coupling the test compound with a radioisotope or enzymatic label such that binding of the test compound to the kinase protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase protein to bind to or interact with a kinase target molecule. By "target molecule" is intended a molecule with which a kinase protein binds or interacts in nature. In a preferred embodiment, the ability of the kinase protein to bind to or interact with a kinase target molecule can be determined by monitoring the activity of the target molecule. For example, the activity of the target molecule can be monitored by detecting induction of a cellular second messenger of the target (e.g., intracellular Ca2+, diacylglycerol, IP3, etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, cellular differentiation or cell proliferation.

In yet another embodiment, an assay of the present invention is a cell-free assay comprising contacting a kinase protein or biologically active portion thereof with a test compound and determining the ability of the test compound to bind to the kinase protein or biologically active portion thereof. Binding of the test compound to the kinase protein can be determined either directly or indirectly as described above. In a preferred embodiment, the assay includes contacting the kinase protein or biologically active portion thereof with a known compound that binds kinase protein to form an assay mixture, contacting the assay mixture with a test compound, and determining the ability of the test compound to preferentially bind to kinase protein or biologically active portion thereof as compared to the known compound.

In another embodiment, an assay is a cell-free assay comprising contacting kinase protein or biologically active portion thereof with a test compound and determining the ability of the test compound to modulate (e.g., stimulate or inhibit) the activity of the kinase protein or biologically active portion thereof. Determining the ability of the test compound to modulate the activity of a kinase protein can be accomplished, for example, by determining the ability of the kinase protein to bind to a kinase target molecule as described above for determining direct binding. In an alternative embodiment, determining the ability of the test compound to modulate the activity of a kinase protein can be accomplished by determining the ability of the kinase protein to further modulate a kinase target molecule. For example, the catalytic/enzymatic activity of the target molecule on an appropriate substrate can be determined as previously described.

In yet another embodiment, the cell-free assay comprises contacting the kinase protein or biologically active portion thereof with a known compound that binds a kinase protein to form an assay mixture, contacting the assay mixture with a test compound, and determining the ability of the test compound to preferentially bind to or modulate the activity of a kinase target molecule.

In the above-mentioned assays, it may be desirable to immobilize either a kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either kinase protein or its target molecule can be immobilized utilizing conjugation of biotin and streptavidin. Biotinylated kinase molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase protein or target molecules but which do not interfere with binding of the kinase protein to its target molecule can be derivatized to the wells of the plate, and unbound target or kinase protein trapped in the wells by antibody conjugation. Methods for detecting such complexes, in addition to those described above for the GST-immobilized complexes, include immunodetection of complexes using antibodies reactive with the kinase protein or target molecule, as well as enzyme-linked assays that rely on detecting an enzymatic activity associated with the kinase protein or target molecule.

In another embodiment, modulators of kinase expression are identified in a method in which a cell is contacted with a candidate compound and the expression of kinase mRNA or protein in the cell is determined relative to expression of kinase mRNA or protein in a cell in the absence of the candidate compound. When expression is greater (statistically significantly greater) in the presence of the candidate compound than in its absence, the candidate compound is identified as a stimulator of kinase mRNA or protein expression. Alternatively, when expression is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/techniques* 14:920-924; Iwabuchi et al. (1993) *Oncogene* 8:1693-1696; and PCT Publication No. WO 94/10300), to identify other proteins, which bind to or interact with kinase protein ("kinase-binding proteins" or "kinase-bp") and modulate kinase activity. Such kinase-binding proteins are also likely to be involved in the propagation of signals by the kinase proteins as, for example, upstream or downstream elements of a signaling pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial kinase gene sequences of the invention can be used to map their respective kinase genes on a chromosome, thereby facilitating the location of gene regions associated with genetic disease. Computer analysis of kinase sequences can be used to rapidly select PCR primers (preferably 15-25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919-924). Somatic cell hybrids containing only fragments of human chromosomes can also be produced by using human chromosomes with translocations and deletions.

Other mapping strategies that can similarly be used to map a kinase sequence to its chromosome include in situ hybridization (described in Fan et al. (1990) *Proc. Natl. Acad. Sci. USA* 87:6223-27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection.

Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with the kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the kinase sequences of the invention can be used to prepare two PCR primers from the 5☐ and 3☐ ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1, 3, 5, 7, 9, 11, or 13 can comfortably provide positive individual identification with a panel of perhaps 10 to 1,000 primers that each yield a noncoding amplified sequence of 100 bases. If predicted coding sequences, such as those in SEQ ID NO:1, 3 5, 7, 9, 11, or 13 are used, a more appropriate number of primers for positive individual identification would be 500 to 2,000.

3. Use of Partial kinase Sequences in Forensic Biology

DNA-based identification techniques can also be used in forensic biology. In this manner, PCR technology can be used to amplify DNA sequences taken from very small biological samples such as tissues, e.g., hair, skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1, 3, 5, 7, 9, 11, or 13 are particularly appropriate for this use as greater numbers of polymorphisms occur in the noncoding regions, making it easier to differentiate individuals using this technique. Examples of polynucleotide reagents include the kinase sequences or portions thereof, e.g., fragments derived from the noncoding regions of SEQ ID NO:1, 3, 5, 7, 9, 11, or 13 having a length of at least 20 or 30 bases.

The kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase probes, can be used to identify tissue by species and/or by organ type.

In a similar fashion, these reagents, e.g., kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting kinase protein and/or nucleic acid expression as well as kinase activity, in the context of a biological sample. An exemplary method for detecting the presence or absence of kinase proteins in a biological sample involves obtaining a biological sample from a test subject and contacting the biological sample with a compound or an agent capable of detecting kinase protein or nucleic acid (e.g., mRNA, genomic DNA) that encodes kinase protein such that the presence of kinase protein is detected in the biological sample. Results obtained with a biological sample from the test subject may be compared to results obtained with a biological sample from a control subject.

A preferred agent for detecting kinase mRNA or genomic DNA is a labeled nucleic acid probe capable of hybridizing to kinase mRNA or genomic DNA. The nucleic acid probe can be, for example, a full-length or partial kinase nucleic acid, such as the nucleic acid of SEQ ID NO:1, 3, 5, 7, 9, 11, or 13, or a portion thereof, such as a nucleic acid molecule of at least 15, 30, 50, 100, 250, or 500 nucleotides in length and sufficient to specifically hybridize under stringent conditions to kinase mRNA or genomic DNA. Other suitable probes for use in the diagnostic assays of the invention are described herein.

A preferred agent for detecting kinase protein is an antibody capable of binding to kinase protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of kinase protein include enzyme linked immunosorbent assays (ELISAs), Western blots, immunoprecipitations, and immunofluorescence. In vitro techniques for detection of kinase genomic DNA include Southern hybridizations. Furthermore, in vivo techniques for detection of kinase protein include introducing into a subject a labeled anti-kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase proteins in a biological sample (a test sample). Such kits can be used to determine if a subject is suffering from or is at increased risk of developing a disorder associated with aberrant expression of kinase protein. For example, the kit can comprise a labeled compound or agent capable of detecting kinase protein or mRNA in a biological sample and means for determining the amount of a kinase protein in the sample (e.g., an anti-kinase antibody or an oligonucleotide probe that binds to DNA encoding a kinase protein, e.g., SEQ ID NO:1, 3, 5, 7, 9, 11, or 13). Kits can also include instructions for observing that the tested subject is suffering from or is at risk of developing a disorder associated with aberrant expression of kinase sequences if the amount of kinase protein or mRNA is above or below a normal level.

For antibody-based kits, the kit can comprise, for example: (1) a first antibody (e.g., attached to a solid support) that binds to kinase protein; and, optionally, (2) a second, different antibody that binds to kinase protein or the first antibody and is conjugated to a detectable agent. For oligonucleotide-based kits, the kit can comprise, for example: (1) an oligonucleotide, e.g., a detectably labeled oligonucleotide, that hybridizes to a kinase nucleic acid sequence or (2) a pair of primers useful for amplifying a kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase proteins.

2. Prognostic Assays

The methods described herein can furthermore be utilized as diagnostic or prognostic assays to identify subjects having or at risk of developing a disease or disorder associated with kinase protein, kinase nucleic acid expression, or kinase activity. Prognostic assays can be used for prognostic or predictive purposes to thereby prophylactically treat an individual prior to the onset of a disorder characterized by or associated with kinase protein, kinase nucleic acid expression, or kinase activity.

Thus, the present invention provides a method in which a test sample is obtained from a subject, and kinase protein or nucleic acid (e.g., mRNA, genomic DNA) is detected, wherein the presence of kinase protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase activity) to effectively treat a disease or disorder associated with aberrant kinase expression or activity. In this manner, a test sample is obtained and kinase protein or nucleic acid is detected. The presence of kinase protein or nucleic acid is diagnostic for a subject that can be administered the agent to treat a disorder associated with aberrant kinase expression or activity.

The methods of the invention can also be used to detect genetic lesions or mutations in a kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a kinase-protein, or the misexpression of the kinase gene. For example, such genetic lesions or mutations can be detected by ascertaining the existence of at least one of: (1) a deletion of one or more nucleotides from a kinase gene; (2) an addition of one or more nucleotides to a kinase gene; (3) a substitution of one or more nucleotides of a kinase gene; (4) a chromosomal rearrangement of a kinase gene; (5) an alteration in the level of a messenger RNA transcript of a kinase gene; (6) an aberrant modification of a kinase gene, such as of the methylation pattern of the genomic DNA; (7) the presence of a non-wild-type splicing pattern of a messenger RNA transcript of a kinase gene; (8) a non-wild-type level of a kinase-protein; (9) an allelic loss of a kinase gene; and (10) an inappropriate post-translational modification of a kinase-protein. As described herein, there are a large number of assay techniques known in the art that can be used for detecting lesions in a kinase gene. Any cell type or tissue in which kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the kinase-gene (see, e.g., Abravaya et al. (1995) *Nucleic Acids Res.* 23:675-682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase molecule can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). In yet another embodiment, any of a variety of sequencing reactions known in the art can be used to directly sequence the kinase gene and detect mutations by comparing the sequence of the sample kinase gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the kinase gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in kinase cDNAs obtained from samples of cells. See, e.g., Hsu et al. (1994) *Carcinogenesis* 15:1657-1662. According to an exemplary embodiment, a probe based on a kinase sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA*

88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a kinase gene.

3. Pharmacogenomics

Agents or modulators that have a stimulatory or inhibitory effect on kinase activity (e.g., kinase gene expression) as identified by a screening assay described herein, can be administered to individuals to treat (prophylactically or therapeutically) disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase protein, expression of kinase nucleic acid, or mutation content of kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase protein, expression of kinase nucleic acid, or mutation content of kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase modulator, such as a modulator identified by one of the exemplary screening assays described herein.

4. Monitoring of Effects During Clinical Trials

Monitoring the influence of agents (e.g., drugs, compounds) on the expression or activity of kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase gene expression, protein levels, or protein activity, can be monitored in clinical trials of subjects exhibiting decreased or increased kinase gene expression, protein levels, or protein activity. In such clinical trials, kinase expression or activity and preferably that of other genes that have been implicated in for example, a cellular proliferation disorder, can be used as a marker of cellular growth and differentiation.

For example, and not by way of limitation, genes that are modulated in cells by treatment with an agent (e.g., compound, drug, or small molecule) that modulates kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase protein, mRNA, or genomic DNA in the preadministration sample; (3) obtaining one or more postadministration samples from the subject; (4) detecting the level of expression or activity of the kinase protein, mRNA, or genomic DNA in the postadministration samples; (5) comparing the level of expression or activity of the kinase protein, mRNA, or genomic DNA in the preadministration sample with the kinase protein, mRNA, or genomic DNA in the postadministration sample or samples; and (vi) altering the administration of the agent to the subject accordingly to bring about the desired effect, i.e., for example, an increase or a decrease in the expression or activity of a kinase protein.

C. Methods of Treatment

The present invention provides for both prophylactic and therapeutic methods of treating a subject at risk of (or susceptible to) a disorder or having a disorder associated with aberrant kinase expression or activity. Additionally, the compositions of the invention find use in the treatment of disorders described herein.

1. Prophylactic Methods

In one aspect, the invention provides a method for preventing in a subject a disease or condition associated with an aberrant kinase expression or activity by administering to the subject an agent that modulates kinase expression or at least one kinase gene activity. Subjects at risk for a disease that is caused, or contributed to, by aberrant kinase expression or activity can be identified by, for example, any or a combination of diagnostic or prognostic assays as described herein. Administration of a prophylactic agent can occur prior to the manifestation of symptoms characteristic of the kinase aberrancy, such that a disease or disorder is prevented or, alternatively, delayed in its progression. Depending on the type of kinase aberrancy, for example, a kinase agonist or kinase antagonist agent can be used for treating the subject. The appropriate agent can be determined based on screening assays described herein.

2. Therapeutic Methods

Another aspect of the invention pertains to methods of modulating kinase expression or activity for therapeutic purposes. The modulatory method of the invention involves contacting a cell with an agent that modulates one or more of the activities of kinase protein activity associated with the cell. An agent that modulates kinase protein activity can be an agent as described herein, such as a nucleic acid or a protein, a naturally-occurring cognate ligand of a kinase protein, a peptide, a kinase peptidomimetic, or other small molecule. In one embodiment, the agent stimulates one or more of the biological activities of kinase protein. Examples of such stimulatory agents include active kinase protein and a nucleic acid molecule encoding a kinase protein that has been introduced into the cell. In another embodiment, the agent inhibits one or more of the biological activities of kinase protein. Examples of such inhibitory agents include antisense kinase nucleic acid molecules and anti-kinase antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a kinase protein or nucleic acid molecule. In one embodiment, the method involves administering an agent (e.g., an agent identified by a screening assay described herein), or a combination of agents, that modulates (e.g., upregulates or downregulates) kinase expression or activity. In another embodiment, the method involves administering a kinase protein or nucleic acid molecule as therapy to compensate for reduced or aberrant kinase expression or activity.

Stimulation of kinase activity is desirable in situations in which a kinase protein is abnormally downregulated and/or in which increased kinase activity is likely to have a beneficial effect. Conversely, inhibition of kinase activity is desirable in situations in which kinase activity is abnormally upregulated and/or in which decreased kinase activity is likely to have a beneficial effect.

This invention is further illustrated by the following examples, which should not be construed as limiting.

EXAMPLES

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using $\beta$-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Novel kinase expression was measured by TaqMan® quantitative PCR (Perkin Elmer Applied Biosystems) in cDNA prepared from the following normal human tissues: lymph node, spleen, thymus, brain, lung, skeletal muscle, fetal liver, tonsil, colon, heart, and liver from one or two adult donors; fibrotic liver samples prepared from two to seven different donors; resting and phytohemaglutinin activated peripheral blood mononuclear cells (PBMC); $CD3^+$, $CD4^+$, and $CD8^+$ T cells; Th1 and Th2 cells stimulated for six or 48 hours with anti-CD3 antibody; resting and lipopolysaccharide activated $CD19^+B$ cells; $CD34^+$ cells from mobilized peripheral blood (mPB $CD34^+$), adult resting bone marrow (ABM $CD34^+$), G-CSF mobilized bone marrow (mBM $CD34^+$), and neonatal umbilical cord blood (CB $CD34^+$); G-CSF mobilized peripheral blood leukocytes (mPB leukocytes) and $CD34^-$ cells purified from mPB leukocytes (mPB $CD34^-$); $CD14^+$ cells; and granulocytes. Transformed human cell lines included K526, an erythroleukemia; HL60, an acute promyelocytic leukemia; Jurkat, a T cell leukemia; HEK 293, epithelial cells from embryonic kidney transformed with adenovirus 5 DNA; and Hep3B hepatocellular liver carcinoma cells cultured in normal (HepB normoxia) or reduced oxygen tension (Hep3B hypoxia).

Probes were designed by PrimerExpress software (PE Biosystems) based on the sequence of each kinase gene. The primers and probes for expression analysis of h12832, h14138, h14833, h15990, h16341, and h2252, respectively, and for $\beta$-2 microglobulin were as follows:

```
h12832 Forward Primer:
TTTTCACCTCCGACCTTTCCT                   (SEQ ID NO:56)

h12832 Reverse Primer:
ATCCCTTCCATTGTGAAAGCC                   (SEQ ID NO:57)

h12832 TaqMan Probe:
CCAGGCGGTGAGACTCTGGACTGAG               (SEQ ID NO:58)

h14138 Forward Primer:
CACGAGGCTAGACTAAAAGGAAAATT              (SEQ ID NO:59)
```

-continued

```
h14138 Reverse Primer:
TGAAGCCAGGAATACTGCTCAG                      (SEQ ID NO:60)

h14138 TaqMan Prober:
TTGTGCTACAGACTAAATCCAGATACGGTCAG-GT         (SEQ ID NO:61)

h14833 Forward Primer:
CCTGCCTCCCACTCATCG                          (SEQ ID NO:62)

h14833 Reverse Primer:
CAGCTGGTTCTGTAGAGGACGAA                     (SEQ ID NO:63)

h14833 TaqMan Probe:
ATGCTCTGACTGCTCACTGCCTGGATC                 (SEQ ID NO:64)

h15990 Forward Primer:
GGCAAAGGCGGGTTCG                            (SEQ ID NO:65)

h15990 Reverse Primer:
TTGACCGCCACATCGTAGC                         (SEQ ID NO:66)

h15990 TaqMan Probe:
CCGGGCGCAACATAGGAAGTGG                      (SEQ ID NO:67)

h16341 Forward Primer:
CAGTTGCTAGACAGTAACCTGCATT                   (SEQ ID NO:68)

h16341 Reverse Primer:
TGAGGCCCACTGCTATGTCA                        (SEQ ID NO:69)

h16341 TaqMan Probe:
CCTTGGACTGTGAGGGTAAAACTGGCC                 (SEQ ID NO:70)

h2252 Forward Primer:
TCTGATTCCGAGGGCTCTGA                        (SEQ ID NO:71)

h2252 Reverse Primer:
ACGGTGGTAAAGTCTCATTCA                       (SEQ ID NO:72)

h2252 TaqMan Probe:
CGGAATCTACCAGCAGGGAAAACAATACTCAT-C          (SEQ ID NO:73)

β-2 microglobulin Forward Primer
CACCCCCACTGAAAAAGATGA                       (SEQ ID NO:74)

β-2 microglobulin Reverse Primer
CTTAACTATCTTGGGCTGTGACAAAG                  (SEQ ID NO:75)

β-2 microglobulin TaqMan Prober
TATGCCTGCCGTGTGAACCACGTG                    (SEQ ID NO:76)
```

Each kinase gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate kinase gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the kinase gene is normalized by subtracting the Ct value of the β-2 microglobulin gene to obtain a $_\Delta$Ct value using the following formula: $_\Delta Ct = Ct_{kinase} - Ct_{\beta-2\ microglobulin}$. Expression is then calibrated against a cDNA sample showing a comparatively low level of expression of the kinase gene. The $_\Delta$Ct value for the calibrator sample is then subtracted from $_\Delta$Ct for each tissue sample according to the following formula: $_{\Delta\Delta}Ct = {_\Delta Ct_{sample}} - {_\Delta Ct_{Calibrator}}$. Relative expression is then calculated using the arithmetic formula given by $2^{-\Delta\Delta Ct}$. Expression of the target kinase gene in each of the tissues tested is then graphically represented as discussed in more detail below.

Figure 22:
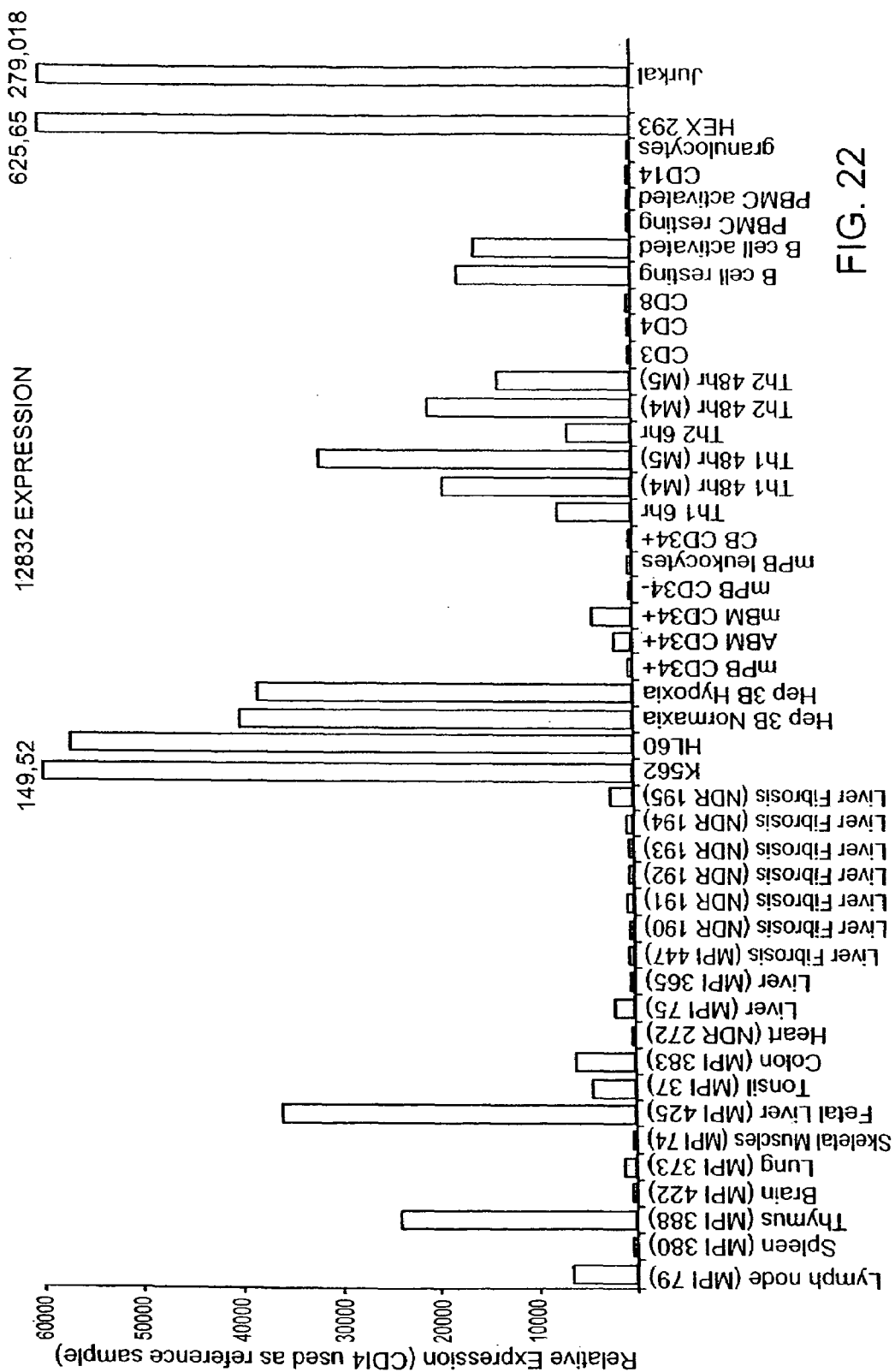
FIG. 22 shows expression of h12832 in various tissues and cell types relative to expression in human CD14.

FIG. 22 shows expression of h12832 in various tissues and cell lines as described above, relative to expression in CD14$^+$ cells. The results indicate significant expression in thymus, fetal liver, B cells, Th1 and Th2 samples, and the K562, HL60, HEK 293, and Jurkat cell lines.

Figure 23:
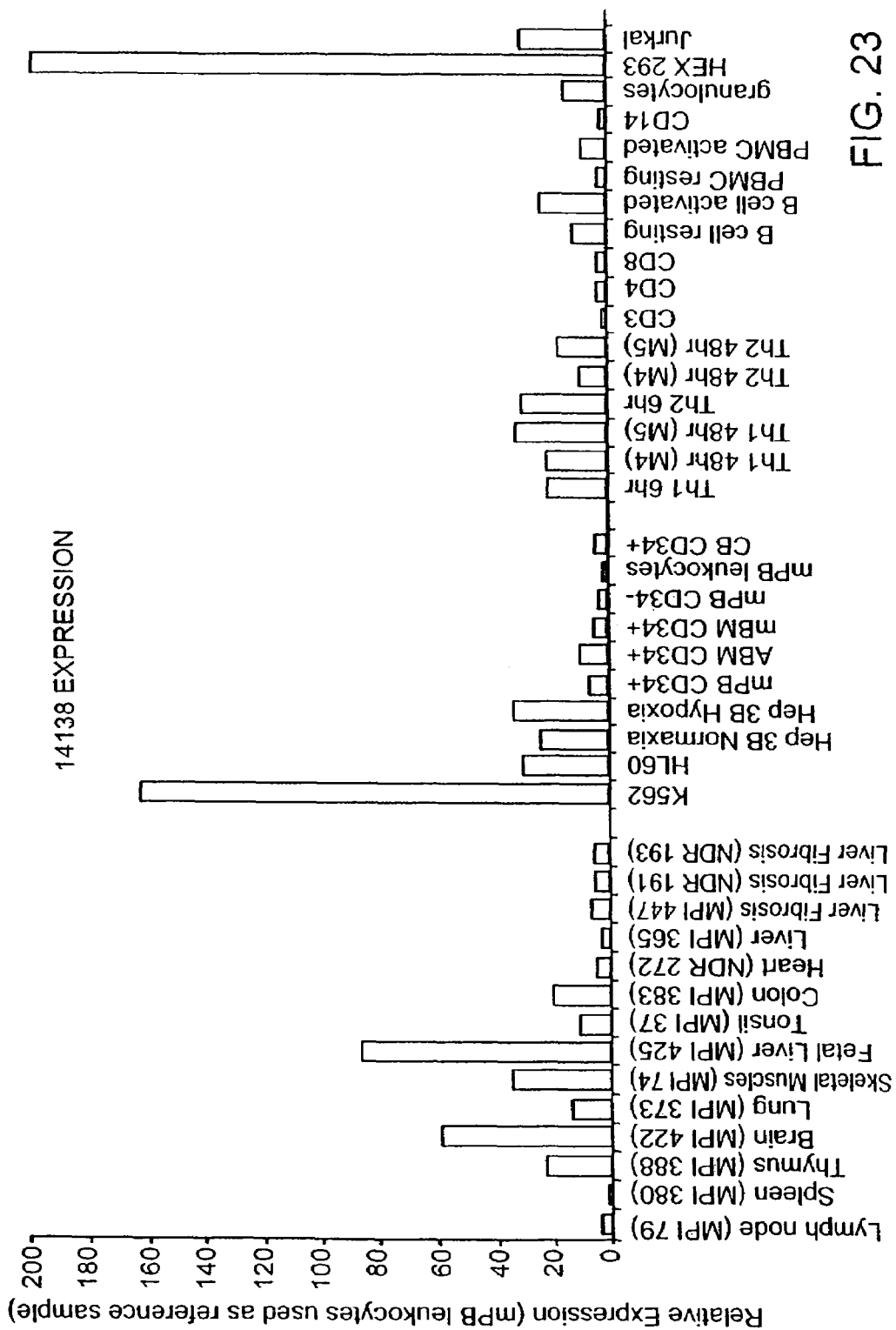
FIG. 23 shows expression of h14138 in various tissues and cell types relative to expression in human mPB leukocytes.

FIG. 23 shows expression of h14138 in various tissues and cell lines as described above, relative to expression in mPB leukocytes. The results indicate broad tissue expression and significant expression in Th1 and Th2 cells, and the K562, HL60, HEK 293, and Jurkat cell lines.

Figure 24:
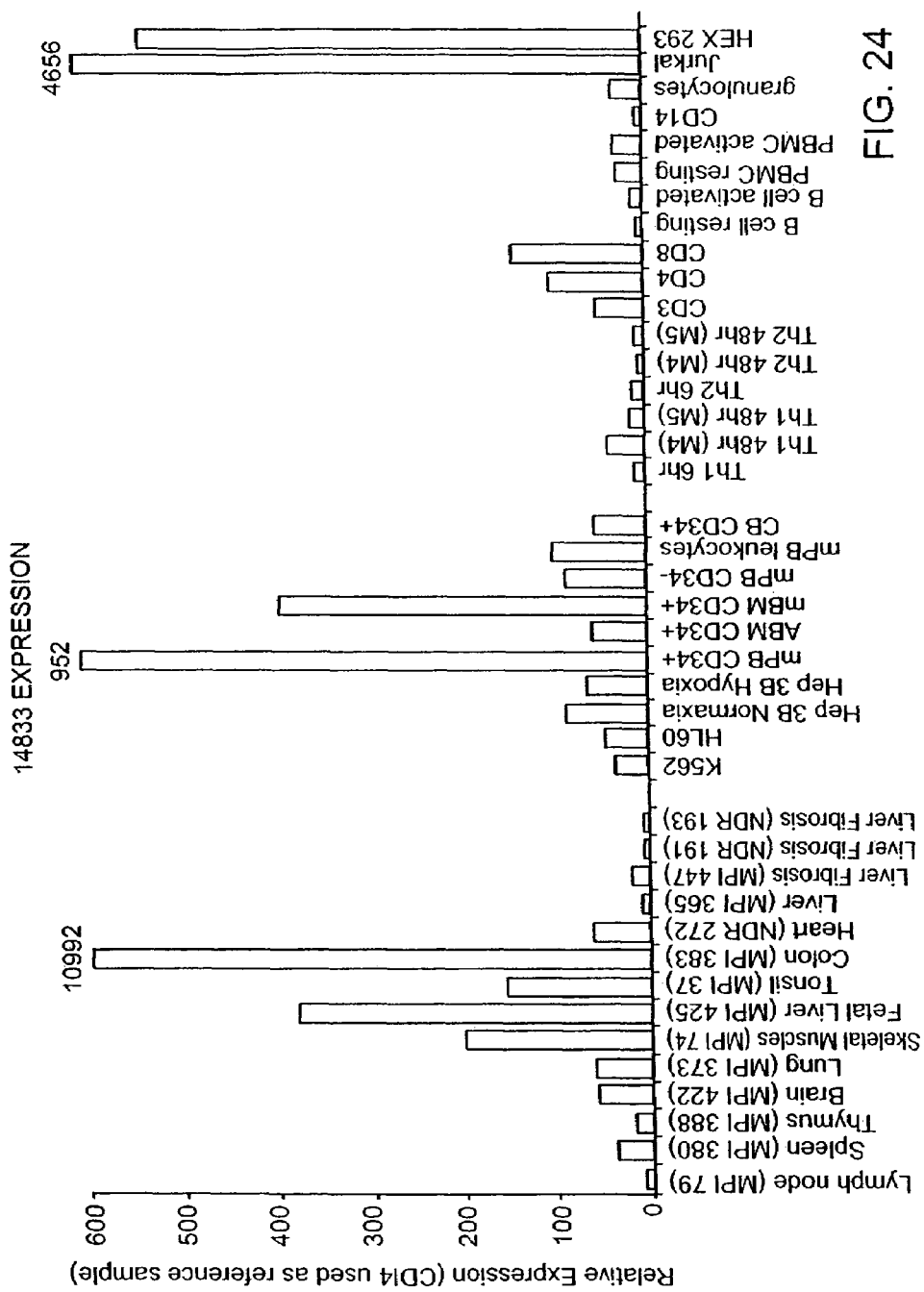
FIG. 24 shows expression of h14833 in various tissues and cell types relative to expression in human CD14.

FIG. 24 shows expression of h14833 in various tissues and cell lines as described above, relative to expression in CD14$^+$ cells. The results show broad tissue expression with high levels in skeletal muscle, fetal liver, and tonsil. Significantly high expression is seen in the CD34$^+$ cells from mobilized peripheral blood and mobilized bone marrow, as well as in colon, and the Jurkat and HEK 293 cell lines.

Figure 25:
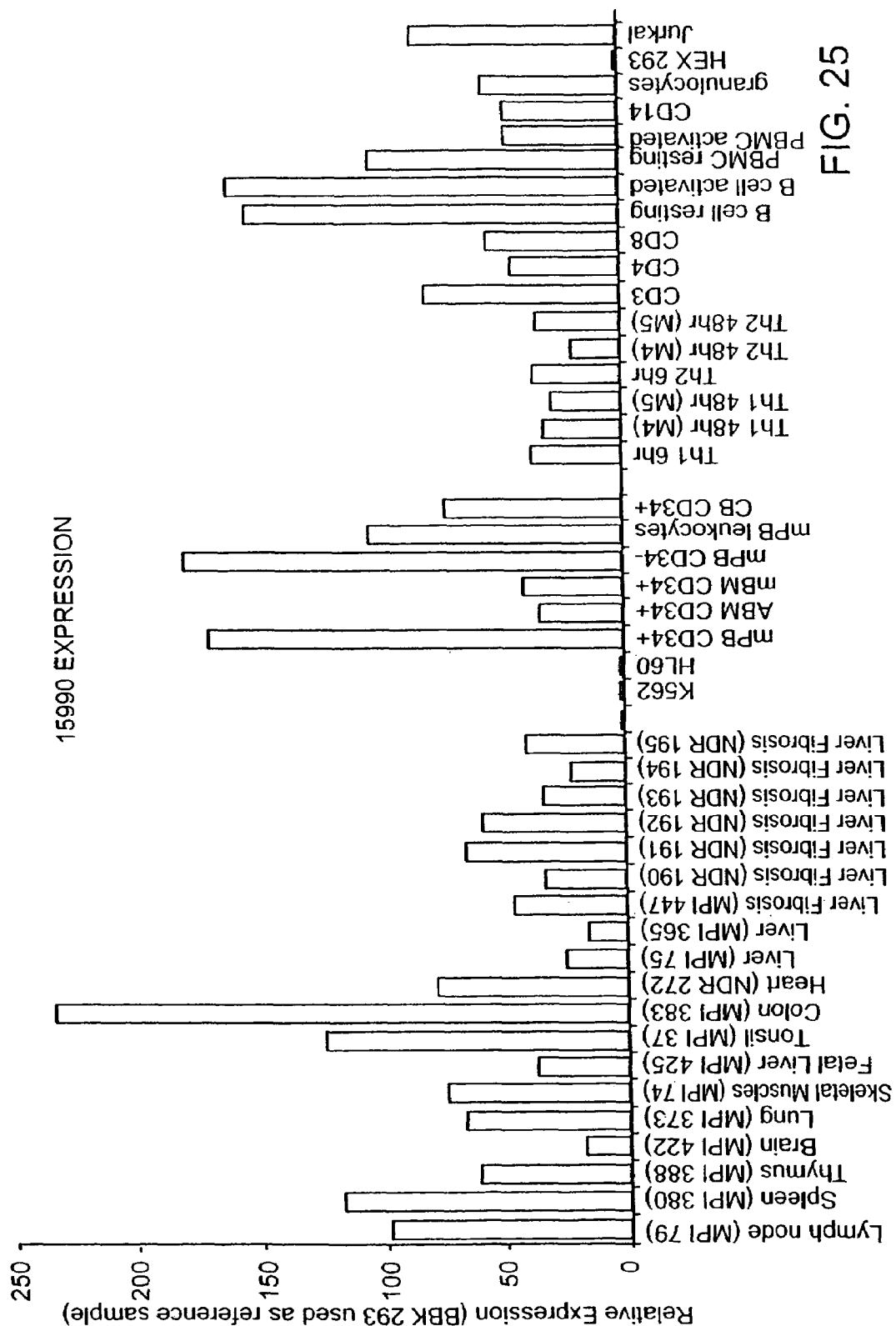
FIG. 25 shows expression of h15990 in various tissues and cell types relative to expression in human HEK 293.

FIG. 25 shows expression of h15990 in various tissues and cell lines as described above, relative to expression in HEK 293 cells. The results show that expression of h15990 is broadly distributed among the tissues examined with a significantly high level of expression in colon.

Figure 26:
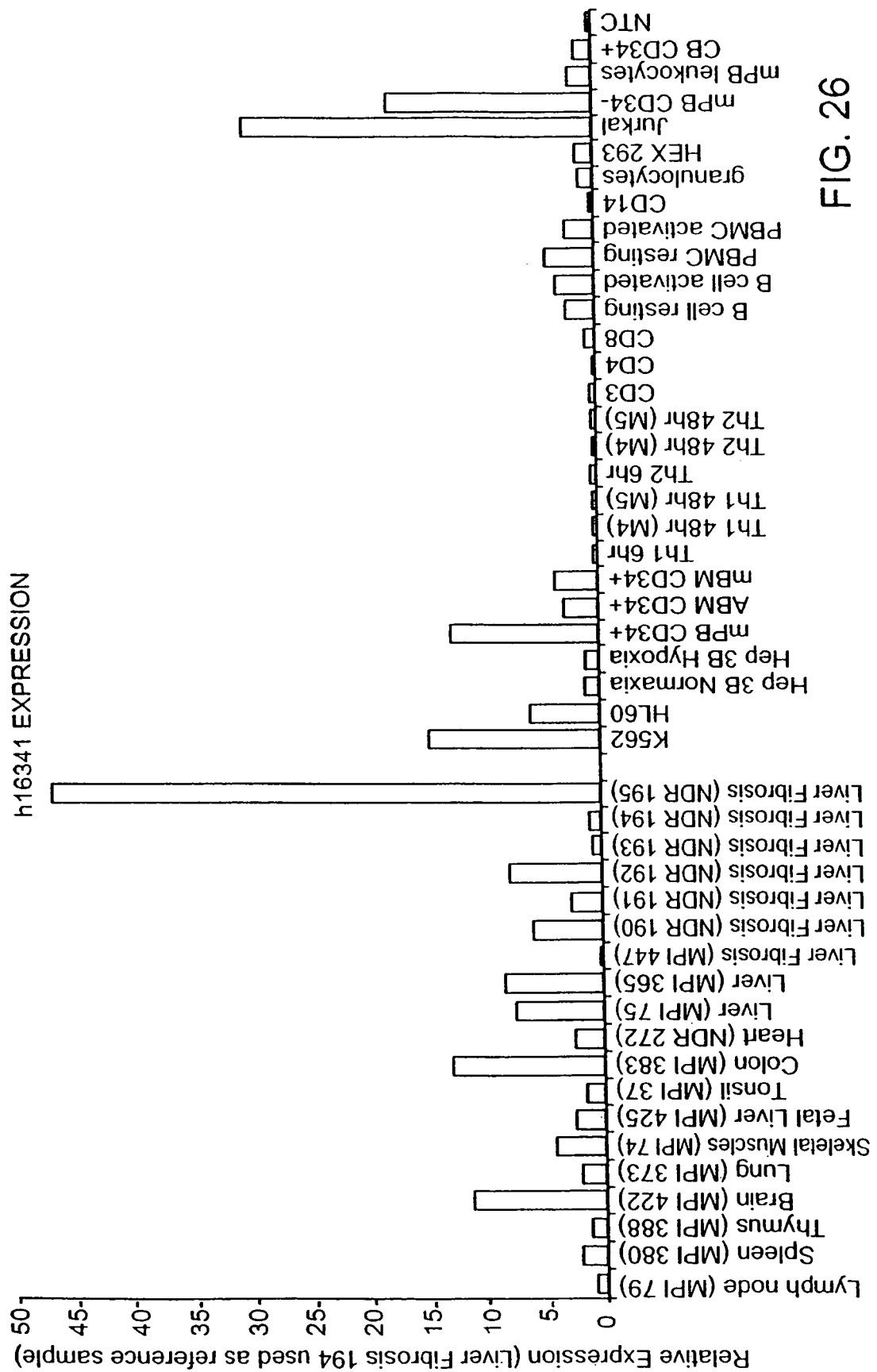
FIG. 26 shows expression of h16341 in various tissues and cell types relative to expression in human liver fibrosis 194.

FIG. 26 shows expression of h16341 in various tissues and cell lines as described above, relative to expression in fibrotic liver cells (sample NDR 194). The results indicate expression at low or barely detectable levels in the tissues examined.

Figure 27:
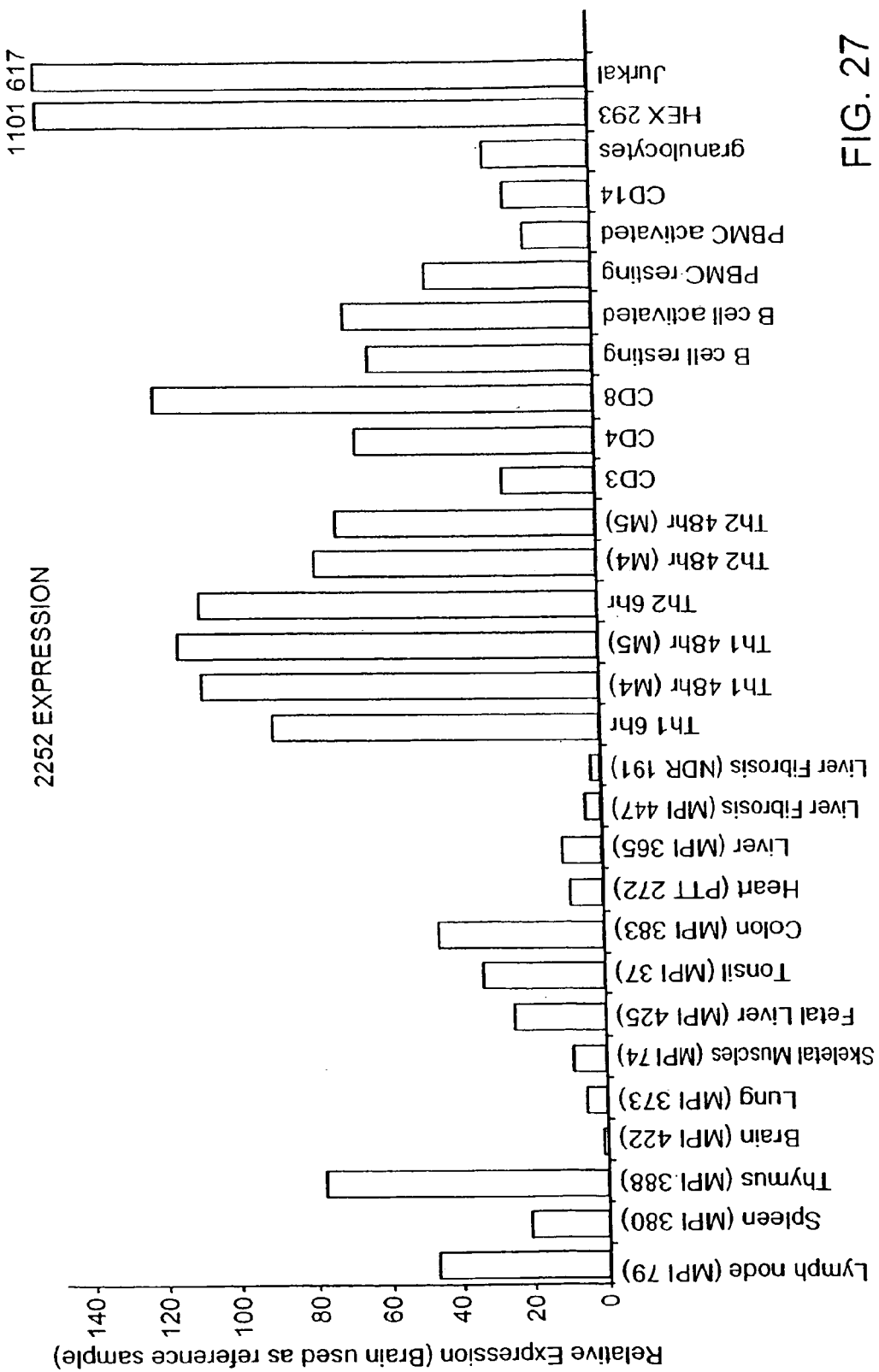
FIG. 27 shows expression of h2252 in various tissues and cell types relative to expression in human brain tissue.

FIG. 27 shows expression of h2252 in various tissues and cell lines as described above, relative to brain tissue. The results indicate that h2252 is expressed lymphocytic cells, particularly in the T and B lymphocyte subpopulations, as well as in the HEK 293 and Jurkat cell lines.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which binds to a polypeptide selected from the group consisting of:
   a) a polypeptide comprising the amino acid sequence of SEQ ID NO:4; and
   b) a polypeptide encoded by a nucleic acid molecule comprising the nucleotide sequence of SEQ ID NO:3;
   the method comprising the steps of:
   i) combining a cell expressing the polypeptide selected from the group consisting of a K562 cell, a HL60 cell, a HEK 293 cell, a Jurkat cell, a Th1 cell, a Th2 cell, a B cell, a fetal liver cell, and a thymus cell, with a test compound; and
   ii) determining whether the polypeptide binds to the test compound.

2. The method of claim 1, wherein the binding of the test compound to the polypeptide is detected by a method detection of binding by direct detecting of test compound/polypeptide binding.

3. The method claim 1, wherein the compound identified is an agent that inhibits the activity of the polypeptide.

4. The method of claim 1, wherein the polypeptide comprises the amino acid sequence of SEQ ID NO:4.

5. The method of claim 1, wherein the polypeptide is encoded by a nucleic acid molecule comprising the nucleotide sequence of SEQ ID NO:3.

* * * * *

SEQUENCE LISTING

<160> NUMBER OF SEQ ID NOS: 89

<210> SEQ ID NO 1
<211> LENGTH: 1586
<212> TYPE: DNA
<213> ORGANISM: Homo sapiens
<220> FEATURE:
<221> NAME/KEY: CDS
<222> LOCATION: (191)...(1156)

<400> SEQUENCE: 1

```
gtcgacccac gcgtccggtt cgaattgcaa cggcagctgc cgggcgtatg tgttggtgct      60
agaggcagct gcagggtctc gctgggggcc gctcgggacc aattttgaag aggtacttgg     120
ccacgactta ttttcacctc cgacctttcc ttccaggcgg tgagactctg gactgagagt     180
ggctttcaca atg gaa ggg atc agt aat ttc aag aca cca agc aaa tta        229
            Met Glu Gly Ile Ser Asn Phe Lys Thr Pro Ser Lys Leu
              1               5                  10 tca gaa aaa aag aaa tct gta tta tgt tca act cca act ata aat atc       277
Ser Glu Lys Lys Lys Ser Val Leu Cys Ser Thr Pro Thr Ile Asn Ile
 15                  20                  25 ccg gcc tct ccg ttt atg cag aag ctt ggc ttt ggt act ggg gta aat       325
Pro Ala Ser Pro Phe Met Gln Lys Leu Gly Phe Gly Thr Gly Val Asn
 30                  35                  40                  45 gtg tac cta atg aaa aga tct cca aga ggt ttg tct cat tct cct tgg       373
Val Tyr Leu Met Lys Arg Ser Pro Arg Gly Leu Ser His Ser Pro Trp
                 50                  55                  60 gct gta aaa aag att aat cct ata tgt aat gat cat tat cga agt gtg       421
Ala Val Lys Lys Ile Asn Pro Ile Cys Asn Asp His Tyr Arg Ser Val
             65                  70                  75 tat caa aag aga cta atg gat gaa gct aag att ttg aaa agc ctt cat       469
Tyr Gln Lys Arg Leu Met Asp Glu Ala Lys Ile Leu Lys Ser Leu His
         80                  85                  90 cat cca aac att gtt ggt tat cgt gct ttt act gaa gcc aat gat ggc       517
His Pro Asn Ile Val Gly Tyr Arg Ala Phe Thr Glu Ala Asn Asp Gly
     95                 100                 105 agt ctg tgt ctt gct atg gaa tat gga ggt gaa aag tct cta aat gac       565
Ser Leu Cys Leu Ala Met Glu Tyr Gly Gly Glu Lys Ser Leu Asn Asp
110                 115                 120                 125 tta ata gaa gaa cga tat aaa gcc agc caa gat cct ttt cca gca gcc       613
Leu Ile Glu Glu Arg Tyr Lys Ala Ser Gln Asp Pro Phe Pro Ala Ala
                130                 135                 140 ata att tta aaa gtt gct ttg aat atg gca aga ggg tta aag tat ctg       661
Ile Ile Leu Lys Val Ala Leu Asn Met Ala Arg Gly Leu Lys Tyr Leu
            145                 150                 155 cac caa gaa aag aaa ctg ctt cat gga gac ata aag tct tca aat gtt       709
His Gln Glu Lys Lys Leu Leu His Gly Asp Ile Lys Ser Ser Asn Val
        160                 165                 170 gta att aaa ggc gat ttt gaa aca att aaa atc tgt gat gta gga gtc       757
Val Ile Lys Gly Asp Phe Glu Thr Ile Lys Ile Cys Asp Val Gly Val
    175                 180                 185 tct cta cca ctg gat gaa aat atg act gtg act gac cct gag gct tgt       805
Ser Leu Pro Leu Asp Glu Asn Met Thr Val Thr Asp Pro Glu Ala Cys
190                 195                 200                 205 tac att ggc aca gag cca tgg aaa ccc aaa gaa gct gtg gag gag aat       853
Tyr Ile Gly Thr Glu Pro Trp Lys Pro Lys Glu Ala Val Glu Glu Asn
                210                 215                 220
```

```
ggt gtt att act gac aag gca gac ata ttt gcc ttt ggc ctt act ttg    901
Gly Val Ile Thr Asp Lys Ala Asp Ile Phe Ala Phe Gly Leu Thr Leu
        225                 230                 235 tgg gaa atg atg act tta tcg att cca cac att aat ctt tca aat gat    949
Trp Glu Met Met Thr Leu Ser Ile Pro His Ile Asn Leu Ser Asn Asp
            240                 245                 250 gat gat gat gaa gat aaa act ttt gat gaa agt gat ttt gat gat gaa    997
Asp Asp Asp Glu Asp Lys Thr Phe Asp Glu Ser Asp Phe Asp Asp Glu
        255                 260                 265 gca tac tat gca gcg ttg gga act agg cca cct att aat atg gaa gaa    1045
Ala Tyr Tyr Ala Ala Leu Gly Thr Arg Pro Pro Ile Asn Met Glu Glu
270                 275                 280                 285 ctg gat gaa tca tac cag aaa gta att gaa ctc ttc tct gta tgc act    1093
Leu Asp Glu Ser Tyr Gln Lys Val Ile Glu Leu Phe Ser Val Cys Thr
                290                 295                 300 aat gaa gac cct aaa gat cgt cct tct gct gca cac att gtt gaa gct    1141
Asn Glu Asp Pro Lys Asp Arg Pro Ser Ala Ala His Ile Val Glu Ala
            305                 310                 315 ctg gaa aca gat gtc tagtgatcat ctcagctgaa gtgtggcttg cgtaaataac    1196
Leu Glu Thr Asp Val
            320 tgtttattcc aaatattta catagttact atcagtagtt attagactct aaaattggca    1256 tatttgagga ccatagtttc ttgttaacat atggataact atttctaata tgaaatatgc    1316 ttatattggc tataagcact tggaattgta ctgggttttc tgtaaagttt tagaaactag    1376 ctacataagt actttgatac tgctcatgct gacttaaaac actagcagta aaacgctgta    1436 aactgtaaca ttaaattgaa tgaccattac ttttattaat gatctttctt aaatattcta    1496 tatttttaatg gatctactga cattagcact ttgtacagta caaaataaag tctacatttg    1556 tttaaaaaaa aaaaaaaaaa gggcggccgc                                    1586

<210> SEQ ID NO 2
<211> LENGTH: 322
<212> TYPE: PRT
<213> ORGANISM: Homo sapiens

<400> SEQUENCE: 2

Met Glu Gly Ile Ser Asn Phe Lys Thr Pro Ser Lys Leu Ser Glu Lys
1               5                   10                  15

Lys Lys Ser Val Leu Cys Ser Thr Pro Thr Ile Asn Ile Pro Ala Ser
                20                  25                  30

Pro Phe Met Gln Lys Leu Gly Phe Gly Thr Gly Val Asn Val Tyr Leu
            35                  40                  45

Met Lys Arg Ser Pro Arg Gly Leu Ser His Ser Pro Trp Ala Val Lys
        50                  55                  60

Lys Ile Asn Pro Ile Cys Asn Asp His Tyr Arg Ser Val Tyr Gln Lys
65                  70                  75                  80

Arg Leu Met Asp Glu Ala Lys Ile Leu Lys Ser Leu His His Pro Asn
                85                  90                  95

Ile Val Gly Tyr Arg Ala Phe Thr Glu Ala Asn Asp Gly Ser Leu Cys
            100                 105                 110

Leu Ala Met Glu Tyr Gly Gly Glu Lys Ser Leu Asn Asp Leu Ile Glu
        115                 120                 125

Glu Arg Tyr Lys Ala Ser Gln Asp Pro Phe Pro Ala Ala Ile Ile Leu
    130                 135                 140

Lys Val Ala Leu Asn Met Ala Arg Gly Leu Lys Tyr Leu His Gln Glu
145                 150                 155                 160
```

```
Lys Lys Leu Leu His Gly Asp Ile Lys Ser Ser Asn Val Val Ile Lys
                165                 170                 175

Gly Asp Phe Glu Thr Ile Lys Ile Cys Asp Val Gly Val Ser Leu Pro
            180                 185                 190

Leu Asp Glu Asn Met Thr Val Thr Asp Pro Glu Ala Cys Tyr Ile Gly
                195                 200                 205

Thr Glu Pro Trp Lys Pro Lys Glu Ala Val Glu Glu Asn Gly Val Ile
210                 215                 220

Thr Asp Lys Ala Asp Ile Phe Ala Phe Gly Leu Thr Leu Trp Glu Met
225                 230                 235                 240

Met Thr Leu Ser Ile Pro His Ile Asn Leu Ser Asn Asp Asp Asp
                245                 250                 255

Glu Asp Lys Thr Phe Asp Glu Ser Asp Phe Asp Asp Glu Ala Tyr Tyr
                260                 265                 270

Ala Ala Leu Gly Thr Arg Pro Pro Ile Asn Met Glu Glu Leu Asp Glu
                275                 280                 285

Ser Tyr Gln Lys Val Ile Glu Leu Phe Ser Val Cys Thr Asn Glu Asp
                290                 295                 300

Pro Lys Asp Arg Pro Ser Ala Ala His Ile Val Glu Ala Leu Glu Thr
305                 310                 315                 320

Asp Val

<210> SEQ ID NO 3
<211> LENGTH: 831
<212> TYPE: DNA
<213> ORGANISM: Homo sapiens
<220> FEATURE:
<221> NAME/KEY: CDS
<222> LOCATION: (1)...(522)

<400> SEQUENCE: 3 tac tat agg gaa ttt ggc cct cga ggc cag aat tcg gca cga gac cga    48
Tyr Tyr Arg Glu Phe Gly Pro Arg Gly Gln Asn Ser Ala Arg Asp Arg
  1               5                  10                  15 act ccg aag agt gtg aga aga ggg gtg gcc ccc gtt gat gat ggg cga    96
Thr Pro Lys Ser Val Arg Arg Gly Val Ala Pro Val Asp Asp Gly Arg
             20                  25                  30 att cta gga acc cca gac tac ctt gca cct gag ctg tta cta ggc agg   144
Ile Leu Gly Thr Pro Asp Tyr Leu Ala Pro Glu Leu Leu Leu Gly Arg
         35                  40                  45 gcc cat ggt cct gcg gta gac tgg tgg gca ctt gga gtt tgc ttg ttt   192
Ala His Gly Pro Ala Val Asp Trp Trp Ala Leu Gly Val Cys Leu Phe
     50                  55                  60 gaa ttt cta aca gga att ccc cct ttc aat gat gaa aca cca caa caa   240
Glu Phe Leu Thr Gly Ile Pro Pro Phe Asn Asp Glu Thr Pro Gln Gln
 65                  70                  75                  80 gta ttc cag aat att ctg aaa aga gat atc cct tgg cca gaa ggt gaa   288
Val Phe Gln Asn Ile Leu Lys Arg Asp Ile Pro Trp Pro Glu Gly Glu
                 85                  90                  95 gaa aag tta tct gat aat gct caa agt gca gta gaa ata ctt tta acc   336
Glu Lys Leu Ser Asp Asn Ala Gln Ser Ala Val Glu Ile Leu Leu Thr
            100                 105                 110 att gat gat aca aag aga gct gga atg aaa gag cta aaa cgt cat cct   384
Ile Asp Asp Thr Lys Arg Ala Gly Met Lys Glu Leu Lys Arg His Pro
        115                 120                 125 ctc ttc agt gat gtg gac tgg gaa aat ctg cag cat cag act atg cct   432
Leu Phe Ser Asp Val Asp Trp Glu Asn Leu Gln His Gln Thr Met Pro
    130                 135                 140
```

```
ttc atc ccc cag cca gat gat gaa aca gat acc tcc tat ttt gaa gcc    480
Phe Ile Pro Gln Pro Asp Asp Glu Thr Asp Thr Ser Tyr Phe Glu Ala
145                 150                 155                 160 agg aat act gct cag cac ctg acc gta tct gga ttt agt ctg            522
Arg Asn Thr Ala Gln His Leu Thr Val Ser Gly Phe Ser Leu
                165                 170 tagcacaaaa attttccttt tagtctagcc tcgtgttata gaatgaactt gcataattat    582
atactcctta atactagatt gatctaaggg ggaaagatca ttatttaacc tagttcaatg    642 tgctttttaat gtacgttaca gctttcacag agttaaaagg ctgaaaggaa tatagtcagt   702
aatttatctt aacctcaaaa ctgtatataa atcttcaaag cttttttcat ctatttattt    762
tgtttattgc actttatgaa aactgaagca tcaataaaat tagaggacac tattgagagt    822
gagccacta                                                           831

<210> SEQ ID NO 4
<211> LENGTH: 174
<212> TYPE: PRT
<213> ORGANISM: Homo sapiens

<400> SEQUENCE: 4

Tyr Tyr Arg Glu Phe Gly Pro Arg Gly Gln Asn Ser Ala Arg Asp Arg
1               5                   10                  15

Thr Pro Lys Ser Val Arg Arg Gly Val Ala Pro Val Asp Asp Gly Arg
            20                  25                  30

Ile Leu Gly Thr Pro Asp Tyr Leu Ala Pro Glu Leu Leu Leu Gly Arg
        35                  40                  45

Ala His Gly Pro Ala Val Asp Trp Trp Ala Leu Gly Val Cys Leu Phe
    50                  55                  60

Glu Phe Leu Thr Gly Ile Pro Pro Phe Asn Asp Glu Thr Pro Gln Gln
65                  70                  75                  80

Val Phe Gln Asn Ile Leu Lys Arg Asp Ile Pro Trp Pro Glu Gly Glu
                85                  90                  95

Glu Lys Leu Ser Asp Asn Ala Gln Ser Ala Val Glu Ile Leu Leu Thr
            100                 105                 110

Ile Asp Asp Thr Lys Arg Ala Gly Met Lys Glu Leu Lys Arg His Pro
        115                 120                 125

Leu Phe Ser Asp Val Asp Trp Glu Asn Leu Gln His Gln Thr Met Pro
    130                 135                 140

Phe Ile Pro Gln Pro Asp Asp Glu Thr Asp Thr Ser Tyr Phe Glu Ala
145                 150                 155                 160

Arg Asn Thr Ala Gln His Leu Thr Val Ser Gly Phe Ser Leu
                165                 170

<210> SEQ ID NO 5
<211> LENGTH: 2060
<212> TYPE: DNA
<213> ORGANISM: Homo sapiens
<220> FEATURE:
<221> NAME/KEY: CDS
<222> LOCATION: (154)...(780)
<220> FEATURE:
<221> NAME/KEY: misc_feature
<222> LOCATION: (1)...(2060)
<223> OTHER INFORMATION: n = A,T,C or G

<400> SEQUENCE: 5
tttttgcctt cattcactcc catgtggggc cttgagaatt aacatcttaa gttgcctcct    60
gctccctgcc tcccactcat cgaggatgct ctgactgctc actgcctgga tctttcgtcc   120
```

```
tctacagaac cagctgggct ccatgaggat gtg atg act atg gat ggt ctt ctc      174
                                 Met Thr Met Asp Gly Leu Leu
                                  1               5 tat gat ctc aca gaa aaa caa gta tat cac atc gga aag cag gtc ctt      222
Tyr Asp Leu Thr Glu Lys Gln Val Tyr His Ile Gly Lys Gln Val Leu
         10                  15                  20 ttg gcg ctg gaa ttc ctg cag gag aag cat ttg ttc cat ggg gat gtg      270
Leu Ala Leu Glu Phe Leu Gln Glu Lys His Leu Phe His Gly Asp Val
 25                  30                  35 gca gcc agg aat att ctg atg caa agt gat ctc act gct aag ctc tgt      318
Ala Ala Arg Asn Ile Leu Met Gln Ser Asp Leu Thr Ala Lys Leu Cys
 40                  45                  50                  55 gga tta ggc ctg gct tat gaa gtt tac acc cga ggg gcc atc tcc tct      366
Gly Leu Gly Leu Ala Tyr Glu Val Tyr Thr Arg Gly Ala Ile Ser Ser
                 60                  65                  70 act caa acc ata cct ctc aag tgg ctt gcc cca gaa cgg ctt ctc ctg      414
Thr Gln Thr Ile Pro Leu Lys Trp Leu Ala Pro Glu Arg Leu Leu Leu
                 75                  80                  85 aga cct gct agc atc aga gca gat gtc tgg tct ttt ggg atc ctg ctc      462
Arg Pro Ala Ser Ile Arg Ala Asp Val Trp Ser Phe Gly Ile Leu Leu
         90                  95                 100 tat gag atg gtg act cta gga gca cca ccg tat cct gaa gtc cct cct      510
Tyr Glu Met Val Thr Leu Gly Ala Pro Pro Tyr Pro Glu Val Pro Pro
         105                 110                 115 acc agc atc cta gag cat ctc caa aga agg aaa atc atg aag aga ccc      558
Thr Ser Ile Leu Glu His Leu Gln Arg Arg Lys Ile Met Lys Arg Pro
120                 125                 130                 135 agt agc tgc aca cat acc atg tac agt atc atg aag tcc tgc tgg cgc      606
Ser Ser Cys Thr His Thr Met Tyr Ser Ile Met Lys Ser Cys Trp Arg
                 140                 145                 150 tgg cgt gag gct gac cgc ccc tca cct aga gag ctg cgc ttg cgc cta      654
Trp Arg Glu Ala Asp Arg Pro Ser Pro Arg Glu Leu Arg Leu Arg Leu
         155                 160                 165 gaa gct gcc att aaa act gca gat gac gag gct gtg tta caa gta cca      702
Glu Ala Ala Ile Lys Thr Ala Asp Asp Glu Ala Val Leu Gln Val Pro
         170                 175                 180 gag ttg gtg gta cct gaa ctg tat gca gct gtg gcc ggc atc aga gtg      750
Glu Leu Val Val Pro Glu Leu Tyr Ala Ala Val Ala Gly Ile Arg Val
         185                 190                 195 gag agc ctc ttc tac aac tat agc atg ctt tgaagagtct cgggcaagaa        800
Glu Ser Leu Phe Tyr Asn Tyr Ser Met Leu
200                 205 acattcatgc atgagtatat gttcttggaa tcaattcctc taagaacaga gaatggtctt    860
tcccagggac acaagggag aaatgggaca tggattcttg atcttccttt acacatttct    920
cgggaaatct gaaatgatgc tggatgggac tctacacatc ctgagctaag acatactgtc    980
agtctcactt ctgctgtccc agtcctagaa atcctgggta gaagtggtgg acctgtgcaa   1040
aggaggtttt agaactctgc agtatttgtt ggggcatggc acaaataagc tcatccctcc   1100
cgtccgaggc tagtttcctc tggaaccaca ttttatcta gatgaaaatt tggaatgaaa    1160
tgaaggaata gaaatccaat aaaagagttg aagggaaaga aaatttaagg ttcttcttgc   1220
tcaggattac agatatggac caacacctcc ttcaagaaaa ggtggtagga cacaaagttc   1280
ttcagtcctg agccctacat gtggggttgg aggagaacta taacgaaaaa acctctgagt   1340
ttcaccttag gtatagataa agaaagatg gtccccttt atctgattct gagacaggta    1400
aattctgttt gttactacgt ttaattagaa ggtggaggag tcatttcatg attaagaaca   1460
ttcaacatgt attgttcatt aagctagctt cctagttccg attagactaa ggagactaag   1520
```

-continued

```
cctagagagt caatgttaga acagtgaaaa gaattctgtg tgtgtgtgtg tgtgtgtgca    1580
caataaatag gaaatgtaga aaccaagcaa gaaggcttag tagctcagtc tttaacaagg    1640
gctagaaaag aatgtaatct gatatggaag gatagcagct tctaattttc aatcatctgt    1700
tgatatactg tgaaacttat tttattaaat taatatttat taaatggaaa tatgcttttc    1760
tggtttataa ctactaaaaa tatcataggg aggataaaag taaataagtg aaagttaatg    1820
ccaatagaaa aattcaagag ataatgtaca atgtcagaaa agggattctt tatgtgtaaa    1880
tggggataat acctatttca caaggttgtt ctgaggattg atacgttttg agtatgtatt    1940
tgtacactat ctggcacata tgcgctcaat aaacgtgttt ctcctttaaa aaaaaaaaa    2000 aaaaaaaaa aaaaaaaaa aaaaaaaaa aaaanaaaa taaaaaaaaa gggcggccgc    2060
```

<210> SEQ ID NO 6
<211> LENGTH: 209
<212> TYPE: PRT
<213> ORGANISM: Homo sapiens

<400> SEQUENCE: 6

```
Met Thr Met Asp Gly Leu Leu Tyr Asp Leu Thr Glu Lys Gln Val Tyr
 1               5                  10                  15

His Ile Gly Lys Gln Val Leu Ala Leu Glu Phe Leu Gln Glu Lys
             20                  25                  30

His Leu Phe His Gly Asp Val Ala Ala Arg Asn Ile Leu Met Gln Ser
         35                  40                  45

Asp Leu Thr Ala Lys Leu Cys Gly Leu Gly Leu Ala Tyr Glu Val Tyr
     50                  55                  60

Thr Arg Gly Ala Ile Ser Ser Thr Gln Thr Ile Pro Leu Lys Trp Leu
 65                  70                  75                  80

Ala Pro Glu Arg Leu Leu Arg Pro Ala Ser Ile Arg Ala Asp Val
             85                  90                  95

Trp Ser Phe Gly Ile Leu Leu Tyr Glu Met Val Thr Leu Gly Ala Pro
            100                 105                 110

Pro Tyr Pro Glu Val Pro Pro Thr Ser Ile Leu Glu His Leu Gln Arg
            115                 120                 125

Arg Lys Ile Met Lys Arg Pro Ser Ser Cys Thr His Thr Met Tyr Ser
            130                 135                 140

Ile Met Lys Ser Cys Trp Arg Trp Arg Glu Ala Asp Arg Pro Ser Pro
145                 150                 155                 160

Arg Glu Leu Arg Leu Arg Leu Glu Ala Ala Ile Lys Thr Ala Asp Asp
                165                 170                 175

Glu Ala Val Leu Gln Val Pro Glu Leu Val Val Pro Glu Leu Tyr Ala
            180                 185                 190

Ala Val Ala Gly Ile Arg Val Glu Ser Leu Phe Tyr Asn Tyr Ser Met
            195                 200                 205

Leu
```

<210> SEQ ID NO 7
<211> LENGTH: 1697
<212> TYPE: DNA
<213> ORGANISM: Homo sapiens
<220> FEATURE:
<221> NAME/KEY: CDS
<222> LOCATION: (2)...(1492)

<400> SEQUENCE: 7

```
g gag aac cag gag ctc gtc ggc aaa ggc ggg ttc ggc aca gtg ttc cgg      49
  Glu Asn Gln Glu Leu Val Gly Lys Gly Gly Phe Gly Thr Val Phe Arg
  1               5                   10                  15 gcg caa cat agg aag tgg ggc tac gat gtg gcg gtc aag atc gta aac        97
Ala Gln His Arg Lys Trp Gly Tyr Asp Val Ala Val Lys Ile Val Asn
                20                  25                  30 tcg aag gcg ata tcc agg gag gtc aag gcc atg gca agt ctg gat aac       145
Ser Lys Ala Ile Ser Arg Glu Val Lys Ala Met Ala Ser Leu Asp Asn
            35                  40                  45 gaa ttc gtg ctg cgc cta gaa ggg gtt atc gag aag gtg aac tgg gac       193
Glu Phe Val Leu Arg Leu Glu Gly Val Ile Glu Lys Val Asn Trp Asp
    50                  55                  60 caa gat ccc aag ccg gct ctg gtg act aaa ttc atg gag aac ggc tcc       241
Gln Asp Pro Lys Pro Ala Leu Val Thr Lys Phe Met Glu Asn Gly Ser
65                  70                  75                  80 ttg tcg ggg ctg ctg cag tcc cag tgc cct cgg ccc tgg ccg ctc ctt       289
Leu Ser Gly Leu Leu Gln Ser Gln Cys Pro Arg Pro Trp Pro Leu Leu
                85                  90                  95 tgc cgc ctg ctg aaa gaa gtg gtg ctt ggg atg ttt tac ctg cac gac       337
Cys Arg Leu Leu Lys Glu Val Val Leu Gly Met Phe Tyr Leu His Asp
                100                 105                 110 cag aac ccg gtg ctc ctg cac cgg gac ctc aag cca tcc aac gtc ctg       385
Gln Asn Pro Val Leu Leu His Arg Asp Leu Lys Pro Ser Asn Val Leu
            115                 120                 125 ctg gac cca gag ctg cac gtc aag ctg gca gat ttt ggc ctg tcc aca       433
Leu Asp Pro Glu Leu His Val Lys Leu Ala Asp Phe Gly Leu Ser Thr
130                 135                 140 ttt cag gga ggc tca cag tca ggg aca ggg tcc ggg gag cca ggg ggc       481
Phe Gln Gly Gly Ser Gln Ser Gly Thr Gly Ser Gly Glu Pro Gly Gly
145                 150                 155                 160 acc ctg ggc tac ttg gcc cca gaa ctg ttt gtt aac gta aac cgg aag       529
Thr Leu Gly Tyr Leu Ala Pro Glu Leu Phe Val Asn Val Asn Arg Lys
                165                 170                 175 gcc tcc aca gcc agt gac gtc tac agc ttc ggg atc cta atg tgg gca       577
Ala Ser Thr Ala Ser Asp Val Tyr Ser Phe Gly Ile Leu Met Trp Ala
            180                 185                 190 gtg ctt gct gga aga gaa gtt gag ttg cca acc gaa cca tca ctc gtg       625
Val Leu Ala Gly Arg Glu Val Glu Leu Pro Thr Glu Pro Ser Leu Val
        195                 200                 205 tac gaa gca gtg tgc aac agg cag aac cgg cct tca ttg gct gag ctg       673
Tyr Glu Ala Val Cys Asn Arg Gln Asn Arg Pro Ser Leu Ala Glu Leu
    210                 215                 220 ccc caa gcc ggg cct gag act ccc ggc tta gaa gga ctg aag gag cta       721
Pro Gln Ala Gly Pro Glu Thr Pro Gly Leu Glu Gly Leu Lys Glu Leu
225                 230                 235                 240 atg cag ctc tgc tgg agc agt gag ccc aag gac aga ccc tcc ttc cag       769
Met Gln Leu Cys Trp Ser Ser Glu Pro Lys Asp Arg Pro Ser Phe Gln
                245                 250                 255 gaa tgc cta cca aaa act gat gaa gtc ttc cag atg gtg gag aac aat       817
Glu Cys Leu Pro Lys Thr Asp Glu Val Phe Gln Met Val Glu Asn Asn
            260                 265                 270 atg aat gct gct gtc tcc acg gta aag gat ttc ctg tct cag ctc agg       865
Met Asn Ala Ala Val Ser Thr Val Lys Asp Phe Leu Ser Gln Leu Arg
        275                 280                 285 agc agc aat agg aga ttt tct atc cca gag tca ggc caa gga ggg aca       913
Ser Ser Asn Arg Arg Phe Ser Ile Pro Glu Ser Gly Gln Gly Gly Thr
    290                 295                 300
```

```
gaa atg gat ggc ttt agg aga acc ata gaa aac cag cac tct cgt aat      961
Glu Met Asp Gly Phe Arg Arg Thr Ile Glu Asn Gln His Ser Arg Asn
305                 310                 315                 320 gat gtc atg gtt tct gag tgg cta aac aaa ctg aat cta gag gag cct     1009
Asp Val Met Val Ser Glu Trp Leu Asn Lys Leu Asn Leu Glu Glu Pro
                325                 330                 335 ccc agc tct gtt cct aaa aaa tgc ccg agc ctt acc aag agg agc agg     1057
Pro Ser Ser Val Pro Lys Lys Cys Pro Ser Leu Thr Lys Arg Ser Arg
            340                 345                 350 gca caa gag gag cag gtt cca caa gcc tgg aca gca ggc aca tct tca     1105
Ala Gln Glu Glu Gln Val Pro Gln Ala Trp Thr Ala Gly Thr Ser Ser
        355                 360                 365 gat tcg atg gcc caa cct ccc cag act cca gag acc tca act ttc aga     1153
Asp Ser Met Ala Gln Pro Pro Gln Thr Pro Glu Thr Ser Thr Phe Arg
    370                 375                 380 aac cag atg ccc agc cct acc tca act gga aca cca agt cct gga ccc     1201
Asn Gln Met Pro Ser Pro Thr Ser Thr Gly Thr Pro Ser Pro Gly Pro
385                 390                 395                 400 cga ggg aat cag ggg gct gag aga caa ggc atg aac tgg tcc tgc agg     1249
Arg Gly Asn Gln Gly Ala Glu Arg Gln Gly Met Asn Trp Ser Cys Arg
                405                 410                 415 acc ccg gag cca aat cca gta aca ggg cga ccg ctc gtt aac ata tac     1297
Thr Pro Glu Pro Asn Pro Val Thr Gly Arg Pro Leu Val Asn Ile Tyr
            420                 425                 430 aac tgc tct ggg gtg caa gtt gga gac aac aac tac ttg act atg caa     1345
Asn Cys Ser Gly Val Gln Val Gly Asp Asn Asn Tyr Leu Thr Met Gln
        435                 440                 445 cag aca act gcc ttg ccc aca tgg ggc ttg gca cct tcg ggc aag ggg     1393
Gln Thr Thr Ala Leu Pro Thr Trp Gly Leu Ala Pro Ser Gly Lys Gly
    450                 455                 460 agg ggc ttg cag cac ccc cca cca gta ggt tcg caa gaa ggc cct aaa     1441
Arg Gly Leu Gln His Pro Pro Pro Val Gly Ser Gln Glu Gly Pro Lys
465                 470                 475                 480 gat cct gaa gcc tgg agc agg cca cag ggt tgg tat aat cat agc ggg     1489
Asp Pro Glu Ala Trp Ser Arg Pro Gln Gly Trp Tyr Asn His Ser Gly
                485                 490                 495 aaa taaagcacct tccaagcttg cctccaagag ttacgagtta aggaagagtg         1542
Lys ccaccccttg aggcccctga cttccttcta gggcagtctg gcctgccac aaactgactt     1602 tgtgacctgt cccccaggag tcaataaaca tgatggaatg ctaaaaaaaa aaaaaaaaa    1662 aaaaaaaaaa aaaaaaaaaa aaaagggggcg gccgc                             1697

<210> SEQ ID NO 8
<211> LENGTH: 497
<212> TYPE: PRT
<213> ORGANISM: Homo sapiens

<400> SEQUENCE: 8

Glu Asn Gln Glu Leu Val Gly Lys Gly Gly Phe Gly Thr Val Phe Arg
1               5                   10                  15

Ala Gln His Arg Lys Trp Gly Tyr Asp Val Ala Val Lys Ile Val Asn
            20                  25                  30

Ser Lys Ala Ile Ser Arg Glu Val Lys Ala Met Ala Ser Leu Asp Asn
        35                  40                  45

Glu Phe Val Leu Arg Leu Glu Gly Val Ile Glu Lys Val Asn Trp Asp
    50                  55                  60

Gln Asp Pro Lys Pro Ala Leu Val Thr Lys Phe Met Glu Asn Gly Ser
65                  70                  75                  80
```

-continued

```
Leu Ser Gly Leu Leu Gln Ser Gln Cys Pro Arg Pro Trp Pro Leu Leu
                85                  90                  95

Cys Arg Leu Leu Lys Glu Val Val Leu Gly Met Phe Tyr Leu His Asp
            100                 105                 110

Gln Asn Pro Val Leu Leu His Arg Asp Leu Lys Pro Ser Asn Val Leu
        115                 120                 125

Leu Asp Pro Glu Leu His Val Lys Leu Ala Asp Phe Gly Leu Ser Thr
    130                 135                 140

Phe Gln Gly Gly Ser Gln Ser Gly Thr Gly Ser Gly Glu Pro Gly Gly
145                 150                 155                 160

Thr Leu Gly Tyr Leu Ala Pro Glu Leu Phe Val Asn Val Asn Arg Lys
                165                 170                 175

Ala Ser Thr Ala Ser Asp Val Tyr Ser Phe Gly Ile Leu Met Trp Ala
            180                 185                 190

Val Leu Ala Gly Arg Glu Val Glu Leu Pro Thr Glu Pro Ser Leu Val
        195                 200                 205

Tyr Glu Ala Val Cys Asn Arg Gln Asn Arg Pro Ser Leu Ala Glu Leu
    210                 215                 220

Pro Gln Ala Gly Pro Glu Thr Pro Gly Leu Glu Gly Leu Lys Glu Leu
225                 230                 235                 240

Met Gln Leu Cys Trp Ser Ser Glu Pro Lys Asp Arg Pro Ser Phe Gln
                245                 250                 255

Glu Cys Leu Pro Lys Thr Asp Glu Val Phe Gln Met Val Glu Asn Asn
            260                 265                 270

Met Asn Ala Ala Val Ser Thr Val Lys Asp Phe Leu Ser Gln Leu Arg
        275                 280                 285

Ser Ser Asn Arg Arg Phe Ser Ile Pro Glu Ser Gly Gln Gly Gly Thr
    290                 295                 300

Glu Met Asp Gly Phe Arg Arg Thr Ile Glu Asn Gln His Ser Arg Asn
305                 310                 315                 320

Asp Val Met Val Ser Glu Trp Leu Asn Lys Leu Asn Leu Glu Glu Pro
                325                 330                 335

Pro Ser Ser Val Pro Lys Lys Cys Pro Ser Leu Thr Lys Arg Ser Arg
            340                 345                 350

Ala Gln Glu Glu Gln Val Pro Gln Ala Trp Thr Ala Gly Thr Ser Ser
        355                 360                 365

Asp Ser Met Ala Gln Pro Pro Gln Thr Pro Glu Thr Ser Thr Phe Arg
    370                 375                 380

Asn Gln Met Pro Ser Pro Thr Ser Thr Gly Thr Pro Ser Pro Gly Pro
385                 390                 395                 400

Arg Gly Asn Gln Gly Ala Glu Arg Gln Gly Met Asn Trp Ser Cys Arg
                405                 410                 415

Thr Pro Glu Pro Asn Pro Val Thr Gly Arg Pro Leu Val Asn Ile Tyr
            420                 425                 430

Asn Cys Ser Gly Val Gln Val Gly Asp Asn Asn Tyr Leu Thr Met Gln
        435                 440                 445

Gln Thr Thr Ala Leu Pro Thr Trp Gly Leu Ala Pro Ser Gly Lys Gly
    450                 455                 460

Arg Gly Leu Gln His Pro Pro Val Gly Ser Gln Glu Gly Pro Lys
465                 470                 475                 480

Asp Pro Glu Ala Trp Ser Arg Pro Gln Gly Trp Tyr Asn His Ser Gly
                485                 490                 495

Lys
```

<210> SEQ ID NO 9
<211> LENGTH: 981
<212> TYPE: DNA
<213> ORGANISM: Homo sapiens
<220> FEATURE:
<221> NAME/KEY: misc_feature
<222> LOCATION: (1)...(981)
<223> OTHER INFORMATION: n=A,T,C or G

<400> SEQUENCE: 9

```
cgcgcagagg gcggtggcct gggctggccg aaccatggcg gccccggagc cggcgccgag      60
gcgggcccgg gaacgggagc gggagcggga ggacgagagc gaggacgaga gcgacatcct     120
ggaggaaagc ccgtgtggtc gctggcaaaa gcgacgggag caggtaaacc aagggaacat     180
gccagggctt cagagcacct tcctagccat ggacacggag gaggggtag aggtggtgtg      240
gaacgagctc cacttcggag acaggaaggc cttcgcggcg cacgaggaga gatccagac     300
cgtgttcgag cagctggtgc tggtggacca cccgaacatc gtgaagttgc acaagtactg     360
gctggatacc tctgaggcct cgcgagggt catcttcatc acagagtacg tgtcatcagg     420
cagcctcaag caattcctca aaagaccaa gaagaaccac aaggccatga acgcccgggc     480
ctggaagcgc tggtgcacgc agatcctgtc tgcgctcagc ttcctgcacg cctgcagccc     540
cccaatcatc acgggaacc tgaccagcga caccatcttc attcagcaca acggcctcat     600
caagatcggc tccgtgtggc accgaatctt ctccaatgca cttccagatg atctccgaag     660
ccccatccgc gctgagcgag aggaacttcg gaacctgcac ttcttccccc cagagtatgg     720
agaggtggcc gatgggaccg ctgtggacat cttcttcttt gggatgtgtg cgctggagat     780
ggctgtactg gaaatccaga ccaatgggga cacccgggtc acagaggagg ccattgctcg     840
cgccaggcac tcgctgagtg accccaacat gcgggagttc atcctttgct gcctggcccg     900
ggaccctgcc cgncggccct ctgtccacag cctcctcttc cacncgcgtg ctcttngagg     960
tgcactcgct gaagctcctg g                                               981
```

<210> SEQ ID NO 10
<211> LENGTH: 326
<212> TYPE: PRT
<213> ORGANISM: Homo sapiens
<220> FEATURE:
<221> NAME/KEY: VARIANT
<222> LOCATION: (1)...(326)
<223> OTHER INFORMATION: Xaa = Any Amino Acid

<400> SEQUENCE: 10

```
Ala Gln Arg Ala Val Ala Trp Ala Gly Arg Thr Met Ala Ala Pro Glu
  1               5                  10                  15

Pro Ala Pro Arg Arg Ala Arg Glu Arg Glu Arg Glu Arg Glu Asp Glu
             20                  25                  30

Ser Glu Asp Glu Ser Asp Ile Leu Glu Glu Ser Pro Cys Gly Arg Trp
         35                  40                  45

Gln Lys Arg Arg Glu Gln Val Asn Gln Gly Asn Met Pro Gly Leu Gln
     50                  55                  60

Ser Thr Phe Leu Ala Met Asp Thr Glu Glu Gly Val Glu Val Val Trp
 65                  70                  75                  80

Asn Glu Leu His Phe Gly Asp Arg Lys Ala Phe Ala Ala His Glu Glu
                 85                  90                  95

Lys Ile Gln Thr Val Phe Glu Gln Leu Val Leu Val Asp His Pro Asn
            100                 105                 110
```

-continued

Ile Val Lys Leu His Lys Tyr Trp Leu Asp Thr Ser Glu Ala Cys Ala
            115                 120                 125

Arg Val Ile Phe Ile Thr Glu Tyr Val Ser Ser Gly Ser Leu Lys Gln
        130                 135                 140

Phe Leu Lys Lys Thr Lys Lys Asn His Lys Ala Met Asn Ala Arg Ala
145                 150                 155                 160

Trp Lys Arg Trp Cys Thr Gln Ile Leu Ser Ala Leu Ser Phe Leu His
                165                 170                 175

Ala Cys Ser Pro Pro Ile Ile His Gly Asn Leu Thr Ser Asp Thr Ile
            180                 185                 190

Phe Ile Gln His Asn Gly Leu Ile Lys Ile Gly Ser Val Trp His Arg
        195                 200                 205

Ile Phe Ser Asn Ala Leu Pro Asp Asp Leu Arg Ser Pro Ile Arg Ala
210                 215                 220

Glu Arg Glu Glu Leu Arg Asn Leu His Phe Phe Pro Pro Glu Tyr Gly
225                 230                 235                 240

Glu Val Ala Asp Gly Thr Ala Val Asp Ile Phe Phe Gly Met Cys
                245                 250                 255

Ala Leu Glu Met Ala Val Leu Glu Ile Gln Thr Asn Gly Asp Thr Arg
            260                 265                 270

Val Thr Glu Glu Ala Ile Ala Arg Ala Arg His Ser Leu Ser Asp Pro
        275                 280                 285

Asn Met Arg Glu Phe Ile Leu Cys Cys Leu Ala Arg Asp Pro Ala Arg
290                 295                 300

Arg Pro Ser Val His Ser Leu Leu Phe His Xaa Arg Ala Leu Xaa Gly
305                 310                 315                 320

Ala Leu Ala Glu Ala Pro
            325

<210> SEQ ID NO 11
<211> LENGTH: 518
<212> TYPE: DNA
<213> ORGANISM: Homo sapiens
<220> FEATURE:
<221> NAME/KEY: misc_feature
<222> LOCATION: (1)...(518)
<223> OTHER INFORMATION: n=A,T,C or G

<400> SEQUENCE: 11
aaacggaatt caattgcagg atttcctcca cgtgtggagc cgtcttgaag agtttgangg      60
aggtggtgga ggagaaggaa atgtgagcca ggtgggaaga gtttggccat cttcgtatcg     120
agctcttata agtgcctttt ccagactgac gcgtttggat gatttcacct gtgaaaaaat    180
agggtctggc ttctttttctg aagtgttcaa ggtacgacac cgagcttctg gtcaggtgat    240
ggctcttaag atgaacacat tgagcagtaa ccgggcaaac atgctgaaag aagtacagct     300
catgaataga ctctcccatc ccaacatcct taggttcatg ggtgtatgtg ttcatcaagg    360
acaattgcat gcacttacag agtatatcaa ctccgggaac ctggaacagt tgctagacag    420
taacctgcat ttgccttgga ctgtgagggt aaaactggcc tatgacatag cagtgggcct    480
cagctacctt cacttcaaag gcattttttca tcgggacc                            518

<210> SEQ ID NO 12
<211> LENGTH: 172
<212> TYPE: PRT
<213> ORGANISM: Homo sapiens

```
<220> FEATURE:
<221> NAME/KEY: VARIANT
<222> LOCATION: (1)...(172)
<223> OTHER INFORMATION: Xaa = Any Amino Acid

<400> SEQUENCE: 12

Asn Gly Ile Gln Leu Gln Asp Phe Leu His Val Trp Ser Arg Leu Glu
 1               5                  10                  15

Glu Phe Xaa Gly Gly Gly Gly Glu Gly Asn Val Ser Gln Val Gly
            20                  25                  30

Arg Val Trp Pro Ser Ser Tyr Arg Ala Leu Ile Ser Ala Phe Ser Arg
            35                  40                  45

Leu Thr Arg Leu Asp Asp Phe Thr Cys Glu Lys Ile Gly Ser Gly Phe
 50                  55                  60

Phe Ser Glu Val Phe Lys Val Arg His Arg Ala Ser Gly Gln Val Met
 65                  70                  75                  80

Ala Leu Lys Met Asn Thr Leu Ser Ser Asn Arg Ala Asn Met Leu Lys
                85                  90                  95

Glu Val Gln Leu Met Asn Arg Leu Ser His Pro Asn Ile Leu Arg Phe
                100                 105                 110

Met Gly Val Cys Val His Gln Gly Gln Leu His Ala Leu Thr Glu Tyr
            115                 120                 125

Ile Asn Ser Gly Asn Leu Glu Gln Leu Leu Asp Ser Asn Leu His Leu
    130                 135                 140

Pro Trp Thr Val Arg Val Lys Leu Ala Tyr Asp Ile Ala Val Gly Leu
145                 150                 155                 160

Ser Tyr Leu His Phe Lys Gly Ile Phe His Arg Asp
                165                 170

<210> SEQ ID NO 13
<211> LENGTH: 1737
<212> TYPE: DNA
<213> ORGANISM: Homo sapiens
<220> FEATURE:
<221> NAME/KEY: CDS
<222> LOCATION: (275)...(1522)

<400> SEQUENCE: 13
accctactaa agggaacaaa agctggagct ccaccgcggt ggcggccgct ctagaactag      60
tggatccccc gggctgcagg aattcggcac gagtaacagc ccacctccta gccccgggct     120
acgcgccgcc agcccagtaa ccccactttt gtgtgtcctc ccaggccccg atcgaaaagc     180
ctgggagggc cgccgaacta ccccggagg gaggagccag tccgaaccca aggcgccacc     240
gccgcagaag cggagcgagg cagcattcgc ctcc atg gcc cac tcg ccg gtg gct    295
                                      Met Ala His Ser Pro Val Ala
                                        1               5 gtc caa gtg cct ggg atg cag aat aac ata gct gat cca gaa gaa ctg      343
Val Gln Val Pro Gly Met Gln Asn Asn Ile Ala Asp Pro Glu Glu Leu
            10                  15                  20 ttc aca aaa tta gag cgc att ggg aaa ggc tca ttt ggg gaa gtt ttc      391
Phe Thr Lys Leu Glu Arg Ile Gly Lys Gly Ser Phe Gly Glu Val Phe
        25                  30                  35 aaa gga att gat aac cgt acc cag caa gtc gtt gct att aaa atc ata      439
Lys Gly Ile Asp Asn Arg Thr Gln Gln Val Val Ala Ile Lys Ile Ile
 40                  45                  50                  55 gac ctt gag gaa gcc gaa gat gaa ata gaa gac att cag caa gaa ata      487
Asp Leu Glu Glu Ala Glu Asp Glu Ile Glu Asp Ile Gln Gln Glu Ile
                60                  65                  70
```

```
act gtc ttg agt caa tgt gac agc tca tat gta aca aaa tac tat ggg        535
Thr Val Leu Ser Gln Cys Asp Ser Ser Tyr Val Thr Lys Tyr Tyr Gly
         75                  80                  85 tca tat tta aag ggg tct aaa tta tgg ata ata atg gaa tac ctg ggc        583
Ser Tyr Leu Lys Gly Ser Lys Leu Trp Ile Ile Met Glu Tyr Leu Gly
     90                  95                 100 ggt ggt tca gca ctg gat ctt ctt cga gct ggt cca ttt gat gag ttc        631
Gly Gly Ser Ala Leu Asp Leu Leu Arg Ala Gly Pro Phe Asp Glu Phe
105                 110                 115 cag att gct acc atg cta aag gaa att tta aaa ggt ctg gac tat ctg        679
Gln Ile Ala Thr Met Leu Lys Glu Ile Leu Lys Gly Leu Asp Tyr Leu
120                 125                 130                 135 cat tca gaa aag aaa att cac cga gac ata aaa gct gcc aat gtc ttg        727
His Ser Glu Lys Lys Ile His Arg Asp Ile Lys Ala Ala Asn Val Leu
             140                 145                 150 ctc tca gaa caa gga gat gtt aaa ctt gct gat ttt gga gtt gct ggt        775
Leu Ser Glu Gln Gly Asp Val Lys Leu Ala Asp Phe Gly Val Ala Gly
                 155                 160                 165 cag ctg aca gat aca cag att aaa aga aat acc ttt gtg gga act cca        823
Gln Leu Thr Asp Thr Gln Ile Lys Arg Asn Thr Phe Val Gly Thr Pro
         170                 175                 180 ttt tgg atg gct cct gaa gtt att caa cag tca gct tat gac tca aaa        871
Phe Trp Met Ala Pro Glu Val Ile Gln Gln Ser Ala Tyr Asp Ser Lys
185                 190                 195 gct gac att tgg tca ttg gga att act gct att gaa cta gcc aag gga        919
Ala Asp Ile Trp Ser Leu Gly Ile Thr Ala Ile Glu Leu Ala Lys Gly
200                 205                 210                 215 gag cca cct aac tcc gat atg cat cca atg aga gtt ctg ttt ctt att        967
Glu Pro Pro Asn Ser Asp Met His Pro Met Arg Val Leu Phe Leu Ile
             220                 225                 230 ccc aaa aac aat cct cca act ctt gtt gga gac ttt act aag tct ttt       1015
Pro Lys Asn Asn Pro Pro Thr Leu Val Gly Asp Phe Thr Lys Ser Phe
                 235                 240                 245 aag gag ttt att gat gct tgc ctg aac aaa gat cca tca ttt cgt cct       1063
Lys Glu Phe Ile Asp Ala Cys Leu Asn Lys Asp Pro Ser Phe Arg Pro
         250                 255                 260 aca gca aaa gaa ctt ctg aaa cac aaa ttc att gta aaa aat tca aag       1111
Thr Ala Lys Glu Leu Leu Lys His Lys Phe Ile Val Lys Asn Ser Lys
265                 270                 275 aag act tct tat ctg act gaa ctg ata gat cgt ttt aag aga tgg aag       1159
Lys Thr Ser Tyr Leu Thr Glu Leu Ile Asp Arg Phe Lys Arg Trp Lys
280                 285                 290                 295 gca gaa gga cac agt gat gat gaa tct gat tcc gag ggc tct gat tcg       1207
Ala Glu Gly His Ser Asp Asp Glu Ser Asp Ser Glu Gly Ser Asp Ser
             300                 305                 310 gaa tct acc agc agg gaa aac aat act cat cct gaa tgg agc ttt acc       1255
Glu Ser Thr Ser Arg Glu Asn Asn Thr His Pro Glu Trp Ser Phe Thr
                 315                 320                 325 acc gta cga aag aag cct gat cca aag aaa gta cag aat ggg gca gag       1303
Thr Val Arg Lys Lys Pro Asp Pro Lys Lys Val Gln Asn Gly Ala Glu
         330                 335                 340 caa gat ctt gtg caa acc ctg agt tgt ttg tct atg ata atc aca cct       1351
Gln Asp Leu Val Gln Thr Leu Ser Cys Leu Ser Met Ile Ile Thr Pro
345                 350                 355 gca ttt gct gaa ctt aaa cag cag gac gag aat aac gct agc agg aat       1399
Ala Phe Ala Glu Leu Lys Gln Gln Asp Glu Asn Asn Ala Ser Arg Asn
360                 365                 370                 375 cag gcg att gaa gaa ctc gag aaa agt att gct gtg gct gaa gcc gcc       1447
Gln Ala Ile Glu Glu Leu Glu Lys Ser Ile Ala Val Ala Glu Ala Ala
             380                 385                 390
```

-continued

```
tgt ccc ggc atc aca gat aaa atg gtg aag aaa cta att gaa aaa ttt       1495
Cys Pro Gly Ile Thr Asp Lys Met Val Lys Lys Leu Ile Glu Lys Phe
        395                 400                 405 caa aag tgt tca gca gac gaa tcc ccc taagaaactt attattggct             1542
Gln Lys Cys Ser Ala Asp Glu Ser Pro
        410                 415 tctgkttcat atggacccag agagccccac caaacctacg tcaagataac aatgcttaac     1602
ccatgagctc catgtgcctt ttggatcttt gcaacacttg aagatttgga agaagctatt     1662
aaactatttt ggggatggcg gttatcattt tatattttgg aaggattatt tgtaagggat     1722
aacttttaat actat                                                      1737
```

<210> SEQ ID NO 14
<211> LENGTH: 416
<212> TYPE: PRT
<213> ORGANISM: Homo sapiens

<400> SEQUENCE: 14

```
Met Ala His Ser Pro Val Ala Val Gln Val Pro Gly Met Gln Asn Asn
  1               5                  10                  15

Ile Ala Asp Pro Glu Glu Leu Phe Thr Lys Leu Glu Arg Ile Gly Lys
             20                  25                  30

Gly Ser Phe Gly Glu Val Phe Lys Gly Ile Asp Asn Arg Thr Gln Gln
         35                  40                  45

Val Val Ala Ile Lys Ile Ile Asp Leu Glu Glu Ala Glu Asp Glu Ile
     50                  55                  60

Glu Asp Ile Gln Gln Glu Ile Thr Val Leu Ser Gln Cys Asp Ser Ser
 65                  70                  75                  80

Tyr Val Thr Lys Tyr Tyr Gly Ser Tyr Leu Lys Gly Ser Lys Leu Trp
                 85                  90                  95

Ile Ile Met Glu Tyr Leu Gly Gly Gly Ser Ala Leu Asp Leu Leu Arg
            100                 105                 110

Ala Gly Pro Phe Asp Glu Phe Gln Ile Ala Thr Met Leu Lys Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu Gln Gly Asp Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Gln
            180                 185                 190

Gln Ser Ala Tyr Asp Ser Lys Ala Asp Ile Trp Ser Leu Gly Ile Thr
        195                 200                 205

Ala Ile Glu Leu Ala Lys Gly Glu Pro Pro Asn Ser Asp Met His Pro
    210                 215                 220

Met Arg Val Leu Phe Leu Ile Pro Lys Asn Asn Pro Pro Thr Leu Val
225                 230                 235                 240

Gly Asp Phe Thr Lys Ser Phe Lys Glu Phe Ile Asp Ala Cys Leu Asn
                245                 250                 255

Lys Asp Pro Ser Phe Arg Pro Thr Ala Lys Glu Leu Leu Lys His Lys
            260                 265                 270

Phe Ile Val Lys Asn Ser Lys Lys Thr Ser Tyr Leu Thr Glu Leu Ile
        275                 280                 285
```

```
Asp Arg Phe Lys Arg Trp Lys Ala Glu Gly His Ser Asp Glu Ser
        290                 295                 300

Asp Ser Glu Gly Ser Asp Ser Glu Ser Thr Ser Arg Glu Asn Asn Thr
305                 310                 315                 320

His Pro Glu Trp Ser Phe Thr Thr Val Arg Lys Lys Pro Asp Pro Lys
                325                 330                 335

Lys Val Gln Asn Gly Ala Glu Gln Asp Leu Val Gln Thr Leu Ser Cys
            340                 345                 350

Leu Ser Met Ile Ile Thr Pro Ala Phe Ala Glu Leu Lys Gln Gln Asp
        355                 360                 365

Glu Asn Asn Ala Ser Arg Asn Gln Ala Ile Glu Glu Leu Glu Lys Ser
370                 375                 380

Ile Ala Val Ala Glu Ala Ala Cys Pro Gly Ile Thr Asp Lys Met Val
385                 390                 395                 400

Lys Lys Leu Ile Glu Lys Phe Gln Lys Cys Ser Ala Asp Glu Ser Pro
                405                 410                 415

<210> SEQ ID NO 15
<211> LENGTH: 645
<212> TYPE: PRT
<213> ORGANISM: Arabidopsis thaliana

<400> SEQUENCE: 15

Met Phe Phe Leu Val Phe Ala Phe Phe Leu Ile Ser Pro Val Arg Ser
1               5                   10                  15

Ser Asp Val Glu Ala Leu Leu Ser Leu Lys Ser Ser Ile Asp Pro Ser
            20                  25                  30

Asn Ser Ile Pro Trp Arg Gly Thr Asp Pro Cys Asn Trp Glu Gly Val
        35                  40                  45

Lys Lys Cys Met Lys Gly Arg Val Ser Lys Leu Val Leu Glu Asn Leu
    50                  55                  60

Asn Leu Ser Gly Ser Leu Asn Gly Lys Ser Leu Asn Gln Leu Asp Gln
65                  70                  75                  80

Leu Arg Val Leu Ser Phe Lys Gly Asn Ser Leu Ser Gly Ser Ile Pro
                85                  90                  95

Asn Leu Ser Gly Leu Val Asn Leu Lys Ser Leu Tyr Leu Asn Asp Asn
            100                 105                 110

Asn Phe Ser Gly Glu Phe Pro Glu Ser Leu Thr Ser Leu His Arg Leu
        115                 120                 125

Lys Thr Val Val Leu Ser Arg Asn Arg Phe Ser Gly Lys Ile Pro Ser
    130                 135                 140

Ser Leu Leu Arg Leu Ser Arg Leu Tyr Thr Phe Tyr Val Gln Asp Asn
145                 150                 155                 160

Leu Phe Ser Gly Ser Ile Pro Pro Leu Asn Gln Ala Thr Leu Arg Phe
                165                 170                 175

Phe Asn Val Ser Asn Asn Gln Leu Ser Gly His Ile Pro Pro Thr Gln
            180                 185                 190

Ala Leu Asn Arg Phe Asn Glu Ser Ser Phe Thr Asp Asn Ile Ala Leu
        195                 200                 205

Cys Gly Asp Gln Ile Gln Asn Ser Cys Asn Asp Thr Thr Gly Ile Thr
    210                 215                 220

Ser Thr Pro Ser Ala Lys Pro Ala Ile Pro Val Ala Lys Thr Arg Ser
225                 230                 235                 240

Arg Thr Lys Leu Ile Gly Ile Ile Ser Gly Ser Ile Cys Gly Gly Ile
                245                 250                 255
```

-continued

```
Leu Ile Leu Leu Leu Thr Phe Leu Leu Ile Cys Leu Leu Trp Arg Arg
            260                 265                 270

Lys Arg Ser Lys Ser Lys Arg Glu Glu Arg Arg Ser Lys Arg Val Ala
        275                 280                 285

Glu Ser Lys Glu Ala Lys Thr Ala Glu Thr Glu Gly Thr Ser Asp
290                 295                 300

Gln Lys Asn Lys Arg Phe Ser Trp Glu Lys Glu Ser Glu Glu Gly Ser
305                 310                 315                 320

Val Gly Thr Leu Val Phe Leu Gly Arg Asp Ile Thr Val Val Arg Tyr
            325                 330                 335

Thr Met Asp Asp Leu Leu Lys Ala Ser Ala Glu Thr Leu Gly Arg Gly
            340                 345                 350

Thr Leu Gly Ser Thr Tyr Lys Ala Val Met Glu Ser Gly Phe Ile Ile
            355                 360                 365

Thr Val Lys Arg Leu Lys Asp Ala Gly Phe Pro Arg Met Asp Glu Phe
        370                 375                 380

Lys Arg His Ile Glu Ile Leu Gly Arg Leu Lys His Pro Asn Leu Val
385                 390                 395                 400

Pro Leu Arg Ala Tyr Phe Gln Ala Lys Glu Glu Cys Leu Leu Val Tyr
            405                 410                 415

Asp Tyr Phe Pro Asn Gly Ser Leu Phe Ser Leu Ile His Gly Ser Lys
            420                 425                 430

Val Ser Gly Ser Gly Lys Pro Leu His Trp Thr Ser Cys Leu Lys Ile
        435                 440                 445

Ala Glu Asp Leu Ala Met Gly Leu Val Tyr Ile His Gln Asn Pro Gly
        450                 455                 460

Leu Thr His Gly Asn Leu Lys Ser Ser Asn Val Leu Leu Gly Pro Asp
465                 470                 475                 480

Phe Glu Ser Cys Leu Thr Asp Tyr Gly Leu Ser Asp Leu His Asp Pro
            485                 490                 495

Tyr Ser Ile Glu Asp Thr Ser Ala Ala Ser Leu Phe Tyr Lys Ala Pro
            500                 505                 510

Glu Cys Arg Asp Leu Arg Lys Ala Ser Thr Gln Pro Ala Asp Val Tyr
        515                 520                 525

Ser Phe Gly Val Leu Leu Leu Glu Leu Leu Thr Gly Arg Thr Ser Phe
530                 535                 540

Lys Asp Leu Val His Lys Tyr Gly Ser Asp Ile Ser Thr Trp Val Arg
545                 550                 555                 560

Ala Val Arg Glu Glu Glu Thr Glu Val Ser Glu Glu Leu Asn Ala Ser
            565                 570                 575

Glu Glu Lys Leu Gln Ala Leu Leu Thr Ile Ala Thr Ala Cys Val Ala
            580                 585                 590

Val Lys Pro Glu Asn Arg Pro Ala Met Arg Glu Val Leu Lys Met Val
        595                 600                 605

Lys Asp Ala Arg Ala Glu Ala Ala Leu Phe Ser Phe Asn Ser Ser Asp
        610                 615                 620

His Ser Pro Gly Arg Trp Ser Asp Thr Ile Gln Ser Leu Pro Arg Glu
625                 630                 635                 640

Asp His Met Ser Ile
            645
```

<210> SEQ ID NO 16
<211> LENGTH: 645
<212> TYPE: PRT
<213> ORGANISM: Arabidopsis thaliana

<400> SEQUENCE: 16

| Met | Phe | Phe | Leu | Val | Phe | Ala | Phe | Phe | Leu | Ile | Ser | Pro | Val | Arg | Ser |
|---|---|---|---|---|---|---|---|---|---|---|---|---|---|---|---|
| 1 | | | | 5 | | | | | 10 | | | | | 15 | |

Ser Asp Val Glu Ala Leu Leu Ser Leu Lys Ser Ser Ile Asp Pro Ser
            20                  25                  30

Asn Ser Ile Pro Trp Arg Gly Thr Asp Pro Cys Asn Trp Glu Gly Val
        35                  40                  45

Lys Lys Cys Met Lys Gly Arg Val Ser Lys Leu Val Leu Glu Asn Leu
    50                  55                  60

Asn Leu Ser Gly Ser Leu Asn Gly Lys Ser Leu Asn Gln Leu Asp Gln
65                  70                  75                  80

Leu Arg Val Leu Ser Phe Lys Gly Asn Ser Leu Ser Gly Ser Ile Pro
                85                  90                  95

Asn Leu Ser Gly Leu Val Asn Leu Lys Ser Leu Tyr Leu Asn Asp Asn
            100                 105                 110

Asn Phe Ser Gly Glu Phe Pro Glu Ser Leu Thr Ser Leu His Arg Leu
        115                 120                 125

Lys Thr Val Val Leu Ser Arg Asn Arg Phe Ser Gly Lys Ile Pro Ser
    130                 135                 140

Ser Leu Leu Arg Leu Ser Arg Leu Tyr Thr Phe Tyr Val Gln Asp Asn
145                 150                 155                 160

Leu Phe Ser Gly Ser Ile Pro Pro Leu Asn Gln Ala Thr Leu Arg Phe
                165                 170                 175

Phe Asn Val Ser Asn Asn Gln Leu Ser Gly His Ile Pro Pro Thr Gln
            180                 185                 190

Ala Leu Asn Arg Phe Asn Glu Ser Ser Phe Thr Asp Asn Ile Ala Leu
        195                 200                 205

Cys Gly Asp Gln Ile Gln Asn Ser Cys Asn Asp Thr Thr Gly Ile Thr
    210                 215                 220

Ser Thr Pro Ser Ala Lys Pro Ala Ile Pro Val Ala Lys Thr Arg Ser
225                 230                 235                 240

Arg Thr Lys Leu Ile Gly Ile Ile Ser Gly Ser Ile Cys Gly Gly Ile
                245                 250                 255

Leu Ile Leu Leu Leu Thr Phe Leu Leu Ile Cys Leu Leu Trp Arg Arg
            260                 265                 270

Lys Arg Ser Lys Ser Lys Arg Glu Glu Arg Ser Lys Arg Val Ala
        275                 280                 285

Glu Ser Lys Glu Ala Lys Thr Ala Glu Thr Glu Gly Thr Ser Asp
    290                 295                 300

Gln Lys Asn Lys Arg Phe Ser Trp Glu Lys Glu Ser Glu Gly Ser
305                 310                 315                 320

Val Gly Thr Leu Val Phe Leu Gly Arg Asp Ile Thr Val Val Arg Tyr
                325                 330                 335

Thr Met Asp Asp Leu Leu Lys Ala Ser Ala Glu Thr Leu Gly Arg Gly
            340                 345                 350

Thr Leu Gly Ser Thr Tyr Lys Ala Val Met Glu Ser Gly Phe Ile Ile
        355                 360                 365

Thr Val Lys Arg Leu Lys Asp Ala Gly Phe Pro Arg Met Asp Glu Phe
    370                 375                 380

-continued

```
Lys Arg His Ile Glu Ile Leu Gly Arg Leu Lys His Pro Asn Leu Val
385                 390                 395                 400

Pro Leu Arg Ala Tyr Phe Gln Ala Lys Glu Glu Cys Leu Leu Val Tyr
            405                 410                 415

Asp Tyr Phe Pro Asn Gly Ser Leu Phe Ser Leu Ile His Gly Ser Lys
        420                 425                 430

Val Ser Gly Ser Gly Lys Pro Leu His Trp Thr Ser Cys Leu Lys Ile
    435                 440                 445

Ala Glu Asp Leu Ala Met Gly Leu Val Tyr Ile His Gln Asn Pro Gly
450                 455                 460

Leu Thr His Gly Asn Leu Lys Ser Ser Asn Val Leu Leu Gly Pro Asp
465                 470                 475                 480

Phe Glu Ser Cys Leu Thr Asp Tyr Gly Leu Ser Asp Leu His Asp Pro
            485                 490                 495

Tyr Ser Ile Glu Asp Thr Ser Ala Ala Ser Leu Phe Tyr Lys Ala Pro
        500                 505                 510

Glu Cys Arg Asp Leu Arg Lys Ala Ser Thr Gln Pro Ala Asp Val Tyr
    515                 520                 525

Ser Phe Gly Val Leu Leu Leu Glu Leu Leu Thr Gly Arg Thr Ser Phe
530                 535                 540

Lys Asp Leu Val His Lys Tyr Gly Ser Asp Ile Ser Thr Trp Val Arg
545                 550                 555                 560

Ala Val Arg Glu Glu Thr Glu Val Ser Glu Glu Leu Asn Ala Ser
            565                 570                 575

Glu Glu Lys Leu Gln Ala Leu Leu Thr Ile Ala Thr Ala Cys Val Ala
            580                 585                 590

Val Lys Pro Glu Asn Arg Pro Ala Met Arg Glu Val Leu Lys Met Val
            595                 600                 605

Lys Asp Ala Arg Ala Glu Ala Ala Leu Phe Ser Phe Asn Ser Ser Asp
    610                 615                 620

His Ser Pro Gly Arg Trp Ser Asp Thr Ile Gln Ser Leu Pro Arg Glu
625                 630                 635                 640

Asp His Met Ser Ile
            645

<210> SEQ ID NO 17
<211> LENGTH: 604
<212> TYPE: PRT
<213> ORGANISM: Arabidopsis thaliana

<400> SEQUENCE: 17

Ser Leu Lys Ser Ser Ile Asp Pro Ser Asn Ser Ile Ser Trp Arg Gly
1               5                   10                  15

Thr Asp Leu Cys Asn Trp Gln Gly Val Arg Glu Cys Met Asn Gly Arg
            20                  25                  30

Val Ser Lys Leu Val Leu Glu Tyr Leu Asn Leu Thr Gly Ser Leu Asn
        35                  40                  45

Glu Lys Ser Leu Asn Gln Leu Asp Gln Leu Arg Val Leu Ser Phe Lys
    50                  55                  60

Ala Asn Ser Leu Ser Gly Ser Ile Pro Asn Leu Ser Gly Leu Val Asn
65                  70                  75                  80

Leu Lys Ser Val Tyr Leu Asn Asp Asn Phe Ser Gly Asp Phe Pro
            85                  90                  95

Glu Ser Leu Thr Ser Leu His Arg Leu Lys Thr Ile Phe Leu Ser Gly
        100                 105                 110
```

```
Asn Arg Leu Ser Gly Arg Ile Pro Ser Ser Leu Leu Arg Leu Ser Arg
        115                 120                 125

Leu Tyr Thr Leu Asn Val Glu Asp Asn Leu Phe Thr Gly Ser Ile Pro
130                 135                 140

Pro Leu Asn Gln Thr Ser Leu Arg Tyr Phe Asn Val Ser Asn Asn Lys
145                 150                 155                 160

Leu Ser Gly Gln Ile Pro Leu Thr Arg Ala Leu Lys Gln Phe Asp Glu
                165                 170                 175

Ser Ser Phe Thr Gly Asn Val Ala Leu Cys Gly Asp Gln Ile Gly Lys
            180                 185                 190

Glu Gln Ser Glu Leu Ile Gly Ile Ala Gly Ser Val Ala Gly Gly
        195                 200                 205

Val Leu Val Leu Ile Leu Leu Leu Thr Leu Leu Ile Val Cys Trp Arg
210                 215                 220

Arg Lys Arg Arg Asn Gln Ala Pro Arg Glu Asp Arg Lys Gly Lys Gly
225                 230                 235                 240

Ile Ala Glu Ala Glu Gly Ala Thr Thr Ala Glu Thr Glu Arg Asp Ile
                245                 250                 255

Glu Arg Lys Asp Arg Gly Phe Ser Trp Glu Arg Gly Glu Glu Gly Ala
            260                 265                 270

Val Gly Thr Leu Val Phe Leu Gly Thr Ser Asp Ser Gly Glu Thr Val
        275                 280                 285

Val Arg Tyr Thr Met Glu Asp Leu Leu Lys Ala Ser Ala Glu Thr Leu
290                 295                 300

Gly Arg Gly Thr Leu Gly Ser Thr Tyr Lys Ala Val Met Glu Ser Gly
305                 310                 315                 320

Phe Ile Val Thr Val Lys Arg Leu Lys Asn Ala Arg Tyr Pro Arg Met
                325                 330                 335

Glu Glu Phe Lys Arg His Val Glu Ile Leu Gly Gln Leu Lys His Pro
            340                 345                 350

Asn Leu Val Pro Leu Arg Ala Tyr Phe Gln Ala Lys Glu Glu Arg Leu
        355                 360                 365

Leu Val Tyr Asp Tyr Phe Pro Asn Gly Ser Leu Phe Thr Leu Ile His
370                 375                 380

Gly Thr Arg Ala Ser Gly Ser Gly Lys Pro Leu His Trp Thr Ser Cys
385                 390                 395                 400

Leu Lys Ile Ala Glu Asp Leu Ala Ser Ala Leu Leu Tyr Ile His Gln
                405                 410                 415

Asn Pro Gly Leu Thr His Gly Asn Leu Lys Ser Ser Asn Val Leu Leu
            420                 425                 430

Gly Pro Asp Phe Glu Ser Cys Leu Thr Asp Tyr Gly Leu Ser Thr Leu
        435                 440                 445

His Asp Pro Asp Ser Val Glu Glu Thr Ser Ala Val Ser Leu Phe Tyr
450                 455                 460

Lys Ala Pro Glu Cys Arg Asp Pro Arg Lys Ala Ser Thr Gln Pro Ala
465                 470                 475                 480

Asp Val Tyr Ser Phe Gly Val Leu Leu Leu Glu Leu Leu Thr Gly Arg
                485                 490                 495

Thr Pro Phe Gln Asp Leu Val Gln Glu Tyr Gly Ser Asp Ile Ser Arg
            500                 505                 510

Trp Val Arg Ala Val Arg Glu Glu Glu Thr Glu Ser Gly Glu Glu Pro
        515                 520                 525
```

```
Thr Ser Ser Gly Asn Glu Ala Ser Glu Glu Lys Leu Gln Ala Leu Leu
        530                 535                 540

Ser Ile Ala Thr Val Cys Val Thr Ile Gln Pro Asp Asn Arg Pro Val
545                 550                 555                 560

Met Arg Glu Val Leu Lys Met Val Arg Asp Ala Arg Ala Glu Ala Pro
                565                 570                 575

Phe Ser Ser Asn Ser Ser Glu His Ser Pro Gly Arg Trp Ser Asp Thr
                580                 585                 590

Val Gln Ser Leu Pro Arg Asp Asp Gln Val Ser Ile
        595                 600

<210> SEQ ID NO 18
<211> LENGTH: 328
<212> TYPE: PRT
<213> ORGANISM: C. elegans

<400> SEQUENCE: 18

Met Ser Arg Asn His Glu Glu Asn Lys Arg Lys Thr Lys Asn Lys Glu
  1               5                  10                  15

Tyr Lys Cys Met Lys Met Ser Thr Pro Thr Ser Asn Glu Ser Thr Ser
                 20                  25                  30

Ser Ser Ser Asn Asn Ser Asp Gln Arg Val Leu Phe Pro Asp Ile Gln
             35                  40                  45

Arg Asp Asp Ile Gln Val Gly Asp His Ile Gly Val Gly Thr Phe Gly
         50                  55                  60

Ala Val Phe Ser Gly Asn Trp Thr Leu Pro Asp Gly Ser Gln Arg Thr
 65                  70                  75                  80

Ile Ala Leu Lys Lys Val Phe Val Leu Glu Lys Glu Ala Glu Ile Leu
                 85                  90                  95

Ser Lys Ile Arg His Lys Asn Ile Ile Gln Phe Tyr Gly Ile Cys Lys
                100                 105                 110

Ala Thr Gly Asn Asp Phe Phe Ile Val Thr Glu Tyr Ala Glu Lys Gly
                115                 120                 125

Ser Leu Tyr Asp Phe Ile His Ser Glu Glu Ser Gln Ser Phe Ala Ser
            130                 135                 140

Ser Ser Gly Gly Asn Ser Phe Asp Val Val Lys Trp Ala Ser Gln
145                 150                 155                 160

Ile Ala Ser Gly Ile Gln Tyr Leu His Tyr Asp Ala Val Asp Thr Ile
                165                 170                 175

Ile His Arg Asp Leu Lys Ser Lys Asn Val Val Leu Asp Lys Asn Leu
            180                 185                 190

Val Cys Lys Ile Cys Asp Phe Gly Thr Ser Lys Asp Leu Thr His Ser
            195                 200                 205

Cys Thr Ala Pro Ser Trp Gly Gly Thr Ala Ala Trp Met Ser Pro Glu
210                 215                 220

Met Ile Leu Gln Ser Glu Gly Leu Thr Thr Ala Thr Asp Val Trp Ser
225                 230                 235                 240

Tyr Gly Val Val Leu Trp Glu Ile Leu Ser Lys Glu Val Pro Tyr Lys
                245                 250                 255

Asp Tyr Ser Glu Phe Arg Ile Phe Thr Met Ile Thr Gln Ser Gly Ile
            260                 265                 270

Thr Leu Ala Ile Pro Pro Ser Cys Pro Ala Pro Leu Lys Gln Leu Met
        275                 280                 285

Ser Asn Cys Trp Lys Met Thr Pro Lys Asp Arg Ala Asn Met Arg Gln
290                 295                 300
```

```
Ile Gln Gly Glu Leu Asn Arg Leu Ala Gly Asn Gln Lys Val Arg Val
305                 310                 315                 320

Ser Lys Leu Ser Leu Ser Ser Val
                325

<210> SEQ ID NO 19
<211> LENGTH: 394
<212> TYPE: PRT
<213> ORGANISM: Homo sapiens

<400> SEQUENCE: 19

Ala Glu Leu Thr Leu Glu Glu Ile Ile Gly Ile Gly Gly Phe Gly Lys
  1               5                  10                  15

Val Tyr Arg Ala Phe Trp Ile Gly Asp Glu Val Ala Val Lys Ala Ala
             20                  25                  30

Arg His Asp Pro Asp Glu Asp Ile Ser Gln Thr Ile Glu Asn Val Arg
         35                  40                  45

Gln Glu Ala Lys Leu Phe Ala Met Leu Lys His Pro Asn Ile Ile Ala
     50                  55                  60

Leu Arg Gly Val Cys Leu Lys Glu Pro Asn Leu Cys Leu Val Met Glu
 65                  70                  75                  80

Phe Ala Arg Gly Gly Pro Leu Asn Arg Val Leu Ser Gly Lys Arg Ile
                 85                  90                  95

Pro Pro Asp Ile Leu Val Asn Trp Ala Val Gln Ile Ala Arg Gly Met
            100                 105                 110

Asn Tyr Leu His Asp Glu Ala Ile Val Pro Ile Ile His Arg Asp Leu
        115                 120                 125

Lys Ser Ser Asn Ile Leu Ile Leu Gln Lys Val Glu Asn Gly Asp Leu
    130                 135                 140

Ser Asn Lys Ile Leu Lys Ile Thr Asp Phe Gly Leu Ala Arg Glu Trp
145                 150                 155                 160

His Arg Thr Thr Lys Met Ser Ala Ala Gly Thr Tyr Ala Trp Met Ala
                165                 170                 175

Pro Glu Val Ile Arg Ala Ser Met Phe Ser Lys Gly Ser Asp Val Trp
            180                 185                 190

Ser Tyr Gly Val Leu Leu Trp Glu Leu Leu Thr Gly Glu Val Pro Phe
        195                 200                 205

Arg Gly Ile Asp Gly Leu Arg Val Ala Tyr Gly Val Ala Met Asn Lys
    210                 215                 220

Leu Ala Leu Pro Ile Pro Ser Thr Cys Pro Glu Pro Phe Ala Lys Leu
225                 230                 235                 240

Met Glu Asp Cys Trp Asn Pro Asp Pro His Ser Arg Pro Ser Phe Thr
                245                 250                 255

Asn Ile Leu Asp Gln Leu Thr Thr Ile Glu Glu Ser Gly Phe Phe Glu
            260                 265                 270

Met Pro Lys Asp Ser Phe His Cys Leu Gln Asp Asn Trp Lys His Glu
        275                 280                 285

Ile Gln Glu Met Phe Asp Gln Leu Arg Ala Lys Glu Lys Glu Leu Arg
    290                 295                 300

Thr Trp Glu Glu Glu Leu Thr Arg Ala Ala Leu Gln Gln Lys Asn Gln
305                 310                 315                 320

Glu Glu Leu Leu Arg Arg Arg Glu Gln Leu Ala Glu Arg Glu Ile
                325                 330                 335

Asp Ile Leu Glu Arg Glu Leu Asn Ile Ile Ile His Gln Leu Cys Gln
            340                 345                 350
```

```
Glu Lys Pro Arg Val Lys Lys Arg Lys Gly Lys Phe Arg Lys Ser Arg
            355                 360                 365

Leu Ala Gln Pro Val Leu Pro Phe Pro His Gly His Ser Arg Cys Pro
    370                 375                 380

Gly Gly Thr Gly Ser Ser Trp Gly Gly Gln
385                 390

<210> SEQ ID NO 20
<211> LENGTH: 370
<212> TYPE: PRT
<213> ORGANISM: avian

<400> SEQUENCE: 20

Ala Asp Ser Pro Gly Leu Ala Arg Pro His Ala His Phe Ala Ser Ala
1               5                   10                  15

Gly Ala Asp Ala Ala Gly Gly Ser Pro Val Leu Leu Leu Arg Thr
            20                  25                  30

Thr Ser Cys Cys Leu Glu Asp Leu Arg Pro Glu Leu Leu Glu Glu Val
        35                  40                  45

Lys Asp Ile Leu Ile Pro Glu Glu Arg Leu Ile Thr His Arg Ser Arg
50                  55                  60

Val Ile Gly Arg Gly His Phe Gly Ser Val Tyr His Gly Thr Tyr Met
65                  70                  75                  80

Asp Pro Leu Leu Gly Asn Leu His Cys Ala Val Lys Ser Leu His Arg
                85                  90                  95

Ile Thr Tyr Leu Glu Glu Val Glu Phe Leu Arg Glu Gly Ile Leu
            100                 105                 110

Met Lys Gly Phe His His Pro Gln Val Leu Ser Leu Leu Gly Val Cys
        115                 120                 125

Leu Pro Arg His Gly Leu Pro Leu Val Val Leu Pro Tyr Met Arg His
    130                 135                 140

Gly Asp Leu Arg His Phe Val Arg Ala Gln Glu Arg Ser Pro Thr Val
145                 150                 155                 160

Lys Glu Leu Ile Gly Phe Gly Leu Gln Val Ala Leu Gly Met Glu Tyr
                165                 170                 175

Leu Ala Gln Lys Lys Phe Val His Arg Asp Leu Ala Ala Arg Asn Cys
            180                 185                 190

Met Leu Asp Glu Thr Leu Thr Val Lys Val Ala Asp Phe Gly Leu Ala
        195                 200                 205

Arg Asp Val Phe Gly Lys Glu Tyr Tyr Ser Ile Arg Gln His Arg His
    210                 215                 220

Ala Lys Leu Pro Val Arg Trp Met Ala Leu Glu Ser Leu Gln Thr Gln
225                 230                 235                 240

Lys Phe Thr Thr Lys Ser Asp Val Trp Ser Phe Gly Val Leu Met Trp
                245                 250                 255

Glu Leu Leu Thr Arg Gly Ala Ser Pro Tyr Pro Glu Val Asp Pro Tyr
            260                 265                 270

Asp Met Ala Arg Tyr Leu Leu Arg Gly Arg Arg Leu Pro Gln Pro Gln
        275                 280                 285

Pro Cys Pro Asp Thr Leu Tyr Gly Val Met Leu Ser Cys Trp Ala Pro
    290                 295                 300

Thr Pro Glu Glu Arg Pro Ser Phe Ser Gly Leu Val Cys Glu Leu Glu
305                 310                 315                 320

Arg Val Leu Ala Ser Leu Glu Gly Glu His Tyr Ile Asn Met Ala Val
                325                 330                 335
```

Thr Tyr Val Asn Leu Glu Ser Gly Pro Pro Phe Pro Ala Pro Arg
                340                 345                 350

Gly Gln Leu Pro Asp Ser Glu Asp Glu Asp Glu Glu Glu Val
            355                 360                 365

Ala Glu
    370

<210> SEQ ID NO 21
<211> LENGTH: 596
<212> TYPE: PRT
<213> ORGANISM: avian

<400> SEQUENCE: 21

Lys Leu Thr Met Leu Ala Pro Asn His Thr Asp Ile Leu Lys Val Leu
  1               5                  10                  15

Ala Asn Ser Ser Arg Thr Gly Ile Arg Arg Lys Arg Asn Thr Ser His
                 20                  25                  30

Leu Asp Asp Thr Cys Ser Asp Glu Val Gln Leu Trp Gly Pro Thr Ala
             35                  40                  45

Arg Ile Phe Ala Ser Ile Leu Ala Pro Gly Val Ala Ala Thr Gln Ala
         50                  55                  60

Leu Arg Glu Ile Glu Arg Leu Ala Cys Trp Ser Val Lys Gln Ala Asn
 65                  70                  75                  80

Leu Thr Thr Ser Leu Leu Gly Asp Leu Leu Asp Asp Val Thr Ser Ile
                 85                  90                  95

Arg His Ala Val Leu Gln Asn Arg Ala Ala Ile Asp Phe Leu Leu Leu
            100                 105                 110

Ala His Gly His Gly Cys Glu Asp Ile Ala Gly Met Cys Cys Phe Asn
        115                 120                 125

Leu Ser Asp His Ser Glu Ser Ile Gln Lys Lys Phe Gln Leu Met Lys
    130                 135                 140

Lys His Val Asn Lys Ile Gly Val Asp Ser Asp Pro Ile Gly Ser Trp
145                 150                 155                 160

Leu Arg Gly Leu Phe Gly Gly Ile Gly Glu Trp Ala Val His Leu Leu
                165                 170                 175

Lys Gly Leu Leu Leu Gly Leu Val Val Ile Leu Leu Leu Val Val Cys
            180                 185                 190

Leu Pro Cys Leu Leu Gln Phe Val Ser Ser Ile Arg Lys Met Ile
        195                 200                 205

Asp Asn Ser Leu Gly Tyr Arg Glu Glu Cys Arg Lys Leu Gln Glu Ala
    210                 215                 220

Asn Arg Ala Asp Ser Pro Gly Leu Ala Arg Pro His Ala His Phe Ala
225                 230                 235                 240

Ser Ala Gly Ala Asp Ala Ala Gly Gly Ser Pro Val Leu Leu Leu
                245                 250                 255

Arg Thr Thr Ser Cys Cys Leu Glu Asp Leu Arg Pro Glu Leu Leu Glu
            260                 265                 270

Glu Val Lys Asp Ile Leu Ile Pro Glu Glu Arg Leu Ile Thr His Arg
        275                 280                 285

Ser Arg Val Ile Gly Arg Gly His Phe Gly Ser Val Tyr His Gly Thr
    290                 295                 300

Tyr Met Asp Pro Leu Leu Gly Asn Leu His Cys Ala Val Lys Ser Leu
305                 310                 315                 320

His Arg Ile Thr Asp Leu Glu Glu Val Glu Glu Phe Leu Arg Glu Gly
                325                 330                 335

Ile Leu Met Lys Gly Phe His His Pro Gln Val Leu Ser Leu Leu Gly
                340                 345                 350

Val Cys Leu Pro Arg His Gly Leu Pro Leu Val Val Leu Pro Tyr Met
            355                 360                 365

Arg His Gly Asp Leu Arg His Phe Val Arg Ala Gln Glu Arg Ser Pro
        370                 375                 380

Thr Val Lys Glu Leu Ile Gly Phe Gly Leu Gln Val Ala Leu Gly Met
385                 390                 395                 400

Glu Tyr Leu Ala Gln Lys Lys Phe Val His Arg Asp Leu Ala Ala Arg
                405                 410                 415

Asn Cys Met Leu Asp Glu Thr Leu Thr Val Lys Val Ala Asp Phe Gly
            420                 425                 430

Leu Ala Arg Asp Val Phe Gly Lys Glu Tyr Tyr Ser Ile Arg Gln His
        435                 440                 445

Arg His Ala Lys Leu Pro Val Arg Trp Met Ala Leu Glu Ser Leu Gln
    450                 455                 460

Thr Gln Lys Phe Thr Thr Lys Ser Asp Val Trp Ser Phe Gly Val Leu
465                 470                 475                 480

Met Trp Glu Leu Leu Thr Arg Gly Ala Ser Pro Tyr Pro Glu Val Asp
                485                 490                 495

Pro Tyr Asp Met Ala Arg Tyr Leu Leu Arg Gly Arg Arg Leu Pro Gln
            500                 505                 510

Pro Gln Pro Cys Pro Asp Thr Leu Tyr Gly Val Met Leu Ser Cys Trp
        515                 520                 525

Ala Pro Thr Pro Glu Glu Arg Pro Ser Phe Ser Gly Leu Val Cys Glu
    530                 535                 540

Leu Glu Arg Val Leu Ala Ser Leu Glu Gly Glu His Tyr Ile Asn Met
545                 550                 555                 560

Ala Val Thr Tyr Val Asn Leu Glu Ser Gly Pro Pro Phe Pro Pro Ala
                565                 570                 575

Pro Arg Gly Gln Leu Pro Asp Ser Glu Asp Glu Asp Glu Glu Glu Glu
            580                 585                 590

Glu Val Ala Glu
        595

<210> SEQ ID NO 22
<211> LENGTH: 430
<212> TYPE: PRT
<213> ORGANISM: C. elegans

<400> SEQUENCE: 22

Met Ile Ile Gly Ile Val Ile Gly Ser Leu Val Val Ile Leu Val Ala
1               5                   10                  15

Ile Val Val Ile Trp Phe Tyr Phe Arg Lys Lys Ser Glu Asn Met Lys
            20                  25                  30

Phe Lys Phe Gln Met Glu Gln Val Gly Lys Asn Asn Met Asn Arg Tyr
        35                  40                  45

Ile Asp Phe Pro Ile Met Ala Ala Lys Asn Asp Ile Trp Glu Ile Glu
    50                  55                  60

Arg Arg Asn Leu Ile Ile His Asn Asp Lys Lys Leu Gly Ser Gly Ala
65                  70                  75                  80

Phe Gly Ala Val Tyr Leu Gly Lys Leu Ile Gly Lys Ser Leu Ala His
                85                  90                  95

Lys Asp Ala Asn Ser Pro Leu Gly Ile Asn Leu Met Arg Ala Glu Asn
            100                 105                 110

```
Cys Gln Val Ala Val Lys Met Leu Pro Glu Tyr Ala Asp Glu Met Ser
        115                 120                 125

Lys His Glu Phe Leu Arg Glu Ile Ala Leu Met Lys Thr Leu Gly Tyr
        130                 135                 140

His Glu Arg Leu Val Asn Met Leu Ala Cys Val Thr Glu Ser Glu Pro
145                 150                 155                 160

Leu Cys Leu Val Val Glu Tyr Cys Asp Asn Gly Asp Leu Leu Lys Phe
                165                 170                 175

Leu Arg Glu Arg Cys Lys Tyr Met Met Lys Leu Asp Asp Leu Gly Ile
                180                 185                 190

Asn Tyr His Asp Pro Pro Glu Asn Glu Asn Tyr Asp Thr Asn Met Ile
                195                 200                 205

Val Thr Leu Lys Gln Leu Leu Gln Phe Ala Val Gln Ile Ser Tyr Gly
        210                 215                 220

Leu Glu Tyr Leu Ser Gln Lys Gly Phe Val His Arg Asp Val Ala Ala
225                 230                 235                 240

Arg Asn Val Leu Val His Gly Thr Ala Cys Lys Ile Gly Asp Phe
                245                 250                 255

Gly Leu Cys Arg Tyr Ile Tyr Ala Asp Gln Ser Gln Tyr Lys Ser Lys
                260                 265                 270

Gly Gly Lys Leu Pro Leu Lys Trp Met Ser Pro Glu Ala Ile Arg His
        275                 280                 285

Tyr Glu Phe Ser Ile Lys Ser Asp Ile Trp Ser Phe Gly Ile Leu Leu
        290                 295                 300

Phe Glu Val Ile Thr Leu Gly Gly Ser Pro Tyr Pro Gly Met Pro Pro
305                 310                 315                 320

Glu Asp Val Leu Pro Phe Leu Glu Gly Gly Arg Ile Glu Lys Pro
                325                 330                 335

Asp Asn Cys Pro Glu Asn Phe Tyr Asp Val Met Met Gln Cys Trp Asn
                340                 345                 350

Ala Asp Pro Asp Asp Arg Ile Glu Phe Ser Asp Val Arg Met Gln Leu
                355                 360                 365

Ala Thr Gln Leu Glu Asp Ile Thr Glu Asp Tyr Ser Tyr Leu Lys Leu
        370                 375                 380

Asp Ala Ala Lys Asp Tyr Tyr Asn Val Gln Tyr Gly Asp Glu Lys Lys
385                 390                 395                 400

Thr Asp Val Val Ile Ile Pro Asp Glu Ile Ile Lys Pro Ser Lys Leu
                405                 410                 415

Ile Met Asp Asp Ile Ser Glu Lys Asn Leu Val Ile Glu Gln
                420                 425                 430

<210> SEQ ID NO 23
<211> LENGTH: 923
<212> TYPE: PRT
<213> ORGANISM: Drosophila melanogaster

<400> SEQUENCE: 23

Met Leu Ile Phe Tyr Ala Lys Tyr Ala Phe Ile Phe Trp Phe Phe Val
1               5                   10                  15

Gly Ser Asn Gln Gly Glu Met Leu Leu Met Asp Lys Ile Ser His Asp
                20                  25                  30

Lys Thr Leu Leu Asn Val Thr Ala Cys Thr Gln Asn Cys Leu Glu Lys
        35                  40                  45

Gly Gln Met Asp Phe Arg Ser Cys Leu Lys Asp Cys Arg Ile Asn Gly
50                  55                  60
```

-continued

```
Thr Phe Pro Gly Ala Leu Arg Lys Val Gln Glu Asn Tyr Gln Met Asn
 65              70                  75                  80

Met Ile Cys Arg Thr Glu Ser Glu Ile Val Phe Gln Ile Asp Trp Val
                 85                  90                  95

Gln His Ser Arg Gly Thr Glu Pro Ala Pro Asn Ala Thr Tyr Ile Ile
                100                 105                 110

Arg Val Asp Ala Val Lys Asp Asp Asn Lys Glu Thr Thr Leu Tyr Leu
                115                 120                 125

Ser Asp Asp Asn Phe Leu Ile Leu Pro Gly Leu Glu Ser Asn Ser Thr
                130                 135                 140

His Asn Ile Thr Ala Leu Ala Met His Gly Asp Gly Ser Tyr Ser Leu
145                 150                 155                 160

Ile Ala Lys Asp Gln Thr Phe Ala Thr Leu Ile Arg Gly Tyr Gln Pro
                165                 170                 175

Ser Lys Met Gly Ala Val Asn Leu Leu Arg Phe Val Pro Gln Pro Asp
                180                 185                 190

Asp Leu His His Ile Ala Ala Glu Ile Glu Trp Lys Pro Ser Ala Glu
                195                 200                 205

Ser Asn Cys Tyr Phe Asp Met Val Ser Tyr Ser Thr Asn Ser Val Asn
                210                 215                 220

Met Asp Glu Pro Leu Glu Val Gln Phe Arg Asp Arg Lys Lys Leu Tyr
225                 230                 235                 240

Arg His Thr Val Asp Asn Leu Glu Phe Asp Lys Gln Tyr His Val Gly
                245                 250                 255

Val Arg Thr Val Asn Ile Met Asn Arg Leu Glu Ser Asp Leu Gln Trp
                260                 265                 270

Leu Pro Ile Ala Val Pro Ser Cys Leu Asp Trp Tyr Pro Tyr Asn Tyr
                275                 280                 285

Thr Leu Cys Pro Pro His Lys Pro Glu Asn Leu Thr Val Thr Gln Lys
                290                 295                 300

Gln Tyr Leu Pro Asn Ile Leu Ala Leu Asn Ile Thr Trp Ala Arg Pro
305                 310                 315                 320

Arg Tyr Leu Pro Asp Asn Tyr Thr Leu His Ile Phe Asp Leu Phe Lys
                325                 330                 335

Gly Gly Thr Glu Leu Asn Tyr Thr Leu Asp Gln Asn Arg Ser His Phe
                340                 345                 350

Tyr Val Pro Lys Ile Thr Val Leu Gly Ser His Phe Glu Val His Leu
                355                 360                 365

Val Ala Gln Ser Ala Gly Gly Lys Asn Val Ser Gly Leu Thr Leu Asp
                370                 375                 380

Lys Val Pro Arg Gly Val Leu Leu Ser Glu Gly Asn Met Val Lys Leu
385                 390                 395                 400

Val Leu Phe Ile Ile Val Pro Ile Cys Cys Ile Leu Met Leu Cys Ser
                405                 410                 415

Leu Thr Phe Cys Arg Arg Asn Arg Ser Glu Val Gln Ala Leu Gln Met
                420                 425                 430

Asp Ala Lys Asp Ala Lys Ala Ser Glu Phe His Leu Ser Leu Met Asp
                435                 440                 445

Ser Ser Gly Leu Leu Val Thr Leu Ser Ala Asn Glu Ser Leu Glu Val
                450                 455                 460

Met Asp Glu Leu Glu Val Glu Pro His Ser Val Leu Leu Gln Asp Val
465                 470                 475                 480
```

-continued

```
Leu Gly Glu Gly Ala Phe Gly Leu Val Arg Gly Val Tyr Lys Lys
                485                 490                 495

Arg Gln Val Ala Val Lys Leu Leu Lys Asp Glu Pro Asn Asp Glu Asp
                500                 505                 510

Val Tyr Ala Phe Lys Cys Glu Ile Gln Met Leu Lys Ala Val Gly Lys
                515                 520                 525

His Pro Asn Ile Val Gly Ile Val Gly Tyr Ser Thr Arg Phe Ser Asn
                530                 535                 540

Gln Met Met Leu Leu Ile Glu Tyr Cys Ser Leu Gly Ser Leu Gln Asn
545                 550                 555                 560

Phe Leu Arg Glu Glu Trp Lys Phe Arg Gln Glu Gln Asn Ala Ile Gly
                565                 570                 575

Leu Lys Lys Asn Leu Glu Gln Asn Val Asp Asn Arg Arg Phe Asn Arg
                580                 585                 590

Leu Pro Arg Asn Ser Ile His Asp Arg Ile Glu Asp Ile Asn Asn Ser
                595                 600                 605

Met Leu Ser Thr Val Glu Glu Ser Glu Ser Asp Gln Thr His Ser
610                 615                 620

Ser Arg Cys Glu Thr Tyr Thr Leu Thr Arg Ile Thr Asn Ala Ala Asp
625                 630                 635                 640

Asn Lys Gly Tyr Gly Leu Glu Asp Ile Glu Asn Ile Gly Gly Ser Tyr
                645                 650                 655

Ile Pro Lys Thr Ala Glu Ala Pro Lys Asp Gln Pro Lys Arg Lys Leu
                660                 665                 670

Lys Pro Gln Pro Lys Lys Asp Ser Lys Gln Asp Phe Lys Ser Asp Asn
                675                 680                 685

Lys Lys Arg Ile Phe Glu Asn Lys Glu Tyr Phe Asp Cys Leu Asp Ser
                690                 695                 700

Ser Asp Thr Lys Pro Arg Ile Pro Leu Lys Tyr Ala Asp Leu Leu Asp
705                 710                 715                 720

Ile Ala Gln Gln Val Ala Val Gly Met Glu Phe Leu Ala Gln Asn Lys
                725                 730                 735

Val Val His Arg Asp Leu Ala Ala Arg Asn Val Leu Ile Ser Val Asp
                740                 745                 750

Arg Ser Ile Lys Ile Ala Asp Phe Gly Leu Ser Arg Asp Val Tyr His
                755                 760                 765

Glu Asn Val Tyr Arg Lys Ser Gly Gly Ser Gly Lys Leu Pro Ile Lys
                770                 775                 780

Trp Leu Ala Leu Glu Ser Leu Thr His Gln Val Tyr Thr Ser Gln Ser
785                 790                 795                 800

Asp Val Trp Ser Phe Gly Val Leu Leu Tyr Glu Ile Thr Thr Leu Gly
                805                 810                 815

Gly Met Pro Tyr Pro Ser Val Ser Pro Ser Asp Leu Leu Gln Leu Leu
                820                 825                 830

Arg Gln Gly His Arg Met Lys Arg Pro Glu Gly Cys Thr Gln Glu Met
                835                 840                 845

Phe Ser Leu Met Glu Ser Cys Trp Ser Ser Val Pro Ser His Arg Pro
                850                 855                 860

Thr Phe Ser Ala Leu Lys His Arg Leu Gly Gly Met Ile Leu Ala Thr
865                 870                 875                 880

Asn Asp Val Pro Glu Arg Leu Lys Gln Leu Gln Ala Ala Thr Glu Ser
                885                 890                 895
```

```
Lys Leu Lys Ser Cys Asp Gly Leu Asn Ser Lys Val Glu Gln Val Pro
            900                 905                 910

Cys Glu Glu Leu Tyr Leu Glu Pro Leu Asn
            915                 920

<210> SEQ ID NO 24
<211> LENGTH: 1404
<212> TYPE: PRT
<213> ORGANISM: Gallus gallus

<400> SEQUENCE: 24

Met Gly Pro Arg Cys Leu Val Cys Leu Leu Leu Leu Ala Pro Ser
 1               5                  10                  15

Leu Leu Gln Ala Gly Ala Trp Gln Cys Arg Arg Ile Pro Phe Ser Ser
            20                  25                  30

Thr Arg Asn Phe Ser Val Pro Tyr Thr Leu Pro Ser Leu Asp Ala Gly
            35                  40                  45

Ser Pro Val Gln Asn Ile Ala Val Phe Pro Asp Pro Thr Val Phe
        50                  55                  60

Val Ala Val Arg Asn Arg Ile Leu Val Val Asp Pro Glu Leu Arg Leu
 65                  70                  75                  80

Arg Ser Val Leu Val Thr Gly Pro Thr Gly Ser Ala Pro Cys Glu Ile
                    85                  90                  95

Cys Arg Leu Cys Pro Ala Ala Val Asp Ala Pro Gly Pro Glu Asp Val
                100                 105                 110

Asp Asn Val Leu Leu Leu Asp Pro Val Glu Pro Trp Leu Tyr Ser
            115                 120                 125

Cys Gly Thr Ala Arg Arg Gly Leu Cys Tyr Leu His Gln Leu Asp Val
        130                 135                 140

Arg Gly Ser Glu Val Thr Ile Ala Ser Thr Arg Cys Leu Tyr Ser Ala
145                 150                 155                 160

Ala Ala Asn Ser Pro Val Asn Cys Pro Asp Cys Val Ala Ser Pro Leu
                165                 170                 175

Gly Ser Thr Ala Thr Val Val Ala Asp Arg Tyr Thr Ala Ser Phe Tyr
            180                 185                 190

Leu Gly Ser Thr Val Asn Ser Ser Val Ala Ala Arg Tyr Ser Pro Arg
        195                 200                 205

Ser Val Ser Val Arg Arg Leu Lys Gly Thr Arg Asp Gly Phe Ala Asp
210                 215                 220

Pro Phe His Ser Leu Thr Val Leu Pro His Tyr Gln Asp Val Tyr Pro
225                 230                 235                 240

Ile His Tyr Val His Ser Phe Thr Asp Gly Asp His Val Tyr Leu Val
                245                 250                 255

Thr Val Gln Pro Glu Phe Pro Gly Ser Ser Thr Phe His Thr Arg Leu
            260                 265                 270

Val Arg Leu Ser Ala His Glu Pro Glu Leu Arg Arg Tyr Arg Glu Ile
        275                 280                 285

Val Leu Asp Cys Arg Tyr Glu Ser Lys Arg Arg Arg Arg Arg Gly
290                 295                 300

Ala Glu Glu Glu Thr Glu Arg Asp Val Ala Tyr Asn Val Leu Gln Ala
305                 310                 315                 320

Ala His Ala Ala Arg Pro Gly Ala Arg Leu Ala Arg Asp Leu Gly Ile
                325                 330                 335

Asp Gly Thr Glu Thr Val Leu Phe Gly Ala Phe Ala Glu Ser His Pro
            340                 345                 350
```

-continued

```
Glu Ser Arg Ala Pro Gln His Asn Ser Ala Val Cys Ala Phe Pro Leu
    355                 360                 365
Arg Leu Leu Asn Gln Ala Ile Arg Glu Gly Met Asp Lys Cys Cys Gly
    370                 375                 380
Thr Gly Thr Gln Thr Leu Lys Arg Gly Leu Ala Phe Phe Gln Pro Gln
385                 390                 395                 400
Gln Tyr Cys Pro His Ser Val Asn Leu Ser Ala Pro Val Thr Asn Thr
                405                 410                 415
Ser Cys Trp Asp Gln Pro Thr Leu Val Pro Ala Ala Ser His Lys Val
            420                 425                 430
Asp Leu Phe Asn Gly Arg Leu Ser Gly Thr Leu Leu Thr Ser Ile Phe
        435                 440                 445
Val Thr Val Leu Gln Asn Val Thr Val Ala His Leu Gly Thr Ala Gln
    450                 455                 460
Gly Arg Val Leu Gln Met Val Leu Gln Arg Ser Ser Tyr Val Val
465                 470                 475                 480
Ala Leu Thr Asn Phe Ser Leu Gly Glu Pro Gly Leu Val Gln His Ala
                485                 490                 495
Thr Gly Leu Gln Gly His Ser Leu Leu Phe Ala Ala Gly Thr Lys Val
            500                 505                 510
Trp Arg Val Asn Val Thr Gly Pro Gly Cys Arg His Phe Ser Thr Cys
        515                 520                 525
Asp Arg Cys Leu Arg Ala Glu Arg Phe Met Gly Cys Gly Trp Cys Gly
    530                 535                 540
Asn Gly Cys Thr Arg His His Glu Cys Ala Gly Pro Trp Val Gln Asp
545                 550                 555                 560
Ser Cys Pro Pro Val Leu Thr Asp Phe His Pro Arg Ser Ala Pro Leu
                565                 570                 575
Arg Gly Gln Thr Arg Val Thr Leu Cys Gly Met Thr Phe His Ser Pro
            580                 585                 590
Pro Asp Pro Thr Ala His His Ser Leu Pro Gly Pro Tyr Arg Val Ala
        595                 600                 605
Val Gly Gly Arg Ser Cys Thr Val Leu Leu Asp Glu Ser Glu Ser Tyr
    610                 615                 620
Arg Pro Leu Pro Thr Phe Arg Arg Lys Asp Phe Val Asp Val Leu Val
625                 630                 635                 640
Cys Val Leu Glu Pro Gly Glu Pro Ala Val Ala Ala Gly Pro Ala Asp
                645                 650                 655
Val Val Leu Asn Val Thr Glu Ser Ala Gly Thr Ser Arg Phe Arg Val
            660                 665                 670
Gln Gly Ser Ser Thr Leu Ser Gly Phe Val Phe Val Glu Pro His Ile
        675                 680                 685
Ser Thr Leu His Pro Ser Phe Gly Pro Gln Gly Gly Gly Thr Leu Met
    690                 695                 700
Ser Leu Tyr Gly Thr His Leu Ser Ala Gly Ser Ser Trp Arg Val Thr
705                 710                 715                 720
Ile Asn Gly Ser Glu Cys Leu Leu Asp Gly Gln Pro Ser Glu Gly Asp
                725                 730                 735
Gly Glu Ile Arg Cys Thr Ala Pro Ala Ala Thr Ser Leu Gly Ala Ala
            740                 745                 750
Pro Val Ala Leu Trp Ile Asp Gly Glu Glu Phe Leu Ala Pro Leu Pro
        755                 760                 765
```

-continued

```
Phe Glu Tyr Arg Pro Asp Pro Ser Val Leu Thr Val Pro Asn Cys
    770                 775                 780

Ser Tyr Gly Gly Ser Thr Leu Thr Leu Ile Gly Thr His Leu Asp Ser
785                 790                 795                 800

Val Tyr Arg Ala Lys Ile Gln Phe Gln Gly Gly Gly Gly Lys Thr
            805                 810                 815

Glu Ala Thr Glu Cys Glu Gly Pro Gln Ser Pro Asn Trp Leu Leu Cys
        820                 825                 830

Arg Ser Pro Ala Phe Pro Ile Glu Ile Lys Pro Val Pro Gly Asn Leu
        835                 840                 845

Ser Val Leu Leu Asp Gly Ala Ala Asp Arg Trp Leu Phe Arg Leu Arg
    850                 855                 860

Tyr Phe Pro Gln Pro Gln Met Phe Ser Phe Gly Gln Gln Gly Glu Arg
865                 870                 875                 880

Tyr Gln Leu Lys Pro Gly Asp Asn Glu Ile Lys Val Asn Gln Leu Gly
            885                 890                 895

Leu Asp Ser Val Ala Gly Cys Met Asn Ile Thr Met Thr Val Gly Gly
        900                 905                 910

Arg Asp Cys His Pro Asn Val Leu Lys Asn Glu Val Thr Cys Arg Val
    915                 920                 925

Pro Arg Asp Val Asp Leu Thr Pro Ala Gly Ala Pro Val Gln Ile Cys
930                 935                 940

Val Asn Gly Asp Cys Gln Ala Leu Gly Leu Val Leu Pro Ala Ser Ser
945                 950                 955                 960

Leu Asp Met Ala Ala Ser Leu Ala Leu Gly Thr Gly Val Thr Phe Leu
            965                 970                 975

Val Cys Cys Val Leu Ala Ala Val Leu Leu Arg Trp Arg Trp Arg Lys
        980                 985                 990

Arg Arg Gly Leu Glu Asn Leu Glu Leu Val His Pro Pro Arg Ile
    995                 1000                1005

Glu His Pro Ile Thr Ile Gln Arg Pro Asn Val Asp Tyr Arg Glu Val
    1010                1015                1020

Gln Val Leu Pro Val Ala Asp Ser Pro Gly Leu Ala Arg Pro His Ala
1025                1030                1035                1040

His Phe Ala Ser Ala Gly Ala Asp Ala Ala Gly Gly Ser Pro Val
            1045                1050                1055

Pro Leu Leu Arg Thr Thr Ser Cys Cys Leu Glu Asp Leu Arg Pro Glu
        1060                1065                1070

Leu Leu Glu Glu Val Lys Asp Ile Leu Ile Pro Glu Glu Arg Leu Ile
    1075                1080                1085

Thr His Arg Ser Arg Val Ile Gly Arg Gly His Phe Gly Ser Val Tyr
    1090                1095                1100

His Gly Thr Tyr Met Asp Pro Leu Leu Gly Asn Leu His Cys Ala Val
1105                1110                1115                1120

Lys Ser Leu His Arg Ile Thr Asp Leu Glu Glu Val Glu Glu Phe Leu
            1125                1130                1135

Arg Glu Gly Ile Leu Met Lys Ser Phe His His Pro Gln Val Leu Ser
        1140                1145                1150

Leu Leu Gly Val Cys Leu Pro Arg His Gly Leu Pro Leu Val Val Leu
    1155                1160                1165

Pro Tyr Met Arg His Gly Asp Leu Arg His Phe Ile Arg Ala Gln Glu
    1170                1175                1180
```

-continued

```
Arg Ser Pro Thr Val Lys Glu Leu Ile Gly Phe Gly Leu Gln Val Ala
1185                1190                1195                1200

Leu Gly Met Glu Tyr Leu Ala Gln Lys Lys Phe Val His Arg Asp Leu
            1205                1210                1215

Ala Ala Arg Asn Cys Met Leu Asp Glu Thr Leu Thr Val Lys Val Ala
        1220                1225                1230

Asp Phe Gly Leu Ala Arg Asp Val Phe Gly Lys Glu Tyr Tyr Ser Ile
    1235                1240                1245

Arg Gln His Arg His Ala Lys Leu Pro Val Lys Trp Met Ala Leu Glu
1250                1255                1260

Ser Leu Gln Thr Gln Lys Phe Thr Thr Lys Ser Asp Val Trp Ser Phe
1265                1270                1275                1280

Gly Val Leu Met Trp Glu Leu Leu Thr Arg Gly Ala Ser Pro Tyr Pro
            1285                1290                1295

Glu Val Asp Pro Tyr Asp Met Ala Arg Tyr Leu Leu Arg Gly Arg Arg
        1300                1305                1310

Leu Pro Gln Pro Gln Pro Cys Pro Asp Thr Leu Tyr Gly Val Met Leu
    1315                1320                1325

Ser Cys Trp Ala Pro Thr Pro Glu Glu Arg Pro Ser Phe Ser Gly Leu
1330                1335                1340

Val Cys Glu Leu Glu Arg Val Leu Ala Ser Leu Glu Gly Glu Arg Tyr
1345                1350                1355                1360

Val Asn Leu Ala Val Thr Tyr Val Asn Leu Glu Ser Gly Pro Pro Phe
            1365                1370                1375

Pro Pro Ala Pro Arg Gly Gln Leu Pro Asp Ser Glu Asp Glu Glu Asp
        1380                1385                1390

Glu Glu Asp Glu Glu Asp Glu Asp Ala Ala Val Arg
    1395                1400
```

<210> SEQ ID NO 25
<211> LENGTH: 891
<212> TYPE: PRT
<213> ORGANISM: Hydra vulgaris

<400> SEQUENCE: 25

```
Met Leu Phe Met Lys Ile Ile Leu Leu Asn Phe Val Leu Leu Asn Val
1               5                   10                  15

Ser Asn Ile Ala Glu Ala Leu Gln Phe Ile Ala Lys Pro Phe Ser Gly
            20                  25                  30

Gly Ile Trp His Val Asn Lys Asp Asp Asn Ile Thr Ile Ser Cys Leu
        35                  40                  45

Thr Asp Asp Ser Ser Ala Asn Val Thr Leu Leu Val Gly Glu Lys Thr
    50                  55                  60

Ile Gln Asp Gln Phe Ile Lys Arg Lys Gly Leu Leu Lys Ile Asp Gly
65                  70                  75                  80

Gln Ile Phe Lys Leu His Leu Ile Thr Ser Ser Asp Trp Asn Thr Tyr
                85                  90                  95

Gln Cys Met Ala Arg Ala Glu Asp Lys Asn Leu Val Leu Lys Leu Gly
            100                 105                 110

Thr Leu Ile Val Asn Pro Ala Pro Cys Asn Lys Ala Pro Asp Leu Gln
        115                 120                 125

Arg Phe Gly Lys Thr Leu Asn Tyr Ser Val Asp Val Glu Tyr Glu Leu
    130                 135                 140

Phe Asp Glu Ile Ile Ile Val Cys Ser Thr Pro Gly Ile Asp Gly Ile
145                 150                 155                 160
```

-continued

```
Lys Asn Ile Leu Thr Trp Val Asn Lys Asn Ile Ser Ser Asp Leu Lys
            165                 170                 175

Gln Thr Val Leu Pro Asp Glu Arg Asp Gln Val Thr Tyr Ile Asp Arg
            180                 185                 190

Leu Gln Leu Lys Ile Ser Tyr Ala Asn Leu Met Asn Glu Gly Glu Tyr
            195                 200                 205

Ile Cys Lys Arg Ser Leu Cys Asn Ile Thr Ser Ser Arg Ser Ile Lys
            210                 215                 220

Leu Lys Tyr Lys Asn Pro Tyr Lys Pro Ile Ile Ser Leu Ser Tyr Ser
225                 230                 235                 240

Gly Lys Pro Gln Lys Gly Arg Ser Ile Lys Ile Gln Cys Leu Val Asp
            245                 250                 255

Ser Ser Pro Ser Ser Thr Ile Glu Trp Tyr Ser Gly Asp Ser Leu Leu
            260                 265                 270

Leu Val Cys Lys Ser Ser Lys Lys Pro Tyr Thr Asp Leu Gln Ile Pro
            275                 280                 285

Cys Glu Tyr Thr Ile Gln Asp Phe Asn Arg Asn Thr Asn Phe Thr Cys
            290                 295                 300

Ile Ala Lys Asn Ala Ala Gly Asn Ser Ser Gln Ser Leu Ile Ile Tyr
305                 310                 315                 320

Val Leu Val Pro Pro Leu Ile Ser Pro Ser Lys Ala Glu Ser Gln Arg
            325                 330                 335

Phe Glu Cys Thr Val Thr Gln Gly Asn Pro Leu Pro Phe Ile Tyr Trp
            340                 345                 350

Glu Arg Lys Val Leu Ser Cys Lys Asn Cys Glu Ser Gln Trp Val Asn
            355                 360                 365

Phe Ser Ser Glu Asn Val Lys Val Val Pro Pro Thr Tyr Glu Pro Ser
            370                 375                 380

Ser Gln Ser Ala Leu Ile Phe Gln Asn Ser Phe Lys Asp Ile Gly Ser
385                 390                 395                 400

Ile Arg Cys His Ala Tyr Asn Ser Glu Gly Asn Ser Ser Ala Val Ile
            405                 410                 415

Ser Leu Asn Tyr Ser Ala Gly Lys Glu Pro Arg Phe Pro Thr Val Gly
            420                 425                 430

Ile Ile Cys Gly Phe Leu Val Ile Phe Ile Phe Leu Ile Ile Ile
            435                 440                 445

Phe Phe Tyr Lys Arg Tyr Thr Asn Lys Lys Phe Ala Leu Phe Met Glu
            450                 455                 460

Pro Asn Pro Lys Phe Lys Leu Asp Pro Ser Arg Thr Ile Phe Glu Gln
465                 470                 475                 480

Ser Ile Glu Leu Pro Tyr Asp Leu Ser Trp Glu Phe Pro Arg His Arg
            485                 490                 495

Leu Asp Phe Val Arg Val Ile Gly Ser Gly Ala Phe Gly Gln Val Trp
            500                 505                 510

Phe Ala His Ala Arg Gly Ile Leu Ala Leu Cys Pro Arg Asp Lys Ser
            515                 520                 525

Ala Ser Ala Ala Arg Gln Arg Ala Lys Leu Tyr Phe Asn Thr Lys Val
            530                 535                 540

Pro Lys Ser Leu Thr Lys Leu Phe Thr Asn Gly Ser Met Cys Asp His
545                 550                 555                 560

Asp Thr Phe Val Ala Val Lys Thr Leu Lys Ser Ser Ala Ser Asp Val
            565                 570                 575
```

-continued

```
Glu Tyr Arg Asp Leu Ser Ser Glu Ile Lys Val Leu Ile His Leu Gly
                580                 585                 590

Glu His Pro Asn Ile Val Asn Leu Leu Gly Ser Cys Thr Lys Asp Gly
            595                 600                 605

Arg Leu Cys Ala Ile Met Glu Tyr Cys Pro His Gly Asn Leu Val Gly
        610                 615                 620

Phe Leu Arg Pro Arg Arg His Val Phe Ser Leu Gln Trp Glu Lys Gln
625                 630                 635                 640

Ala Leu Asn Tyr Asp Glu Asp Phe Cys Trp Leu Asp Ala Ala Thr Ala
                645                 650                 655

Ala Phe Gln Ile Ala Ser Gly Met Leu Phe Leu Ser Glu Lys Lys Leu
            660                 665                 670

Val His Arg Asp Leu Ala Ala Arg Asn Val Leu Val Gly Pro Asp Tyr
        675                 680                 685

Ile Met Lys Leu Ala Asp Phe Gly Leu Ala Arg Asp Ile Tyr Leu Ser
    690                 695                 700

Gly Val Tyr Ile Lys Glu Ser Cys Gly Ile Leu Pro Val Lys Trp Met
705                 710                 715                 720

Ala Pro Glu Ser Leu Phe Asp Lys Val Tyr Thr Ile Lys Ser Asp Val
                725                 730                 735

Trp Ser Phe Gly Ile Val Leu Trp Glu Ile Cys Thr Met Gly Gly Ser
            740                 745                 750

Pro Tyr Pro Gly Leu Pro Thr Glu Asp Leu Phe Glu Tyr Leu Thr Ala
        755                 760                 765

Gly Lys Arg Met Cys Gln Pro Val Thr Cys Pro Asp Glu Leu Tyr Glu
    770                 775                 780

Ile Met Leu Gln Cys Trp Gln Glu Arg Pro Glu Glu Arg Pro Trp Phe
785                 790                 795                 800

His Glu Ile Val Ser Gln Leu Gln Arg Ile Ile Glu Ser Lys Asn Glu
                805                 810                 815

Pro Pro Asn Asn Leu Ser Ala Phe Asp Arg Ile Gln Ser Val Ser Asp
            820                 825                 830

Glu Thr Asp Cys Leu Val Pro Leu Ser Pro Leu Lys Lys Lys Lys Ser
        835                 840                 845

Ser Asp Val Ile Phe Thr Lys Lys Asp Ser Leu Lys Thr Lys Ile Asp
    850                 855                 860

Cys Val Phe Asn Phe Pro Pro Ile Glu Asp Asn Ser Asp Lys Asn Gly
865                 870                 875                 880

Asn Ser Val Asn Lys Glu Gln Leu Asn Thr Thr
                885                 890

<210> SEQ ID NO 26
<211> LENGTH: 355
<212> TYPE: PRT
<213> ORGANISM: Arabidopsis thaliana

<400> SEQUENCE: 26

Met Ala Asn Ala Lys Glu Thr Thr Phe Tyr Ile Thr Ile Ser Val Val
 1               5                   10                  15

Ala Phe Val Ile Gly Lys Ile Val Ile Ala Leu Leu Phe Tyr Lys Arg
                20                  25                  30

Trp Lys Arg Lys His Thr Ile His Glu Asn Gly Phe Pro Val Lys Gly
            35                  40                  45

Gly Gly Lys Met Val Met Phe Arg Ser Gln Leu Leu Asn Ser Val Ser
        50                  55                  60
```

```
Ser Asp Met Phe Met Lys Lys Thr His Lys Leu Ser Asn Lys Asp Ile
 65                  70                  75                  80

Leu Gly Ser Gly Gly Phe Gly Thr Val Tyr Arg Leu Val Ile Asp Asp
                 85                  90                  95

Ser Thr Thr Phe Ala Val Lys Arg Leu Asn Arg Gly Thr Ser Glu Arg
            100                 105                 110

Asp Arg Gly Phe His Arg Glu Leu Glu Ala Met Ala Asp Ile Lys His
        115                 120                 125

Arg Asn Ile Val Thr Leu His Gly Tyr Phe Thr Ser Pro His Tyr Asn
130                 135                 140

Leu Leu Ile Tyr Glu Leu Met Pro Asn Gly Ser Leu Asp Ser Phe Leu
145                 150                 155                 160

His Gly Arg Lys Ala Leu Asp Trp Ala Ser Arg Tyr Arg Ile Ala Val
                165                 170                 175

Gly Ala Ala Arg Gly Ile Ser Tyr Leu His His Asp Cys Ile Pro His
            180                 185                 190

Ile Ile His Arg Asp Ile Lys Ser Ser Asn Ile Leu Leu Asp His Asn
        195                 200                 205

Met Glu Ala Arg Val Ser Asp Phe Gly Leu Ala Thr Leu Met Glu Pro
210                 215                 220

Asp Lys Thr His Val Ser Thr Phe Val Ala Gly Thr Phe Gly Tyr Leu
225                 230                 235                 240

Ala Pro Glu Tyr Phe Asp Thr Gly Lys Ala Thr Met Lys Gly Asp Val
                245                 250                 255

Tyr Ser Phe Gly Val Val Leu Leu Glu Leu Leu Thr Gly Arg Lys Pro
            260                 265                 270

Thr Asp Asp Glu Phe Phe Glu Glu Gly Thr Lys Leu Val Thr Trp Val
        275                 280                 285

Lys Gly Val Val Arg Asp Gln Arg Glu Glu Val Val Ile Asp Asn Arg
290                 295                 300

Leu Arg Gly Ser Ser Val Gln Glu Asn Glu Glu Met Asn Asp Val Phe
305                 310                 315                 320

Gly Ile Ala Met Met Cys Leu Glu Pro Glu Pro Ala Ile Arg Pro Ala
                325                 330                 335

Met Thr Glu Val Val Lys Leu Leu Glu Tyr Ile Lys Leu Ser Thr Arg
            340                 345                 350

Ser Ser Phe
        355

<210> SEQ ID NO 27
<211> LENGTH: 669
<212> TYPE: PRT
<213> ORGANISM: Arabidopsis thaliana

<400> SEQUENCE: 27

Met Lys Phe Phe Val Leu Val Leu Leu Val Leu Gln Phe Phe Ser
 1               5                  10                  15

Asn Lys Ala Leu Ser Gln Ser Glu Glu Gly Glu Phe Gly Phe Asn Gly
                 20                  25                  30

Tyr Leu Tyr Asp Asn Ser Gly Ile Ala Ile Thr Asn Ser Lys Gly Leu
            35                  40                  45

Met Lys Leu Thr Asn Ser Ser Glu Phe Ser Tyr Gly His Val Phe Tyr
        50                  55                  60

Asn Ser Pro Val Arg Phe Lys Asn Ser Pro Asn Gly Thr Val Ser Ser
 65                  70                  75                  80
```

```
Phe Ser Thr Thr Phe Val Phe Ala Ile Val Ser Asn Val Asn Ala Leu
             85                  90                  95

Asp Gly His Gly Leu Ala Phe Val Ile Ser Pro Thr Lys Gly Leu Pro
            100                 105                 110

Tyr Ser Ser Ser Ser Gln Tyr Leu Gly Leu Phe Asn Leu Thr Asn Asn
            115                 120                 125

Gly Asp Pro Ser Asn His Ile Val Ala Val Glu Phe Asp Thr Phe Gln
130                 135                 140

Asn Gln Glu Phe Asp Asp Met Asp Asn Asn His Val Gly Ile Asp Ile
145                 150                 155                 160

Asn Ser Leu Ser Ser Glu Lys Ala Ser Thr Ala Gly Tyr Tyr Glu Asp
                165                 170                 175

Asp Asp Gly Thr Phe Lys Asn Ile Arg Leu Ile Asn Gln Lys Pro Ile
            180                 185                 190

Gln Ala Trp Ile Glu Tyr Asp Ser Ser Arg Arg Gln Leu Asn Val Thr
            195                 200                 205

Ile His Pro Ile His Leu Pro Lys Pro Lys Ile Pro Leu Leu Ser Leu
        210                 215                 220

Thr Lys Asp Leu Ser Pro Tyr Leu Phe Asp Ser Met Tyr Val Gly Phe
225                 230                 235                 240

Thr Ser Ala Thr Gly Arg Leu Arg Ser Ser His Tyr Ile Leu Gly Trp
                245                 250                 255

Thr Phe Lys Leu Asn Gly Thr Ala Ser Asn Ile Asp Ile Ser Arg Leu
            260                 265                 270

Pro Lys Leu Pro Arg Asp Ser Arg Ser Thr Ser Val Lys Lys Ile Leu
        275                 280                 285

Ala Ile Ser Leu Ser Leu Thr Ser Leu Ala Ile Leu Val Phe Leu Thr
        290                 295                 300

Ile Ser Tyr Met Leu Phe Leu Lys Arg Lys Lys Leu Met Glu Val Leu
305                 310                 315                 320

Glu Asp Trp Glu Val Gln Phe Gly Pro His Arg Phe Ala Tyr Lys Asp
                325                 330                 335

Leu Tyr Ile Ala Thr Lys Gly Phe Arg Asn Ser Glu Leu Leu Gly Lys
            340                 345                 350

Gly Gly Phe Gly Lys Val Tyr Lys Gly Thr Leu Ser Thr Ser Asn Met
        355                 360                 365

Asp Ile Ala Val Lys Lys Val Ser His Asp Ser Arg Gln Gly Met Arg
370                 375                 380

Glu Phe Val Ala Glu Ile Ala Thr Ile Gly Arg Leu Arg His Pro Asn
385                 390                 395                 400

Leu Val Arg Leu Leu Gly Tyr Cys Arg Arg Lys Gly Glu Leu Tyr Leu
                405                 410                 415

Val Tyr Asp Cys Met Pro Lys Gly Ser Leu Asp Lys Phe Leu Tyr His
            420                 425                 430

Gln Pro Glu Gln Ser Leu Asp Trp Ser Gln Arg Phe Lys Ile Ile Lys
        435                 440                 445

Asp Val Ala Ser Gly Leu Cys Tyr Leu His His Gln Trp Val Gln Val
        450                 455                 460

Ile Ile His Arg Asp Ile Lys Pro Ala Asn Val Leu Leu Asp Asp Ser
465                 470                 475                 480

Met Asn Gly Lys Leu Gly Asp Phe Gly Leu Ala Lys Leu Cys Glu His
                485                 490                 495
```

```
Gly Phe Asp Pro Gln Thr Ser Asn Val Ala Gly Thr Phe Gly Tyr Ile
                500                 505                 510

Ser Pro Glu Leu Ser Arg Thr Gly Lys Ala Ser Thr Ser Ser Asp Val
            515                 520                 525

Phe Ala Phe Gly Ile Leu Met Leu Glu Ile Thr Cys Gly Arg Arg Pro
530                 535                 540

Val Leu Pro Arg Ala Ser Ser Pro Ser Glu Met Val Leu Thr Asp Trp
545                 550                 555                 560

Val Leu Asp Cys Trp Glu Asp Ile Leu Gln Val Val Asp Glu Arg
                565                 570                 575

Val Lys Gln Asp Asp Lys Tyr Leu Glu Gln Val Ala Leu Val Leu
                580                 585                 590

Lys Leu Gly Leu Phe Cys Ser His Pro Val Ala Val Arg Pro Ser
                595                 600                 605

Met Ser Ser Val Ile Gln Phe Leu Asp Gly Val Ala Gln Leu Pro Asn
                610                 615                 620

Asn Leu Phe Asp Ile Val Lys Ala Arg Glu Asn Val Gly Ala Ile Glu
625                 630                 635                 640

Gly Phe Gly Glu Ala Ala Glu Ser Leu Ala Glu Pro Cys Ser Val Ala
                645                 650                 655

Thr Leu Thr Phe Thr Glu Pro Phe Val Ser His Gly Arg
                660                 665

<210> SEQ ID NO 28
<211> LENGTH: 540
<212> TYPE: PRT
<213> ORGANISM: Homo sapiens

<400> SEQUENCE: 28

Met Asn Gly Glu Ala Ile Cys Ser Ala Leu Pro Thr Ile Pro Tyr His
1               5                   10                  15

Lys Leu Ala Asp Leu Arg Tyr Leu Ser Arg Gly Ala Ser Gly Thr Val
                20                  25                  30

Ser Ser Ala Arg His Ala Asp Trp Arg Val Gln Val Ala Val Lys His
            35                  40                  45

Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
                100                 105                 110

Tyr Pro Asp Val Ala Trp Pro Leu Arg Phe Arg Ile Leu His Glu Ile
            115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
                180                 185                 190

Met Pro Pro Glu Asn Tyr Glu Pro Gly Gln Lys Ser Arg Ala Ser Ile
            195                 200                 205
```

```
Lys His Asp Ile Tyr Ser Tyr Ala Val Ile Thr Trp Glu Val Leu Ser
210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
            245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
            275                 280                 285

Glu Leu Glu Pro Val Leu Arg Thr Phe Glu Glu Ile Thr Phe Leu Glu
290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
            325                 330                 335

Val Asn His Gly Pro Gln Glu Ser Cys Gly Ser Ser Gln Leu His
            340                 345                 350

Glu Asn Ser Gly Ser Pro Glu Thr Ser Arg Ser Leu Pro Ala Pro Gln
            355                 360                 365

Asp Asn Asp Phe Leu Ser Arg Lys Ala Gln Asp Cys Tyr Phe Met Lys
370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Thr Pro Cys Ser Ser
                405                 410                 415

Ala Ile Ile Asn Pro Leu Ser Thr Ala Gly Asn Ser Glu Arg Leu Gln
                420                 425                 430

Pro Gly Ile Ala Gln Gln Trp Ile Gln Ser Lys Arg Glu Asp Ile Val
            435                 440                 445

Asn Gln Met Thr Glu Ala Cys Leu Asn Gln Ser Leu Asp Ala Leu Leu
450                 455                 460

Ser Arg Asp Leu Ile Met Lys Glu Asp Tyr Glu Leu Val Ser Thr Lys
465                 470                 475                 480

Pro Thr Arg Thr Ser Lys Val Arg Gln Leu Leu Asp Thr Thr Asp Ile
                485                 490                 495

Gln Gly Glu Glu Phe Ala Lys Val Ile Val Gln Lys Leu Lys Asp Asn
                500                 505                 510

Lys Gln Met Gly Leu Gln Pro Tyr Pro Glu Ile Leu Val Val Ser Arg
            515                 520                 525

Ser Pro Ser Leu Asn Leu Gln Asn Lys Ser Met
            530                 535                 540

<210> SEQ ID NO 29
<211> LENGTH: 671
<212> TYPE: PRT
<213> ORGANISM: Homo sapiens

<400> SEQUENCE: 29

Met Gln Pro Asp Met Ser Leu Asn Val Ile Lys Met Lys Ser Ser Asp
1               5                   10                  15

Phe Leu Glu Ser Ala Glu Leu Asp Ser Gly Gly Phe Gly Lys Val Ser
                20                  25                  30

Leu Cys Phe His Arg Thr Gln Gly Leu Met Ile Met Lys Thr Val Tyr
            35                  40                  45
```

```
Lys Gly Pro Asn Cys Ile Glu His Asn Glu Ala Leu Leu Glu Glu Ala
 50                  55                  60

Lys Met Met Asn Arg Leu Arg His Ser Arg Val Val Lys Leu Leu Gly
 65                  70                  75                  80

Val Ile Ile Glu Glu Gly Lys Tyr Ser Leu Val Met Glu Tyr Met Glu
                 85                  90                  95

Lys Gly Asn Leu Met His Val Leu Lys Ala Glu Met Ser Thr Pro Leu
                100                 105                 110

Ser Val Lys Gly Arg Ile Ile Leu Glu Ile Ile Glu Gly Met Cys Tyr
            115                 120                 125

Leu His Gly Lys Gly Val Ile His Lys Asp Leu Lys Pro Glu Asn Ile
    130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
            195                 200                 205

Ser Asp Val Tyr Ser Phe Ala Val Val Leu Trp Ala Ile Phe Ala Asn
210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270

Glu Ala Arg Pro Thr Phe Pro Gly Ile Glu Glu Lys Phe Arg Pro Phe
            275                 280                 285

Tyr Leu Ser Gln Leu Glu Glu Ser Val Glu Glu Asp Val Lys Ser Leu
290                 295                 300

Lys Lys Glu Tyr Ser Asn Glu Asn Ala Val Val Lys Arg Met Gln Ser
305                 310                 315                 320

Leu Gln Leu Asp Cys Val Ala Val Pro Ser Ser Arg Ser Asn Ser Ala
                325                 330                 335

Thr Glu Gln Pro Gly Ser Leu His Ser Ser Gln Gly Leu Gly Met Gly
            340                 345                 350

Pro Val Glu Glu Ser Trp Phe Ala Pro Ser Leu Glu His Pro Gln Glu
            355                 360                 365

Glu Asn Glu Pro Ser Leu Gln Ser Lys Leu Gln Asp Glu Ala Asn Tyr
            370                 375                 380

His Leu Tyr Gly Ser Arg Met Asp Arg Gln Thr Lys Gln Gln Pro Arg
385                 390                 395                 400

Gln Asn Val Ala Tyr Asn Arg Glu Glu Glu Arg Arg Arg Arg Val Ser
                405                 410                 415

His Asp Pro Phe Ala Gln Gln Arg Pro Tyr Glu Asn Phe Gln Asn Thr
            420                 425                 430

Glu Gly Lys Gly Thr Val Tyr Ser Ser Ala Ala Ser His Gly Asn Ala
            435                 440                 445

Val His Gln Pro Ser Gly Leu Thr Ser Gln Pro Gln Val Leu Tyr Gln
            450                 455                 460
```

-continued

```
Asn Asn Gly Leu Tyr Ser Ser His Gly Phe Gly Thr Arg Pro Leu Asp
465                 470                 475                 480

Pro Gly Thr Ala Gly Pro Arg Val Trp Tyr Arg Pro Ile Pro Ser His
            485                 490                 495

Met Pro Ser Leu His Asn Ile Pro Val Pro Glu Thr Asn Tyr Leu Gly
        500                 505                 510

Asn Thr Pro Thr Met Pro Phe Ser Ser Leu Pro Pro Thr Asp Glu Ser
    515                 520                 525

Ile Lys Tyr Thr Ile Tyr Asn Ser Thr Gly Ile Gln Ile Gly Ala Tyr
530                 535                 540

Asn Tyr Met Glu Ile Gly Gly Thr Ser Ser Ser Leu Leu Asp Ser Thr
545                 550                 555                 560

Asn Thr Asn Phe Lys Glu Glu Pro Ala Ala Lys Tyr Gln Ala Ile Phe
                565                 570                 575

Asp Asn Thr Thr Ser Leu Thr Asp Lys His Leu Asp Pro Ile Arg Glu
            580                 585                 590

Asn Leu Gly Lys His Trp Lys Asn Cys Ala Arg Lys Leu Gly Phe Thr
        595                 600                 605

Gln Ser Gln Ile Asp Glu Ile Asp His Asp Tyr Glu Arg Asp Gly Leu
    610                 615                 620

Lys Glu Lys Val Tyr Gln Met Leu Gln Lys Trp Val Met Arg Glu Gly
625                 630                 635                 640

Ile Lys Gly Ala Thr Val Gly Lys Leu Ala Gln Ala Leu His Gln Cys
                645                 650                 655

Ser Arg Ile Asp Leu Leu Ser Ser Leu Ile Tyr Val Ser Gln Asn
            660                 665                 670

<210> SEQ ID NO 30
<211> LENGTH: 656
<212> TYPE: PRT
<213> ORGANISM: Mus musculus

<400> SEQUENCE: 30

Met Gln Pro Asp Met Ser Leu Asp Asn Ile Lys Met Ala Ser Ser Asp
  1               5                  10                  15

Leu Leu Glu Lys Thr Asp Leu Asp Ser Gly Gly Phe Gly Lys Val Ser
                20                  25                  30

Leu Cys Tyr His Arg Ser His Gly Phe Val Ile Leu Lys Lys Val Tyr
            35                  40                  45

Thr Gly Pro Asn Arg Ala Glu Tyr Asn Glu Val Leu Leu Glu Glu Gly
        50                  55                  60

Lys Met Met His Arg Leu Arg His Ser Arg Val Val Lys Leu Leu Gly
 65                 70                  75                  80

Ile Ile Ile Glu Glu Gly Asn Tyr Ser Leu Val Met Glu Tyr Met Glu
                85                  90                  95

Lys Gly Asn Leu Met His Val Leu Lys Thr Gln Ile Asp Val Pro Leu
            100                 105                 110

Ser Leu Lys Gly Arg Ile Ile Val Glu Ala Ile Glu Gly Met Cys Tyr
        115                 120                 125

Leu His Asp Lys Gly Val Ile His Lys Asp Leu Lys Pro Glu Asn Ile
    130                 135                 140

Leu Val Asp Arg Asp Phe His Ile Lys Ile Ala Asp Leu Gly Val Ala
145                 150                 155                 160

Ser Phe Lys Thr Trp Ser Lys Leu Thr Lys Glu Lys Asp Asn Lys Gln
                165                 170                 175
```

```
Lys Glu Val Ser Ser Thr Thr Lys Lys Asn Asn Gly Gly Thr Leu Tyr
            180                 185                 190

Tyr Met Ala Pro Glu His Leu Asn Asp Ile Asn Ala Lys Pro Thr Glu
        195                 200                 205

Lys Ser Asp Val Tyr Ser Phe Gly Ile Val Leu Trp Ala Ile Phe Ala
    210                 215                 220

Lys Lys Glu Pro Tyr Glu Asn Val Ile Cys Thr Glu Gln Phe Val Ile
225                 230                 235                 240

Cys Ile Lys Ser Gly Asn Arg Pro Asn Val Glu Glu Ile Leu Glu Tyr
            245                 250                 255

Cys Pro Arg Glu Ile Ile Ser Leu Met Glu Arg Cys Trp Gln Ala Ile
        260                 265                 270

Pro Glu Asp Arg Pro Thr Phe Leu Gly Ile Glu Glu Phe Arg Pro
    275                 280                 285

Phe Tyr Leu Ser His Phe Glu Glu Tyr Val Glu Glu Asp Val Ala Ser
    290                 295                 300

Leu Lys Lys Glu Tyr Pro Asp Gln Ser Pro Val Leu Gln Arg Met Phe
305                 310                 315                 320

Ser Leu Gln His Asp Cys Val Pro Leu Pro Pro Ser Arg Ser Asn Ser
            325                 330                 335

Glu Gln Pro Gly Ser Leu His Ser Ser Gln Gly Leu Gln Met Gly Pro
        340                 345                 350

Val Glu Glu Ser Trp Phe Ser Ser Pro Glu Tyr Pro Gln Asp Glu
    355                 360                 365

Asn Asp Arg Ser Val Gln Ala Lys Leu Gln Glu Glu Ala Ser Tyr His
370                 375                 380

Ala Phe Gly Ile Phe Ala Glu Lys Gln Thr Lys Pro Gln Pro Arg Gln
385                 390                 395                 400

Asn Glu Ala Tyr Asn Arg Glu Glu Arg Lys Arg Arg Val Ser His
            405                 410                 415

Asp Pro Phe Ala Gln Gln Arg Ala Arg Glu Asn Ile Lys Ser Ala Gly
        420                 425                 430

Ala Arg Gly His Ser Asp Pro Ser Thr Thr Ser Arg Gly Ile Ala Val
            435                 440                 445

Gln Gln Leu Ser Trp Pro Ala Thr Gln Thr Val Trp Asn Asn Gly Leu
    450                 455                 460

Tyr Asn Gln His Gly Phe Gly Thr Thr Gly Thr Gly Val Trp Tyr Pro
465                 470                 475                 480

Pro Asn Leu Ser Gln Met Tyr Ser Thr Tyr Lys Thr Pro Val Pro Glu
            485                 490                 495

Thr Asn Ile Pro Gly Ser Thr Pro Thr Met Pro Tyr Phe Ser Gly Pro
        500                 505                 510

Val Ala Asp Asp Leu Ile Lys Tyr Thr Ile Phe Asn Ser Ser Gly Ile
            515                 520                 525

Gln Ile Gly Asn His Asn Tyr Met Asp Val Gly Leu Asn Ser Gln Pro
    530                 535                 540

Pro Asn Asn Thr Cys Lys Glu Glu Ser Thr Ser Arg His Gln Ala Ile
545                 550                 555                 560

Phe Asp Asn Thr Thr Ser Leu Thr Asp Glu His Leu Asn Pro Ile Arg
            565                 570                 575

Glu Asn Leu Gly Arg Gln Trp Lys Asn Cys Ala Arg Lys Leu Gly Phe
        580                 585                 590
```

```
Thr Glu Ser Gln Ile Asp Glu Ile Asp His Asp Tyr Glu Arg Asp Gly
            595                 600                 605

Leu Lys Glu Lys Val Tyr Gln Met Leu Gln Lys Trp Leu Met Arg Glu
        610                 615                 620

Gly Thr Lys Gly Ala Thr Val Gly Lys Leu Ala Gln Ala Leu His Gln
625                 630                 635                 640

Cys Cys Arg Ile Asp Leu Leu Asn His Leu Ile Arg Ala Ser Gln Ser
            645                 650                 655

<210> SEQ ID NO 31
<211> LENGTH: 142
<212> TYPE: PRT
<213> ORGANISM: Rattus norvegicus

<400> SEQUENCE: 31

Met Cys Tyr Leu His Ser Leu Asn Pro Ser Leu Leu His Arg Asp Leu
1               5                   10                  15

Lys Pro Ser Asn Val Leu Leu Asp Leu Glu Leu His Ala Lys Leu Ala
            20                  25                  30

Asp Phe Gly Leu Ser Thr Phe Gln Gly Gly Ser Gln Ser Gly Ser Gly
        35                  40                  45

Ser Gly Ser Arg Asp Ser Gly Gly Thr Leu Ala Tyr Leu Ala Pro Glu
    50                  55                  60

Leu Leu Asp Asn Asp Gly Lys Ala Ser Lys Ala Ser Asp Val Tyr Ser
65                  70                  75                  80

Phe Gly Val Leu Val Trp Thr Val Leu Ala Gly Arg Glu Ala Glu Val
                85                  90                  95

Val Asp Lys Thr Ser Leu Ile Arg Gly Ala Val Cys Asn Arg Gln Arg
            100                 105                 110

Arg Pro Pro Leu Thr Glu Leu Pro Pro Asp Ser Pro Glu Thr Pro Gly
        115                 120                 125

Leu Glu Gly Leu Lys Glu Leu Met Thr His Cys Trp Ser Tyr
    130                 135                 140

<210> SEQ ID NO 32
<211> LENGTH: 549
<212> TYPE: PRT
<213> ORGANISM: Arabidopsis thaliana

<400> SEQUENCE: 32

Met Tyr Met Glu Ile Ser Ser Ala Ser Asp Ser Ile Ala Tyr Val
1               5                   10                  15

Glu Thr Asp Pro Ser Gly Arg Tyr Gly Arg Phe Arg Glu Val Leu Gly
            20                  25                  30

Lys Gly Ala Met Lys Thr Val Tyr Lys Ala Phe Asp Gln Val Leu Gly
        35                  40                  45

Met Glu Val Ala Trp Asn Gln Val Lys Leu Asn Glu Val Phe Arg Ser
    50                  55                  60

Pro Glu Pro Leu Gln Arg Leu Tyr Ser Glu Val His Leu Leu Lys Asn
65                  70                  75                  80

Leu Asn His Glu Ser Ile Ile Arg Tyr Cys Thr Ser Trp Ile Asp Val
                85                  90                  95

Asn Arg Arg Thr Phe Asn Phe Ile Thr Glu Leu Phe Thr Ser Gly Thr
            100                 105                 110

Leu Arg Glu Tyr Arg Arg Lys Tyr Gln Lys Val Asp Ile Arg Ala Ile
        115                 120                 125
```

-continued

```
Lys Ser Trp Ala Arg Gln Ile Leu Asn Gly Leu Ala Tyr Leu His Gly
130                 135                 140

His Asp Pro Pro Val Ile His Arg Asp Leu Lys Cys Asp Asn Ile Phe
145                 150                 155                 160

Val Asn Gly His Leu Gly Gln Val Lys Ile Gly Asp Leu Gly Leu Ala
                165                 170                 175

Ala Ile Leu Arg Gly Ser Gln Asn Ala His Ser Val Ile Gly Thr Pro
            180                 185                 190

Glu Phe Met Ala Pro Glu Leu Tyr Glu Glu Asp Tyr Asn Glu Leu Val
        195                 200                 205

Asp Ile Tyr Ser Phe Gly Met Cys Val Leu Glu Met Leu Thr Gly Glu
210                 215                 220

Tyr Pro Tyr Ser Glu Cys Thr Asn Pro Ala Gln Ile Tyr Lys Lys Val
225                 230                 235                 240

Thr Ser Gly Lys Leu Pro Asp Ser Phe His Leu Ile Gln His Thr Glu
                245                 250                 255

Ala Gln Arg Phe Val Gly Lys Cys Leu Glu Thr Val Ser Arg Arg Leu
            260                 265                 270

Pro Ala Lys Glu Leu Leu Ala Asp Pro Phe Leu Ala Ala Thr Asp Glu
        275                 280                 285

Arg Asp Leu Ala Pro Leu Phe Arg Leu Pro Gln Gln Leu Ala Ile Gln
290                 295                 300

Asn Leu Ala Ala Asn Gly Thr Val Val Glu His Leu Pro Ser Thr Thr
305                 310                 315                 320

Asp Pro Thr Arg Thr Thr Asp Met Ser Ile Thr Gly Lys Met Asn Ser
                325                 330                 335

Glu Asp His Thr Ile Phe Leu Gln Val Gln Ile Leu Asp Gly Asp Gly
            340                 345                 350

His Met Arg Asn Ile Gln Phe Pro Phe Asn Ile Leu Ser Asp Thr Pro
        355                 360                 365

Leu Glu Val Ala Leu Glu Met Val Lys Glu Leu Glu Ile Thr Asp Trp
370                 375                 380

Asp Pro Leu Glu Ile Ala Ala Met Ile Glu Asn Glu Ile Ser Leu Leu
385                 390                 395                 400

Val Pro Asn Trp Arg Ala Asn Asp Ser Ser Ile Arg His Glu Ser Phe
                405                 410                 415

Gly His Glu Asp Asp Glu Asp Asn Gly Asp Thr Glu Gly Arg Thr Arg
            420                 425                 430

Leu Phe Ser Ser Ala Ser Ser His Asp Ser Pro Val Ala Val Arg
        435                 440                 445

Glu Asn Asn Asp Asp Ser Ser Asp Val Ile Pro Asp Met Asp Asp
450                 455                 460

Gly Asn Arg Ser Ser Asn Arg Leu Leu Asn Ser Ser Thr Tyr His Tyr
465                 470                 475                 480

Ser Pro Ala Ile Asp Asp Gln Asn Gln Gln Arg Arg Val
                485                 490                 495

Arg Leu Gln Gln Lys Met Arg Ser Leu Val Asp Thr Thr Gln Val
        500                 505                 510

Leu His Arg Ser Leu Met Glu Leu Ile Asn Lys Arg Gly Arg Gly
515                 520                 525
```

```
Phe Asp Pro Asn Thr Asn Glu Leu Gln Pro Gln Pro Ser Ser Thr Asp
    530                 535                 540

Phe Ile Arg Arg Cys
545

<210> SEQ ID NO 33
<211> LENGTH: 553
<212> TYPE: PRT
<213> ORGANISM: Arabidopsis thaliana

<400> SEQUENCE: 33

Met Ala Gly Ser Ser Thr Lys Arg Phe Pro Leu Tyr Ala Lys Asp Tyr
  1               5                  10                  15

Glu Leu Phe Glu Glu Val Gly Glu Gly Val Ser Ala Thr Val Tyr Arg
             20                  25                  30

Ala Arg Cys Ile Ala Leu Asn Glu Ile Val Ala Val Lys Ile Leu Asp
         35                  40                  45

Leu Glu Lys Cys Arg Asn Asp Leu Glu Thr Ile Arg Lys Glu Val His
     50                  55                  60

Ile Met Ser Leu Ile Asp His Pro Asn Leu Leu Lys Ala His Cys Ser
 65                  70                  75                  80

Phe Ile Asp Ser Ser Ser Leu Trp Ile Val Met Pro Tyr Met Ser Gly
                 85                  90                  95

Gly Ser Cys Phe His Leu Met Lys Ser Val Tyr Pro Glu Gly Leu Glu
            100                 105                 110

Gln Pro Ile Ile Ala Thr Leu Leu Arg Glu Val Leu Lys Ala Leu Val
        115                 120                 125

Tyr Leu His Arg Gln Gly His Ile His Arg Asp Val Lys Ala Gly Asn
    130                 135                 140

Ile Leu Ile His Ser Lys Gly Val Val Lys Leu Gly Asp Phe Gly Val
145                 150                 155                 160

Ser Ala Cys Met Phe Asp Ser Gly Glu Arg Met Gln Thr Arg Asn Thr
                165                 170                 175

Phe Val Gly Thr Pro Cys Trp Met Ala Pro Glu Val Met Gln Gln Leu
            180                 185                 190

Asp Gly Tyr Asp Phe Lys Leu Trp Ser Phe Gly Ile Thr Ala Leu Glu
        195                 200                 205

Leu Ala His Gly His Ala Pro Phe Ser Lys Tyr Pro Pro Met Lys Val
    210                 215                 220

Leu Leu Met Thr Leu Gln Asn Ala Pro Pro Arg Leu Asp Tyr Asp Arg
225                 230                 235                 240

Asp Lys Lys Phe Ser Lys Ser Phe Arg Glu Leu Ile Ala Ala Cys Leu
                245                 250                 255

Val Lys Asp Pro Lys Lys Arg Pro Thr Ala Ala Lys Leu Leu Lys His
            260                 265                 270

Pro Phe Phe Lys His Ala Arg Ser Thr Asp Tyr Leu Ser Arg Lys Ile
        275                 280                 285

Leu His Gly Leu Ser Pro Leu Gly Glu Arg Phe Lys Lys Leu Lys Glu
    290                 295                 300

Ala Glu Ala Glu Leu Phe Lys Gly Ile Asn Gly Asp Lys Glu Gln Leu
305                 310                 315                 320

Ser Gln His Glu Tyr Met Arg Gly Ile Ser Ala Trp Asn Phe Asp Leu
                325                 330                 335

Glu Ala Leu Arg Arg Gln Ala Ser Leu Val Ile Val Ser Lys Glu Leu
            340                 345                 350
```

```
Asn Arg Asn Gly Asp Val Pro Lys Gly Lys Pro Val Ile Gln Arg Ser
            355                 360                 365

Gln Thr Met Pro Leu Glu Tyr Phe Ser Glu Lys Asp Met Val Ser Glu
        370                 375                 380

Ser Ser Ser Gln Leu Thr Gly Ser Leu Pro Ser Phe His Arg Lys
385                 390                 395                 400

Phe Leu Pro Ala Leu Gly Tyr Gln Val Gly Ile Ile Ser Asn Glu Ser
                405                 410                 415

Asn Ala Cys Asn Ser Ser Asp Arg Ala Ala Glu Lys Leu Ala Phe Glu
            420                 425                 430

Glu Pro Arg Gln Val Leu His Pro Leu Ala Asp Thr Lys Lys Ile Arg
        435                 440                 445

Lys Ala Gly Ser Asp Gln Gln Glu Lys Pro Lys Asn Gly Tyr Ala Asp
    450                 455                 460

Ser Pro Val Asn Arg Glu Ser Ser Thr Leu Ser Lys Glu Pro Leu Ala
465                 470                 475                 480

Asp Thr Lys Gln Val Arg Lys Pro Gly Asn Glu Gln Glu Lys Pro Lys
                485                 490                 495

Asn Gly Tyr Ile Val Ser His Val Asn Arg Glu Ser Ser Thr Ser Glu
            500                 505                 510

Glu Ile Leu Pro Leu Leu Gln Ser Leu Leu Val Gln Asn Asp Ile Gln
        515                 520                 525

Arg Val Cys Val Leu Ser Val Ser Thr Ala Ser Cys Gly Tyr Thr Ser
    530                 535                 540

Pro Lys Trp Leu Leu Arg Phe Gly Phe
545                 550

<210> SEQ ID NO 34
<211> LENGTH: 516
<212> TYPE: PRT
<213> ORGANISM: Arabidopsis thaliana

<400> SEQUENCE: 34

Met Arg Gln Asp Glu Asn Asn Ser Glu Glu Phe Val Glu Ile Asp
 1               5                  10                  15

Pro Thr Gly Arg Tyr Gly Arg Tyr Lys Glu Val Leu Gly Lys Gly Ala
                20                  25                  30

Phe Lys Glu Val Tyr Arg Ala Phe Asp Gln Leu Glu Gly Ile Glu Val
            35                  40                  45

Ala Trp Asn Gln Val Lys Leu Asp Asp Lys Phe Cys Ser Ser Glu Asp
    50                  55                  60

Leu Asp Arg Leu Tyr Ser Glu Val His Leu Leu Lys Thr Leu Lys His
65                  70                  75                  80

Lys Ser Ile Ile Lys Phe Tyr Thr Ser Trp Ile Asp His Gln His Met
                85                  90                  95

Thr Ile Asn Leu Ile Thr Glu Val Phe Thr Ser Gly Asn Leu Arg Gln
            100                 105                 110

Tyr Arg Lys Lys His Lys Cys Val Asp Leu Arg Ala Leu Lys Lys Trp
        115                 120                 125

Ser Arg Gln Ile Leu Glu Gly Leu Val Tyr Leu His Ser His Asp Pro
    130                 135                 140

Pro Val Ile His Arg Asp Leu Lys Cys Asp Asn Ile Phe Ile Asn Gly
145                 150                 155                 160

Asn Gln Gly Glu Val Lys Ile Gly Asp Leu Gly Leu Ala Ala Ile Leu
                165                 170                 175
```

```
His Arg Ala Arg Ser Ala His Ser Val Ile Gly Thr Pro Glu Phe Met
            180                 185                 190

Ala Pro Glu Leu Tyr Glu Asp Tyr Asn Val Leu Val Asp Ile Tyr
        195                 200                 205

Ala Phe Gly Met Cys Leu Leu Glu Leu Val Thr Phe Glu Tyr Pro Tyr
    210                 215                 220

Ser Glu Cys Thr Asn Ala Ala Gln Ile Tyr Arg Lys Val Thr Ser Gly
225                 230                 235                 240

Ile Lys Pro Ala Ala Leu Leu Asn Val Thr Asp Pro Gln Val Arg Ala
                245                 250                 255

Phe Ile Glu Lys Cys Ile Ala Lys Val Ser Gln Arg Leu Ser Ala Lys
            260                 265                 270

Glu Leu Leu Asp Asp Pro Phe Leu Lys Cys Tyr Lys Glu Asn Thr Glu
        275                 280                 285

Asn Val Ser Ser His Lys Glu Asn Gly Tyr Asn Gly Asn Gly Ile Val
    290                 295                 300

Asp Lys Leu Ser Asp Ser Glu Val Gly Leu Leu Thr Val Glu Gly Gln
305                 310                 315                 320

Arg Lys Asp Leu Asn Thr Ile Phe Leu Lys Leu Arg Ile Thr Asp Ser
                325                 330                 335

Lys Gly Gln Ile Arg Asn Ile His Phe Pro Phe Asn Ile Glu Thr Asp
            340                 345                 350

Thr Ser Phe Ser Val Ala Ile Glu Met Val Glu Glu Leu Asp Leu Thr
        355                 360                 365

Asp Asp Gln Asp Ile Ser Thr Ile Ala Lys Met Ile Asp Thr Glu Ile
    370                 375                 380

His Ser His Ile Pro Asp Trp Thr Pro Ser Arg Leu Ile Gly Asp Asp
385                 390                 395                 400

Ser Ala Val Gln Lys Cys Leu Ser Ser Pro Glu Thr Leu His Leu Asp
                405                 410                 415

Arg Phe Pro Ser Gly Arg Lys Phe Trp Ser Ser Pro Lys Ala Gly Ala
            420                 425                 430

Gly Asp Ser Arg Ser Pro Phe Ala Pro Arg Ser Asn Ser Lys Leu Ser
        435                 440                 445

Ser Ala Gln Gly Pro Ile Asn Gln Glu Val Gly Val Ile Val Glu Lys
    450                 455                 460

Leu Glu Ser Leu Leu Arg Lys Gln Arg Glu Glu Ile Glu Glu Met Gln
465                 470                 475                 480

Arg Asp Gln Glu Arg Ile Val Thr Glu Phe Leu Lys Glu Phe Pro Pro
                485                 490                 495

Glu Ile Cys Glu Glu Ala Leu Val Arg Leu Gln Val Lys Asp Ser Asp
            500                 505                 510

Asn Leu Leu Cys
        515

<210> SEQ ID NO 35
<211> LENGTH: 461
<212> TYPE: PRT
<213> ORGANISM: C. elegans

<400> SEQUENCE: 35

Met Cys Lys Asp Val Ser Gly Gln Asn Leu Leu Val Ala Pro Asp Ala
1               5                   10                  15

Ile Asn His His Val Lys Thr Cys Arg Glu Asn Met Arg Tyr Met His
            20                  25                  30
```

```
Tyr Ile Ala Pro Glu Tyr Glu Asn Asn Thr Glu Leu Thr Ser Ala Ala
         35                  40                  45

Asp Ile Tyr Ser Phe Gly Ile Cys Ser Leu Glu Ile Ala Val Ile Gly
 50                  55                  60

Gly Leu Ser Gly Cys Gln Asn Gly Ser Ser Glu Gly Pro Val Thr Glu
 65                  70                  75                  80

Asp Val Ile Glu Lys Ala Ile Arg Ser Leu Glu Asp Pro Met Gln Gln
                 85                  90                  95

Asp Phe Ile Arg Gln Cys Leu Arg Lys Asp Pro Ala Glu Arg Pro Ser
                100                 105                 110

Ala Arg Glu Leu Leu Phe His Gln Ile Leu Phe Glu Val His Ser Leu
            115                 120                 125

Lys Leu Leu Ser Ala His Ala Ile Val Asp Ser Lys Lys Tyr Glu Asp
130                 135                 140

Val Ser Glu Ser Ala Phe Arg Ile Lys Asp Asn Glu Thr Ile Ala Ala
145                 150                 155                 160

Thr Ser Lys Leu Arg Glu Met Ala Tyr Cys Gln Val Ala Ala Phe Gln
                165                 170                 175

Val Asp Leu Glu Lys Phe Leu Asp Asp Val Arg Asn Gly Ile Tyr Pro
            180                 185                 190

Leu Thr Ala Phe Ala Pro Leu Ala His Gln Pro Ser Thr Thr Leu Arg
            195                 200                 205

Ala Tyr Ser Asn Thr Asn Pro Ser Thr Leu Ile Thr Thr Asp Ile Ser
210                 215                 220

Ala Pro Ser Ser Thr His Pro Ser Ala Asn Ser Thr Ile Thr Ala Glu
225                 230                 235                 240

Thr Ser Val Asn Thr Ser Leu Pro Gly Gln Ser Ser Gln Pro Ser Gly
                245                 250                 255

Thr Thr Thr Asn Thr Asn Gly Pro Ser Ser Ile Gly Lys Ser Ala Ser
            260                 265                 270

Pro Glu Ala Val Asp Lys Lys Ile Gly Glu Val Thr Ser Thr Glu Ser
            275                 280                 285

Thr Ser Lys Val Glu Val Glu Val Asn Gly Ala Asn Val Thr Ile Gly
290                 295                 300

Ser Ser Asn Gly Arg Asp Ala Gly Ser Pro Thr Pro Glu Glu Glu Gly
305                 310                 315                 320

Glu Pro Asn Gly Glu Arg Asp Met Arg Leu Glu Asn Arg His Ile Leu
                325                 330                 335

Glu Ile Asn Val His Ile Glu Asn Glu Glu Met Ser Ile Val Leu Leu
            340                 345                 350

Leu Glu Asp Gln Met His Arg Gln Leu Thr Thr Ser Ile Asn Lys Gly
            355                 360                 365

Asp Asn Pro Glu Thr Leu Thr Glu Asn Leu Ile Thr His Gly Phe Met
370                 375                 380

Cys Gln Leu Asp Ser Glu Gly Val Glu Lys Ala Ile Ala Val Ala Phe
385                 390                 395                 400

Asp Ile Arg Ala Ala Arg Ile Ala Glu Gly Val Gln Glu Glu Asn
                405                 410                 415

Glu Thr Ser Thr Arg Glu Ser Asn Ser Glu Ala Pro Ile Glu His Gly
                420                 425                 430
```

```
Thr Ser Ser Ser Ile Thr Asn Ser Val Lys Pro Ile Val Asp Ser Val
        435                 440                 445

Ala Pro Ser Ser Gln Thr Pro Thr Thr Thr Ser Ser
450                 455                 460

<210> SEQ ID NO 36
<211> LENGTH: 231
<212> TYPE: PRT
<213> ORGANISM: C. elegans

<400> SEQUENCE: 36

Met Val Ser Ser Gly Glu Glu Arg Thr Ala Ala Gly Lys Thr Pro Ile
1               5                   10                  15

Gly Asp Asp Ala Ala Ser Asp Ser Asp Ala Asp Gly Ala Glu Glu Ile
            20                  25                  30

Leu Glu Glu Ser Pro Asp Lys Arg Trp Ser Lys Arg Glu Gln Val
        35                  40                  45

Lys Gln Arg Asp Val Pro Gly Ile Asp Val Ala Tyr Leu Ala Met Asp
50                  55                  60

Asn Glu Thr Gly Asn Glu Val Val Trp Asn Glu Val Gln Phe Ser Glu
65                  70                  75                  80

Arg Lys Asn Phe Arg Ala Gln Glu Glu Lys Ile Asn Ala Val Phe Asp
                85                  90                  95

Asn Leu Thr Gln Leu Val His Thr Asn Leu Val Lys Phe His Lys Tyr
            100                 105                 110

Trp Thr Asp Ser Lys Ser Glu Lys Pro Arg Ile Phe Ile Thr Glu
        115                 120                 125

Tyr Met Ser Ser Gly Ser Met Ser Ala Phe Leu Gln Arg Thr Arg Lys
130                 135                 140

Ala Gly Ser Ser Leu Ser Ile Lys Ala Trp Lys Lys Trp Thr Thr Gln
145                 150                 155                 160

Ile Leu Ser Ala Leu Asn Tyr Leu His Ser Ser Asp Pro Pro Ile Ile
                165                 170                 175

His Gly Asn Leu Thr Cys Asn Thr Val Phe Ile Gln Gln Asn Gly Leu
            180                 185                 190

Ile Lys Ile Gly Cys Gly Glu Phe Gln Phe Ala Val Ile Phe Ile
        195                 200                 205

Leu Ile Asp Gln Phe Glu Lys Phe Thr Gly Tyr Cys Arg Lys Tyr Ser
210                 215                 220

Asp Lys Met Val Lys Asn His
225                 230

<210> SEQ ID NO 37
<211> LENGTH: 309
<212> TYPE: PRT
<213> ORGANISM: Homo sapiens

<400> SEQUENCE: 37

Asp Arg Lys Leu Thr Lys Leu Glu Arg Gln Arg Phe Lys Glu Glu Ala
1               5                   10                  15

Glu Met Leu Lys Gly Leu Gln His Pro Asn Ile Val Arg Phe Tyr Asp
            20                  25                  30

Phe Trp Glu Ser Ser Ala Lys Gly Lys Arg Cys Ile Val Leu Val Thr
        35                  40                  45

Glu Leu Met Thr Ser Gly Thr Leu Lys Thr Tyr Leu Lys Arg Phe Lys
50                  55                  60
```

-continued

```
Val Met Lys Pro Lys Val Leu Arg Ser Trp Cys Arg Gln Ile Leu Lys
 65                  70                  75                  80

Gly Leu Leu Phe Leu His Thr Arg Thr Pro Ile Ile His Arg Asp
                 85                  90                  95

Leu Lys Cys Asp Asn Ile Phe Ile Thr Gly Pro Thr Gly Ser Val Lys
            100                 105                 110

Ile Gly Asp Leu Gly Leu Ala Thr Leu Lys Arg Ala Ser Phe Ala Lys
            115                 120                 125

Ser Val Ile Gly Thr Pro Glu Phe Met Val Pro Glu Met Tyr Glu Glu
            130                 135                 140

His Tyr Asp Glu Ser Val Asp Val Tyr Ala Phe Gly Met Cys Met Leu
145                 150                 155                 160

Glu Met Ala Thr Ser Glu Tyr Pro Tyr Ser Glu Cys Gln Asn Ala Ala
                165                 170                 175

Gln Ile Tyr Arg Lys Val Thr Cys Gly Ile Lys Pro Ala Ser Phe Glu
            180                 185                 190

Lys Val His Asp Pro Glu Ile Lys Glu Ile Gly Glu Cys Ile Cys
            195                 200                 205

Lys Asn Arg Glu Glu Arg Tyr Glu Ile Lys Asp Leu Leu Ser His Ala
210                 215                 220

Phe Phe Ala Glu Asp Thr Gly Val Arg Val Glu Leu Ala Glu Glu Asp
225                 230                 235                 240

His Gly Arg Lys Ser Thr Ile Ala Leu Arg Leu Trp Val Glu Asp Pro
                245                 250                 255

Lys Lys Leu Lys Gly Lys Pro Lys Asp Asn Gly Ala Thr Glu Phe Thr
            260                 265                 270

Phe Asp Leu Glu Lys Glu Thr Pro Asp Glu Val Ala Gln Glu Met Ile
            275                 280                 285

Glu Ser Gly Phe Phe His Glu Ser Asp Val Lys Ile Val Ala Lys Ser
290                 295                 300

Ile Arg Asp Arg Val
305

<210> SEQ ID NO 38
<211> LENGTH: 677
<212> TYPE: PRT
<213> ORGANISM: Oryza sativa

<400> SEQUENCE: 38

Met Gly Pro Lys Ala Asn Ala Ala Ala Gly Asp Leu Pro Glu Tyr
  1               5                  10                  15

Ala Glu Val Asp Pro Thr Gly Arg Tyr Gly Arg Tyr Asn Asp Val Leu
                 20                  25                  30

Gly Lys Gly Ala Ser Lys Thr Val Tyr Arg Ala Phe Asp Glu Tyr Gln
             35                  40                  45

Gly Met Glu Val Ala Trp Asn Gln Val Lys Leu His Asp Phe Leu Gln
         50                  55                  60

Ser Pro Glu Asp Leu Glu Arg Leu Tyr Cys Glu Ile His Leu Leu Lys
 65                  70                  75                  80

Thr Leu Lys His Arg Asn Ile Met Lys Phe Tyr Thr Ser Trp Val Asp
                 85                  90                  95

Val Ser Arg Arg Asn Ile Asn Phe Ile Thr Glu Met Phe Thr Ser Gly
            100                 105                 110

Thr Leu Arg Gln Tyr Arg Gln Lys His Met Arg Val Asn Ile Trp Ala
            115                 120                 125
```

```
Val Lys His Trp Cys Arg Gln Ile Leu Ser Gly Leu Leu Tyr Leu His
130                 135                 140

Ser His Asp Pro Pro Ile Ile His Arg Asp Leu Lys Cys Asp Asn Ile
145                 150                 155                 160

Phe Val Asn Gly Asn Gln Gly Glu Val Lys Ile Gly Asp Leu Gly Leu
                165                 170                 175

Ala Ala Ile Leu Arg Lys Ser His Ala Val His Cys Val Gly Thr Pro
            180                 185                 190

Glu Phe Met Ala Pro Glu Val Tyr Glu Glu Tyr Asn Glu Leu Val
        195                 200                 205

Asp Ile Tyr Ser Phe Gly Met Cys Val Leu Glu Met Val Thr Phe Glu
210                 215                 220

Tyr Pro Tyr Ser Glu Cys Thr His Pro Val Gln Ile Tyr Lys Lys Val
225                 230                 235                 240

Ile Ser Gly Thr Lys Pro Glu Ala Leu Tyr Lys Val Lys Asp Pro Met
                245                 250                 255

Val Arg Gln Phe Val Glu Lys Cys Leu Ala Thr Ala Ser Arg Arg Leu
            260                 265                 270

Ser Ala Arg Glu Val Leu Lys Asp Pro Phe Leu Gln Val Asp Asp Leu
        275                 280                 285

Val Phe Cys Pro Gly Asp Gly Asn Tyr Ser Leu Met Asn Tyr Leu Arg
290                 295                 300

Gln Pro Tyr Leu Gln His Ala Tyr Ser Thr Val Ser Met Met Ser Asn
305                 310                 315                 320

Gly Leu Ser Glu Ser Ile Asp Glu Asp Ser Pro Thr Glu Asp Arg Trp
                325                 330                 335

Asp Cys Glu Asp Asp Ile Lys Ala Asp Gly Ile Asp Leu Phe Asn
            340                 345                 350

Gly His Glu Asp Glu Pro Leu Gly Asn Val Asp Ile Thr Ile Lys Gly
        355                 360                 365

Arg Lys Ser Glu Asp Gly Ser Ile Phe Leu Arg Leu Arg Ile Ala Asp
370                 375                 380

Asn Asp Gly His Val Arg Asn Ile Tyr Phe Pro Phe Asp Ile Glu Ala
385                 390                 395                 400

Asp Thr Ala Leu Ser Val Ala Thr Glu Met Val Ala Glu Leu Asp Ile
                405                 410                 415

Thr Asp His Glu Val Thr Arg Ile Ala Glu Met Ile Asp Gly Glu Val
            420                 425                 430

Ser Ala Leu Val Pro Asp Trp Arg Pro Gly Pro Gly Ile Glu Glu Ser
        435                 440                 445

Gln Asp Thr Thr Tyr Cys His Asn Cys Gly Ser Asn Val Ser Ser Cys
450                 455                 460

Gly Ser Leu Tyr Ala Tyr Met Ser Cys Ala Ala Arg Gly Cys His Cys
465                 470                 475                 480

Ala Asp Leu His Gly Arg Phe Glu Asp Ile Thr Phe Gln Ala Asn Gly
                485                 490                 495

Glu Gln Thr Asp Leu Gln Asp Ser Gly Gly Ser Ser Asp Gly Gly
            500                 505                 510

Gly Gln Thr Gln His Val Lys Asp Gln Glu Ala Val His Ser Asn Gly
        515                 520                 525

Phe Val Gln Met Gly Thr Thr Arg Pro Arg Asp Gln Phe Cys Phe Ser
530                 535                 540
```

```
Ser Phe Gln Glu Gln Ser Cys Ser Pro Arg His Tyr Glu Tyr Asp Thr
545                 550                 555                 560

Ser Leu Gln Ala Lys Gly Phe Asp Met Lys His Glu Val Lys Met Ala
                565                 570                 575

Lys Tyr Lys Ala Arg Lys Met Ala His Leu Arg Arg Gly Ile His Pro
            580                 585                 590

Ser Leu Asp Phe Asp Asn Leu Asn Gly Glu Arg Arg Met Lys Ser Ser
        595                 600                 605

Leu Asn Lys Leu Gln Ser Phe His Ile Gly Lys Asn His Asn Phe Arg
610                 615                 620

Ile Pro Thr Cys Glu Arg Ser Pro Gly Ala Arg Asp Ala Glu Glu Asp
625                 630                 635                 640

Pro Asp Ile Phe Asn Leu Ala Tyr His Ser Arg His Pro Asp Pro Gly
                645                 650                 655

Ala Gln Arg Ala Arg His Cys Glu Val Asp Ala Gln Ser Ser Pro Asp
            660                 665                 670

Gly His Val Tyr Ser
        675

<210> SEQ ID NO 39
<211> LENGTH: 613
<212> TYPE: PRT
<213> ORGANISM: Phycomyces blakesleeanus

<400> SEQUENCE: 39

Met Pro Asp Tyr Glu Lys Val Ile Glu Ala Ser Gly Asn Gly Arg Tyr
1               5                   10                  15

Ser Lys Leu Asn Thr Val Leu Gly Lys Gly Ala Tyr Lys Val Val Tyr
            20                  25                  30

Lys Ala Ile Asp Arg Glu Glu Ala Ile Asn Asp Asn Glu Ile Thr Asn
        35                  40                  45

Val Lys Val Thr Arg Gln Glu Phe Lys Asp Leu Gly His Glu Ile Asp
    50                  55                  60

Ile Leu Lys Ser Val Arg His Pro Asn Ile Ile Thr Phe His Asp Ala
65                  70                  75                  80

Trp Tyr Asn Glu Thr Glu Phe Val Phe Ile Thr Glu Leu Met Thr Ser
                85                  90                  95

Gly Thr Leu Arg Glu Tyr Ile Arg Lys Leu Thr Pro Leu Pro Asn Ile
            100                 105                 110

Lys Ile Val Lys Arg Trp Cys Arg Gln Ile Leu Lys Gly Leu Ala Tyr
        115                 120                 125

Leu His Gly His Glu Pro Pro Ile Ile His Arg Asp Ile Lys Cys Asp
    130                 135                 140

Asn Ile Phe Ile Asn Gly Ala His Gly Glu Ile Lys Ile Gly Asp Met
145                 150                 155                 160

Gly Thr Ala Glu Met Lys Asn Gly Lys Lys Tyr Thr Val Ile Gly Thr
                165                 170                 175

Pro Glu Phe Met Ala Pro Glu Met Tyr Glu Glu Gln Gly Tyr Asn Glu
            180                 185                 190

Lys Val Asp Ile Tyr Ala Phe Gly Met Cys Leu Leu Glu Met Ala Thr
        195                 200                 205

Gly Glu Tyr Pro Tyr Gly Glu Cys Thr Asn Ala Val Gln Val Phe Lys
    210                 215                 220

Lys Val Thr Gln Thr Ile Lys Pro Glu Cys Leu Ser Arg Val Gln Asp
225                 230                 235                 240
```

```
Pro Glu Leu Leu Thr Leu Val Asn Ile Cys Leu Thr Pro Glu Asp Glu
            245                 250                 255

Arg Met Thr Ala Gln Glu Ile Leu Glu His Arg Phe Leu Ala Val Glu
            260                 265                 270

Pro Glu Val Val Leu Val Ser Lys Asp Met Thr Met Lys Leu Leu Thr
            275                 280             285

Leu Gln Val Val Phe Lys Gly Met Asp Lys Leu Ser Val Lys Phe Glu
        290                 295                 300

Phe Asn Ala Asp Thr Asp Thr Ala Ala Asp Val Val Ala Glu Met Ile
305                 310                 315                 320

Glu Glu Gln Val Leu Gln Asn Cys Tyr Gln Gln Leu Ile Thr Cys Glu
                325                 330                 335

Ile Asn Arg Ile Leu Arg Asp Ile Ala Arg Asn Gln Gly Pro Pro Asp
            340                 345                 350

Lys Gly Glu Asp Glu Lys Ile Val Trp Arg Arg Glu Asn Asp Ile Arg
            355                 360                 365

Ser Glu Leu Glu Arg Ala Lys Lys Asp Leu Ala Leu Ala Val Glu Arg
        370                 375                 380

Val Phe Glu Ala Glu Lys Lys Cys Glu Leu Leu Glu Gln His Asn Ile
385                 390                 395                 400

Ile Ala Glu Glu Arg Cys Lys Glu Thr Ile Phe Ala Leu Glu Gln Ala
                405                 410                 415

Lys Phe Gln Ile Pro Asp Leu Leu Gln Pro Gln Pro Gln Pro Gln Pro
            420                 425                 430

Gln Pro Gln Pro Gln Pro Gln Pro Gln Phe Gln Leu Gln Pro
        435                 440                 445

Gln Leu Gln Tyr Leu Ser Pro Gln Ser Thr Thr Ser Pro Gly Pro Thr
        450                 455                 460

Ser Asp Asp Asn Ser Thr Asn Ser Thr Met Leu Ser Ser Leu Glu Ser
465                 470                 475                 480

Glu Leu Ser Lys Leu Cys Val Ser Gly Asp Glu Gln Val Glu Thr Thr
                485                 490                 495

Thr His Ser Ala Leu Met Glu Asn Val Leu Ala Gly Lys Ala Lys Tyr
            500                 505                 510

Tyr Glu Tyr Ser Asn Asp Thr Ser Ile Asp Lys Phe Val Met Asp Thr
        515                 520                 525

Ala Gly Ala Thr Asn Arg Ser Lys Asp Lys Gln Lys Gln Trp Ala Ala
        530                 535                 540

Lys Leu Gln Asp Gln Asp Ile Met Thr Val Gly Asp Leu Arg Asp Leu
545                 550                 555                 560

His Asp Glu Asp Trp Ser Gly Ile Gly Leu Thr Val Phe Ala Leu Arg
                565                 570                 575

Ala Leu Lys Asn Met Leu Ala Gly Lys Lys Ala Ala Val Thr Gln Arg
            580                 585                 590

Gly Leu Gln Gly Thr Arg Ser Gly Ala Ser Thr Pro Val Glu Glu Gln
        595                 600                 605

Glu Gln Glu Leu Met
        610

<210> SEQ ID NO 40
<211> LENGTH: 1601
<212> TYPE: PRT
<213> ORGANISM: C. elegans
```

```
<400> SEQUENCE: 40

Ser Ser Ser Ser Pro Ser Asp Ala Ala Asn Asn Asp Lys Pro Ile Gln
  1               5                  10                  15

Gln Arg His Ser Ile Leu Ser Asn Val Arg Thr Leu Thr Gln Ala Met
             20                  25                  30

Val Asn Asp Gly Pro Arg Thr Leu Thr Gly Asp Asp Met Asp Lys Met
         35                  40                  45

Val Ser Glu Glu Glu Arg Ala Arg Lys Glu Gln Glu Lys Arg Glu Glu
     50                  55                  60

Glu Glu Lys Ala Ala Arg Arg Ile Asp Val Asp Asp Phe Asp Ala
 65                  70                  75                  80

Gln Glu Lys Pro Ile Asp Lys Ser Lys Asn Gly Arg Phe Leu Lys Phe
                 85                  90                  95

Asp Glu Glu Leu Gly Arg Gly Ser Phe Lys Thr Val Phe Arg Gly Leu
                100                 105                 110

Asp Thr Glu Thr Gly Val Ala Val Ala Trp Cys Glu Leu Gln Glu Ser
                115                 120                 125

Lys Leu Asn Lys Thr Glu Arg Gln Arg Phe Arg Glu Glu Ala Glu Met
    130                 135                 140

Leu Lys Asp Leu Gln His Pro Asn Ile Val Arg Phe Tyr Asp Tyr Trp
145                 150                 155                 160

Glu Ser Ala Asp Leu Cys Gly Lys Arg Lys Tyr Ile Val Leu Val Thr
                165                 170                 175

Glu Leu Met Thr Ser Gly Thr Leu Lys Met Tyr Leu Lys Arg Phe Lys
                180                 185                 190

Arg Ile Asn Ile Lys Val Val Leu Lys Ser Trp Cys Arg Gln Ile Leu
                195                 200                 205

Lys Gly Leu Ser Phe Leu His Thr Arg Asn Pro Pro Val Ile His Arg
    210                 215                 220

Asp Leu Lys Cys Asp Asn Ile Phe Ile Thr Gly Thr Thr Gly Ser Val
225                 230                 235                 240

Lys Ile Gly Asp Leu Gly Leu Ala Thr Leu Lys Asn Lys Ser Phe Ala
                245                 250                 255

Lys Ser Val Ile Gly Thr Pro Glu Phe Met Ala Pro Glu Met Tyr Glu
                260                 265                 270

Glu Met Tyr Asp Glu Ser Val Asp Val Tyr Ala Phe Gly Met Cys Leu
                275                 280                 285

Leu Glu Met Val Thr Gly Glu Tyr Pro Tyr Ser Glu Cys Met Asn Pro
    290                 295                 300

Ala Thr Ile Tyr Arg Lys Val Ile Ser Gly Val Lys Pro Glu Cys Phe
305                 310                 315                 320

Ser Arg Ile Pro Ala Gln Tyr Pro Glu Ile Arg Glu Ile Ile Asp Arg
                325                 330                 335

Cys Ile Arg Val Arg Arg Glu Glu Arg Ser Thr Val Lys Gln Leu Leu
                340                 345                 350

Val Asp Asp Phe Phe Thr Pro Glu Asp Leu Ile Gly Ile Arg Val Glu
                355                 360                 365

Ile Lys Asn Arg Asp Ala Asp Leu Asn Asp Leu Asn Val Glu Ile Gln
    370                 375                 380

Met Gln Leu Arg Val Tyr Asp Glu Lys Lys Arg Lys Gln Tyr Arg Phe
385                 390                 395                 400

Lys Glu Asn Glu Gly Leu Gln Phe Ala Phe Asp Ile Glu Asn Asp Ser
                405                 410                 415
```

-continued

```
Pro Asp Glu Val Val Gln Gln Met Ile Glu Gln Gln His Ile Pro Asp
            420                 425                 430
Glu Asp Thr Arg Met Ile Thr Lys Leu Ile Lys Asp Lys Val Asp Ala
        435                 440                 445
Phe Arg Arg Asp Arg Asp His Arg Leu Leu Glu Ile Lys Arg Ala Lys
    450                 455                 460
Glu Glu Glu Glu Arg Ile Arg Glu Ala Glu Ile Lys Glu Glu Leu
465                 470                 475                 480
Arg Leu Arg Ala Glu Ala Lys Glu Lys Glu Lys Glu Arg Leu Glu Lys
                485                 490                 495
Glu Arg Leu Glu Lys Lys Ala Ala Ala Ala Ala Ala Asn Pro Asn
            500                 505                 510
Pro Thr Pro Ile Pro Pro Thr Pro Ala Thr Pro His Ser Ser Ala Gln
        515                 520                 525
Gln Gln Pro Ile Pro Pro Leu Ser Thr Gln Thr Ser Ala Glu Ile
    530                 535                 540
Gln Gln Ser Ala Gln Gln Pro Ser Val Pro Val Thr Met Ile Ala Asn
545                 550                 555                 560
Ile Pro Ala Met Ser Pro Thr Ser Ala Gln Pro Gln Pro Val Leu Ser
                565                 570                 575
Pro Thr Ser Ala Ala Val Pro Val Pro Thr Thr Met Ile His Val Pro
            580                 585                 590
Lys Pro Ser Glu Ile Pro Val Gln Asn Val Ala Thr Ala Ala Pro
        595                 600                 605
Val Ala Ala Asn Asn Val Pro Pro Ser Pro Ala Pro Phe Lys Thr Glu
    610                 615                 620
Asp Ile Gln Thr Pro Thr Leu Ala Gln Asn Thr Val Pro Arg Thr Ile
625                 630                 635                 640
Ser Thr Asp Ala Ser Gly Leu Val Ile Asn Thr Pro Ala Ser Ile Ala
                645                 650                 655
Ser Pro Ser Pro Ala Pro Ser Ala Thr Asp Val Ala Ser Thr Thr Ala
            660                 665                 670
Pro Val Thr Pro Ala Pro Thr Pro Thr Thr Thr Asp Gly Gly Ala
        675                 680                 685
Ala Ala Ala Ser Thr Thr Thr Glu Asn Lys Glu Glu Lys Arg Lys Ser
    690                 695                 700
Asn Lys Arg Lys Val Val Met Glu Ile Leu Gly Cys Asp Glu Ser Arg
705                 710                 715                 720
Asn Phe Ala Leu Val Ser Cys Arg Leu Asp Thr Ser His Lys Ser Val
                725                 730                 735
Thr Phe Gln Phe Ala Pro Gly Thr Asp Lys Pro Cys Thr Ile Ala Thr
            740                 745                 750
Lys Leu Leu Ala Glu Asp Cys Leu Leu Lys Val His Val His Ile Val
        755                 760                 765
Glu Ala Gln Leu Gly Glu Val Ile Gln Leu Ile Asn Ser Asp Gly Lys
    770                 775                 780
Lys Gly Val Gly Thr Lys Leu Thr Val Leu Asp Pro Asn Ser Thr
785                 790                 795                 800
Glu Pro Pro Thr Ile Thr Ala Val Met Pro Lys Asp Ser Ser Ala Ala
                805                 810                 815
Thr Ala Ser Asn Thr Lys Pro Lys Ile Glu Ile Glu Lys Thr Pro Pro
            820                 825                 830
```

```
Thr Arg Asp Ala Ser Gln Glu Pro Asn Asn Val Gln Val Thr Asn Val
        835                 840                 845

Arg Lys Val Ser Gln Glu Ser Asn Ala Glu Ser Val Gln Ser Ile Pro
    850                 855                 860

Arg Pro Gly Gly Ile Ile Val Met Ser Pro Thr Asn Gln Thr Asp Ser
865                 870                 875                 880

Ala Pro Pro Thr Gly Ala Ala Lys Pro Ser Arg Phe Gln Val
            885                 890                 895

Thr Lys Ser Ala Asp Pro Ile Ala Thr Pro Ile Ser Ser Ile Ser
        900                 905                 910

Thr Ala Thr Val Ile Pro Ile Val Ala Ala Thr Pro Thr Asn Ile Thr
        915                 920                 925

Ser Glu Pro Val Ile Val Gln Pro Ile Thr Ala Gln Val Ile Thr His
    930                 935                 940

Leu Ala Thr Pro Ser Pro Val Ser His Ser Leu Ser Ser Asn Ser Ser
945                 950                 955                 960

Pro Ser Ala Thr Thr His Ser Asn Met Ser Ser Ile Gln Ser Thr Thr
            965                 970                 975

Ser Val Pro Gly Arg Arg Phe Thr Val Gln Pro Val Ser Gln Ala Glu
        980                 985                 990

Ser Gly Ile Ser Ser Ser Ile Ser Thr Pro His Pro Glu Pro Thr Pro
    995                 1000                1005

Ala Ile Thr Ser Cys Pro Pro Val Pro Ser Val Pro Pro Val Val
        1010                1015                1020

Ser Asn Gly Thr Leu Asn Leu Glu Val Ala Pro Lys Gln Thr Pro Ser
1025                1030                1035                1040

Ala Thr Asn Gln Asn Val Asp Thr Gln His Ser Ser Ser Thr Ala Ser
            1045                1050                1055

Thr Ala Thr Leu Val Ser Glu Thr Pro Ala Thr Val His Val Thr Pro
            1060                1065                1070

Ile Ser Val Pro Ala Pro Val Gln Glu Pro Leu Val Ile Asp His His
        1075                1080                1085

Ser Asp Val Leu Thr Gln Leu Asp Ser Glu Leu Arg Lys Val Ser Gly
        1090                1095                1100

Val Ser His Ser Ala Ser Pro Ser Thr Val Val Glu Ser Leu Thr Ser
1105                1110                1115                1120

Met Thr Pro Gln Thr Ile Pro Leu Ala Cys Gln Thr Val Pro Ala Ser
            1125                1130                1135

Ile Gly Gln Ala Pro Ala Val Ile Ala Ala His Ala Ala Ser Leu
            1140                1145                1150

Ile Pro Asn Ala Ser Val Pro Gln Ser Pro Ser Arg Leu Asp Ala Glu
            1155                1160                1165

Thr Gly Leu Ala Gly Leu His Glu Lys Leu Glu Ala Leu Lys Met Glu
            1170                1175                1180

Gln Asp Arg Arg Glu Asp Met Gly Asp Asp Ala Ile Gly Thr Thr Thr
1185                1190                1195                1200

Thr Asp Gly Lys Asp Glu Ile Pro Ile Asp Thr Leu Lys Gly Leu Ala
            1205                1210                1215

Glu Ala Leu Gly Lys Val Ile His Ala Asp Gly Arg Glu Thr Thr Pro
            1220                1225                1230

Met Pro Pro Asp His Pro Asp Leu Thr Asp Ala Ser Thr Gln Gln Leu
            1235                1240                1245
```

```
Ile Ser Pro Ser Asn Pro Asp Val Leu Thr Thr Met Ser Ala Val
1250                1255                1260

Glu Gly Ser Ala Ser Ser Thr Met Ile Glu Asp Ile Asp Ala Ser Thr
1265                1270                1275                1280

Ser Ala Val Asp Ala Ser Met Met Asn Ser Met Pro Pro Gly Ala Gln
            1285                1290                1295

Asn Ser Thr Asp Gln Ile Pro Ala Ala Met Thr Leu Ser Met Asp Gln
            1300                1305                1310

Glu Cys Ala Gln Ser Met Thr Ser Ser Ile Thr Arg Asn Thr Thr Gly
            1315                1320                1325

Thr Lys Leu Ala Thr Phe Glu Asn Leu Glu Thr Ala Leu Ser Ser Thr
1330                1335                1340

Leu Gly Thr His Ile Arg Gln Pro Asn Ala Pro Ser Ser Arg Asp Glu
1345                1350                1355                1360

Thr Thr Ala Pro Met Thr Pro Ser Phe Thr Asn Glu Arg Ile Gly Gly
                1365                1370                1375

Gly Gly Gly Gly Gly Ala Thr Ser Phe Ser Ile Gly Thr Pro Pro Ser
            1380                1385                1390

His Ser Pro Phe Pro Val Ser Glu Cys Asp Tyr Asp Leu Lys Gly Gln
            1395                1400                1405

Met Asp Leu Glu Ser Glu Asp Pro Glu Val Ile Gln Met Ile Val Arg
            1410                1415                1420

His Arg Met Glu Gln His Lys Leu Leu Glu Lys Gln Arg Val Glu Ile
1425                1430                1435                1440

Glu Arg Leu Arg Ser Lys Ile Arg Val Pro Arg Ala Thr Ser Val Asn
                1445                1450                1455

Pro Glu Met Ile Gly Asp Asp Glu Ala Asp Thr Thr Leu Thr Ala Leu
                1460                1465                1470

Gln Ser Ala Leu Gly Asn Ala Ser Leu Ser Leu Pro Ala Ser Pro Pro
            1475                1480                1485

Pro Asn Thr Glu Thr Thr Lys Val Asn Thr Thr Val Ile Pro Ser Asp
            1490                1495                1500

Val Leu Ala Thr Arg Met Thr Met Ser Gln Ser Ser Thr Lys Ser Ser
1505                1510                1515                1520

Asn Val Ser Val Ser Ser Arg His Arg Asp Asn Gln Ser Ala Pro Pro
                1525                1530                1535

Arg His His His His Gln Pro His Pro Pro His His Pro His Leu Gln
            1540                1545                1550

Asn His Tyr His Pro Pro Gln Asn His Thr Ser Ala Thr Ala Pro Cys
            1555                1560                1565

Pro Ser Ala Met Val Gln Leu Gln Ala Val Ser Asn Asn Asn Val Asn
            1570                1575                1580

Pro Leu His Gln Pro Pro His Pro Val Ser Ser Gln Ile Pro Pro Gln
1585                1590                1595                1600

Ala

<210> SEQ ID NO 41
<211> LENGTH: 638
<212> TYPE: PRT
<213> ORGANISM: Homo sapiens
```

<400> SEQUENCE: 41

```
Met Ser Ala Leu Ala Gly Glu Asp Val Trp Arg Cys Pro Gly Cys Gly
 1               5                  10                  15

Asp His Ile Ala Pro Ser Gln Ile Trp Tyr Arg Thr Val Asn Glu Thr
            20                  25                  30

Trp His Gly Ser Cys Phe Arg Cys Ser Glu Cys Gln Asp Ser Leu Thr
        35                  40                  45

Asn Trp Tyr Tyr Glu Lys Asp Gly Lys Leu Tyr Cys Pro Lys Asp Tyr
50                  55                  60

Trp Gly Lys Phe Gly Glu Phe Cys His Gly Cys Ser Leu Leu Met Thr
65                  70                  75                  80

Gly Pro Phe Met Val Ala Gly Glu Phe Lys Tyr His Pro Glu Cys Phe
                85                  90                  95

Ala Cys Met Ser Cys Lys Val Ile Ile Glu Asp Gly Asp Ala Tyr Ala
            100                 105                 110

Leu Val Gln His Ala Thr Leu Tyr Cys Gly Lys Cys His Asn Glu Val
        115                 120                 125

Val Leu Ala Pro Met Phe Glu Arg Leu Ser Thr Glu Ser Val Gln Glu
130                 135                 140

Gln Leu Pro Tyr Ser Val Thr Leu Ile Ser Met Pro Ala Thr Thr Glu
145                 150                 155                 160

Gly Arg Arg Gly Phe Ser Val Ser Val Glu Ser Ala Cys Ser Asn Tyr
                165                 170                 175

Ala Thr Thr Val Gln Val Lys Glu Val Asn Arg Met His Ile Ser Pro
            180                 185                 190

Asn Asn Arg Asn Ala Ile His Pro Gly Asp Arg Ile Leu Glu Ile Asn
        195                 200                 205

Gly Thr Pro Val Arg Thr Leu Arg Val Glu Glu Val Glu Asp Ala Ile
210                 215                 220

Ser Gln Thr Ser Gln Thr Leu Gln Leu Leu Ile Glu His Asp Pro Val
225                 230                 235                 240

Ser Gln Arg Leu Asp Gln Leu Arg Leu Glu Ala Arg Leu Ala Pro His
                245                 250                 255

Met Gln Asn Ala Gly His Pro His Ala Leu Ser Thr Leu Asp Thr Lys
            260                 265                 270

Glu Asn Leu Glu Gly Thr Leu Arg Arg Arg Ser Leu Arg Arg Ser Asn
        275                 280                 285

Ser Ile Ser Lys Ser Pro Gly Pro Ser Ser Pro Lys Glu Pro Leu Leu
290                 295                 300

Phe Ser Arg Asp Ile Ser Arg Ser Glu Ser Leu Arg Cys Ser Ser Ser
305                 310                 315                 320

Tyr Ser Gln Gln Ile Phe Arg Pro Cys Asp Leu Ile His Gly Glu Val
                325                 330                 335

Leu Gly Lys Gly Phe Phe Gly Gln Ala Ile Lys Val Thr His Lys Ala
            340                 345                 350

Thr Gly Lys Val Met Val Met Lys Glu Leu Ile Arg Cys Asp Glu Glu
        355                 360                 365

Thr Gln Lys Thr Phe Leu Thr Glu Val Lys Val Met Arg Ser Leu Asp
370                 375                 380

His Pro Asn Val Leu Lys Phe Ile Gly Val Leu Tyr Lys Asp Lys Lys
385                 390                 395                 400

Leu Asn Leu Leu Thr Glu Tyr Ile Glu Gly Gly Thr Leu Lys Asp Phe
                405                 410                 415
```

```
Leu Arg Ser Met Asp Pro Phe Pro Trp Gln Gln Lys Val Arg Phe Ala
            420                 425                 430

Lys Gly Ile Ala Ser Gly Met Ala Tyr Leu His Ser Met Cys Ile Ile
            435                 440                 445

His Arg Asp Leu Asn Ser His Asn Cys Leu Ile Lys Leu Asp Lys Thr
        450                 455                 460

Val Val Val Ala Asp Phe Gly Leu Ser Arg Leu Ile Val Glu Glu Arg
465                 470                 475                 480

Lys Arg Ala Pro Met Glu Lys Ala Thr Thr Lys Lys Arg Thr Leu Arg
                485                 490                 495

Lys Asn Asp Arg Lys Lys Arg Tyr Thr Val Val Gly Asn Pro Tyr Trp
            500                 505                 510

Met Ala Pro Glu Met Leu Asn Gly Lys Ser Tyr Asp Glu Thr Val Asp
            515                 520                 525

Ile Phe Ser Phe Gly Ile Val Leu Cys Glu Ile Ile Gly Gln Val Tyr
        530                 535                 540

Ala Asp Pro Asp Cys Leu Pro Arg Thr Leu Asp Phe Gly Leu Asn Val
545                 550                 555                 560

Lys Leu Phe Trp Glu Lys Phe Val Pro Thr Asp Cys Pro Pro Ala Phe
                565                 570                 575

Phe Pro Leu Ala Ala Ile Cys Cys Arg Leu Glu Pro Glu Ser Arg Pro
            580                 585                 590

Ala Phe Ser Lys Leu Glu Asp Ser Phe Glu Ala Leu Ser Leu Tyr Leu
            595                 600                 605

Gly Glu Leu Gly Ile Pro Leu Pro Ala Glu Leu Glu Glu Leu Asp His
        610                 615                 620

Thr Val Ser Met Gln Tyr Gly Leu Thr Arg Asp Ser Pro
625                 630                 635

<210> SEQ ID NO 42
<211> LENGTH: 733
<212> TYPE: PRT
<213> ORGANISM: Homo sapiens

<400> SEQUENCE: 42

Met Gly Ser Tyr Leu Ser Val Pro Ala Tyr Phe Thr Ser Arg Asp Leu
1               5                   10                  15

Phe Arg Cys Ser Glu Cys Gln Asp Ser Leu Thr Asn Trp Tyr Tyr Glu
                20                  25                  30

Lys Asp Gly Lys Leu Tyr Cys Pro Lys Asp Tyr Trp Gly Lys Phe Gly
            35                  40                  45

Glu Phe Cys His Gly Cys Ser Leu Leu Met Thr Gly Pro Phe Met Val
    50                  55                  60

Ala Gly Glu Phe Lys Tyr His Pro Glu Cys Phe Ala Cys Met Ser Cys
65                  70                  75                  80

Lys Val Ile Ile Glu Asp Gly Asp Ala Tyr Ala Leu Val Gln His Ala
                85                  90                  95

Thr Leu Tyr Cys Gly Lys Cys His Asn Glu Val Val Leu Ala Pro Met
            100                 105                 110

Phe Glu Arg Leu Ser Thr Glu Ser Val Gln Glu Gln Leu Pro Tyr Ser
        115                 120                 125

Val Thr Leu Ile Ser Met Pro Ala Thr Thr Glu Gly Arg Arg Gly Phe
    130                 135                 140

Ser Val Ser Val Glu Ser Ala Cys Ser Asn Tyr Ala Thr Thr Val Gln
145                 150                 155                 160
```

```
Val Lys Glu Val Asn Arg Met His Ile Ser Pro Asn Arg Asn Ala
            165                 170                 175

Ile His Pro Gly Asp Arg Ile Leu Glu Ile Asn Gly Thr Pro Val Arg
            180                 185                 190

Thr Leu Arg Val Glu Glu Val Glu Asp Ala Ile Ser Gln Thr Ser Gln
            195                 200                 205

Thr Leu Gln Leu Leu Ile Glu His Asp Pro Val Ser Gln Arg Leu Asp
            210                 215                 220

Gln Leu Arg Leu Glu Ala Arg Leu Ala Pro His Met Gln Asn Ala Gly
225                 230                 235                 240

His Pro His Ala Leu Ser Thr Leu Asp Thr Lys Glu Asn Leu Glu Gly
                245                 250                 255

Thr Leu Arg Arg Arg Ser Leu Arg Arg Ser Asn Ser Ile Ser Lys Ser
            260                 265                 270

Pro Gly Pro Ser Ser Pro Lys Glu Pro Leu Leu Phe Ser Arg Asp Ile
            275                 280                 285

Ser Arg Ser Glu Ser Leu Arg Cys Ser Ser Ser Tyr Ser Gln Gln Ile
            290                 295                 300

Phe Arg Pro Cys Asp Leu Ile His Gly Glu Val Leu Gly Lys Gly Phe
305                 310                 315                 320

Phe Gly Gln Ala Ile Lys Val Thr His Lys Ala Thr Gly Lys Val Met
                325                 330                 335

Val Met Lys Glu Leu Ile Arg Cys Asp Glu Glu Thr Gln Lys Thr Phe
            340                 345                 350

Leu Thr Glu Val Lys Val Met Arg Ser Leu Asp His Pro Asn Val Leu
            355                 360                 365

Lys Phe Ile Gly Val Leu Tyr Lys Asp Lys Lys Leu Asn Leu Leu Thr
            370                 375                 380

Glu Tyr Ile Glu Gly Gly Thr Leu Lys Asp Phe Leu Arg Ser Met Asp
385                 390                 395                 400

Pro Phe Pro Trp Gln Gln Lys Val Arg Phe Ala Lys Gly Ile Ala Ser
                405                 410                 415

Gly Met Ala Tyr Leu His Ser Met Cys Ile Ile His Arg Asp Leu Asn
            420                 425                 430

Ser His Asn Cys Leu Ile Lys Leu Asp Lys Thr Val Val Val Ala Asp
            435                 440                 445

Phe Gly Leu Ser Arg Leu Ile Val Glu Glu Arg Lys Arg Ala Pro Met
            450                 455                 460

Glu Lys Ala Thr Thr Lys Lys Arg Thr Leu Arg Lys Asn Asp Arg Lys
465                 470                 475                 480

Lys Arg Tyr Thr Val Val Gly Asn Pro Tyr Trp Met Ala Pro Glu Met
                485                 490                 495

Leu Asn Gly Lys Ser Tyr Asp Glu Thr Val Asp Ile Phe Ser Phe Gly
            500                 505                 510

Ile Val Leu Cys Glu Ile Ile Gly Gln Val Tyr Ala Asp Pro Asp Cys
            515                 520                 525

Leu Pro Arg Thr Leu Asp Phe Gly Leu Asn Val Lys Leu Phe Trp Glu
            530                 535                 540

Lys Phe Val Pro Thr Asp Cys Pro Pro Ala Phe Phe Pro Leu Ala Ala
545                 550                 555                 560

Ile Cys Cys Arg Leu Glu Pro Glu Ser Arg Ala Pro Pro Gly Ala Ala
                565                 570                 575
```

```
Gly Glu Gly Pro Gly Cys Ala Asp Asp Glu Gly Pro Val Arg Arg Gln
            580                 585                 590

Gly Lys Val Thr Ile Lys Tyr Asp Pro Lys Glu Leu Arg Lys His Leu
        595                 600                 605

Asn Leu Glu Glu Trp Ile Leu Glu Gln Leu Thr Arg Leu Tyr Asp Cys
    610                 615                 620

Gln Glu Glu Glu Ile Ser Glu Leu Glu Ile Asp Val Asp Glu Leu Leu
625                 630                 635                 640

Asp Met Glu Ser Asp Asp Ala Trp Ala Ser Arg Val Lys Glu Leu Leu
                645                 650                 655

Val Asp Cys Tyr Lys Pro Thr Glu Ala Phe Ile Ser Gly Leu Leu Asp
            660                 665                 670

Lys Ile Arg Ala Met Gln Lys Leu Ser Thr Pro Gln Lys Lys Pro Ala
        675                 680                 685

Phe Ser Lys Leu Glu Asp Ser Phe Glu Ala Leu Ser Leu Tyr Leu Gly
    690                 695                 700

Glu Leu Gly Ile Pro Leu Pro Ala Glu Leu Glu Glu Leu Asp His Thr
705                 710                 715                 720

Val Ser Met Gln Tyr Gly Leu Thr Arg Asp Ser Pro Pro
                725                 730

<210> SEQ ID NO 43
<211> LENGTH: 626
<212> TYPE: PRT
<213> ORGANISM: Homo sapiens

<400> SEQUENCE: 43

Met Ala Gly Glu Arg Pro Pro Leu Arg Gly Pro Gly Pro Gly Pro Gly
 1               5                  10                  15

Glu Val Pro Gly Glu Gly Pro Pro Gly Pro Gly Thr Gly Gly Gly
            20                  25                  30

Pro Gly Arg Gly Arg Pro Ser Ser Tyr Arg Val Leu Arg Ser Ala Val
        35                  40                  45

Ser Ser Leu Ala Arg Val Asp Asp Phe His Cys Ala Glu Lys Ile Gly
    50                  55                  60

Ala Gly Phe Phe Ser Glu Val Tyr Lys Val Arg His Arg Gln Ser Gly
65                  70                  75                  80

Gln Val Met Val Leu Lys Met Asn Lys Leu Pro Ser Asn Arg Gly Asn
                85                  90                  95

Thr Leu Arg Glu Val Gln Leu Met Asn Arg Leu Arg His Pro Asn Ile
            100                 105                 110

Leu Arg Phe Met Gly Val Cys Val His Gln Gly Gln Leu His Ala Leu
        115                 120                 125

Thr Glu Tyr Met Asn Gly Gly Thr Leu Glu Gln Leu Leu Ser Ser Pro
    130                 135                 140

Glu Pro Leu Ser Trp Pro Val Arg Leu His Leu Ala Leu Asp Ile Ala
145                 150                 155                 160

Arg Gly Leu Arg Tyr Leu His Ser Lys Gly Val Phe His Arg Asp Leu
                165                 170                 175

Thr Ser Lys Asn Cys Leu Val Arg Arg Glu Asp Arg Gly Phe Thr Ala
            180                 185                 190

Val Val Gly Asp Phe Gly Leu Ala Glu Lys Ile Pro Val Tyr Arg Glu
        195                 200                 205

Gly Ala Arg Lys Glu Pro Leu Ala Val Val Gly Ser Pro Tyr Trp Met
    210                 215                 220
```

```
Ala Pro Glu Val Leu Arg Gly Glu Leu Tyr Asp Glu Lys Ala Asp Val
225                 230                 235                 240

Phe Ala Phe Gly Ile Val Leu Cys Glu Leu Ile Ala Arg Val Pro Ala
            245                 250                 255

Asp Pro Asp Tyr Leu Pro Arg Thr Glu Asp Phe Gly Leu Asp Val Pro
        260                 265                 270

Ala Phe Arg Thr Leu Val Gly Asp Asp Cys Pro Leu Pro Phe Leu Leu
        275                 280                 285

Leu Ala Ile His Cys Cys Asn Leu Glu Pro Ser Thr Arg Ala Pro Phe
        290                 295                 300

Thr Glu Ile Thr Gln His Leu Glu Trp Ile Leu Glu Gln Leu Pro Glu
305                 310                 315                 320

Pro Ala Pro Leu Thr Arg Thr Ala Leu Thr His Asn Gln Gly Ser Val
                325                 330                 335

Ala Arg Gly Gly Pro Ser Ala Thr Leu Pro Arg Pro Asp Pro Arg Leu
            340                 345                 350

Ser Arg Ser Arg Ser Asp Leu Phe Leu Pro Ser Pro Glu Ser Pro
        355                 360                 365

Pro Asn Trp Gly Asp Asn Leu Thr Arg Val Asn Pro Phe Ser Leu Arg
        370                 375                 380

Glu Asp Leu Arg Gly Gly Lys Ile Lys Leu Leu Asp Thr Pro Ser Lys
385                 390                 395                 400

Pro Val Leu Pro Leu Val Pro Pro Ser Pro Phe Pro Ser Thr Gln Leu
                405                 410                 415

Pro Leu Val Thr Thr Pro Glu Thr Leu Val Gln Pro Gly Thr Pro Ala
                420                 425                 430

Arg Arg Cys Arg Ser Leu Pro Ser Ser Pro Glu Leu Pro Arg Arg Met
        435                 440                 445

Glu Thr Ala Leu Pro Gly Pro Gly Pro Pro Ala Val Gly Pro Ser Ala
450                 455                 460

Glu Glu Lys Met Glu Cys Glu Gly Ser Ser Pro Glu Pro Glu Pro Pro
465                 470                 475                 480

Gly Pro Ala Pro Gln Leu Pro Leu Ala Val Ala Thr Asp Asn Phe Ile
                485                 490                 495

Ser Thr Cys Ser Ser Ala Ser Gln Pro Trp Ser Pro Arg Ser Gly Pro
            500                 505                 510

Val Leu Asn Asn Asn Pro Pro Ala Val Val Asn Ser Pro Gln Gly
            515                 520                 525

Trp Ala Gly Glu Pro Trp Asn Arg Ala Gln His Ser Leu Pro Arg Ala
530                 535                 540

Ala Ala Leu Glu Arg Thr Glu Pro Ser Pro Pro Ser Ala Pro Arg
545                 550                 555                 560

Glu Pro Asp Glu Gly Leu Pro Cys Pro Gly Cys Cys Leu Gly Pro Phe
            565                 570                 575

Ser Phe Gly Phe Leu Ser Met Cys Pro Arg Pro Thr Pro Ala Val Ala
        580                 585                 590

Arg Tyr Arg Asn Leu Asn Cys Glu Ala Gly Ser Leu Leu Cys His Arg
        595                 600                 605

Gly His His Ala Lys Pro Pro Thr Pro Ser Leu Gln Leu Pro Gly Ala
    610                 615                 620

Arg Ser
625
```

```
<210> SEQ ID NO 44
<211> LENGTH: 617
<212> TYPE: PRT
<213> ORGANISM: Mus musculus

<400> SEQUENCE: 44
```

| | | | | | | | | | | | | | | |
|---|---|---|---|---|---|---|---|---|---|---|---|---|---|---|
| Met | Gly | Ser | Tyr | Leu | Ser | Val | Pro | Ala | Tyr | Phe | Thr | Ser | Arg | Asp | Pro |
| 1 | | | | 5 | | | | | 10 | | | | | 15 | |
| Phe | Arg | Cys | Ser | Glu | Cys | Gln | Glu | Ser | Leu | Thr | Asn | Trp | Tyr | Tyr | Glu |
| | | | 20 | | | | | 25 | | | | | 30 | | |
| Lys | Asp | Gly | Lys | Leu | Tyr | Cys | His | Lys | Asp | Tyr | Trp | Ala | Lys | Phe | Gly |
| | | 35 | | | | | 40 | | | | | 45 | | | |
| Glu | Phe | Cys | His | Gly | Cys | Ser | Leu | Leu | Met | Thr | Gly | Pro | Ala | Met | Val |
| | 50 | | | | | 55 | | | | | 60 | | | | |
| Ala | Gly | Glu | Phe | Lys | Tyr | His | Pro | Glu | Cys | Phe | Ala | Cys | Met | Ser | Cys |
| 65 | | | | | 70 | | | | | 75 | | | | | 80 |
| Lys | Val | Ile | Ile | Glu | Asp | Gly | Asp | Ala | Tyr | Ala | Leu | Val | Gln | His | Ala |
| | | | | 85 | | | | | 90 | | | | | 95 | |
| Thr | Leu | Tyr | Cys | Gly | Lys | Cys | His | Asn | Glu | Val | Val | Leu | Ala | Pro | Met |
| | | | 100 | | | | | 105 | | | | | 110 | | |
| Phe | Glu | Arg | Leu | Ser | Thr | Glu | Ser | Val | Gln | Asp | Gln | Leu | Pro | Tyr | Ser |
| | | 115 | | | | | 120 | | | | | 125 | | | |
| Val | Thr | Leu | Ile | Ser | Met | Pro | Ala | Thr | Thr | Glu | Cys | Arg | Arg | Gly | Phe |
| | 130 | | | | | 135 | | | | | 140 | | | | |
| Ser | Val | Thr | Val | Glu | Ser | Ala | Ser | Ser | Asn | Tyr | Ala | Thr | Thr | Val | Gln |
| 145 | | | | | 150 | | | | | 155 | | | | | 160 |
| Val | Lys | Glu | Val | Asn | Arg | Met | His | Ile | Ser | Pro | Asn | Arg | Asn | Ala |
| | | | | 165 | | | | | 170 | | | | | 175 |
| Ile | His | Pro | Gly | Asp | Arg | Ile | Leu | Glu | Ile | Asn | Gly | Thr | Pro | Val | Arg |
| | | | 180 | | | | | 185 | | | | | 190 | | |
| Thr | Leu | Arg | Val | Glu | Glu | Val | Glu | Asp | Ala | Ile | Lys | Gln | Thr | Ser | Gln |
| | | 195 | | | | | 200 | | | | | 205 | | | |
| Thr | Leu | Gln | Leu | Leu | Ile | Glu | His | Asp | Pro | Val | Pro | Gln | Arg | Leu | Asp |
| | 210 | | | | | 215 | | | | | 220 | | | | |
| Gln | Leu | Arg | Leu | Asp | Ala | Arg | Leu | Pro | Pro | His | Met | Gln | Ser | Thr | Gly |
| 225 | | | | | 230 | | | | | 235 | | | | | 240 |
| His | Thr | Leu | Met | Leu | Ser | Thr | Leu | Asp | Thr | Lys | Glu | Asn | Gln | Glu | Gly |
| | | | | 245 | | | | | 250 | | | | | 255 | |
| Thr | Leu | Arg | Arg | Arg | Ser | Leu | Arg | Arg | Ser | Asn | Ser | Ile | Ser | Lys | Ser |
| | | | 260 | | | | | 265 | | | | | 270 | | |
| Pro | Gly | Pro | Ser | Ser | Pro | Lys | Glu | Pro | Leu | Leu | Ser | Arg | Asp | Ile |
| | | 275 | | | | | 280 | | | | | 285 | | | |
| Ser | Arg | Ser | Glu | Ser | Leu | Arg | Cys | Ser | Ser | Ser | Tyr | Ser | Gln | Gln | Ile |
| | 290 | | | | | 295 | | | | | 300 | | | | |
| Phe | Arg | Pro | Cys | Asp | Leu | Ile | His | Gly | Glu | Val | Leu | Gly | Lys | Gly | Phe |
| 305 | | | | | 310 | | | | | 315 | | | | | 320 |
| Phe | Gly | Gln | Ala | Ile | Lys | Val | Thr | His | Lys | Ala | Thr | Gly | Lys | Val | Met |
| | | | | 325 | | | | | 330 | | | | | 335 | |
| Val | Met | Lys | Glu | Leu | Ile | Arg | Cys | Asp | Glu | Glu | Thr | Gln | Lys | Thr | Phe |
| | | | 340 | | | | | 345 | | | | | 350 | | |
| Leu | Thr | Glu | Val | Lys | Val | Met | Arg | Ser | Leu | Asp | His | Pro | Asn | Val | Leu |
| | | 355 | | | | | 360 | | | | | 365 | | | |
| Lys | Phe | Ile | Gly | Val | Leu | Tyr | Lys | Asp | Lys | Lys | Leu | Asn | Leu | Leu | Thr |
| | 370 | | | | | 375 | | | | | 380 | | | | |

-continued

```
Glu Tyr Ile Glu Gly Gly Thr Leu Lys Asp Phe Leu Arg Ser Val Asp
385                 390                 395                 400

Pro Phe Pro Trp Gln Gln Lys Val Arg Phe Ala Lys Gly Ile Ser Ser
            405                 410                 415

Gly Met Ala Tyr Leu His Ser Met Cys Ile Ile His Arg Asp Leu Asn
            420                 425                 430

Ser His Asn Cys Leu Ile Lys Leu Asp Lys Thr Val Val Ala Asp
            435                 440                 445

Phe Gly Leu Ser Arg Leu Ile Val Glu Glu Arg Lys Arg Pro Val
    450                 455                 460

Glu Lys Ala Thr Thr Lys Lys Arg Thr Leu Arg Lys Ser Asp Arg Lys
465                 470                 475                 480

Lys Arg Tyr Thr Val Val Gly Asn Pro Tyr Trp Met Ala Pro Glu Met
                485                 490                 495

Leu Asn Gly Lys Ser Tyr Asp Glu Thr Val Asp Val Phe Ser Phe Gly
            500                 505                 510

Ile Val Leu Cys Glu Ile Ile Gly Gln Val Tyr Ala Asp Pro Asp Cys
            515                 520                 525

Leu Pro Arg Thr Leu Asp Phe Gly Leu Asn Val Lys Leu Phe Trp Glu
    530                 535                 540

Lys Phe Val Pro Thr Asp Cys Pro Pro Ala Phe Phe Pro Leu Ala Ala
545                 550                 555                 560

Ile Cys Cys Lys Leu Glu Pro Glu Ser Arg Pro Ala Phe Ser Lys Leu
                565                 570                 575

Glu Asp Ser Phe Glu Ala Leu Ser Leu Phe Leu Gly Glu Leu Ala Ile
            580                 585                 590

Pro Leu Pro Ala Glu Leu Glu Asp Leu Asp His Thr Val Ser Met Glu
    595                 600                 605

Tyr Gly Leu Thr Arg Asp Ser Pro Pro
    610                 615

<210> SEQ ID NO 45
<211> LENGTH: 451
<212> TYPE: PRT
<213> ORGANISM: Mus musculus

<400> SEQUENCE: 45

Met His Ile Ser Pro Asn Asn Arg Asn Ala Ile His Pro Gly Asp Arg
1               5                   10                  15

Ile Leu Glu Ile Asn Gly Thr Pro Val Arg Thr Leu Arg Val Glu Glu
            20                  25                  30

Val Glu Asp Ala Ile Lys Gln Thr Ser Gln Thr Leu Gln Leu Leu Ile
        35                  40                  45

Glu His Asp Pro Val Pro Gln Arg Leu Asp Gln Leu Arg Leu Asp Ala
    50                  55                  60

Arg Leu Pro Pro His Met Gln Ser Thr Gly His Thr Leu Met Leu Ser
65                  70                  75                  80

Thr Leu Asp Thr Lys Glu Asn Gln Glu Gly Thr Leu Arg Arg Arg Ser
                85                  90                  95

Leu Arg Arg Ser Asn Ser Ile Ser Lys Ser Pro Gly Pro Ser Ser Pro
            100                 105                 110

Lys Glu Pro Leu Leu Leu Ser Arg Asp Ile Ser Arg Ser Glu Ser Leu
        115                 120                 125

Arg Cys Ser Ser Ser Tyr Ser Gln Gln Ile Phe Arg Pro Cys Asp Leu
    130                 135                 140
```

```
Ile His Gly Glu Val Leu Gly Lys Gly Phe Phe Gly Gln Ala Ile Lys
145                 150                 155                 160

Val Thr His Lys Ala Thr Gly Lys Val Met Val Lys Glu Leu Ile
            165                 170                 175

Arg Cys Asp Glu Glu Thr Gln Lys Thr Phe Leu Thr Glu Val Lys Val
            180                 185                 190

Met Arg Ser Leu Asp His Pro Asn Val Leu Lys Phe Ile Gly Val Leu
            195                 200                 205

Tyr Lys Asp Lys Lys Leu Asn Leu Leu Thr Glu Tyr Ile Glu Gly Gly
    210                 215                 220

Thr Leu Lys Asp Phe Leu Arg Ser Val Asp Pro Phe Pro Trp Gln Gln
225                 230                 235                 240

Lys Val Arg Phe Ala Lys Gly Ile Ser Ser Gly Met Ala Tyr Leu His
                245                 250                 255

Ser Met Cys Ile Ile His Arg Asp Leu Asn Ser His Asn Cys Leu Ile
            260                 265                 270

Lys Leu Asp Lys Thr Val Val Ala Asp Phe Gly Leu Ser Arg Leu
    275                 280                 285

Ile Val Glu Glu Arg Lys Arg Pro Pro Val Lys Ala Thr Thr Lys
    290                 295                 300

Lys Arg Thr Leu Arg Lys Ser Asp Arg Lys Lys Arg Tyr Thr Val Val
305                 310                 315                 320

Gly Asn Pro Tyr Trp Met Ala Pro Glu Met Leu Asn Gly Lys Ser Tyr
                325                 330                 335

Asp Glu Thr Val Asp Val Phe Ser Phe Gly Ile Val Leu Cys Glu Ile
            340                 345                 350

Ile Gly Gln Val Tyr Ala Asp Pro Asp Cys Leu Pro Arg Thr Leu Asp
            355                 360                 365

Phe Gly Leu Asn Val Lys Leu Phe Trp Glu Lys Phe Val Pro Thr Asp
    370                 375                 380

Cys Pro Pro Ala Phe Phe Pro Leu Ala Ala Ile Cys Cys Lys Leu Glu
385                 390                 395                 400

Pro Glu Ser Arg Pro Ala Phe Ser Lys Leu Glu Asp Ser Phe Glu Ala
                405                 410                 415

Leu Ser Leu Phe Leu Gly Glu Leu Ala Ile Pro Leu Pro Ala Glu Leu
            420                 425                 430

Glu Asp Leu Asp His Thr Val Ser Met Glu Tyr Gly Leu Thr Arg Asp
            435                 440                 445

Ser Pro Pro
    450

<210> SEQ ID NO 46
<211> LENGTH: 627
<212> TYPE: PRT
<213> ORGANISM: Mus musculus

<400> SEQUENCE: 46

Met Ala Gly Glu Arg Pro Pro Leu Arg Gly Pro Gly Pro Gly Glu Ala
1               5                   10                  15

Pro Gly Glu Gly Pro Gly Gly Ala Gly Gly Pro Gly Arg Gly Arg
            20                  25                  30

Pro Ser Ser Tyr Arg Ala Leu Arg Ser Ala Val Ser Ser Leu Ala Arg
        35                  40                  45

Val Asp Asp Phe Asp Cys Ala Glu Lys Ile Gly Ala Gly Phe Phe Ser
    50                  55                  60
```

-continued

```
Glu Val Tyr Lys Val Arg His Arg Gln Ser Gly Gln Val Met Val Leu
 65                  70                  75                  80

Lys Met Asn Lys Leu Pro Ser Asn Arg Ser Asn Thr Leu Arg Glu Val
                 85                  90                  95

Gln Leu Met Asn Arg Leu Arg His Pro Asn Ile Leu Arg Phe Met Gly
            100                 105                 110

Val Cys Val His Gln Gly Gln Leu His Ala Leu Thr Glu Tyr Met Asn
            115                 120                 125

Gly Gly Thr Leu Glu Gln Leu Leu Ser Ser Pro Glu Pro Leu Ser Trp
130                 135                 140

Pro Val Arg Leu His Leu Ala Leu Asp Ile Ala Gln Gly Leu Arg Tyr
145                 150                 155                 160

Leu His Ala Lys Gly Val Phe His Arg Asp Leu Thr Ser Lys Asn Cys
                165                 170                 175

Leu Val Arg Arg Glu Asp Arg Gly Phe Thr Ala Val Val Gly Asp Phe
            180                 185                 190

Gly Leu Ala Glu Lys Ile Pro Val Tyr Arg Lys Gly Gln Gly Arg Ser
            195                 200                 205

Pro Trp Leu Trp Trp Ala Pro Arg Thr Gly Trp Leu Gln Arg Cys Cys
210                 215                 220

Gly Glu Ser Cys Met Met Arg Arg Pro Met Ser Ser Pro Ser Gly Ser
225                 230                 235                 240

Ser Ser Val Ser Ser Pro Glu Tyr Leu Gln Thr Leu Thr Thr Tyr
                245                 250                 255

Pro Val Leu Arg Asp Phe Gly Leu Asp Val Pro Ala Phe Arg Thr Leu
            260                 265                 270

Val Gly Asn Asp Cys Pro Leu Pro Phe Leu Leu Leu Ala Ile His Cys
            275                 280                 285

Cys Ser Met Glu Pro Ser Thr Arg Ala Pro Phe Thr Glu Ile Thr Gln
290                 295                 300

His Leu Glu Gln Ile Leu Glu Gln Gln Pro Glu Ala Thr Pro Leu Ala
305                 310                 315                 320

Lys Pro Pro Leu Thr Lys Ala Pro Leu Thr Tyr Asn Gln Gly Ser Val
                325                 330                 335

Pro Arg Gly Gly Pro Ser Ala Thr Leu Pro Arg Pro Asp Pro Arg Leu
            340                 345                 350

Ser Arg Ser Arg Ser Asp Leu Phe Leu Pro Pro Ser Pro Glu Ser Pro
            355                 360                 365

Pro Ser Trp Gly Asp Asn Leu Thr Arg Val Asn Pro Phe Ser Leu Arg
370                 375                 380

Glu Asp Leu Arg Gly Gly Lys Ile Lys Leu Leu Asp Thr Pro Cys Lys
385                 390                 395                 400

Pro Ala Thr Pro Leu Pro Leu Val Pro Pro Ser Pro Leu Thr Ser Thr
                405                 410                 415

Gln Leu Pro Leu Val Thr Thr Pro Asp Ile Leu Val Gln Pro Glu Thr
            420                 425                 430

Pro Val Arg Arg Cys Arg Ser Leu Pro Ser Ser Pro Glu Leu Pro Arg
            435                 440                 445

Arg Met Glu Thr Ala Leu Pro Gly Pro Gly Ser Pro Met Gly Pro
450                 455                 460

Thr Glu Glu Arg Met Asp Cys Glu Gly Ser Ser Pro Glu Pro Glu Pro
465                 470                 475                 480
```

```
Pro Gly Leu Ala Pro Gln Leu Pro Leu Ala Val Ala Thr Asp Asn Phe
                485                 490                 495
Ile Ser Thr Cys Ser Ser Ala Ser Gln Pro Trp Ser Pro Arg Ser Gly
                500                 505                 510
Pro Pro Leu Asn Asn Pro Ala Val Val Asn Ser Pro Gln
                515                 520                 525
Gly Trp Ala Arg Glu Pro Trp Asn Arg Ala Gln His Ser Leu Pro Arg
                530                 535                 540
Ala Ala Ala Leu Glu Gln Thr Glu Pro Ser Pro Pro Ser Ala Pro
545                 550                 555                 560
Arg Glu Pro Glu Glu Gly Leu Pro Cys Pro Gly Cys Cys Leu Gly Pro
                565                 570                 575
Phe Ser Phe Gly Phe Leu Ser Met Cys Pro Arg Pro Thr Pro Ala Val
                580                 585                 590
Ala Arg Tyr Arg Asn Leu Asn Cys Glu Ala Gly Ser Leu Leu Cys His
                595                 600                 605
Arg Gly His His Ala Lys Pro Pro Thr Pro Ser Leu Gln Leu Pro Gly
                610                 615                 620
Ala Arg Ser
625

<210> SEQ ID NO 47
<211> LENGTH: 627
<212> TYPE: PRT
<213> ORGANISM: Mus musculus

<400> SEQUENCE: 47

Met Ala Gly Glu Arg Pro Pro Leu Arg Gly Pro Gly Pro Gly Glu Ala
1               5                   10                  15
Pro Gly Glu Gly Pro Gly Gly Ala Gly Gly Pro Gly Arg Gly Arg
                20                  25                  30
Pro Ser Ser Tyr Arg Ala Leu Arg Ser Ala Val Ser Ser Leu Ala Arg
                35                  40                  45
Val Asp Asp Phe Asp Cys Ala Glu Lys Ile Gly Ala Gly Phe Phe Ser
50                  55                  60
Glu Val Tyr Lys Val Arg His Arg Gln Ser Gly Gln Val Met Val Leu
65                  70                  75                  80
Lys Met Asn Lys Leu Pro Ser Asn Arg Ser Asn Thr Leu Arg Glu Val
                85                  90                  95
Gln Leu Met Asn Arg Leu Arg His Pro Asn Ile Leu Arg Phe Met Gly
                100                 105                 110
Val Cys Val His Gln Gly Gln Leu His Ala Leu Thr Glu Tyr Met Asn
                115                 120                 125
Gly Gly Thr Leu Glu Gln Leu Leu Ser Ser Pro Glu Pro Leu Ser Trp
                130                 135                 140
Pro Val Arg Leu His Leu Ala Leu Asp Ile Ala Gln Gly Leu Arg Tyr
145                 150                 155                 160
Leu His Ala Lys Gly Val Phe His Arg Asp Leu Thr Ser Lys Asn Cys
                165                 170                 175
Leu Val Arg Arg Glu Asp Arg Gly Phe Thr Ala Val Val Gly Asp Phe
                180                 185                 190
Gly Leu Ala Glu Lys Ile Pro Val Tyr Arg Glu Gly Thr Arg Lys Glu
                195                 200                 205
Pro Leu Ala Val Val Gly Ser Pro Tyr Trp Met Ala Pro Glu Val Leu
210                 215                 220
```

```
Arg Gly Glu Leu Tyr Asp Glu Lys Ala Asp Val Phe Ala Phe Gly Ile
225                 230                 235                 240

Val Leu Cys Glu Leu Ile Ala Arg Val Pro Ala Asp Pro Asp Tyr Leu
                245                 250                 255

Pro Arg Thr Glu Asp Phe Gly Leu Asp Val Pro Ala Phe Arg Thr Leu
            260                 265                 270

Val Gly Asn Asp Cys Pro Leu Pro Phe Leu Leu Ala Ile His Cys
        275                 280                 285

Cys Ser Met Glu Pro Ser Thr Arg Ala Pro Phe Thr Glu Ile Thr Gln
    290                 295                 300

His Leu Glu Gln Ile Leu Glu Gln Gln Pro Glu Ala Thr Pro Leu Ala
305                 310                 315                 320

Lys Pro Pro Leu Thr Lys Ala Pro Leu Thr Tyr Asn Gln Gly Ser Val
                325                 330                 335

Pro Arg Gly Gly Pro Ser Ala Thr Leu Pro Arg Pro Asp Pro Arg Leu
            340                 345                 350

Ser Arg Ser Arg Ser Asp Leu Phe Leu Pro Ser Pro Glu Ser Pro
        355                 360                 365

Pro Ser Trp Gly Asp Asn Leu Thr Arg Val Asn Pro Phe Ser Leu Arg
    370                 375                 380

Glu Asp Leu Arg Gly Gly Lys Ile Lys Leu Leu Asp Thr Pro Cys Lys
385                 390                 395                 400

Pro Ala Thr Pro Leu Pro Leu Val Pro Pro Ser Pro Leu Thr Ser Thr
                405                 410                 415

Gln Leu Pro Leu Val Thr Thr Pro Asp Ile Leu Val Gln Pro Glu Thr
            420                 425                 430

Pro Val Arg Arg Cys Arg Ser Leu Pro Ser Ser Pro Glu Leu Pro Arg
        435                 440                 445

Arg Met Glu Thr Ala Leu Pro Gly Pro Gly Pro Ser Pro Met Gly Pro
    450                 455                 460

Thr Glu Glu Arg Met Asp Cys Glu Gly Ser Ser Pro Glu Pro Glu Pro
465                 470                 475                 480

Pro Gly Leu Ala Pro Gln Leu Pro Leu Ala Val Ala Thr Asp Asn Phe
                485                 490                 495

Ile Ser Thr Cys Ser Ser Ala Ser Gln Pro Trp Ser Pro Arg Ser Gly
            500                 505                 510

Pro Pro Leu Asn Asn Asn Pro Ala Val Val Asn Ser Pro Gln
        515                 520                 525

Gly Trp Ala Arg Glu Pro Trp Asn Arg Ala Gln His Ser Leu Pro Arg
    530                 535                 540

Ala Ala Ala Leu Glu Gln Thr Glu Pro Ser Pro Pro Ser Ala Pro
545                 550                 555                 560

Arg Glu Pro Glu Glu Gly Leu Pro Cys Pro Gly Cys Leu Gly Pro
                565                 570                 575

Phe Ser Phe Gly Phe Leu Ser Met Cys Pro Arg Pro Thr Pro Ala Val
            580                 585                 590

Ala Arg Tyr Arg Asn Leu Asn Cys Glu Ala Gly Ser Leu Leu Cys His
        595                 600                 605

Arg Gly His His Ala Lys Pro Pro Thr Pro Ser Leu Gln Leu Pro Gly
    610                 615                 620

Ala Arg Ser
625
```

<210> SEQ ID NO 48
<211> LENGTH: 628
<212> TYPE: PRT
<213> ORGANISM: Rattus norvegicus

<400> SEQUENCE: 48

Met Ala Glu Arg Pro Pro Leu Arg Gly Pro Gly Glu Thr
1               5                   10                  15

Pro Val Glu Gly Pro Gly Gly Ala Gly Gly Pro Gly Arg Gly Arg
            20                  25                  30

Pro Ser Ser Tyr Arg Ala Leu Arg Ser Ala Val Ser Ser Leu Ala Arg
            35                  40                  45

Val Asp Asp Phe Asp Cys Ala Glu Lys Ile Gly Ala Gly Phe Phe Ser
50                  55                  60

Glu Val Tyr Lys Val Arg His Arg Gln Ser Gly Gln Val Met Val Leu
65                  70                  75                  80

Lys Met Asn Lys Leu Pro Ser Asn Arg Ser Asn Thr Leu Arg Glu Val
                85                  90                  95

Gln Leu Met Asn Arg Leu Arg His Pro Asn Ile Leu Arg Phe Met Gly
            100                 105                 110

Val Cys Val His Gln Gly Gln Leu His Ala Leu Thr Glu Tyr Met Asn
        115                 120                 125

Gly Gly Thr Leu Glu Gln Leu Leu Ser Ser Pro Glu Pro Leu Ser Trp
    130                 135                 140

Pro Val Arg Leu His Leu Ala Leu Asp Ile Ala Gln Gly Leu Arg Tyr
145                 150                 155                 160

Leu His Ala Lys Gly Val Phe His Arg Asp Leu Thr Ser Lys Asn Cys
                165                 170                 175

Leu Val Arg Arg Glu Asp Gly Gly Phe Thr Ala Val Val Gly Asp Phe
            180                 185                 190

Gly Leu Ala Glu Lys Ile Pro Val Tyr Arg Glu Gly Ala Arg Lys Glu
        195                 200                 205

Pro Leu Ala Val Val Gly Ser Pro Tyr Trp Met Ala Pro Glu Val Leu
    210                 215                 220

Arg Gly Glu Leu Tyr Asp Glu Lys Ala Asp Val Phe Ala Phe Gly Ile
225                 230                 235                 240

Val Leu Cys Glu Leu Ile Ala Arg Val Pro Ala Asp Pro Asp Tyr Leu
                245                 250                 255

Pro Arg Thr Glu Asp Phe Gly Leu Asp Val Pro Ala Phe Arg Thr Leu
            260                 265                 270

Val Gly Asn Asp Cys Pro Leu Pro Phe Leu Leu Leu Ala Ile His Cys
        275                 280                 285

Cys Ser Met Glu Pro Ser Ala Arg Ala Pro Phe Thr Glu Ile Thr Gln
    290                 295                 300

His Leu Glu Gln Ile Leu Glu Gln Leu Pro Glu Pro Thr Pro Leu Ala
305                 310                 315                 320

Lys Met Pro Leu Ala Lys Ala Pro Leu Thr Tyr Asn Gln Gly Ser Val
                325                 330                 335

Pro Arg Gly Gly Pro Ser Ala Thr Leu Pro Arg Ser Asp Pro Arg Leu
            340                 345                 350

Ser Arg Ser Arg Ser Asp Leu Phe Leu Pro Pro Ser Pro Glu Ser Pro
        355                 360                 365

Pro Ser Trp Gly Asp Asn Leu Thr Arg Val Asn Pro Phe Ser Leu Arg
    370                 375                 380

Glu Asp Leu Arg Gly Gly Lys Ile Lys Leu Leu Asp Thr Pro Cys Lys
385                 390                 395                 400

Pro Ala Thr Pro Leu Pro Val Pro Ser Pro Leu Thr Ser Thr
            405                 410                 415

Gln Leu Pro Leu Val Ala Ser Pro Glu Ser Leu Val Gln Pro Glu Thr
            420                 425                 430

Pro Val Arg Arg Cys Arg Ser Leu Pro Ser Ser Pro Glu Leu Pro Arg
            435                 440                 445

Arg Met Glu Thr Ala Leu Pro Gly Pro Gly Pro Ser Pro Val Gly Pro
        450                 455                 460

Ser Thr Glu Glu Arg Met Asp Cys Glu Gly Ser Ser Pro Glu Pro Glu
465                 470                 475                 480

Pro Pro Gly Pro Ala Pro Gln Leu Pro Leu Ala Val Ala Thr Asp Asn
                485                 490                 495

Phe Ile Ser Thr Cys Ser Ser Ala Ser Gln Pro Trp Ser Ala Arg Pro
                500                 505                 510

Gly Pro Ser Leu Asn Asn Pro Pro Ala Val Val Asn Ser Pro
            515                 520                 525

Gln Gly Trp Ala Arg Glu Pro Trp Asn Arg Ala Gln His Ser Leu Pro
        530                 535                 540

Arg Ala Ala Leu Glu Arg Thr Glu Pro Ser Pro Pro Ser Ala
545                 550                 555                 560

Pro Arg Glu Gln Glu Glu Gly Leu Pro Cys Pro Gly Cys Cys Leu Ser
                565                 570                 575

Pro Phe Ser Phe Gly Phe Leu Ser Met Cys Pro Arg Pro Thr Pro Ala
                580                 585                 590

Val Ala Arg Tyr Arg Asn Leu Asn Cys Glu Ala Gly Ser Leu Leu Cys
        595                 600                 605

His Arg Gly His His Ala Lys Pro Pro Thr Pro Ser Leu Gln Leu Pro
    610                 615                 620

Gly Ala Arg Ser
625

<210> SEQ ID NO 49
<211> LENGTH: 615
<212> TYPE: PRT
<213> ORGANISM: Xenopus laevis

<400> SEQUENCE: 49

Met Arg Leu Met Leu Leu Cys Cys Ser Trp Ser Glu Glu His Met Gly
1               5                   10                  15

Glu Glu Glu Gly Asn Val Leu Pro Leu Cys Ala Ser Cys Gly Gln Ser
            20                  25                  30

Ile Tyr Asp Gly Cys Tyr Leu Gln Ala Leu Ala Leu Asp Trp His Ser
        35                  40                  45

Asp Cys Phe Arg Cys Ser Asp Cys Gly Val Ser Leu Ser His Arg Tyr
    50                  55                  60

Tyr Glu Lys Asp Gly Arg Leu Phe Cys Lys Lys His Tyr Trp Thr Arg
65                  70                  75                  80

Phe Gly Gly Met Cys Gln Gly Cys Ser Glu Asn Ile Thr Lys Gly Leu
                85                  90                  95

Val Met Val Ala Gly Glu His Lys Tyr His Pro Glu Cys Phe Met Cys
            100                 105                 110

Ser Arg Cys Lys Ala Tyr Ile Gly Asp Gly Glu Thr Tyr Ala Leu Val
        115                 120                 125

-continued

```
Glu Arg Ser Lys Leu Tyr Cys Gly Pro Cys Tyr Tyr Gln Phe Ser Val
    130                 135                 140
Thr Pro Val Ile Asp Ser Pro Gly Ser Arg Ser Pro His Thr Val Thr
145                 150                 155                 160
Leu Val Ser Leu Pro Ala Ser Asp Gly Lys Arg Gly Leu Ser Val Ser
                165                 170                 175
Ile Thr Pro Ser Cys Ala Glu His Ser His Thr Val Arg Val Thr Glu
            180                 185                 190
Leu Asp Ala Asp Phe Leu Gly Pro Asp Ile Gln Ser Ser Ile His Ile
        195                 200                 205
Gly Asp Arg Ile Leu Glu Ile Asn Gly Thr Pro Ile Arg Ser Val Pro
    210                 215                 220
Leu Asp Glu Ile Asp Val Leu Ile Gln Glu Thr Ser Arg Leu Leu Gln
225                 230                 235                 240
Leu Thr Ile Glu His Asp Pro His Glu Thr Pro Thr Met Pro Ser Pro
                245                 250                 255
Cys Ala Glu Ile Ala Val Arg Arg Gln Arg Pro Val Met Arg Ser Cys
            260                 265                 270
Ser Ile Asp Arg Ser Pro Gly Ser Ser Cys Val Gly Ser Pro Ser Cys
        275                 280                 285
Ser Arg Arg Asp Met Ser Arg Ser Glu Ser Val Arg Thr Val Thr Gly
    290                 295                 300
Val His Arg Ile Phe Arg Pro Ser Asp Leu Ile Pro Gly Glu Val Leu
305                 310                 315                 320
Gly Arg Gly Cys Phe Gly Gln Ala Ile Lys Val Thr His Arg Val Thr
                325                 330                 335
Gly Glu Val Met Val Met Lys Glu Leu Ile Arg Phe Asp Glu Glu Thr
            340                 345                 350
Gln Arg Thr Phe Leu Lys Glu Val Lys Val Met Arg Cys Leu Glu His
        355                 360                 365
Pro His Val Leu Lys Phe Ile Gly Val Leu Tyr Lys Asp Lys Arg Leu
    370                 375                 380
Asn Phe Ile Thr Glu Tyr Ile Pro Gly Gly Thr Leu Arg Arg Val Ile
385                 390                 395                 400
Lys Ser Met Asp Thr His Cys Pro Trp Asn Gln Arg Val Ser Phe Ala
                405                 410                 415
Arg Asp Ile Ala Ala Gly Met Thr Tyr Leu His Ser Met Asn Ile Ile
            420                 425                 430
His Arg Asp Leu Asn Ser His Asn Cys Leu Val Arg Glu Asp Gly Gly
        435                 440                 445
Leu Val Val Ala Asn Phe Gly Leu Ser Arg Leu Ile Pro Glu Glu Thr
    450                 455                 460
Arg Asp Leu Arg Lys Asp Arg Arg Lys Arg Tyr Thr Val Val Gly Asn
465                 470                 475                 480
Pro Tyr Trp Met Ala Pro Glu Met Ile Asn Gly Arg Ser Tyr Asp Glu
                485                 490                 495
Ser Val Asp Val Phe Ser Phe Gly Ile Val Ile Cys Glu Ile Ile Gly
            500                 505                 510
Leu Val Asn Ala Asp Pro Asp Tyr Leu Pro Arg Thr Met Asp Phe Gly
        515                 520                 525
Leu Asn Val Arg Ala Phe Leu Asp Arg Phe Cys Pro Pro Asn Cys Pro
    530                 535                 540
```

```
Pro Gly Phe Phe Pro Ser Ala Val Leu Cys Cys Asp Leu Asp Pro Glu
545                 550                 555                 560

Lys Arg Pro Arg Phe Ser Gln Leu Gln Leu Trp Leu Asp Ser Leu Leu
                565                 570                 575

Arg His Leu Asn Leu Gln Leu Pro Leu Ser Ser His Ile Glu Gln Leu
            580                 585                 590

Glu Gln Asn Phe Trp Glu Asn Tyr Arg Arg Gly Asp Ser Thr Leu His
        595                 600                 605

Val His Pro Glu Ile Pro Glu
    610             615

<210> SEQ ID NO 50
<211> LENGTH: 653
<212> TYPE: PRT
<213> ORGANISM: Caenorhabditis elegans

<400> SEQUENCE: 50

Met Thr Thr Thr Ser Ser Asp Glu Leu Pro Arg Gln Ala Asp Asp Asp
 1               5                  10                  15

Ser Met Lys Trp Asp Arg Ile Tyr Ile Gln Lys Leu Asp Pro Glu Val
                20                  25                  30

Ile Phe Thr Lys Gln Glu Arg Ile Gly Arg Gly Ser Phe Gly Glu Val
            35                  40                  45

Tyr Lys Gly Ile Asp Asn Arg Thr Gly Arg Val Val Ala Ile Lys Ile
    50                  55                  60

Ile Asp Leu Glu Gln Ala Glu Asp Glu Ile Glu Asp Ile Gln Gln Glu
65                  70                  75                  80

Ile Gln Val Leu Ser Gln Cys Asp Ser Gln Tyr Val Thr Lys Tyr Phe
                85                  90                  95

Gly Ser Phe Leu Lys Gly Ser Lys Leu Trp Ile Ile Met Glu Tyr Leu
            100                 105                 110

Gly Gly Gly Ser Ala Leu Asp Leu Thr Lys Ser Gly Lys Leu Asp Glu
            115                 120                 125

Ser His Ile Ala Val Ile Leu Arg Glu Ile Leu Lys Gly Leu Glu Tyr
        130                 135                 140

Leu His Ser Glu Arg Lys Ile His Arg Asp Ile Lys Ala Ala Asn Val
145                 150                 155                 160

Leu Val Ser Glu His Gly Asp Val Lys Val Ala Asp Phe Gly Val Ala
                165                 170                 175

Gly Gln Leu Thr Glu Thr Val Lys Lys Arg Ile Thr Phe Val Gly Ser
            180                 185                 190

Pro Phe Trp Met Ala Pro Glu Leu Ile Lys Gln Ser Ser Tyr Asp Tyr
            195                 200                 205

Lys Ala Asp Ile Trp Ser Leu Gly Ile Thr Ala Ile Glu Leu Ala Asn
        210                 215                 220

Gly Glu Pro Pro His Ser Asp Leu His Pro Met Arg Val Leu Phe Leu
225                 230                 235                 240

Ile Pro Lys Asn Pro Pro Val Leu Gln Gly Ser Gln Trp Ser Lys
                245                 250                 255

Pro Phe Lys Glu Phe Val Glu Met Cys Leu Asn Lys Asp Pro Glu Asn
            260                 265                 270

Arg Pro Ser Ala Ser Thr Leu Leu Lys His Gln Phe Ile Lys Arg Ala
        275                 280                 285

Lys Lys Asn Ser Ile Leu Val Asp Leu Ile Glu Arg Ala Ala Glu Tyr
        290                 295                 300
```

```
Arg Leu Arg Thr Gly Val Ser Ser Asp Ser Asp Leu Asp Glu Asp Ser
305                 310                 315                 320

Asp Gly Gly Gly Gly Thr Ser Lys Trp Asp Tyr Pro Thr Val Arg Gly
                325                 330                 335

Pro Arg Val Ser Ala Asp Asp Gly Thr Val Arg Gln Arg Thr Asp
            340                 345                 350

Arg Pro Arg Ala Gln Val Asp Arg Arg Ser Pro Ser Gly Ser Pro Gly
        355                 360                 365

Gly Thr Ile Val Arg Gly Ser Pro Gln Val Ala Ala Val Ala Glu Gln
    370                 375                 380

Leu Arg Asn Ser Ser Val Gly Ser Ser Gly Tyr Gly Ser Gly Gly Asn
385                 390                 395                 400

Ser Ala Ser Ser Gln Tyr Ala Thr Ser Ser Leu Pro Gln Ser His Thr
                405                 410                 415

Ala Ser Ser Gly Gly Ala Thr Thr Ile Thr Leu Gly Ser Pro Asn Gly
            420                 425                 430

Ser Pro Thr Ser Ser Leu Ala Arg Thr Gln Ser Met Val Ser Pro Ser
        435                 440                 445

Gly Gln Arg Ser Gly Ser Ala Gln Ser Trp Glu Leu Glu Arg Gly Asn
    450                 455                 460

Arg Pro Met Ser Glu Arg Val Ser Ser Gln Val Ser Pro Ser Lys Tyr
465                 470                 475                 480

Asn Gln His Arg Thr Ser Ser Asn Gly Val Gln Gly Gly Ser Gly
                485                 490                 495

Gly Arg Arg Glu Tyr Ile Asn Gly Ser Gly Ser Gly Leu Asn Gly Asn
            500                 505                 510

Ser Ser Asn Gln Asn His Ser Glu Tyr Ser Asp Ala Val Arg Gln Arg
        515                 520                 525

Gly Pro Gly Gly Ser Gly Gly Arg Leu Asp Tyr Arg Glu Ser His Val
    530                 535                 540

Pro Thr Ser Ser Gln Glu Asn Leu Asn His Gly Arg Met Tyr Gly Tyr
545                 550                 555                 560

Gly Ala Pro Pro Pro Ser Arg Glu Ala Asn Asn Val Pro Met Pro Arg
                565                 570                 575

Val Lys Gly Ala Leu Asp Cys Ser Leu Leu Pro Ala Ile Glu His Leu
            580                 585                 590

Ser Arg Thr Arg His Ala Thr Ala Ala Leu Asp Gln Leu Arg His Val
        595                 600                 605

Phe Arg Asp Val Glu Asp Ser Cys Pro Gly Ile Cys Asn Glu Leu Ile
    610                 615                 620

Glu Glu Leu Met Gln Arg Ile Ala Val Pro Gln Val Ser Gln Ser Asp
625                 630                 635                 640

Leu Asp Ala Ala Ile Arg Arg Leu Thr Thr Pro Pro Ser
                645                 650

<210> SEQ ID NO 51
<211> LENGTH: 478
<212> TYPE: PRT
<213> ORGANISM: Dictyostelium discoideum

<400> SEQUENCE: 51

Met Ala Ser Lys Lys Gly Asp Pro Glu Glu Leu Tyr Val Arg Gln Glu
1               5                   10                  15

Lys Ile Gly Lys Gly Ser Phe Gly Glu Val Phe Lys Gly Ile Asn Lys
            20                  25                  30
```

-continued

```
Lys Thr Asn Glu Thr Ile Ala Ile Lys Thr Ile Asp Leu Glu Asp Ala
         35                  40                  45

Glu Asp Glu Ile Glu Asp Ile Gln Gln Glu Ile Asn Val Leu Ser Gln
 50                  55                  60

Cys Glu Ser Pro Phe Val Thr Lys Tyr Phe Gly Ser Phe Leu Lys Gly
 65                  70                  75                  80

Ser Lys Leu Trp Ile Ile Met Glu Tyr Leu Ala Gly Gly Ser Val Leu
                 85                  90                  95

Asp Leu Met Lys Pro Gly Pro Phe Asp Glu Gly Tyr Ile Ala Ile Ile
             100                 105                 110

Leu Arg Glu Leu Leu Lys Gly Leu Glu Tyr Leu His Ser Glu Gly Lys
         115                 120                 125

Ile His Arg Asp Ile Lys Ala Ala Asn Val Leu Leu Ser Ala Ser Gly
     130                 135                 140

Asp Val Lys Leu Ala Asp Phe Gly Val Ser Gly Gln Leu Thr Asp Gln
145                 150                 155                 160

Met Thr Lys Arg Asn Thr Phe Val Gly Thr Pro Phe Trp Met Ala Pro
                165                 170                 175

Glu Val Ile Lys Gln Thr Gly Tyr Asp Ser Lys Ala Asp Ile Trp Ser
            180                 185                 190

Met Gly Ile Thr Ala Leu Glu Met Ala Lys Gly Glu Pro Pro Arg Ala
        195                 200                 205

Asp Leu His Pro Met Arg Ala Leu Phe Leu Ile Pro Lys Asp Pro Pro
    210                 215                 220

Pro Thr Leu Glu Gly Asn Phe Ser Lys Gly Phe Lys Glu Phe Cys Ala
225                 230                 235                 240

Leu Cys Leu Asn Lys Asp Pro Asn Gln Arg Pro Thr Ala Lys Asp Leu
                245                 250                 255

Leu Lys His Lys Phe Ile Lys Ala Ala Lys Lys Thr Ser Ser Leu Thr
            260                 265                 270

Asp Leu Ile Glu Arg Arg Gln Lys Trp Leu Gln Leu Asn Gly Asn Asn
        275                 280                 285

Ala Asp Asp Glu Asn Asp Asp Leu Asp Arg Asp Ala Lys Ser Asn Glu
    290                 295                 300

Glu Asp Phe Gly Trp Glu Phe Pro Thr Ile Lys Gln Lys Ser Pro Val
305                 310                 315                 320

Ala Val Gln Glu Gln Gln Thr Pro Gln Lys Pro Thr Val Val Ser
                325                 330                 335

Thr Pro Ile Lys Glu Gln Gln Gln Gln Gln Pro Thr Pro Val Thr
            340                 345                 350

Thr Pro Gln Gln Pro Val Thr Thr Thr Thr Thr Pro Thr Thr Glu
        355                 360                 365

Thr Lys Val Arg Ser Leu Ser Asn Ser Ser Thr Thr Pro Val Lys
    370                 375                 380

Thr Thr Val Ala Ala Thr Thr Ala Pro Ala Thr Thr Pro Ala Ser Asn
385                 390                 395                 400

Ala Pro Thr Ser Thr Thr Pro Asn Gly Ala Ala Val Thr Gln Gln Gln
                405                 410                 415

Ala Pro Arg Ala Ser Ala Leu Thr Ser Val Ile Tyr Pro Val Leu Ser
            420                 425                 430

Lys Leu Leu Lys Asn Thr Ser Asp Glu Asn Val Ile Asn Ala Leu Ala
        435                 440                 445
```

```
Gln Leu Lys Met Ala Phe Asp Asn Ala Glu Lys Ala Lys Pro Gly Ile
    450                 455                 460

Thr His Ser Leu Ile Ala Gln Ile Ile Glu Thr Leu Lys Arg
465                 470                 475

<210> SEQ ID NO 52
<211> LENGTH: 426
<212> TYPE: PRT
<213> ORGANISM: Homo sapiens

<400> SEQUENCE: 52

Met Ala His Leu Arg Gly Phe Ala Asn Gln His Ser Arg Val Asp Pro
1               5                   10                  15

Glu Glu Leu Phe Thr Lys Leu Asp Arg Ile Gly Lys Gly Ser Phe Gly
                20                  25                  30

Glu Val Tyr Lys Gly Ile Asp Asn His Thr Lys Glu Val Val Ala Ile
            35                  40                  45

Lys Ile Ile Asp Leu Glu Ala Glu Asp Ile Glu Asp Ile Gln
    50                  55                  60

Gln Glu Ile Thr Val Leu Ser Gln Cys Asp Ser Pro Tyr Ile Thr Arg
65                  70                  75                  80

Tyr Phe Gly Ser Tyr Leu Lys Ser Thr Lys Leu Trp Ile Ile Met Glu
                85                  90                  95

Tyr Leu Gly Gly Gly Ser Ala Leu Asp Leu Leu Lys Pro Gly Pro Leu
            100                 105                 110

Glu Glu Thr Tyr Ile Ala Thr Ile Leu Arg Glu Ile Leu Lys Gly Leu
        115                 120                 125

Asp Tyr Leu His Ser Glu Arg Lys Ile His Arg Asp Ile Lys Ala Ala
    130                 135                 140

Asn Val Leu Leu Ser Glu Gln Gly Asp Val Lys Leu Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
            180                 185                 190

Asp Phe Lys Ala Asp Ile Trp Ser Leu Gly Ile Thr Ala Ile Glu Leu
        195                 200                 205

Ala Lys Gly Glu Pro Pro Asn Ser Asp Leu His Pro Met Arg Val Leu
    210                 215                 220

Phe Leu Ile Pro Lys Asn Ser Pro Pro Thr Leu Glu Gly Gln His Ser
225                 230                 235                 240

Lys Pro Phe Lys Glu Phe Val Glu Ala Cys Leu Asn Lys Asp Pro Arg
                245                 250                 255

Phe Arg Pro Thr Ala Lys Glu Leu Leu Lys His Lys Phe Ile Thr Arg
            260                 265                 270

Tyr Thr Lys Lys Thr Ser Phe Leu Thr Glu Leu Ile Asp Arg Tyr Lys
        275                 280                 285

Arg Trp Lys Ser Glu Gly His Gly Glu Glu Ser Ser Ser Glu Asp Ser
    290                 295                 300

Asp Ile Asp Gly Glu Ala Glu Asp Gly Glu Gln Gly Pro Ile Trp Thr
305                 310                 315                 320

Phe Pro Pro Thr Ile Arg Pro Ser Pro His Ser Lys Leu His Lys Gly
                325                 330                 335

Thr Ala Leu His Ser Ser Gln Lys Pro Ala Asp Ala Val Lys Arg Gln
            340                 345                 350
```

```
Pro Arg Ser Gln Cys Leu Ser Thr Leu Val Arg Pro Val Phe Gly Glu
        355                 360                 365

Leu Lys Glu Lys His Lys Gln Ser Gly Gly Ser Val Gly Ala Leu Glu
        370                 375                 380

Glu Leu Glu Asn Ala Phe Ser Leu Ala Glu Glu Ser Cys Pro Gly Ile
385                 390                 395                 400

Ser Asp Lys Leu Met Val His Leu Val Glu Arg Val Gln Arg Phe Ser
                405                 410                 415

His Asn Arg Asn His Leu Thr Ser Thr Arg
                420                 425

<210> SEQ ID NO 53
<211> LENGTH: 431
<212> TYPE: PRT
<213> ORGANISM: Homo sapiens

<400> SEQUENCE: 53

Met Ala His Ser Pro Val Gln Ser Gly Leu Pro Gly Met Gln Asn Leu
  1               5                  10                  15

Lys Ala Asp Pro Glu Glu Leu Phe Thr Lys Leu Glu Lys Ile Gly Lys
                 20                  25                  30

Gly Ser Phe Gly Glu Val Phe Lys Gly Ile Asp Asn Arg Thr Gln Lys
             35                  40                  45

Val Val Ala Ile Lys Ile Ile Asp Leu Glu Glu Ala Glu Asp Glu Ile
         50                  55                  60

Glu Asp Ile Gln Gln Glu Ile Thr Val Leu Ser Gln Cys Asp Ser Pro
 65                  70                  75                  80

Tyr Val Thr Lys Tyr Tyr Gly Ser Tyr Leu Lys Asp Thr Lys Leu Trp
                 85                  90                  95

Ile Ile Met Glu Tyr Leu Gly Gly Gly Ser Ala Leu Asp Leu Leu Glu
                100                 105                 110

Pro Gly Pro Leu Asp Glu Thr Gln Ile Ala Thr Ile Leu Arg Glu Ile
            115                 120                 125

Leu Lys Gly Leu Asp Tyr Leu His Ser Glu Lys Lys Ile His Arg Asp
        130                 135                 140

Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Arg Gly Glu Pro Pro His Ser Glu Leu His Pro
210                 215                 220

Met Lys Val Leu Phe Leu Ile Pro Lys Asn Asn Pro Pro Thr Leu Glu
225                 230                 235                 240

Gly Asn Tyr Ser Lys Pro Leu Lys Glu Phe Val Glu Ala Cys Leu Asn
                245                 250                 255

Lys Glu Pro Ser Phe Arg Pro Thr Ala Lys Glu Leu Leu Lys His Lys
            260                 265                 270

Phe Ile Leu Arg Asn Ala Lys Lys Thr Ser Tyr Leu Thr Glu Leu Ile
        275                 280                 285

Asp Arg Tyr Lys Arg Trp Lys Ala Glu Gln Ser His Asp Asp Ser Ser
        290                 295                 300
```

```
Ser Glu Asp Ser Asp Ala Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
                325                 330                 335

Leu Glu Asn Gly Ala Leu Gln Pro Ser Asp Leu Asp Arg Asn Lys Met
                340                 345                 350

Lys Asp Ile Pro Lys Arg Pro Phe Ser Gln Cys Leu Ser Thr Ile Ile
                355                 360                 365

Ser Pro Leu Phe Ala Glu Leu Lys Glu Lys Ser Gln Ala Cys Gly Gly
370                 375                 380

Asn Leu Gly Ser Ile Glu Glu Leu Arg Gly Ala Ile Tyr Leu Ala Glu
385                 390                 395                 400

Glu Val Cys Pro Gly Ile Ser Asp Thr Met Val Ala Gln Leu Val Gln
                405                 410                 415

Arg Leu Gln Arg Tyr Ser Leu Ser Gly Gly Thr Ser Ser His
                420                 425                 430

<210> SEQ ID NO 54
<211> LENGTH: 426
<212> TYPE: PRT
<213> ORGANISM: Homo sapiens

<400> SEQUENCE: 54

Met Ala His Leu Arg Gly Phe Ala Asn Gln His Ser Arg Val Asp Pro
1               5                   10                  15

Glu Glu Leu Phe Thr Lys Leu Asp Arg Ile Gly Lys Gly Ser Phe Gly
                20                  25                  30

Glu Val Tyr Lys Gly Ile Asp Asn His Thr Lys Glu Val Val Ala Ile
                35                  40                  45

Lys Ile Ile Asp Leu Glu Glu Ala Glu Asp Glu Ile Glu Asp Ile Gln
            50                  55                  60

Gln Glu Ile Thr Val Leu Ser Gln Cys Asp Ser Pro Tyr Ile Thr Arg
65                  70                  75                  80

Tyr Phe Gly Ser Tyr Leu Lys Ser Thr Lys Leu Trp Ile Ile Met Glu
                85                  90                  95

Tyr Leu Gly Gly Gly Ser Ala Leu Asp Leu Leu Lys Pro Gly Pro Leu
                100                 105                 110

Glu Glu Thr Tyr Ile Ala Thr Ile Leu Arg Glu Ile Leu Lys Gly Leu
                115                 120                 125

Asp Tyr Leu His Ser Glu Arg Lys Ile His Arg Asp Ile Lys Ala Ala
            130                 135                 140

Asn Val Leu Leu Ser Glu Gln Gly Asp Val Lys Leu Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
                180                 185                 190

Asp Phe Lys Ala Asp Ile Trp Ser Leu Gly Ile Thr Ala Ile Glu Leu
            195                 200                 205

Ala Lys Gly Glu Pro Pro Asn Ser Asp Leu His Pro Met Arg Val Leu
            210                 215                 220

Phe Leu Ile Pro Lys Asn Ser Pro Pro Thr Leu Glu Gly Gln His Ser
225                 230                 235                 240

Lys Pro Phe Lys Glu Phe Val Glu Ala Cys Leu Asn Lys Asp Pro Arg
                245                 250                 255
```

Phe Arg Pro Thr Ala Lys Glu Leu Leu Lys His Lys Phe Ile Thr Arg
            260                 265                 270

Tyr Thr Lys Lys Thr Ser Phe Leu Thr Glu Leu Ile Asp Arg Tyr Lys
        275                 280                 285

Arg Trp Lys Ser Glu Gly His Gly Glu Glu Ser Ser Glu Asp Ser
    290                 295                 300

Asp Ile Asp Gly Glu Ala Glu Asp Gly Glu Gln Gly Pro Ile Trp Thr
305                 310                 315                 320

Phe Pro Pro Thr Ile Arg Pro Ser Pro His Ser Lys Leu His Lys Gly
                325                 330                 335

Thr Ala Leu His Ser Ser Gln Lys Pro Ala Glu Pro Val Lys Arg Gln
            340                 345                 350

Pro Arg Ser Gln Cys Leu Ser Thr Leu Val Arg Pro Val Phe Gly Glu
        355                 360                 365

Leu Lys Glu Lys His Lys Gln Ser Gly Gly Ser Val Gly Ala Leu Glu
    370                 375                 380

Glu Leu Glu Asn Ala Phe Ser Leu Ala Glu Glu Ser Cys Pro Gly Ile
385                 390                 395                 400

Ser Asp Lys Leu Met Val His Leu Val Glu Arg Val Gln Arg Phe Ser
                405                 410                 415

His Asn Arg Asn His Leu Thr Ser Thr Arg
            420                 425

<210> SEQ ID NO 55
<211> LENGTH: 426
<212> TYPE: PRT
<213> ORGANISM: Mus musculus

<400> SEQUENCE: 55

Met Ala His Leu Arg Gly Phe Ala His Gln His Ser Arg Val Asp Pro
 1               5                  10                  15

Glu Glu Leu Phe Thr Lys Leu Asp Arg Ile Gly Lys Gly Ser Phe Gly
             20                  25                  30

Glu Val Tyr Lys Gly Ile Asp Asn His Thr Lys Glu Val Val Ala Ile
         35                  40                  45

Lys Ile Ile Asp Leu Glu Glu Ala Glu Asp Glu Ile Glu Asp Ile Gln
 50                  55                  60

Gln Glu Ile Thr Val Leu Ser Gln Cys Asp Ser Pro Tyr Ile Thr Arg
 65                  70                  75                  80

Tyr Phe Gly Ser Tyr Leu Lys Ser Thr Lys Leu Trp Ile Ile Met Glu
                 85                  90                  95

Tyr Leu Gly Gly Gly Ser Ala Leu Asp Leu Leu Lys Pro Gly Pro Leu
            100                 105                 110

Glu Glu Thr Tyr Ile Ala Thr Ile Leu Arg Glu Ile Leu Lys Gly Leu
        115                 120                 125

Asp Tyr Leu His Ser Glu Arg Lys Ile His Arg Asp Ile Lys Ala Ala
    130                 135                 140

Asn Val Leu Leu Ser Glu Gln Gly Asp Val Lys Met Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
            180                 185                 190

Asp Phe Lys Ala Asp Ile Trp Ser Leu Gly Ile Thr Ala Ile Glu Leu
        195                 200                 205

-continued

```
Ala Lys Gly Glu Pro Pro Asn Ser Asp Leu His Pro Met Arg Val Leu
    210                 215                 220
Phe Leu Ile Pro Lys Asn Asn Pro Pro Thr Leu Glu Gly His His Ser
225                 230                 235                 240
Lys Pro Phe Lys Glu Phe Val Glu Ala Cys Leu Asn Lys Asp Pro Arg
                245                 250                 255
Phe Arg Pro Thr Ala Lys Glu Leu Leu Lys His Lys Phe Ile Thr Arg
            260                 265                 270
Tyr Thr Lys Lys Thr Ser Phe Leu Thr Glu Leu Ile Asp Arg Tyr Lys
        275                 280                 285
Arg Trp Lys Ser Glu Gly His Gly Glu Glu Ser Ser Ser Glu Asp Ser
    290                 295                 300
Asp Ile Asp Gly Glu Ala Glu Asp Gly Glu Gln Gly Pro Ile Trp Thr
305                 310                 315                 320
Phe Pro Pro Thr Ile Arg Pro Ser Pro His Ser Lys Leu His Lys Gly
                325                 330                 335
Thr Ala Leu His Ser Ser Gln Lys Pro Ala Glu Pro Ile Lys Arg Gln
            340                 345                 350
Pro Arg Ser Gln Cys Leu Ser Thr Leu Val Arg Pro Val Phe Gly Glu
        355                 360                 365
Leu Lys Glu Lys His Lys Gln Ser Gly Gly Ser Val Gly Ala Leu Glu
    370                 375                 380
Glu Leu Glu Asn Ala Phe Ser Leu Ala Glu Gly Ser Cys Pro Gly Ile
385                 390                 395                 400
Ser Asp Lys Leu Met Val His Leu Val Glu Arg Val Gln Arg Phe Ser
                405                 410                 415
His Ser Arg Asn His Leu Thr Ser Thr Arg
            420                 425

<210> SEQ ID NO 56
<211> LENGTH: 21
<212> TYPE: DNA
<213> ORGANISM: Artificial Sequence
<220> FEATURE:
<223> OTHER INFORMATION: Oligonucleotide Primer for h12832

<400> SEQUENCE: 56
ttttcacctc cgacctttcc t                                             21

<210> SEQ ID NO 57
<211> LENGTH: 21
<212> TYPE: DNA
<213> ORGANISM: Artificial Sequence
<220> FEATURE:
<223> OTHER INFORMATION: Oligonucleotide Primer for h12832

<400> SEQUENCE: 57
atcccttcca ttgtgaaagc c                                             21

<210> SEQ ID NO 58
<211> LENGTH: 25
<212> TYPE: DNA
<213> ORGANISM: Artificial Sequence
<220> FEATURE:
<223> OTHER INFORMATION: Oligonucleotide Primer for h12832

<400> SEQUENCE: 58
ccaggcggtg agactctgga ctgag                                         25
```

```
<210> SEQ ID NO 59
<211> LENGTH: 26
<212> TYPE: DNA
<213> ORGANISM: Artificial Sequence
<220> FEATURE:
<223> OTHER INFORMATION: Oligonucleotide Primer for h14138

<400> SEQUENCE: 59
cacgaggcta gactaaaagg aaaatt                                              26

<210> SEQ ID NO 60
<211> LENGTH: 22
<212> TYPE: DNA
<213> ORGANISM: Artificial Sequence
<220> FEATURE:
<223> OTHER INFORMATION: Oligonucleotide Primer for h14138

<400> SEQUENCE: 60
tgaagccagg aatactgctc ag                                                  22

<210> SEQ ID NO 61
<211> LENGTH: 34
<212> TYPE: DNA
<213> ORGANISM: Artificial Sequence
<220> FEATURE:
<223> OTHER INFORMATION: Oligonucleotide Primer for h14138

<400> SEQUENCE: 61
ttgtgctaca gactaaatcc agatacggtc aggt                                     34

<210> SEQ ID NO 62
<211> LENGTH: 18
<212> TYPE: DNA
<213> ORGANISM: Artificial Sequence
<220> FEATURE:
<223> OTHER INFORMATION: Oligonucleotide Primer for h14833

<400> SEQUENCE: 62
cctgcctccc actcatcg                                                       18

<210> SEQ ID NO 63
<211> LENGTH: 23
<212> TYPE: DNA
<213> ORGANISM: Artificial Sequence
<220> FEATURE:
<223> OTHER INFORMATION: Oligonucleotide Primer for h14833

<400> SEQUENCE: 63
cagctggttc tgtagaggac gaa                                                 23

<210> SEQ ID NO 64
<211> LENGTH: 27
<212> TYPE: DNA
<213> ORGANISM: Artificial Sequence
<220> FEATURE:
<223> OTHER INFORMATION: Oligonucleotide Primer for h14833

<400> SEQUENCE: 64
atgctctgac tgctcactgc ctggatc                                             27

<210> SEQ ID NO 65
<211> LENGTH: 16
<212> TYPE: DNA
<213> ORGANISM: Artificial Sequence
<220> FEATURE:
<223> OTHER INFORMATION: Oligonucleotide Primer for h15990
```

-continued

```
<400> SEQUENCE: 65
ggcaaaggcg ggttcg                                                   16

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide Primer for h15990

<400> SEQUENCE: 66
ttgaccgcca catcgtagc                                                19

<210> SEQ ID NO 67
<211> LENGTH: 22
<212> TYPE: DNA
<213> ORGANISM: Artificial Sequence
<220> FEATURE:
<223> OTHER INFORMATION: Oligonucleotide Primer for h15990

<400> SEQUENCE: 67
ccgggcgcaa cataggaagt gg                                            22

<210> SEQ ID NO 68
<211> LENGTH: 26
<212> TYPE: DNA
<213> ORGANISM: Artificial Sequence
<220> FEATURE:
<223> OTHER INFORMATION: Oligonucleotide Primer for h16341

<400> SEQUENCE: 68
cagttgctag acagtaacct gcattt                                        26

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide Primer for h16341

<400> SEQUENCE: 69
tgaggcccac tgctatgtca                                               20

<210> SEQ ID NO 70
<211> LENGTH: 27
<212> TYPE: DNA
<213> ORGANISM: Artificial Sequence
<220> FEATURE:
<223> OTHER INFORMATION: Oligonucleotide Primer for h16341

<400> SEQUENCE: 70
ccttggactg tgagggtaaa actggcc                                       27

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide Primer for h2252

<400> SEQUENCE: 71
tctgattccg agggctctga                                               20
```

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide Primer for h2252

<400> SEQUENCE: 72
acggtggtaa agtctcattc a                                              21

<210> SEQ ID NO 73
<211> LENGTH: 33
<212> TYPE: DNA
<213> ORGANISM: Artificial Sequence
<220> FEATURE:
<223> OTHER INFORMATION: Oligonucleotide Primer for h2252

<400> SEQUENCE: 73
cggaatctac cagcagggaa aacaatactc atc                                 33

<210> SEQ ID NO 74
<211> LENGTH: 21
<212> TYPE: DNA
<213> ORGANISM: Artificial Sequence
<220> FEATURE:
<223> OTHER INFORMATION: Oligonucleotide Primer for b-2 microglobulin

<400> SEQUENCE: 74
cacccccact gaaaaagatg a                                              21

<210> SEQ ID NO 75
<211> LENGTH: 26
<212> TYPE: DNA
<213> ORGANISM: Artificial Sequence
<220> FEATURE:
<223> OTHER INFORMATION: Oligonucleotide Primer for b-2 microglobulin

<400> SEQUENCE: 75
cttaactatc ttgggctgtg acaaag                                         26

<210> SEQ ID NO 76
<211> LENGTH: 23
<212> TYPE: DNA
<213> ORGANISM: Artificial Sequence
<220> FEATURE:
<223> OTHER INFORMATION: Oligonucleotide Primer for b-2 microglobulin

<400> SEQUENCE: 76
atgcctgccg tgtgaaccac gtg                                            23

<210> SEQ ID NO 77
<211> LENGTH: 256
<212> TYPE: PRT
<213> ORGANISM: Dictyostelium discoideum

<400> SEQUENCE: 77

Gln Gln Ser Gln Gln Gln Ser Gln Gln Gln Gln Gln Thr Thr Pro Pro
 1               5                  10                  15

Leu Pro Pro His Asn Ile His Arg Lys Leu Ser Cys Val Gly Thr Pro
            20                  25                  30

Asp Tyr Leu Ala Pro Glu Ile Leu Leu Gly Ile Gly His Gly Ala Ser
        35                  40                  45

Ala Asp Trp Phe Ser Leu Gly Val Ile Leu Tyr Glu Phe Leu Cys Gly
    50                  55                  60

```
Val Ser Pro Phe Asn Gly Ser Ser Val Gln Glu Thr Phe Gln Asn Ile
 65                  70                  75                  80

Leu Gln Arg Asn Ile Ser Trp Pro Glu Asp Met Ser Pro Glu Ala Arg
                 85                  90                  95

Asp Leu Ile Asp Lys Leu Leu Ala Leu Asp Pro Arg Gln Arg Leu Gly
            100                 105                 110

Phe Asn Gly Ala Glu Glu Ile Lys Ser His Pro Phe Phe Lys Ser Ile
        115                 120                 125

Asn Trp Lys Thr Ile Leu Thr Gln Glu Pro Tyr Phe Lys Pro Lys Ile
    130                 135                 140

Glu Asn Leu Gln Asp Thr Ser Tyr Phe Asp Pro Arg Lys Glu Ile Tyr
145                 150                 155                 160

Lys Val Ser Asp Asp Phe Ala Glu Ser Cys Lys Pro Phe Val Gln Asn
                165                 170                 175

Gln Asn Gln Asn Lys Glu Ser Ser Thr Ile Leu Thr Thr Ser Pro Pro
            180                 185                 190

Ser Thr Ser Ser Thr Thr Ala Thr Ala Thr Ala Thr Thr Ser Asn Leu
        195                 200                 205

Asp Ser Ile Thr Ile Asn Gln Asn Thr Asn Ala Asn Phe Asp Asp Phe
    210                 215                 220

Leu Tyr Val Asn Phe Gln Ser Leu Leu Glu Leu Asn Lys Asn Tyr Leu
225                 230                 235                 240

Ala Glu Ala Lys Pro Phe Asn Ser Asn His Arg Arg Arg Asn Ser Thr
                245                 250                 255

<210> SEQ ID NO 78
<211> LENGTH: 1237
<212> TYPE: PRT
<213> ORGANISM: Homo sapiens

<400> SEQUENCE: 78

Gly Arg Ser Ser Lys Ala Lys Lys Pro Pro Gly Glu Asn Asp Phe Asp
  1               5                  10                  15

Thr Ile Lys Leu Ile Ser Asn Gly Ala Tyr Gly Ala Val Tyr Leu Val
             20                  25                  30

Arg His Arg Asp Thr Arg Gln Arg Phe Ala Met Lys Lys Ile Asn Lys
         35                  40                  45

Gln Asn Leu Ile Leu Arg Asn Gln Ile Gln Gln Ala Phe Val Glu Arg
     50                  55                  60

Asp Ile Leu Thr Phe Ala Glu Asn Pro Phe Val Val Gly Met Phe Cys
 65                  70                  75                  80

Ser Phe Glu Thr Arg Arg His Leu Cys Met Val Met Glu Tyr Val Glu
                 85                  90                  95

Gly Gly Asp Cys Ala Thr Leu Leu Lys Asn Ile Gly Ala Leu Pro Val
            100                 105                 110

Glu Met Ala Arg Met Tyr Phe Ala Glu Thr Val Leu Ala Leu Glu Tyr
        115                 120                 125

Leu His Asn Tyr Gly Ile Val His Arg Asp Leu Lys Pro Asp Asn Leu
    130                 135                 140

Leu Ile Thr Ser Met Gly His Ile Lys Leu Thr Asp Phe Gly Leu Ser
145                 150                 155                 160

Lys Met Gly Leu Met Ser Leu Thr Thr Asn Leu Tyr Glu Gly His Ile
                165                 170                 175

Glu Lys Asp Ala Arg Glu Phe Leu Asp Lys Gln Val Cys Gly Thr Pro
            180                 185                 190
```

```
Glu Tyr Ile Ala Pro Glu Val Ile Leu Arg Gln Gly Tyr Gly Lys Pro
        195                 200                 205

Val Asp Trp Trp Ala Met Gly Ile Ile Leu Tyr Glu Phe Leu Val Gly
    210                 215                 220

Cys Val Pro Phe Phe Gly Asp Thr Pro Glu Glu Leu Phe Gly Gln Val
225                 230                 235                 240

Ile Ser Asp Asp Ile Leu Trp Pro Glu Gly Asp Glu Ala Leu Pro Thr
                245                 250                 255

Glu Ala Gln Leu Leu Ile Ser Ser Leu Leu Gln Thr Asn Pro Leu Val
            260                 265                 270

Arg Leu Gly Ala Gly Ala Phe Glu Val Lys Gln His Ser Phe Phe
        275                 280                 285

Arg Asp Leu Asp Trp Thr Gly Leu Leu Arg Gln Lys Ala Glu Phe Ile
        290                 295                 300

Pro His Leu Glu Ser Glu Asp Thr Ser Tyr Phe Asp Thr Arg Ser
305                 310                 315                 320

Asp Arg Tyr His His Val Asn Ser Tyr Asp Glu Asp Thr Thr Glu
                325                 330                 335

Glu Glu Pro Val Glu Ile Arg Gln Phe Ser Ser Cys Ser Pro Arg Phe
            340                 345                 350

Ser Lys Val Tyr Ser Ser Met Glu Gln Leu Ser Gln His Glu Pro Lys
        355                 360                 365

Thr Pro Val Ala Ala Gly Ser Ser Lys Arg Glu Pro Ser Thr Lys
    370                 375                 380

Gly Pro Glu Glu Lys Val Ala Gly Lys Arg Glu Gly Leu Gly Gly Leu
385                 390                 395                 400

Thr Leu Arg Glu Lys Thr Trp Arg Gly Gly Ser Pro Glu Ile Lys Arg
                405                 410                 415

Phe Ser Ala Ser Glu Ala Ser Phe Leu Glu Gly Glu Ala Ser Pro Pro
            420                 425                 430

Leu Gly Ala Arg Arg Arg Phe Ser Ala Leu Leu Glu Pro Ser Arg Phe
        435                 440                 445

Ser Ala Pro Gln Glu Asp Glu Asp Glu Ala Arg Leu Arg Arg Pro Pro
    450                 455                 460

Arg Pro Ser Ser Asp Pro Ala Gly Ser Leu Asp Ala Arg Ala Pro Lys
465                 470                 475                 480

Glu Glu Thr Gln Gly Gly Thr Ser Ser Ala Gly Asp Ser Glu Ala
                485                 490                 495

Ser Pro Arg Ala Thr Asn Asp Leu Val Leu Arg Arg Ala Arg His Gln
            500                 505                 510

Gln Met Ser Gly Asp Val Ala Val Glu Lys Arg Pro Ser Arg Thr Gly
        515                 520                 525

Gly Lys Val Ile Lys Ser Ala Ser Ala Thr Ala Leu Ser Ala Gly Pro
    530                 535                 540

Met Arg Gly Cys Ser Ala Thr Ala Leu Gly Gly Arg Ser Arg Tyr
545                 550                 555                 560

Arg Glu Met Ser Ile Phe Leu Val Leu Ile Ser Asp His Gly Cys Val
                565                 570                 575

Ser Val Val Asp Pro His Gly Ser Ser Pro Leu Ala Ser Pro Met Ser
            580                 585                 590

Pro Arg Ser Leu Ser Ser Asn Pro Ser Ser Arg Asp Ser Ser Pro Ser
        595                 600                 605
```

```
Arg Asp Tyr Ser Pro Ala Val Ser Gly Leu Arg Ser Pro Ile Thr Ile
    610                 615                 620

Gln Arg Ser Gly Lys Lys Tyr Gly Phe Thr Leu Arg Ala Ile Arg Val
625                 630                 635                 640

Tyr Met Gly Asp Thr Asp Val Tyr Ser Val His His Ile Val Trp His
            645                 650                 655

Val Glu Glu Gly Gly Pro Ala Gln Glu Ala Gly Leu Cys Ala Gly Asp
                660                 665                 670

Leu Ile Thr His Val Asn Gly Glu Pro Val His Gly Met Val His Pro
            675                 680                 685

Glu Val Val Glu Leu Ile Leu Lys Ser Gly Asn Lys Val Ala Val Thr
690                 695                 700

Thr Thr Pro Phe Glu Asn Thr Ser Ile Arg Ile Gly Pro Ala Arg Arg
705                 710                 715                 720

Ser Ser Tyr Lys Ala Lys Met Ala Arg Arg Asn Lys Arg Pro Ser Ala
                725                 730                 735

Lys Glu Gly Gln Glu Ser Lys Lys Arg Ser Ser Leu Phe Arg Lys Ile
            740                 745                 750

Thr Lys Gln Ser Asn Leu Leu His Thr Ser Arg Ser Leu Ser Ser Leu
            755                 760                 765

Asn Arg Ser Leu Ser Ser Asp Ser Leu Pro Gly Ser Pro Thr His
770                 775                 780

Gly Leu Pro Ala Arg Ser Pro Thr His Ser Tyr Arg Ser Thr Pro Asp
785                 790                 795                 800

Ser Ala Tyr Leu Gly Ile Thr Ser Cys Thr Cys Ala Gly Thr Glu Gln
                805                 810                 815

Arg Gly Val Ala Trp Leu Ser Ser Pro Ala Ser Ser Thr Pro Asn
            820                 825                 830

Ser Pro Ala Ser Ser Ala Ser His His Ile Arg Pro Ser Thr Leu His
835                 840                 845

Gly Leu Ser Pro Lys Leu His Arg Gln Tyr Arg Ser Ala Arg Cys Lys
850                 855                 860

Ser Ala Gly Asn Ile Pro Leu Ser Pro Leu Ala His Thr Pro Ser Pro
865                 870                 875                 880

Thr Gln Ala Ser Pro Pro Leu Pro Gly His Thr Val Gly Ser Ser
            885                 890                 895

His Thr Thr Gln Ser Phe Pro Ala Lys Leu His Ser Ser Pro Pro Val
            900                 905                 910

Val Arg Pro Arg Pro Lys Ser Ala Glu Pro Pro Arg Ser Pro Leu Leu
            915                 920                 925

Lys Arg Val Gln Ser Ala Glu Lys Leu Gly Ala Ser Leu Ser Ala Asp
930                 935                 940

Lys Lys Gly Ala Leu Arg Lys His Ser Leu Glu Val Gly His Pro Asp
945                 950                 955                 960

Phe Arg Lys Asp Phe His Gly Glu Leu Ala Leu His Ser Leu Ala Glu
                965                 970                 975

Ser Asp Gly Glu Thr Pro Pro Val Glu Gly Leu Gly Ala Pro Arg Gln
            980                 985                 990

Val Ala Val Arg Arg Leu Gly Arg Gln Glu Ser Pro Leu Ser Leu Gly
            995                 1000                1005

Ala Asp Pro Leu Leu Pro Glu Gly Ala Ser Arg Pro Pro Val Ser Ser
    1010                1015                1020
```

```
Lys Glu Lys Glu Ser Pro Gly Ala Glu Ala Cys Thr Pro Pro Arg
    1025                1030                1035                1040

Ala Thr Thr Pro Gly Gly Arg Thr Leu Glu Arg Asp Val Gly Cys Thr
                1045                1050                1055

Arg His Gln Ser Val Gln Thr Glu Asp Gly Thr Gly Gly Met Ala Arg
            1060                1065                1070

Ala Val Ala Lys Ala Ala Leu Ser Pro Val Gln Glu His Glu Thr Gly
        1075                1080                1085

Arg Arg Ser Ser Ser Gly Glu Ala Gly Thr Pro Leu Val Pro Ile Val
    1090                1095                1100

Val Glu Pro Ala Arg Pro Gly Ala Lys Ala Val Val Pro Gln Pro Leu
1105                1110                1115                1120

Gly Ala Asp Ser Lys Gly Leu Gln Glu Pro Ala Pro Leu Ala Pro Ser
                1125                1130                1135

Val Pro Glu Ala Pro Arg Gly Arg Glu Arg Trp Val Leu Glu Val Val
            1140                1145                1150

Glu Glu Arg Thr Thr Leu Ser Gly Pro Arg Ser Lys Pro Ala Ser Pro
        1155                1160                1165

Lys Leu Ser Pro Glu Pro Gln Thr Pro Ser Leu Ala Pro Ala Lys Cys
    1170                1175                1180

Ser Ala Pro Ser Ser Ala Val Thr Pro Val Pro Pro Ala Ser Leu Leu
1185                1190                1195                1200

Gly Ser Gly Thr Lys Pro Gln Val Gly Leu Thr Ser Arg Cys Pro Ala
                1205                1210                1215

Glu Ala Val Pro Pro Ala Gly Leu Thr Lys Lys Gly Val Ser Ser Pro
            1220                1225                1230

Ala Pro Pro Gly Pro
        1235

<210> SEQ ID NO 79
<211> LENGTH: 1308
<212> TYPE: PRT
<213> ORGANISM: Homo sapiens

<400> SEQUENCE: 79

Asp Glu Ser Ser Leu Leu Arg Arg Gly Leu Gln Lys Glu Leu Ser
1               5                   10                  15

Leu Pro Arg Arg Gly Arg Gly Cys Arg Ser Gly Asn Arg Lys Ser Leu
            20                  25                  30

Val Val Gly Thr Pro Ser Pro Thr Leu Ser Arg Pro Leu Ser Pro Leu
        35                  40                  45

Ser Val Pro Thr Ala Gly Ser Ser Pro Leu Asp Ser Pro Arg Asn Phe
    50                  55                  60

Ser Ala Ala Ser Ala Leu Asn Phe Pro Phe Ala Arg Arg Ala Asp Gly
65                  70                  75                  80

Arg Arg Trp Ser Leu Ala Ser Leu Pro Ser Ser Gly Tyr Gly Thr Asn
                85                  90                  95

Thr Pro Ser Ser Thr Leu Ser Ser Ser Ser Ser Arg Glu Arg Leu
            100                 105                 110

His Gln Leu Pro Phe Gln Pro Thr Pro Asp Glu Leu His Phe Leu Ser
        115                 120                 125

Lys His Phe Arg Ser Ser Glu Asn Val Leu Asp Glu Glu Gly Gly Arg
    130                 135                 140

Ser Pro Arg Leu Arg Pro Arg Ser Arg Ser Leu Ser Pro Gly Arg Ala
145                 150                 155                 160
```

```
Thr Gly Thr Phe Asp Asn Glu Ile Val Met Met Asn His Val Tyr Arg
                165                 170                 175
Glu Arg Phe Pro Lys Ala Thr Ala Gln Met Glu Gly Arg Leu Gln Glu
            180                 185                 190
Phe Leu Thr Ala Tyr Ala Pro Gly Ala Arg Leu Ala Leu Ala Asp Gly
        195                 200                 205
Val Leu Gly Phe Ile His His Gln Ile Val Glu Leu Ala Arg Asp Cys
    210                 215                 220
Leu Ala Lys Ser Gly Glu Asn Leu Val Thr Ser Arg Tyr Phe Leu Glu
225                 230                 235                 240
Met Gln Glu Lys Leu Glu Arg Leu Leu Gln Asp Ala His Glu Arg Ser
                245                 250                 255
Asp Ser Glu Glu Val Ser Phe Ile Val Gln Leu Val Arg Lys Leu Leu
            260                 265                 270
Ile Ile Ile Ser Arg Pro Ala Arg Leu Leu Glu Cys Leu Glu Phe Asp
        275                 280                 285
Pro Glu Glu Phe Tyr His Leu Leu Glu Ala Ala Glu Gly His Ala Arg
    290                 295                 300
Glu Gly Gln Gly Ile Lys Thr Asp Leu Pro Gln Tyr Ile Ile Gly Gln
305                 310                 315                 320
Leu Gly Leu Ala Lys Asp Pro Leu Glu Glu Met Val Pro Leu Ser His
                325                 330                 335
Leu Glu Glu Gln Pro Pro Ala Pro Glu Ser Pro Glu Ser Arg Ala
            340                 345                 350
Leu Val Gly Gln Ser Arg Arg Lys Pro Cys Glu Ser Asp Phe Glu Thr
        355                 360                 365
Ile Lys Leu Ile Ser Asn Gly Ala Tyr Gly Ala Val Tyr Leu Val Arg
    370                 375                 380
His Arg Asp Thr Arg Gln Arg Phe Ala Ile Lys Lys Ile Asn Lys Gln
385                 390                 395                 400
Asn Leu Ile Leu Arg Asn Gln Ile Gln Gln Val Phe Val Glu Arg Asp
                405                 410                 415
Ile Leu Thr Phe Ala Glu Asn Pro Phe Val Val Ser Met Phe Cys Ser
            420                 425                 430
Phe Glu Thr Arg Arg His Leu Cys Met Val Met Glu Tyr Val Glu Gly
        435                 440                 445
Gly Asp Cys Ala Thr Leu Leu Lys Asn Met Gly Pro Leu Pro Val Asp
    450                 455                 460
Met Ala Arg Leu Tyr Phe Ala Glu Thr Val Leu Ala Leu Glu Tyr Leu
465                 470                 475                 480
His Asn Tyr Gly Ile Val His Arg Asp Leu Lys Pro Asp Asn Leu Leu
                485                 490                 495
Ile Thr Ser Leu Gly His Ile Lys Leu Thr Asp Phe Gly Leu Ser Lys
            500                 505                 510
Ile Gly Leu Met Ser Met Ala Thr Asn Leu Tyr Glu Gly His Ile Glu
        515                 520                 525
Lys Asp Ala Arg Glu Phe Ile Asp Lys Gln Val Cys Gly Thr Pro Glu
    530                 535                 540
Tyr Ile Ala Pro Glu Val Ile Phe Arg Gln Gly Tyr Gly Lys Pro Val
545                 550                 555                 560
Asp Trp Trp Ala Met Gly Val Val Leu Tyr Glu Phe Leu Val Gly Cys
                565                 570                 575
```

```
Val Pro Phe Phe Gly Asp Thr Pro Glu Glu Leu Phe Gly Gln Val Val
            580                 585                 590

Ser Asp Glu Ile Met Trp Pro Glu Gly Asp Glu Ala Leu Pro Ala Asp
    595                 600                 605

Ala Gln Asp Leu Ile Thr Arg Leu Leu Arg Gln Ser Pro Leu Asp Arg
    610                 615                 620

Leu Gly Thr Gly Gly Thr His Glu Val Lys Gln His Pro Phe Phe Leu
625                 630                 635                 640

Ala Leu Asp Trp Ala Gly Leu Leu Arg His Lys Ala Glu Phe Val Pro
                645                 650                 655

Gln Leu Glu Ala Glu Asp Asp Thr Ser Tyr Phe Asp Thr Arg Ser Glu
            660                 665                 670

Arg Tyr Arg His Leu Gly Ser Glu Asp Asp Glu Thr Asn Asp Glu Glu
        675                 680                 685

Ser Ser Thr Glu Ile Pro Gln Phe Ser Ser Cys Ser His Arg Phe Ser
    690                 695                 700

Lys Val Tyr Ser Ser Ser Glu Phe Leu Ala Val Gln Pro Thr Pro Thr
705                 710                 715                 720

Phe Ala Glu Arg Ser Phe Ser Glu Asp Arg Glu Glu Gly Trp Glu Arg
                725                 730                 735

Ser Glu Val Asp Tyr Gly Arg Arg Leu Ser Ala Asp Ile Arg Leu Arg
            740                 745                 750

Ser Trp Thr Ser Ser Gly Ser Ser Cys Gln Ser Ser Ser Ser Gln Pro
        755                 760                 765

Glu Arg Gly Pro Ser Pro Ser Leu Leu Asn Thr Ile Ser Leu Asp Thr
    770                 775                 780

Met Pro Lys Phe Ala Phe Ser Ser Glu Asp Glu Gly Val Gly Pro Gly
785                 790                 795                 800

Pro Ala Gly Pro Lys Arg Pro Val Phe Ile Leu Gly Glu Pro Asp Pro
                805                 810                 815

Pro Pro Ala Ala Thr Pro Val Met Pro Lys Pro Ser Ser Leu Ser Ala
            820                 825                 830

Asp Thr Ala Ala Leu Ser His Ala Arg Leu Arg Ser Asn Ser Ile Gly
        835                 840                 845

Ala Arg His Ser Thr Pro Arg Pro Leu Asp Ala Gly Arg Gly Arg Arg
    850                 855                 860

Leu Gly Gly Pro Arg Asp Pro Ala Pro Glu Lys Ser Arg Ala Ser Ser
865                 870                 875                 880

Ser Gly Gly Ser Gly Gly Gly Ser Gly Gly Arg Val Pro Lys Ser Ala
                885                 890                 895

Ser Val Ser Ala Leu Ser Leu Ile Ile Thr Ala Asp Asp Gly Ser Gly
            900                 905                 910

Gly Pro Leu Met Ser Pro Leu Ser Pro Arg Ser Leu Ser Ser Asn Pro
        915                 920                 925

Ser Ser Arg Asp Ser Ser Pro Ser Arg Asp Pro Ser Pro Val Cys Gly
    930                 935                 940

Ser Leu Arg Pro Pro Ile Val Ile His Ser Ser Gly Lys Lys Tyr Gly
945                 950                 955                 960

Phe Ser Leu Arg Ala Ile Arg Val Tyr Met Gly Asp Ser Asp Val Tyr
                965                 970                 975

Thr Val His His Val Val Trp Ser Val Glu Asp Gly Ser Pro Ala Gln
            980                 985                 990
```

-continued

```
Glu Ala Gly Leu Arg Ala Gly Asp Leu Ile Thr His Ile Asn Gly Glu
        995                1000                1005

Ser Val Leu Gly Leu Val His Met Asp Val Val Glu Leu Leu Leu Lys
    1010                1015                1020

Ser Gly Asn Lys Ile Ser Leu Arg Thr Thr Ala Leu Glu Asn Thr Ser
1025                1030                1035                1040

Ile Lys Val Gly Pro Ala Arg Lys Asn Val Ala Lys Gly Arg Met Ala
                1045                1050                1055

Arg Arg Ser Lys Arg Ser Arg Arg Glu Thr Gln Asp Arg Arg Lys
            1060                1065                1070

Ser Leu Phe Lys Lys Ile Ser Lys Gln Thr Ser Val Leu His Thr Ser
        1075                1080                1085

Arg Ser Phe Ser Ser Gly Leu His His Ser Leu Ser Ser Ser Glu Ser
    1090                1095                1100

Leu Pro Gly Ser Pro Thr His Ser Leu Ser Pro Ser Pro Thr Thr Pro
1105                1110                1115                1120

Cys Arg Ser Pro Ala Pro Asp Val Pro Ala Asp Thr Thr Ala Ser Pro
                1125                1130                1135

Pro Ser Ala Ser Pro Ser Ser Ser Pro Ala Ser Pro Ala Ala Ala
            1140                1145                1150

Gly His Thr Arg Pro Ser Ser Leu His Gly Leu Ala Ala Lys Leu Gly
        1155                1160                1165

Pro Pro Arg Pro Lys Thr Gly Arg Arg Lys Ser Thr Ser Ser Ile Pro
    1170                1175                1180

Pro Ser Pro Leu Ala Cys Pro Pro Ile Ser Ala Pro Pro Arg Ser
1185                1190                1195                1200

Pro Ser Pro Leu Pro Gly His Pro Pro Ala Pro Ala Arg Ser Pro Arg
                1205                1210                1215

Leu Arg Arg Gly Gln Ser Ala Asp Lys Leu Gly Thr Gly Glu Arg Leu
            1220                1225                1230

Asp Gly Glu Ala Gly Arg Arg Thr Arg Gly Pro Glu Ala Glu Leu Val
        1235                1240                1245

Val Met Arg Arg Leu His Leu Ser Glu Arg Arg Asp Ser Phe Lys Lys
    1250                1255                1260

Gln Glu Ala Val Gln Glu Val Ser Phe Asp Glu Pro Gln Glu Ala
1265                1270                1275                1280

Thr Gly Leu Pro Thr Ser Val Pro Gln Ile Ala Val Glu Gly Glu Glu
                1285                1290                1295

Ala Val Pro Val Ala Leu Gly Pro Thr Gly Arg Asp
            1300                1305
```

<210> SEQ ID NO 80
<211> LENGTH: 1265
<212> TYPE: PRT
<213> ORGANISM: Homo sapiens

<400> SEQUENCE: 80

```
Arg Asp Pro Leu Glu Glu Met Ala Gln Leu Ser Ser Cys Asp Ser Pro
 1               5                  10                  15

Asp Thr Pro Glu Thr Asp Ser Ile Glu Gly His Gly Ala Ser Leu
            20                  25                  30

Pro Ser Lys Lys Thr Pro Ser Glu Glu Asp Phe Glu Thr Ile Lys Leu
        35                  40                  45

Ile Ser Asn Gly Ala Tyr Gly Ala Val Phe Leu Val Arg His Lys Ser
    50                  55                  60
```

-continued

```
Thr Arg Gln Arg Phe Ala Met Lys Lys Ile Asn Lys Gln Asn Leu Ile
 65                  70                  75                  80

Leu Arg Asn Gln Ile Gln Gln Ala Phe Val Glu Arg Asp Ile Leu Thr
             85                  90                  95

Phe Ala Glu Asn Pro Phe Val Val Ser Met Phe Cys Ser Phe Asp Thr
            100                 105                 110

Lys Arg His Leu Cys Met Val Met Glu Tyr Val Glu Gly Gly Asp Cys
            115                 120                 125

Ala Thr Leu Leu Lys Asn Ile Gly Ala Leu Pro Val Asp Met Val Arg
        130                 135                 140

Leu Tyr Phe Ala Glu Thr Val Leu Ala Leu Glu Tyr Leu His Asn Tyr
145                 150                 155                 160

Gly Ile Val His Arg Asp Leu Lys Pro Asp Asn Leu Leu Ile Thr Ser
                165                 170                 175

Met Gly His Ile Lys Leu Thr Asp Phe Gly Leu Ser Lys Met Gly Leu
            180                 185                 190

Met Ser Leu Thr Thr Asn Leu Tyr Glu Gly His Ile Glu Lys Asp Ala
        195                 200                 205

Arg Glu Phe Leu Asp Lys Gln Val Cys Gly Thr Pro Glu Tyr Ile Ala
210                 215                 220

Pro Glu Val Ile Leu Arg Gln Gly Tyr Gly Lys Pro Val Asp Trp Trp
225                 230                 235                 240

Ala Met Gly Ile Ile Leu Tyr Glu Phe Leu Val Gly Cys Val Pro Phe
                245                 250                 255

Phe Gly Asp Thr Pro Glu Glu Leu Phe Gly Gln Val Ile Ser Asp Glu
            260                 265                 270

Ile Val Trp Pro Glu Gly Asp Glu Ala Leu Pro Pro Asp Ala Gln Asp
        275                 280                 285

Leu Thr Ser Lys Leu Leu His Gln Asn Pro Leu Glu Arg Leu Gly Thr
    290                 295                 300

Gly Ser Ala Tyr Glu Val Lys Gln His Pro Phe Phe Thr Gly Leu Asp
305                 310                 315                 320

Trp Thr Gly Leu Leu Arg Gln Lys Ala Glu Phe Ile Pro Gln Leu Glu
                325                 330                 335

Ser Glu Asp Asp Thr Ser Tyr Phe Asp Thr Arg Ser Glu Arg Tyr His
            340                 345                 350

His Met Asp Ser Glu Asp Glu Glu Val Ser Glu Asp Gly Cys Leu
        355                 360                 365

Glu Ile Arg Gln Phe Ser Ser Cys Ser Pro Arg Phe Asn Lys Val Tyr
    370                 375                 380

Ser Ser Met Glu Arg Leu Ser Leu Leu Glu Glu Arg Arg Thr Pro Pro
385                 390                 395                 400

Pro Thr Lys Arg Ser Leu Ser Glu Glu Lys Glu Asp His Ser Asp Gly
                405                 410                 415

Leu Ala Gly Leu Lys Gly Arg Asp Arg Ser Trp Val Ile Gly Ser Pro
            420                 425                 430

Glu Ile Leu Arg Lys Arg Leu Ser Val Ser Glu Ser Ser His Thr Glu
        435                 440                 445

Ser Asp Ser Ser Pro Pro Met Thr Val Arg Arg Cys Ser Gly Leu
    450                 455                 460

Leu Asp Ala Pro Arg Phe Pro Glu Gly Pro Glu Glu Ala Ser Ser Thr
465                 470                 475                 480
```

```
Leu Arg Arg Gln Pro Gln Glu Gly Ile Trp Val Leu Thr Pro Pro Ser
                485                 490                 495

Gly Glu Gly Val Ser Gly Pro Val Thr Glu His Ser Gly Glu Gln Arg
            500                 505                 510

Pro Lys Leu Asp Glu Glu Ala Val Gly Arg Ser Ser Gly Ser Ser Pro
        515                 520                 525

Ala Met Glu Thr Arg Gly Arg Gly Thr Ser Gln Leu Ala Glu Gly Ala
    530                 535                 540

Thr Ala Lys Ala Ile Ser Asp Leu Ala Val Arg Arg Ala Arg His Arg
545                 550                 555                 560

Leu Leu Ser Gly Asp Ser Thr Glu Lys Arg Thr Ala Arg Pro Val Asn
                565                 570                 575

Lys Val Ile Lys Ser Ala Ser Ala Thr Ala Leu Ser Leu Leu Ile Pro
            580                 585                 590

Ser Glu His His Thr Cys Ser Pro Leu Ala Ser Pro Met Ser Pro His
        595                 600                 605

Ser Gln Ser Ser Asn Pro Ser Ser Arg Asp Ser Ser Pro Ser Arg Asp
    610                 615                 620

Phe Leu Pro Ala Leu Gly Ser Met Arg Pro Pro Ile Ile Ile His Arg
625                 630                 635                 640

Ala Gly Lys Lys Tyr Gly Phe Thr Leu Arg Ala Ile Arg Val Tyr Met
                645                 650                 655

Gly Asp Ser Asp Val Tyr Thr Val His His Met Val Trp His Val Glu
            660                 665                 670

Asp Gly Gly Pro Ala Ser Glu Ala Gly Leu Arg Gln Gly Asp Leu Ile
        675                 680                 685

Thr His Val Asn Gly Glu Pro Val His Gly Leu Val His Thr Glu Val
    690                 695                 700

Val Glu Leu Ile Leu Lys Ser Gly Asn Lys Val Ala Ile Ser Thr Thr
705                 710                 715                 720

Pro Leu Glu Asn Thr Ser Ile Lys Val Gly Pro Ala Arg Lys Gly Ser
                725                 730                 735

Tyr Lys Ala Lys Met Ala Arg Arg Ser Lys Arg Ser Arg Gly Lys Asp
            740                 745                 750

Gly Gln Glu Ser Arg Lys Arg Ser Ser Leu Phe Arg Lys Ile Thr Lys
        755                 760                 765

Gln Ala Ser Leu Leu His Thr Ser Arg Ser Leu Ser Ser Leu Asn Arg
    770                 775                 780

Ser Leu Ser Ser Gly Glu Ser Gly Pro Gly Ser Pro Thr His Ser His
785                 790                 795                 800

Ser Leu Ser Pro Arg Ser Pro Thr Gln Gly Tyr Arg Val Thr Pro Asp
                805                 810                 815

Ala Val His Ser Val Gly Gly Asn Ser Ser Gln Ser Ser Ser Pro Ser
            820                 825                 830

Ser Ser Val Pro Ser Ser Pro Ala Gly Ser Gly His Thr Arg Pro Ser
        835                 840                 845

Ser Leu His Gly Leu Ala Pro Lys Leu Gln Arg Gln Tyr Arg Ser Pro
    850                 855                 860

Arg Arg Lys Ser Ala Gly Ser Ile Pro Leu Ser Pro Leu Ala His Thr
865                 870                 875                 880

Pro Ser Pro Pro Pro Thr Ala Ser Pro Gln Arg Ser Pro Ser Pro
                885                 890                 895
```

```
Leu Ser Gly His Val Ala Gln Ala Phe Pro Thr Lys Leu His Leu Ser
            900                 905                 910
Pro Pro Leu Gly Arg Gln Leu Ser Arg Pro Lys Ser Ala Glu Pro Pro
        915                 920                 925
Arg Ser Pro Leu Leu Lys Arg Val Gln Ser Ala Glu Lys Leu Ala Ala
    930                 935                 940
Ala Leu Ala Ala Ser Glu Lys Lys Leu Ala Thr Ser Arg Lys His Ser
945                 950                 955                 960
Leu Asp Leu Pro His Ser Glu Leu Lys Lys Glu Leu Pro Pro Arg Glu
                965                 970                 975
Val Ser Pro Leu Glu Val Val Gly Ala Arg Ser Val Leu Ser Gly Lys
            980                 985                 990
Gly Ala Leu Pro Gly Lys Gly Val Leu Gln Pro Ala Pro Ser Arg Ala
        995                 1000                1005
Leu Gly Thr Leu Arg Gln Asp Arg Ala Glu Arg Glu Ser Leu Gln
    1010                1015                1020
Lys Gln Glu Ala Ile Arg Glu Val Asp Ser Ser Glu Asp Asp Thr Glu
1025                1030                1035                1040
Glu Gly Pro Glu Asn Ser Gln Gly Ala Gln Leu Ser Leu Ala Pro
                1045                1050                1055
His Pro Glu Val Ser Gln Ser Val Ala Pro Lys Gly Ala Gly Glu Ser
            1060                1065                1070
Gly Glu Glu Asp Pro Phe Pro Ser Arg Gly Pro Arg Ser Leu Gly Pro
        1075                1080                1085
Met Val Pro Ser Leu Leu Thr Gly Ile Thr Leu Gly Pro Pro Arg Met
    1090                1095                1100
Glu Ser Pro Ser Gly Pro His Arg Arg Leu Gly Ser Pro Gln Ala Ile
1105                1110                1115                1120
Glu Glu Ala Ala Ser Ser Ser Ala Gly Pro Asn Leu Gly Gln Ser
                1125                1130                1135
Gly Ala Thr Asp Pro Ile Pro Pro Glu Gly Cys Trp Lys Ala Gln His
            1140                1145                1150
Leu His Thr Gln Ala Leu Thr Ala Leu Ser Pro Ser Thr Ser Gly Leu
        1155                1160                1165
Thr Pro Thr Ser Ser Cys Ser Pro Ser Ser Thr Ser Gly Lys Leu
    1170                1175                1180
Ser Met Trp Ser Trp Lys Ser Leu Ile Glu Gly Pro Asp Arg Ala Ser
1185                1190                1195                1200
Pro Ser Arg Lys Ala Thr Met Ala Gly Gly Leu Ala Asn Leu Gln Asp
                1205                1210                1215
Leu Glu Thr Gln Leu Gln Pro Ser Leu Arg Thr Cys Leu Pro Gly Ser
            1220                1225                1230
Arg Gly Arg His Ser His Leu Val Pro Pro Asp Trp Pro Ile His Leu
        1235                1240                1245
Met Arg Ile Pro Ala Arg Ala Gly Tyr Gly Ser Leu Ser Val His Lys
    1250                1255                1260
Gln
1265

<210> SEQ ID NO 81
<211> LENGTH: 1734
<212> TYPE: PRT
<213> ORGANISM: Mus musculus
```

<400> SEQUENCE: 81

```
Met Val Thr Gly Leu Ser Pro Leu Leu Phe Arg Lys Leu Ser Asn Pro
 1               5                  10                  15

Asp Ile Phe Ala Pro Thr Gly Lys Val Lys Leu Gln Arg Gln Leu Ser
                20                  25                  30

Gln Asp Asp Cys Lys Leu Arg Arg Gly Ser Leu Ala Ser Ser Leu Ser
            35                  40                  45

Gly Lys Gln Leu Leu Pro Leu Ser Ser Ser Val His Ser Ser Val Gly
        50                  55                  60

Gln Val Thr Trp Gln Ser Thr Gly Glu Ala Ser Asn Leu Val Arg Met
65                  70                  75                  80

Arg Asn Gln Ser Leu Gly Gln Ser Ala Pro Ser Leu Thr Ala Gly Leu
                85                  90                  95

Lys Glu Leu Ser Leu Pro Arg Arg Gly Ser Phe Cys Arg Thr Ser Asn
               100                 105                 110

Arg Lys Ser Leu Ile Val Thr Ser Ser Thr Ser Pro Thr Leu Pro Arg
           115                 120                 125

Pro His Ser Pro Leu His Gly His Thr Gly Asn Ser Pro Leu Asp Ser
       130                 135                 140

Pro Arg Asn Phe Ser Pro Asn Ala Pro Ala His Phe Ser Phe Val Pro
145                 150                 155                 160

Ala Arg Arg Thr Asp Gly Arg Arg Trp Ser Leu Ala Ser Leu Pro Ser
               165                 170                 175

Ser Gly Tyr Gly Thr Asn Thr Pro Ser Ser Thr Val Ser Ser Ser Cys
           180                 185                 190

Ser Ser Gln Glu Lys Leu His Gln Leu Pro Phe Gln Pro Thr Ala Asp
       195                 200                 205

Glu Leu His Phe Leu Thr Lys His Phe Ser Thr Glu Asn Val Pro Asp
   210                 215                 220

Glu Glu Gly Arg Arg Ser Pro Arg Met Arg Pro Arg Ser Arg Ser Leu
225                 230                 235                 240

Ser Pro Gly Arg Ser Pro Val Ser Phe Asp Ser Glu Ile Ile Met Met
               245                 250                 255

Asn His Val Tyr Lys Glu Arg Phe Pro Lys Ala Thr Ala Gln Met Glu
           260                 265                 270

Glu Arg Pro Ser Leu Thr Phe Ile Ser Ser Asn Thr Pro Asp Ser Val
       275                 280                 285

Leu Pro Leu Ala Asp Gly Ala Leu Ser Phe Ile His His Gln Val Ile
   290                 295                 300

Glu Met Ala Arg Asp Cys Leu Asp Lys Ser Arg Ser Gly Leu Ile Thr
305                 310                 315                 320

Ser His Tyr Phe Tyr Glu Leu Gln Glu Asn Leu Glu Lys Leu Leu Gln
               325                 330                 335

Asp Ala His Glu Arg Ser Glu Ser Ser Asp Val Ala Phe Val Ile Gln
           340                 345                 350

Leu Val Lys Lys Leu Met Ile Ile Ile Ala Arg Pro Ala Arg Leu Leu
       355                 360                 365

Glu Cys Leu Glu Phe Asp Pro Glu Glu Phe Tyr His Leu Leu Glu Ala
   370                 375                 380

Ala Glu Gly His Ala Lys Glu Gly His Gly Ile Lys Cys Asp Ile Pro
385                 390                 395                 400

Arg Tyr Ile Val Ser Gln Leu Gly Leu Thr Arg Asp Pro Leu Glu Glu
               405                 410                 415
```

-continued

```
Met Ala Gln Leu Ser Ser Tyr Asp Ser Pro Asp Thr Glu Thr Asp
            420                 425                 430
Asp Ser Val Glu Gly Arg Gly Val Ser Gln Pro Ser Gln Lys Thr Pro
        435                 440                 445
Ser Glu Glu Asp Phe Glu Thr Ile Lys Leu Ile Ser Asn Gly Ala Tyr
    450                 455                 460
Gly Ala Val Phe Leu Val Arg His Lys Ser Thr Arg Gln Arg Phe Ala
465                 470                 475                 480
Met Lys Lys Ile Asn Lys Gln Asn Leu Ile Leu Arg Asn Gln Ile Gln
                485                 490                 495
Gln Ala Phe Val Glu Arg Asp Ile Leu Thr Phe Ala Glu Asn Pro Phe
            500                 505                 510
Val Val Ser Met Phe Cys Ser Phe Glu Thr Lys Arg His Leu Cys Met
        515                 520                 525
Val Met Glu Tyr Val Glu Gly Gly Asp Cys Ala Thr Leu Leu Lys Asn
    530                 535                 540
Ile Gly Ala Leu Pro Val Asp Met Val Arg Leu Tyr Phe Ala Glu Thr
545                 550                 555                 560
Val Leu Ala Leu Glu Tyr Leu His Asn Tyr Gly Ile Val His Arg Asp
                565                 570                 575
Leu Lys Pro Asp Asn Leu Leu Ile Thr Ser Met Gly His Ile Lys Leu
            580                 585                 590
Thr Asp Phe Gly Leu Ser Lys Ile Gly Leu Met Ser Leu Thr Thr Asn
        595                 600                 605
Leu Tyr Glu Gly His Ile Glu Lys Asp Ala Arg Glu Phe Leu Asp Lys
    610                 615                 620
Gln Val Cys Gly Thr Pro Glu Tyr Ile Ala Pro Glu Val Ile Leu Arg
625                 630                 635                 640
Gln Gly Tyr Gly Lys Pro Val Asp Trp Trp Ala Met Gly Ile Ile Leu
                645                 650                 655
Tyr Glu Phe Leu Val Gly Cys Val Pro Phe Phe Gly Asp Thr Pro Glu
            660                 665                 670
Glu Leu Phe Gly Gln Val Ile Ser Asp Glu Ile Val Trp Pro Glu Gly
        675                 680                 685
Asp Asp Ala Leu Pro Pro Asp Ala Gln Asp Leu Thr Ser Lys Leu Leu
    690                 695                 700
His Gln Asn Pro Leu Glu Arg Leu Gly Thr Ser Ser Ala Tyr Glu Val
705                 710                 715                 720
Lys Gln His Pro Phe Phe Met Gly Leu Asp Trp Thr Gly Leu Leu Arg
                725                 730                 735
Gln Lys Ala Glu Phe Ile Pro Gln Leu Glu Ser Glu Asp Thr Ser
            740                 745                 750
Tyr Phe Asp Thr Arg Ser Glu Arg Tyr His His Val Asp Ser Glu Asp
        755                 760                 765
Glu Glu Glu Val Ser Glu Asp Gly Cys Leu Glu Ile Arg Gln Phe Ser
    770                 775                 780
Ser Cys Ser Pro Arg Phe Ser Lys Val Tyr Ser Ser Met Glu Arg Leu
785                 790                 795                 800
Ser Leu Leu Glu Glu Arg Arg Thr Pro Pro Pro Thr Lys Arg Ser Leu
                805                 810                 815
Ser Glu Glu Lys Glu Asp His Ser Asp Gly Leu Ala Gly Leu Lys Gly
            820                 825                 830
```

```
Arg Asp Arg Ser Trp Val Ile Gly Ser Pro Glu Ile Leu Arg Lys Arg
        835                 840                 845

Leu Ser Val Ser Glu Ser Ser His Thr Glu Ser Asp Ser Ser Pro Pro
    850                 855                 860

Met Thr Val Arg His Arg Cys Ser Gly Leu Pro Asp Gly Pro His Cys
865                 870                 875                 880

Pro Glu Glu Thr Ser Ser Thr Pro Arg Lys Gln Gln Gln Gly Ile
                885                 890                 895

Trp Val Leu Ile Pro Pro Ser Gly Glu Gly Ser Ser Arg Pro Val Pro
            900                 905                 910

Glu Arg Pro Leu Glu Arg Gln Leu Lys Leu Asp Glu Pro Pro Gly
        915                 920                 925

Gln Ser Ser Arg Cys Cys Pro Ala Leu Glu Thr Arg Gly Arg Gly Thr
    930                 935                 940

Pro Gln Leu Ala Glu Glu Ala Thr Ala Lys Ala Ile Ser Asp Leu Ala
945                 950                 955                 960

Val Arg Arg Ala Arg His Arg Leu Leu Ser Gly Asp Ser Ile Glu Lys
                965                 970                 975

Arg Thr Thr Arg Pro Val Asn Lys Val Ile Lys Ser Ala Ser Ala Thr
            980                 985                 990

Ala Leu Ser Leu Leu Ile Pro Ser Glu His His Ala Cys Ser Pro Leu
    995                 1000                1005

Ala Ser Pro Met Ser Pro His Ser Gln Ser Ser Asn Pro Ser Ser Arg
    1010                1015                1020

Asp Ser Ser Pro Ser Arg Asp Phe Leu Pro Ala Leu Gly Ser Leu Arg
1025                1030                1035                1040

Pro Pro Ile Ile Ile His Arg Ala Gly Lys Lys Tyr Gly Phe Thr Leu
            1045                1050                1055

Arg Ala Ile Arg Val Tyr Met Gly Asp Thr Asp Val Tyr Thr Val His
            1060                1065                1070

His Met Val Trp His Val Glu Asp Gly Gly Pro Ala Ser Glu Ala Gly
        1075                1080                1085

Leu Arg Gln Gly Asp Leu Ile Thr His Val Asn Gly Glu Pro Val His
        1090                1095                1100

Gly Leu Val His Thr Glu Val Val Glu Leu Val Leu Lys Ser Gly Asn
1105                1110                1115                1120

Lys Val Ser Ile Ser Thr Thr Pro Leu Glu Asn Thr Ser Ile Lys Val
            1125                1130                1135

Gly Pro Ala Arg Lys Gly Ser Tyr Lys Ala Lys Met Ala Arg Arg Ser
            1140                1145                1150

Lys Arg Ser Lys Gly Lys Asp Gly Gln Glu Ser Arg Lys Arg Ser Ser
            1155                1160                1165

Leu Phe Arg Lys Ile Thr Lys Gln Ala Ser Leu Leu His Thr Ser Arg
            1170                1175                1180

Ser Leu Ser Ser Leu Asn Arg Ser Leu Ser Ser Gly Glu Ser Gly Pro
1185                1190                1195                1200

Gly Ser Pro Thr His Ser His Ser Leu Ser Pro Arg Ser Pro Pro Gln
                1205                1210                1215

Gly Tyr Arg Val Ala Pro Asp Ala Val His Ser Val Gly Gly Asn Ser
            1220                1225                1230

Ser Gln Ser Ser Ser Pro Ser Ser Val Pro Ser Ser Pro Ala Gly
            1235                1240                1245
```

```
Ser Gly His Thr Arg Pro Ser Ser Leu His Gly Leu Ala Pro Lys Leu
    1250                1255                1260

Gln Arg Gln Tyr Arg Ser Pro Arg Arg Lys Ser Ala Gly Ser Ile Pro
1265            1270                1275                1280

Leu Ser Pro Leu Ala His Thr Pro Ser Pro Pro Ala Thr Ala Ala Ser
                1285                1290                1295

Pro Gln Arg Ser Pro Ser Pro Leu Ser Gly His Gly Ser Gln Ser Phe
            1300                1305                1310

Pro Thr Lys Leu His Leu Ser Pro Pro Leu Gly Arg Gln Leu Ser Arg
        1315                1320                1325

Pro Lys Ser Ala Glu Pro Pro Arg Ser Pro Leu Leu Lys Arg Val Gln
    1330                1335                1340

Ser Ala Glu Lys Leu Ala Ala Ala Leu Ala Ala Ala Glu Lys Lys Leu
1345                1350                1355                1360

Ala Pro Ser Arg Lys His Ser Leu Asp Leu Pro His Gly Glu Leu Lys
            1365                1370                1375

Lys Glu Leu Thr Pro Arg Glu Ala Ser Pro Leu Glu Val Val Gly Thr
                1380                1385                1390

Arg Ser Val Leu Ser Gly Lys Gly Pro Leu Pro Gly Lys Gly Val Leu
            1395                1400                1405

Gln Pro Ala Pro Ser Arg Ala Leu Gly Thr Leu Arg Gln Asp Arg Ala
        1410                1415                1420

Glu Arg Arg Glu Ser Leu Gln Lys Gln Glu Ala Ile Arg Glu Val Asp
1425                1430                1435                1440

Ser Ser Glu Asp Asp Thr Asp Glu Glu Pro Glu Asn Ser Gln Ala Thr
            1445                1450                1455

Gln Glu Pro Arg Leu Ser Pro His Pro Glu Ala Ser His Asn Leu Leu
        1460                1465                1470

Pro Lys Gly Ser Gly Glu Gly Thr Glu Glu Asp Thr Phe Leu His Arg
    1475                1480                1485

Asp Leu Lys Lys Gln Gly Pro Val Leu Ser Gly Leu Val Thr Gly Ala
        1490                1495                1500

Thr Leu Gly Ser Pro Arg Val Asp Val Pro Gly Leu Ser Pro Arg Lys
1505                1510                1515                1520

Val Ser Arg Pro Gln Ala Phe Glu Ala Thr Asn Pro Leu Gln Val
            1525                1530                1535

Pro Ser Leu Ser Arg Ser Gly Pro Thr Ser Pro Thr Pro Ser Glu Gly
        1540                1545                1550

Cys Trp Lys Ala Gln His Leu His Thr Gln Ala Leu Thr Ala Leu Cys
    1555                1560                1565

Pro Ser Phe Ser Glu Leu Thr Pro Thr Gly Cys Ser Ala Ala Thr Ser
    1570                1575                1580

Thr Ser Gly Lys Pro Gly Thr Trp Ser Trp Lys Phe Leu Ile Glu Gly
1585                1590                1595                1600

Pro Asp Arg Ala Ser Thr Asn Lys Thr Ile Thr Arg Lys Gly Glu Pro
            1605                1610                1615

Ala Asn Ser Gln Asp Thr Asn Thr Val Pro Asn Leu Leu Lys Asn
            1620                1625                1630

Leu Ser Pro Glu Glu Glu Lys Pro Gln Pro Pro Ser Val Pro Gly Leu
        1635                1640                1645

Thr His Pro Leu Leu Glu Val Pro Ser Gln Asn Trp Pro Trp Glu Ser
        1650                1655                1660
```

-continued

```
Glu Cys Glu Gln Met Glu Lys Glu Pro Ser Leu Ser Ile Thr Glu
1665                1670                1675                1680

Val Pro Asp Ser Ser Gly Asp Arg Arg Gln Asp Ile Pro Cys Arg Ala
            1685                1690                1695

His Pro Leu Ser Pro Glu Thr Arg Pro Ser Leu Leu Trp Lys Ser Gln
        1700                1705                1710

Glu Leu Gly Gly Gln Gln Asp His Gln Asp Leu Ala Leu Thr Ser Asp
    1715                1720                1725

Glu Leu Leu Lys Gln Thr
    1730

<210> SEQ ID NO 82
<211> LENGTH: 1309
<212> TYPE: PRT
<213> ORGANISM: Schizosaccharomyces pombe
<220> FEATURE:
<221> NAME/KEY: VARIANT
<222> LOCATION: (1)...(1309)
<223> OTHER INFORMATION: Xaa = Any Amino Acid

<400> SEQUENCE: 82

Met Lys His Ile Lys Asn Glu Arg Glu Val Phe Leu Glu Asp Asp
 1               5                  10                  15

Gln Ala Gln His Ser Gln Ala Glu Leu Leu Ser Ser Lys Asp Glu Asn
            20                  25                  30

Leu Gln Pro Ser Ile Pro Leu Ser Pro Val Ala Phe Glu Leu Asp Phe
        35                  40                  45

Ser Gly Asn Phe Gln Phe Ile Ser Asp Asn Ser Ser Glu Leu Leu Asp
 50                  55                  60

Ile Pro Lys Asp Lys Ile Ile Gly His Ser Val Ala Glu Val Leu Gly
 65                  70                  75                  80

Thr Asp Gly Tyr Asn Ala Phe Met Arg Ala Val Asn Cys Leu Leu Lys
                85                  90                  95

Asp Asp Ser His Ser Tyr His Val Arg Phe Gln His Ser Ile Asn Ala
            100                 105                 110

Asn His Ala Asn Gln Asn Tyr Tyr Thr Ala Lys Gly Asp Leu Pro Ser
        115                 120                 125

Asp Glu Lys Xaa Thr Lys Pro Phe Asp Ala Ile Gly Ile Leu Ile Arg
130                 135                 140

His Pro Gly Xaa Ala Ile Pro Ala His Thr Met Trp Val Val Asn Pro
145                 150                 155                 160

Ala Thr Asn Ser Leu Gly Ser Val Ser Pro Leu Val Thr Lys Leu Leu
                165                 170                 175

Asp Val Ile Gly Phe Gly Ala Ser Leu Leu Asp Lys Tyr Leu Cys Asp
            180                 185                 190

Leu Arg Thr Ser Tyr His Lys His Asn Ser Leu Asp Ala Leu Pro Leu
        195                 200                 205

Pro Thr Pro Glu Phe Cys Gln Ile Cys Glu Arg Glu Ile Gln Ser Trp
    210                 215                 220

Phe Phe Glu Leu His Ser Lys Phe Cys Leu Ser Thr Ser Thr Tyr Glu
225                 230                 235                 240

Ser Val Val Gln Ala Ala Gln Asp Ser Leu Leu Tyr Phe Arg Ser Thr
                245                 250                 255

Leu Leu Glu Ile Gln Glu Gly Met Gln Lys Asp Ser Ser Leu Val Pro
            260                 265                 270
```

-continued

```
Val Tyr Lys Asn Glu Pro Leu Ile Val Asp Ala Asp Tyr Phe Phe
    275                 280                 285

Thr Asp Glu Asn Lys Gln Thr Leu Ser Leu Cys Ser Phe Leu Ser Gln
    290                 295                 300

Val Met Tyr Tyr Leu Glu Val Ala Ile Asp Ile Thr Ile Pro Pro Val
305                 310                 315                 320

Lys Ile Ile Val Asn Phe Asp Lys Val Asp Ser Leu Arg Val Gln Ser
                325                 330                 335

Pro Arg Ser Glu Lys Ala Thr Ile Glu Leu Asp Asn Tyr Asn Pro Ser
            340                 345                 350

Leu Glu Asn Cys Ser Ser Ala Val Ile Ala Leu Trp Glu Asp Ile Lys
        355                 360                 365

Thr Ala Val Asp Thr Lys Ile Thr Gly Val Leu Arg Leu Arg Asn Ala
    370                 375                 380

Ile Tyr Tyr Ser Glu Arg Xaa Arg Leu Glu Ile Asp His His Val Gln
385                 390                 395                 400

Glu Ile Ile Asp Asp Val Val Ser Asn Leu Val Thr Asn His Ser Ser
                405                 410                 415

Thr Ser Leu Gly His Leu Glu Ser Lys Leu Ala Pro Ser Ile Thr Phe
            420                 425                 430

Pro Asp Ala Cys Asp Ala Leu Glu Ala Glu Glu Cys Ile Thr Arg Pro
        435                 440                 445

Gly Ser Ala Thr Asn Thr Pro Gln Ser Asp Arg Ser Leu Asp Ile Asn
    450                 455                 460

Asp Leu Ser Arg Ser Ser Ser Tyr Ser Arg His Leu Ser His Val Ser
465                 470                 475                 480

Leu Ser Asn Pro Asp Phe Ala Ile Gly Ser Pro Met Ser Gln Asp Ser
                485                 490                 495

Ser Asn Tyr Ser Ser Pro Leu His Arg Arg Lys Ala Ser Asp Ser Asn
            500                 505                 510

Phe Ser Asp Pro Arg Phe Asp Asp Leu Lys Tyr Leu Ser Pro Asn Ser
        515                 520                 525

Ser Pro Arg Phe Val Ala Ser Asp Gly Pro Asn Arg Pro Ala Ser Asn
    530                 535                 540

Gly Arg Ser Ser Leu Phe Ser Arg Gly Arg Ala Ser Asn Leu Gly Asp
545                 550                 555                 560

Val Gly Leu Arg Leu Pro Ser Pro Ser Pro Arg Ile His Thr Ile Val
                565                 570                 575

Pro Asn Ser Ala Pro Glu His Pro Ser Ile Asn Asp Tyr Lys Ile Leu
            580                 585                 590

Lys Pro Ile Ser Lys Gly Ala Phe Gly Ser Val Tyr Leu Ala Gln Lys
        595                 600                 605

Arg Thr Thr Gly Asp Tyr Phe Ala Ile Lys Ile Leu Lys Lys Ser Asn
    610                 615                 620

Met Ile Ala Lys Asn Gln Val Ile Asn Val Arg Ala Glu Arg Ala Ile
625                 630                 635                 640

Leu Met Ser Gln Gly Glu Ser Pro Phe Val Ala Lys Leu Tyr Tyr Thr
                645                 650                 655

Phe Gln Ser Lys Asp Tyr Leu Tyr Leu Val Met Glu Tyr Leu Asn Gly
            660                 665                 670

Gly Asp Cys Gly Ser Leu Leu Lys Thr Met Gly Val Leu Asp Leu Asp
        675                 680                 685
```

-continued

```
Trp Ile Arg Thr Tyr Ile Ala Glu Thr Val Leu Cys Leu Gly Asp Leu
690                 695                 700

His Asp Arg Gly Ile Ile His Arg Asp Ile Lys Pro Glu Asn Leu Leu
705                 710                 715                 720

Ile Ser Gln Asn Gly His Leu Lys Leu Thr Asp Phe Gly Leu Ser Arg
            725                 730                 735

Val Gly Tyr Met Lys Arg His Arg Arg Lys Gln Ser Ser Ile Pro
            740                 745                 750

Val Leu Asp Leu Arg Asp Arg Ser Ala Ile Ser Asp Leu Ser Leu
            755                 760                 765

Ser Thr Ala Ser Ser Val Leu Glu Ala Gln Ser Leu Ile Thr Pro Glu
770                 775                 780

Xaa Pro Lys Arg Pro Ser Leu Asn Glu Lys Leu Leu Ser Leu Asp Gly
785                 790                 795                 800

Thr Ser Ile Arg Leu Ala Gly Gln Ser Phe Asn Tyr Glu Asn Ser Ala
            805                 810                 815

Glu Asp Ser Pro Thr Ala Thr Asn Thr Pro Thr Ser Gln Val Asp Glu
            820                 825                 830

Ser Asn Ile Phe Arg Ser Thr Asp Ser Pro Arg Val Gln Pro Phe Phe
            835                 840                 845

Glu Asn Lys Asp Pro Ser Lys Arg Phe Ile Gly Thr Pro Asp Tyr Ile
850                 855                 860

Ala Pro Glu Val Ile Leu Gly Asn Pro Gly Ile Lys Ala Ser Asp Trp
865                 870                 875                 880

Trp Ser Leu Gly Cys Val Val Phe Glu Phe Leu Phe Gly Tyr Pro Pro
            885                 890                 895

Phe Asn Ala Glu Thr Pro Asp Gln Val Phe Gln Asn Ile Leu Ala Arg
            900                 905                 910

Arg Ile Asn Trp Pro Ala Glu Val Phe Thr Ala Glu Ser Ser Val Ala
            915                 920                 925

Leu Asp Leu Ile Asp Arg Leu Leu Cys Met Asn Pro Ala Asn Arg Leu
930                 935                 940

Gly Ala Asn Gly Val Glu Glu Ile Lys Ala His Pro Phe Phe Lys Ser
945                 950                 955                 960

Val Asn Trp Asp Thr Ile Leu Glu Glu Asp Pro Pro Phe Val Pro Lys
            965                 970                 975

Pro Phe Ser Pro Glu Asp Thr Val Tyr Phe Asp Ser Arg Gly Leu Lys
            980                 985                 990

Gly Phe Asp Phe Ser Glu Tyr Tyr Asn Gln Pro Thr Val Thr Glu Ala
            995                 1000                1005

Gln Lys Leu Glu Glu Glu Arg Pro Ala Ser Ser Ile Pro Gln His Val
    1010                1015                1020

Ser Gly Asn Arg Lys Gly Arg Leu Arg Ser Asn Thr Ile Ser Thr Pro
1025                1030                1035                1040

Glu Phe Gly Ser Phe Thr Tyr Arg Asn Leu Asp Phe Leu Asn Lys Ala
            1045                1050                1055

Asn Arg Asn Thr Ile Gln Lys Leu Arg Lys Glu His Met Ala Val Lys
            1060                1065                1070

Ser Ala Lys Thr Ser Val Asp Asp Thr Phe Ser Gln Tyr Met Ser Arg
    1075                1080                1085

Phe Lys Ala Lys Leu Ser Thr Ser Gln Ser Val Gly Pro Val Lys Ser
    1090                1095                1100
```

Ser Arg Arg Ala Ser Met Ala Asp Tyr Glu Ala Ser Thr Thr Thr Arg
1105                1110                1115                1120

Val Gln Asp Ile Thr Thr Asp Ser Ile Asp Ser Ile Asp Asp Phe Asp
            1125                1130                1135

Ser Leu Lys Glu Gly Arg Met Leu Ser Phe Phe Asp Asn Leu Ala Leu
        1140                1145                1150

Glu Asp His Lys Gly Val Ser Ser Thr Met Ser Ala Ser Gln Ser Gln
    1155                1160                1165

Ser Ser Met His Thr Ala Leu Pro Asp Val Thr Glu Gly Thr Ser Ser
1170                1175                1180

Asp Glu His Thr Thr Ile Gln Lys Gly Arg Ile Asp Asn Leu Gln Ala
1185                1190                1195                1200

Gln Ser Leu Thr His Lys Arg Asn Ala Ile Ser Tyr Pro Gly Leu Phe
            1205                1210                1215

Gln Leu Asp Arg Leu Gln Met Ile Ile Pro Lys Asp Glu Ile Glu Leu
        1220                1225                1230

Ala Glu Ile Leu Lys Lys Ile Phe Pro Lys Leu Thr Leu Val Leu Ile
    1235                1240                1245

Asp Asp Pro Trp Ser Ile Leu Lys Lys Leu Leu Gln Asn Glu Gln Phe
1250                1255                1260

Asn Val Val Phe Leu His Phe Gly Asn Asp Lys Val Ser Ser Ser Arg
1265                1270                1275                1280

Leu Met Tyr Ser Val Arg Thr Ser Ala Thr Ile Asn Ser Arg Val Pro
            1285                1290                1295

Val Cys Ile His Leu Arg Gly Arg Asp Leu His Ser Asp
        1300                1305

<210> SEQ ID NO 83
<211> LENGTH: 21
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: Xaa = Leu, Ile or Val
<220> FEATURE:
<221> NAME/KEY: VARIANT
<222> LOCATION: 3, 5
<223> OTHER INFORMATION: Xaa = any amino acid except Pro
<220> FEATURE:
<221> NAME/KEY: VARIANT
<222> LOCATION: 6
<223> OTHER INFORMATION: Xaa = Phe, Tyr, Trp, Met, Gly, Ser,
      Thr, Asn, or His
<220> FEATURE:
<221> NAME/KEY: VARIANT
<222> LOCATION: 7
<223> OTHER INFORMATION: Xaa = Ser, Gly or Ala
<220> FEATURE:
<221> NAME/KEY: VARIANT
<222> LOCATION: 8
<223> OTHER INFORMATION: Xaa = any amino acid except Pro or Trp
<220> FEATURE:
<221> NAME/KEY: VARIANT
<222> LOCATION: 9
<223> OTHER INFORMATION: Xaa = Leu, Ile, Val, Cys, Ala, or Thr
<220> FEATURE:
<221> NAME/KEY: VARIANT
<222> LOCATION: 10
<223> OTHER INFORMATION: Xaa = amino acid except Pro or Asp
<220> FEATURE:
<221> NAME/KEY: VARIANT
<222> LOCATION: 11
<223> OTHER INFORMATION: Xaa = any amino acid

```
<220> FEATURE:
<221> NAME/KEY: VARIANT
<222> LOCATION: 12
<223> OTHER INFORMATION: Xaa = Gly, Ser, Thr, Ala, Cys, Leu,
      Ile, Val, Met, Phe, or Tyr
<220> FEATURE:
<221> NAME/KEY: VARIANT
<222> LOCATION: (13)...(17)
<223> OTHER INFORMATION: Xaa = any amino acid and can be a
      stretch of 5 to 18 residues long
<220> FEATURE:
<221> NAME/KEY: VARIANT
<222> LOCATION: 18
<223> OTHER INFORMATION: Xaa = Leu, Ile, Val, Met, Phe, Tyr,
      Trp, Cys, Ser, Thr, Ala, or Arg
<220> FEATURE:
<221> NAME/KEY: VARIANT
<222> LOCATION: 19
<223> OTHER INFORMATION: Xaa = Ala, Ile, Val, or Pro
<220> FEATURE:
<221> NAME/KEY: VARIANT
<222> LOCATION: 20
<223> OTHER INFORMATION: Xaa = Leu, Ile, Val, Met, Phe, Ala,
      Gly, Cys, Lys, or Arg

<400> SEQUENCE: 83

Xaa Gly Xaa Gly Xaa Xaa Xaa Xaa Xaa Xaa Xaa Xaa Xaa Xaa Xaa
 1               5                   10                  15

Xaa Xaa Xaa Xaa Lys
            20

<210> SEQ ID NO 84
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: Xaa = Leu, Ile, Val, Met, Phe, Tyr, or
      Cys
<220> FEATURE:
<221> NAME/KEY: VARIANT
<222> LOCATION: 2, 4, 8, 9
<223> OTHER INFORMATION: Xaa = any
      amino acid
<220> FEATURE:
<221> NAME/KEY: VARIANT
<222> LOCATION: 3
<223> OTHER INFORMATION: Xaa = His or Tyr
<220> FEATURE:
<221> NAME/KEY: VARIANT
<222> LOCATION: 6
<223> OTHER INFORMATION: Xaa = Leu, Ile, Val, Met, Phe or Tyr
<220> FEATURE:
<221> NAME/KEY: VARIANT
<222> LOCATION: (11)...(13)
<223> OTHER INFORMATION: Xaa = Leu, Ile, Val, Met,
      Phe, Tyr, Cys or Thr.

<400> SEQUENCE: 84

Xaa Xaa Xaa Xaa Asp Xaa Lys Xaa Xaa Asn Xaa Xaa Xaa
 1               5                   10

<210> SEQ ID NO 85
<211> LENGTH: 13
<212> TYPE: PRT
<213> ORGANISM: Artificial Sequence
<220> FEATURE:
<223> OTHER INFORMATION: consensus
```

```
<220> FEATURE:
<221> NAME/KEY: VARIANT
<222> LOCATION: 1
<223> OTHER INFORMATION: Xaa = Leu, Ile, Val, Met, Phe, Tyr or
      Cys
<220> FEATURE:
<221> NAME/KEY: VARIANT
<222> LOCATION: 2, 4, 8, 9
<223> OTHER INFORMATION: Xaa = any amino acid
<220> FEATURE:
<221> NAME/KEY: VARIANT
<222> LOCATION: 3
<223> OTHER INFORMATION: Xaa = His or Tyr
<220> FEATURE:
<221> NAME/KEY: VARIANT
<222> LOCATION: 6
<223> OTHER INFORMATION: Xaa = Leu, Ile, Val, Met, Phe, or Tyr
<220> FEATURE:
<221> NAME/KEY: VARIANT
<222> LOCATION: 7
<223> OTHER INFORMATION: Xaa = Arg, Ser, Thr, Ala or Cys
<220> FEATURE:
<221> NAME/KEY: VARIANT
<222> LOCATION: (11)...(13)
<223> OTHER INFORMATION: Xaa = Leu, Ile, Val, Met, Phe,
      Tyr, or Cys

<400> SEQUENCE: 85

Xaa Xaa Xaa Xaa Asp Xaa Xaa Xaa Xaa Asn Xaa Xaa Xaa
 1               5                  10

<210> SEQ ID NO 86
<211> LENGTH: 12
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)...(3)
<223> OTHER INFORMATION: Xaa = Leu, Ile, Val, Met, Phe,
      Tyr or Trp
<220> FEATURE:
<221> NAME/KEY: VARIANT
<222> LOCATION: 6
<223> OTHER INFORMATION: Xaa = Phe, Tyr or Ile
<220> FEATURE:
<221> NAME/KEY: VARIANT
<222> LOCATION: (9)...(11)
<223> OTHER INFORMATION: Residues 9, 10 and 11 can be any amino acid
<220> FEATURE:
<221> NAME/KEY: VARIANT
<222> LOCATION: 12
<223> OTHER INFORMATION: Xaa = Asn or Gln

<400> SEQUENCE: 86

Xaa Xaa Xaa Asp Gly Xaa Pro Arg Xaa Xaa Xaa Xaa
 1               5                  10

<210> SEQ ID NO 87
<211> LENGTH: 18
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 2
<223> OTHER INFORMATION: Xaa = Ser or Thr
<220> FEATURE:
<221> NAME/KEY: VARIANT
<222> LOCATION: 4, 5, 7, 8, 10, 11, 13, 14, 16
<223> OTHER INFORMATION: Residues 4, 5, 7, 8, 10, 11, 13 and 14 can be
      any amino acid
```

```
<220> FEATURE:
<221> NAME/KEY: VARIANT
<222> LOCATION: 6
<223> OTHER INFORMATION: Xaa = Lys or Arg
<220> FEATURE:
<221> NAME/KEY: VARIANT
<222> LOCATION: 9
<223> OTHER INFORMATION: Xaa = Asp or Glu
<220> FEATURE:
<221> NAME/KEY: VARIANT
<222> LOCATION: 17
<223> OTHER INFORMATION: Xaa = Phe or Tyr
<220> FEATURE:
<221> NAME/KEY: VARIANT
<222> LOCATION: 18
<223> OTHER INFORMATION: Xaa = Leu, Ile, Val, Met, or Lys

<400> SEQUENCE: 87

Thr Xaa Arg Xaa Xaa Xaa Xaa Xaa Xaa Xaa Xaa Gly Xaa Xaa Tyr Xaa
 1               5                  10                  15

Xaa Xaa

<210> SEQ ID NO 88
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: Xaa = Leu, Ile, Val, Ala or Cys
<220> FEATURE:
<221> NAME/KEY: VARIANT
<222> LOCATION: 2, 10
<223> OTHER INFORMATION: Xaa = any amino acid
<220> FEATURE:
<221> NAME/KEY: VARIANT
<222> LOCATION: 3, 4, 13
<223> OTHER INFORMATION: Xaa = Leu, Ile, Val, or Met
<220> FEATURE:
<221> NAME/KEY: VARIANT
<222> LOCATION: 5
<223> OTHER INFORMATION: Xaa = Ser, Ala, Pro, Cys or Val
<220> FEATURE:
<221> NAME/KEY: VARIANT
<222> LOCATION: 7
<223> OTHER INFORMATION: Xaa = Leu, Ile or Val
<220> FEATURE:
<221> NAME/KEY: VARIANT
<222> LOCATION: 9
<223> OTHER INFORMATION: Xaa = Asn, Lys, Arg, Ser or Thr
<220> FEATURE:
<221> NAME/KEY: VARIANT
<222> LOCATION: 11
<223> OTHER INFORMATION: Xaa = Asp, Glu, Gln, or His
<220> FEATURE:
<221> NAME/KEY: VARIANT
<222> LOCATION: 12
<223> OTHER INFORMATION: Xaa = Gly, Ser, Thr or Ala

<400> SEQUENCE: 88

Xaa Xaa Xaa Xaa Xaa Lys Xaa Glu Xaa Xaa Xaa Xaa Xaa
 1               5                  10

<210> SEQ ID NO 89
<211> LENGTH: 35
<212> TYPE: PRT
<213> ORGANISM: Artificial Sequence
<220> FEATURE:
<223> OTHER INFORMATION: consensus
```

```
<220> FEATURE:
<221> NAME/KEY: VARIANT
<222> LOCATION: 1
<223> OTHER INFORMATION: Xaa = Leu, Ile, Val, Met, Phe, Ala or
      Cys
<220> FEATURE:
<221> NAME/KEY: VARIANT
<222> LOCATION: 3
<223> OTHER INFORMATION: Xaa = any amino acid and can be a
      stretch of from 1 to 3 amino acids long
<220> FEATURE:
<221> NAME/KEY: VARIANT
<222> LOCATION: 4
<223> OTHER INFORMATION: Xaa = Asp, Glu or Ala
<220> FEATURE:
<221> NAME/KEY: VARIANT
<222> LOCATION: 5, 9
<223> OTHER INFORMATION: Xaa = Asp or Glu
<220> FEATURE:
<221> NAME/KEY: VARIANT
<222> LOCATION: 6
<223> OTHER INFORMATION: Xaa = Leu, Ile, Val, Met or Cys
<220> FEATURE:
<221> NAME/KEY: VARIANT
<222> LOCATION: 10-13, 16, 18-20, 22, 23, 27, 29, 33, 34
<223> OTHER INFORMATION: Xaa = any amino
      acid
<220> FEATURE:
<221> NAME/KEY: VARIANT
<222> LOCATION: 15
<223> OTHER INFORMATION: Xaa = Gly or Ser
<220> FEATURE:
<221> NAME/KEY: VARIANT
<222> LOCATION: 17
<223> OTHER INFORMATION: Xaa = Ala or Val
<220> FEATURE:
<221> NAME/KEY: VARIANT
<222> LOCATION: 21, 25, 26
<223> OTHER INFORMATION: Xaa = Leu, Ile, Val or
      Met
<220> FEATURE:
<221> NAME/KEY: VARIANT
<222> LOCATION: 24
<223> OTHER INFORMATION: Xaa = Phe, Tyr or His
<220> FEATURE:
<221> NAME/KEY: VARIANT
<222> LOCATION: 28
<223> OTHER INFORMATION: Xaa = Leu, Ile, Val, Met or Phe

<400> SEQUENCE: 89

Xaa Lys Xaa Xaa Xaa Xaa Arg Gln Xaa Xaa Xaa Xaa Xaa Gln Xaa Xaa
1               5                   10                  15

Xaa Xaa Xaa Xaa Xaa Xaa Xaa Xaa Xaa Xaa Xaa Xaa Xaa Asp Arg His
            20                  25                  30

Xaa Xaa Asn
        35
```